(12) United States Patent
Griffin et al.

(10) Patent No.: US 12,331,276 B2
(45) Date of Patent: Jun. 17, 2025

(54) APPARATUS FOR FLUID LINE MANAGEMENT IN A BIOPROCESSING SYSTEM

(71) Applicant: Global Life Sciences Solutions USA LLC, Marlborough, MA (US)

(72) Inventors: Weston Blaine Griffin, Niskayuna, NY (US); Alex D Corwin, Niskayuna, NY (US); Xiaohua Zhang, Niskayuna, NY (US); Reginald Donovan Smith, Niskayuna, NY (US); Zhen Liu, Niskayuna, NY (US); Chengkun Zhang, Niskayuna, NY (US); Vandana Keskar, Niskayuna, NY (US); Brian Michael Davis, Niskayuna, NY (US); Kashan Shaikh, Niskayuna, NY (US)

(73) Assignee: Global Life Sciences Solutions USA, Marlborough, MA (US)

( * ) Notice: Subject to any disclaimer, the term of this patent is extended or adjusted under 35 U.S.C. 154(b) by 0 days.

(21) Appl. No.: 18/651,024

(22) Filed: Apr. 30, 2024

(65) Prior Publication Data
US 2024/0279585 A1    Aug. 22, 2024

Related U.S. Application Data

(63) Continuation of application No. 16/968,333, filed as application No. PCT/EP2019/053206 on Feb. 8, (Continued)

(51) Int. Cl.
C12M 1/34    (2006.01)
C12M 1/00    (2006.01)
(Continued)

(52) U.S. Cl.
CPC ............ *C12M 29/04* (2013.01); *C12M 23/08* (2013.01); *C12M 23/24* (2013.01); *C12M 25/02* (2013.01);
(Continued)

(58) Field of Classification Search
None
See application file for complete search history.

(56) References Cited

U.S. PATENT DOCUMENTS 5,693,537 A    12/1997  Wilson et al.
10,696,961 B2   6/2020  Zhang et al.
(Continued)

FOREIGN PATENT DOCUMENTS

AU    2018376657       12/2018
CN    102504991 A1      6/2012
(Continued)

OTHER PUBLICATIONS

Corresponding Korean Patent Application No. 10-2020-7025578 Office Action dated May 23, 2024.
(Continued)

*Primary Examiner* — Jyoti Nagpaul
(74) *Attorney, Agent, or Firm* — Grogan, Tuccillo & Vanderleeden, LLP

(57) ABSTRACT

In an embodiment, a tubing module for a bioprocessing system includes a first tubing holder block configured to receive at least one pump tube and hold the at least one pump tube in position for selective engagement with a peristaltic pump, a second tubing holder block configured to receive a plurality of pinch valve tubes and hold each pinch valve tube of the plurality of pinch valve tubes in position for selective engagement with a respective actuator of a pinch valve array, and wherein the first tubing holder block and the second tubing holder block are interconnected.

21 Claims, 80 Drawing Sheets

Related U.S. Application Data 2019, now Pat. No. 12,077,743, which is a continuation-in-part of application No. 15/893,336, filed on Feb. 9, 2018, now Pat. No. 10,889,792.

(60) Provisional application No. 62/736,130, filed on Sep. 25, 2018, provisional application No. 62/736,115, filed on Sep. 25, 2018, provisional application No. 62/736,143, filed on Sep. 25, 2018, provisional application No. 62/736,120, filed on Sep. 25, 2018, provisional application No. 62/736,154, filed on Sep. 25, 2018, provisional application No. 62/736,125, filed on Sep. 25, 2018, provisional application No. 62/736,144, filed on Sep. 25, 2018.

(51) Int. Cl.
*C12M 1/04* (2006.01)
*C12M 1/12* (2006.01)
*C12M 1/24* (2006.01)
*C12M 1/26* (2006.01)
*C12N 5/0783* (2010.01)

(52) U.S. Cl.
CPC ............ *C12M 25/06* (2013.01); *C12M 29/18* (2013.01); *C12M 29/26* (2013.01); *C12M 33/00* (2013.01); *C12M 41/46* (2013.01); *C12N 5/0636* (2013.01)

(56) References Cited

U.S. PATENT DOCUMENTS

| | | | |
|---|---|---|---|
| 11,332,732 B2 | 5/2022 | Zhang et al. | |
| 2005/0051723 A1 | 3/2005 | Neagle et al. | |
| 2011/0136225 A1 | 6/2011 | Vunjak-Novakovic et al. | |
| 2016/0123848 A1* | 5/2016 | Griffin | C12M 37/02 |
| | | | 435/308.1 |
| 2017/0253847 A1 | 9/2017 | Koseki | |
| 2021/0087510 A1 | 3/2021 | Griffin et al. | |

FOREIGN PATENT DOCUMENTS

| | | |
|---|---|---|
| CN | 106062185 A | 10/2016 |
| EP | 3717622 | 12/2018 |
| JP | 2002542004 | 12/2002 |
| JP | 2007535965 | 12/2007 |
| JP | 2015-221001 A | 12/2015 |
| JP | 2016153124 | 8/2016 |
| JP | 2017513499 | 6/2017 |
| JP | 7350741 | 9/2023 |
| KR | 10-2008-0072006 A | 8/2008 |
| KR | 10-2016-0145162 A | 12/2016 |
| WO | 2010080032 A2 | 7/2010 |
| WO | 2016118780 | 7/2016 |
| WO | 2016185221 A1 | 11/2016 |
| WO | 2016189159 A1 | 12/2016 |
| WO | 2017035262 A1 | 3/2017 |
| WO | 2017/190254 | 9/2017 |
| WO | 2018005521 | 1/2018 |
| WO | 2018/111931 | 6/2018 |
| WO | 2019/106207 | 6/2019 |

OTHER PUBLICATIONS

Corresponding Chinese Patent Application No. 201980024222.8 Office Action dated May 29, 2024.
Hollyman, Daniel; Title: Manufacturing validation of biologically functional T Cells targeted to CD19 antigen for autologous adoptive cell therapy; Date: Feb. 1, 2010.
United States Office Action dated Oct. 30, 2024 for U.S. Appl. No. 16/968,374.
Mock et al. Automated manufacturing of chimeric antigen receptor T cells for adoptive immunotherapy using CliniMACS Prodigy Cytotherapy, 2016; 18: 1002-1011. (Year: 2016).
GE Application note. "Perfucsion culture of T lymphocytes in the WAVE Bioreactor System 2/10 (software version 2.61)", GE Healthcare Life Sciences, Application note 28-9650-52 AC. Published Jan. 2010, p. 1-9. (Year: 2010).
Mexico Office Action dated Aug. 22, 2024 for Application No. MX/a/2020/008317.
Korea Office Action dated Sep. 5, 2024 for Application No. 10-2020-7018529.
Canadian Examiners Report for corresponding Canada Application No. 3082861, dated Mar. 11, 2025.
Singh, Vijay, Disposable bioreactor for cell culture using wave-induced agitation, Cytotechnology 30: 149-158, 1999; Kluwer Academic Publishers, Printed in the Netherlands.
Japanese Office Action for corresponding Japan Application No. 2023-215870.

* cited by examiner

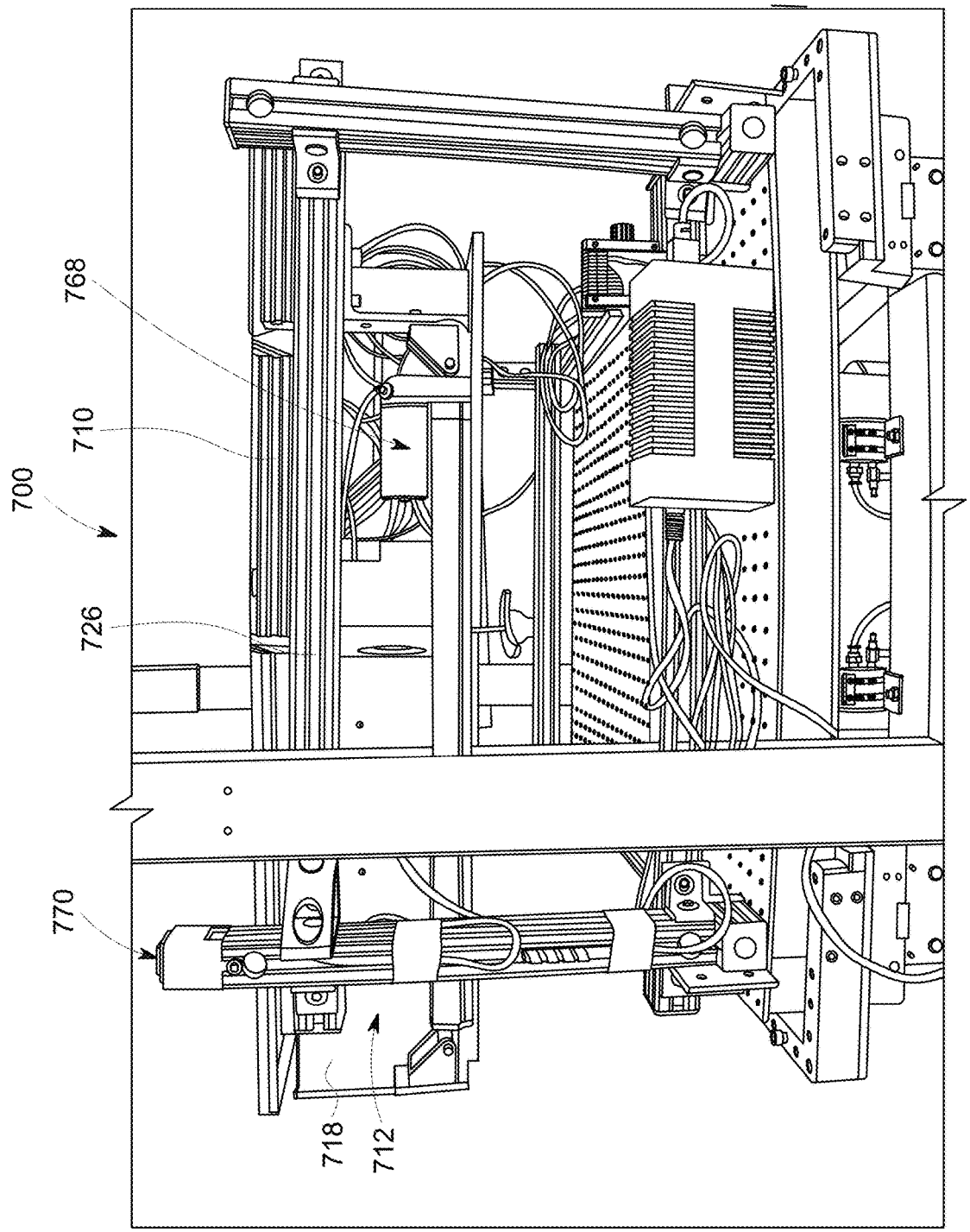

APPARATUS FOR FLUID LINE MANAGEMENT IN A BIOPROCESSING SYSTEM

CROSS-REFERENCE TO RELATED APPLICATIONS

This application is a continuation application of U.S. patent application Ser. No. 16/968,333, filed on Aug. 7, 2020, which is a national stage of International Application No. PCT/EP2019/053206 filed on Feb. 8, 2019, which is a continuation-in-part application of U.S. patent application Ser. No. 15/893,336 filed on Feb. 9, 2018, and claims priority to U.S. Provisional Application No. 62/736,115 filed on Sep. 25, 2018, and U.S. Provisional Application No. 62/736,125 filed Sep. 25, 2018, and U.S. Provisional Application No. 62/736,130 filed on Sep. 25, 2018, and U.S. Provisional Application No. 62/736,120 filed on Sep. 25, 2018, and U.S. Provisional Application No. 62/736,144 filed on Sep. 25, 2018, and U.S. Provisional Application No. 62/736,154 filed on Sep. 25, 2018, and U.S. Provisional Application No. 62/736,143 filed on Sep. 25, 2018, all of which are hereby incorporated by reference in their entireties.

BACKGROUND

Technical Field

Embodiments of the invention relate generally to bioprocessing systems and methods and, more particularly, to a bioprocessing system and methods for the production of cellular immunotherapies.

Discussion of Art

Various medical therapies involve the extraction, culture and expansion of cells for use in downstream therapeutic processes. For example, chimeric antigen receptor (CAR) T cell therapy is a cellular therapy that redirects a patient's T cells to specifically target and destroy tumor cells. The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. CAR-T cells can be derived from either a patient's own blood (autologous) or derived from another healthy donor (allogenic).

The first step in the production of CAR-T cells involves using apheresis, e.g., leukocyte apheresis, to remove blood from a patient's body and separate the leukocytes. After a sufficient quantity of leukocytes have been harvested, the leukapheresis product is enriched for T-cells, which involves washing the cells out of the leukapheresis buffer. T-cell subsets having particular bio-markers are then isolated from the enriched sub-population using specific antibody conjugates or markers.

After isolation of targeted T-cells, the cells are activated in a certain environment in which they can actively proliferate. For example, the cells may be activated using magnetic beads coated with anti-CD3/anti-CD28 monoclonal antibodies or cell-based artificial antigen presenting cells (aAPCs), which can be removed from the culture using magnetic separation. The T-cells are then transduced with CAR genes by either an integrating gammaretrovirus (RV) or by lentivirus (LV) vectors. The viral vector uses viral machinery to attach to the patient cells, and, upon entry into the cells, the vector introduces genetic material in the form of RNA. In the case of CAR-T cell therapy, this genetic material encodes the CAR. The RNA is reverse-transcribed into DNA and permanently integrates into the genome of the patient cells; allowing CAR expression to be maintained as the cells divide and are grown to large numbers in a bioreactor. The CAR is then transcribed and translated by the patient cells, and the CAR is expressed on the cell surface.

After the T cells are activated and transduced with the CAR-encoding viral vector, the cells are expanded to large numbers in a bioreactor to achieve a desired cell density. After expansion, the cells are harvested, washed, concentrated and formulated for infusion into a patient.

Existing systems and methods for manufacturing an infusible dose of CAR T cells require many complex operations involving a large number of human touchpoints, which adds time to the overall manufacturing process and increases the risk of contamination. While recent efforts to automate the manufacturing process have eliminated some human touchpoints, these systems still suffer from high cost, inflexibility and workflow bottlenecks. In particular, systems utilizing increased automation are very costly and inflexible, in that they require customers to adapt their processes to the particular equipment of the system.

In view of the above, there is a need for a bioprocessing system for cellular immunotherapies that reduces contamination risk by increasing automation and decreasing human handling. In addition, there is a need for a bioprocessing system for cell therapy manufacturing that balances the needs of flexibility in development and consistency in volume production, as well as meets the desire for different customers to run different processes.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of the possible embodiments. Indeed, the disclosure may encompass a variety of forms that may be similar to or different from the embodiments set forth below.

In one embodiment, a bioprocessing system includes a first module configured for enriching and isolating a population of cells, a second module configured for activating, genetically transducing and expanding the population of cells, and a third module configured for harvesting the expanded population of cells.

In another embodiment, a bioprocessing system includes a first module configured for enriching and isolating cells, a plurality of second modules, each second module configured for activating, genetically transducing and expanding the cells, and a third module configured for harvesting the cells after expansion. Each second module is configured to support the activation, genetic transduction and expansion of different populations of cells in parallel with one another.

In another embodiment, a method of bioprocessing includes the steps of in a first module, enriching and isolating a population of cells, in a second module, activating, genetically transducing, and expanding the population of cells, and in a third module, harvesting the expanded population of cells. The steps of activating, genetically transducing and expanding the population of cells are carried out without removing the population of cells from the second module.

In another embodiment, an apparatus for bioprocessing includes a housing and a drawer receivable within the housing. The drawer including a plurality of sidewalls and a bottom defining a processing chamber, and a generally open top. The drawer is movable between a closed position in which the drawer is received within the housing, and an open position in which the drawer extends from the housing enabling access to the processing chamber through the open top. The apparatus also includes at least one bed plate positioned within the processing chamber and configured to receive a bioreactor vessel.

In another embodiment, a method of bioprocessing includes the steps of sliding a drawer having a plurality of sidewalls, a bottom and a generally open top from a closed position within a housing to an open position to extend the drawer from the housing, through the generally open top, positioning a bioreactor vessel, through the generally open top, on a static bed plate positioned within the drawer, sliding the drawer to the closed position, and controlling a drawer engagement actuator to engage a plurality of fluid flow lines with at least one pump and a plurality of pinch valve linear actuators.

In another embodiment, a system for bioprocessing includes a housing, a first drawer receivable within the housing, the first drawer including a plurality of sidewalls and a bottom defining a first processing chamber, and a generally open top, at least one first bed plate positioned within the processing chamber of the first drawer and configured to receive or otherwise engage a first bioreactor vessel thereon, a second drawer receivable within the housing in stacked relationship with the first drawer, the second drawer including a plurality of sidewalls and a bottom defining a second processing chamber, and a generally open top, and at least one second bed plate positioned within the processing chamber of the second drawer and configured to receive or otherwise engage a second bioreactor vessel thereon. The first drawer and the second drawer are each movable between a closed position in which the first drawer and/or the second drawer are received within the housing, and an open position in which the first drawer and/or the second drawer extends from the housing enabling access to the processing chambers, respectively, through the open top.

In yet another embodiment, an apparatus for bioprocessing includes a housing, a drawer receivable within the housing, the drawer including a plurality of sidewalls and a bottom surface defining a processing chamber, and a generally open top, the drawer being movable between a closed position in which the drawer is received within the housing, and an open position in which the drawer extends from the housing enabling access to the processing chamber through the open top, at least one bed plate positioned within the processing chamber adjacent to the bottom surface, and a kit receivable within the processing chamber. The kit includes a plurality of sidewalls and a bottom surface defining an interior compartment, and a generally open top, an opening formed in the bottom surface of the kit, the opening having a perimeter, and a bioreactor vessel positioned above the at least one opening within the interior compartment and supported by the bottom surface such that a portion of the bioreactor vessel is accessible through the opening in the bottom surface. The kit is receivable within the processing chamber such that the bed plate extends through the opening in the bottom surface of the tray to support the bioreactor vessel above the bottom surface of the kit.

In yet another embodiment, a system for bioprocessing includes a tray having a plurality of sidewalls and a bottom surface defining an interior compartment, and a generally open top, at least one opening formed in the bottom surface, the at least one opening having a perimeter, a first tubing holder block integrated with the tray and configured to receive at least one pump tube and hold the at least one pump tube in position for selective engagement with a pump, a second tubing holder block integrated with the tray and configured to receive a plurality of pinch valve tubes and hold each pinch valve tube of the plurality of pinch valve tubes in position for selective engagement with a respective actuator of a pinch valve array, and a bioreactor vessel positioned above the at least one opening within the interior compartment and supported by the bottom surface such that a portion of the bioreactor vessel is accessible through the opening in the bottom surface.

In yet another embodiment, a system for bioprocessing includes a processing chamber having a plurality of sidewalls, a bottom surface, and a generally open top, a bed plate positioned within the processing chamber adjacent to the bottom surface, and a tray. The tray includes a plurality of sidewalls and a bottom surface defining an interior compartment, and a generally open top, and an opening in the bottom surface of the tray, the opening having a perimeter. The perimeter of the opening is shaped and/or dimensioned such that a bioreactor vessel can be positioned above the opening and supported by the bottom surface of the tray while a portion of the bioreactor vessel is accessible through the opening in the bottom surface. The tray is receivable within the processing chamber such that the bed plate extends through the opening in the bottom surface of the tray to support the bioreactor vessel.

In yet another embodiment, a system for bioprocessing includes a tray having a plurality of sidewalls and a bottom surface defining an interior compartment, and a generally open top, and at least one opening in the bottom surface, the opening bounded by a perimetrical edge, wherein the opening is shaped and/or dimensioned such that a bioreactor vessel can be positioned above the opening and supported by the bottom surface of the tray within the interior compartment.

In yet another embodiment, a method of bioprocessing includes the steps of placing a bioreactor vessel in a disposable tray, the disposable tray having a plurality of sidewalls and a bottom surface defining an interior compartment, a generally open top, an opening formed in the bottom surface, and a plurality of tabs or projections extending into the opening from the bottom surface, arranging the bioreactor vessel within the tray such that the bioreactor vessel is supported by the plurality of tabs above the opening, and placing the tray into a processing chamber having a bed plate such that the bed plate is received through the opening in the tray and supports the bioreactor vessel.

In yet another embodiment, a tubing module for a bioprocessing system includes a first tubing holder block configured to receive at least one pump tube and hold the at least one pump tube in position for selective engagement with a peristaltic pump, and a second tubing holder block configured to receive a plurality of pinch valve tubes and hold each pinch valve tube of the plurality of pinch valve tubes in position for selective engagement with a respective actuator of a pinch valve array. The first tubing holder block and the second tubing holder block are interconnected.

In yet another embodiment, a system for bioprocessing includes a tray having a plurality of sidewalls and a bottom surface defining an interior compartment, and a generally open top, the tray being configured to receive, support or otherwise engage thereon a bioreactor vessel, a pump assembly positioned adjacent to the rear sidewall of the tray, a pinch valve array positioned adjacent to the rear sidewall of the tray, and a tubing module positioned at a rear of the tray. The tubing module includes a first tubing holder block configured to receive at least one pump tube and hold the at least one pump tube in position for selective engagement with the pump assembly, and a second tubing holder block configured to receive a plurality of pinch valve tubes and hold each pinch valve tube of the plurality of pinch valve tubes in position for selective engagement with a respective actuator of the pinch valve array.

In yet another embodiment, a bioreactor vessel includes a bottom plate, a vessel body coupled to the bottom plate, the vessel body and the bottom plate defining an interior compartment therebetween, and a plurality of recesses formed in the bottom plate, each recess of the plurality of recesses being configured to receive a corresponding alignment pin on a bed plate for aligning the bioreactor vessel on the bed plate.

In yet another embodiment, a method for bioprocessing includes operatively connecting a bottom plate to a vessel body to define an interior compartment therebetween, the bottom plate and the vessel body forming a bioreactor vessel, aligning a recess in the bottom plate with an alignment pin of a bioprocessing system, and seating the bioreactor vessel on a bed plate of the bioprocessing system.

In yet another embodiment, a bioprocessing system includes a first fluid assembly having a first fluid assembly line connected to a first port of a first bioreactor vessel though a first bioreactor line of a first bioreactor vessel, the first bioreactor line of the first bioreactor vessel including a first bioreactor line valve for providing selective fluid communication between the first fluid assembly and the first port of the first bioreactor vessel, a second fluid assembly having a second fluid assembly line connected to a second port of the first bioreactor vessel through a second bioreactor line of the first bioreactor vessel, the second bioreactor line of the first bioreactor vessel including a second bioreactor line valve for providing selective fluid communication between the second fluid assembly and the second port of the first bioreactor vessel, and an interconnect line providing for fluid communication between the first fluid assembly and the second fluid assembly, and for fluid communication between the second bioreactor line of the first bioreactor vessel and the first bioreactor line of the first bioreactor vessel.

In yet another embodiment a method of bioprocessing includes providing a first fluid assembly having a first fluid assembly line connected to a first port of a first bioreactor vessel through a first bioreactor line of the first bioreactor vessel, providing a second fluid assembly having a second fluid assembly line connected to a second port of the first bioreactor vessel through a second bioreactor line of the first bioreactor vessel, and providing an interconnect line between the second bioreactor line of the first bioreactor vessel and the first bioreactor line of the first bioreactor vessel, the interconnecting line allowing for fluid communication between the first fluid assembly and the second fluid assembly, and for fluid communication between the second bioreactor line of the first bioreactor vessel and the first bioreactor line of the first bioreactor vessel.

In yet another embodiment, a bioprocessing method for cell therapy includes genetically modifying a population of cells in a bioreactor vessel to produce a population of genetically modified cells, and expanding the population of genetically modified cells within the bioreactor vessel to generate a number of genetically modified cells sufficient for one or more doses for use in a cell therapy treatment without removing the population of genetically modified cells from the bioreactor vessel.

In yet another embodiment, a bioprocessing method includes coating a bioreactor vessel with a reagent for enhancing efficiency of genetic modification of a population of cells, genetically modifying cells of a population of cells to produce a population of genetically modified cells, and expanding the population of genetically modified cells in the bioreactor vessel without removing the genetically modified cells from the bioreactor vessel.

In yet another embodiment, a bioprocessing method includes activating cells of a population of cells in a bioreactor vessel using magnetic or non-magnetic beads to produce a population of activated cells, genetically modifying the activated cells in the bioreactor vessel to produce a population of genetically modified cells, washing the genetically modified cells in the bioreactor vessel to remove unwanted materials, and expanding the population of genetically modified cells in the bioreactor vessel to produce an expanded population of transduced cells. Activating, genetically modifying, washing, and expanding are carried out in the bioreactor vessel without removing the cells from the bioreactor vessel.

In yet another embodiment, a kit for use in a bioprocessing system includes a process bag, a source bag, a bead addition vessel and a process loop configured to be in fluid communication with the process bag, the source bag and the bead addition vessel. The process loop additionally includes pump tubing configured to in fluid communication with a pump.

In yet another embodiment, an apparatus for bioprocessing includes a kit comprising a process bag, a source bag, and a bead addition vessel configured to be in fluid communication with a process loop, the process loop additionally comprising pump tubing configured to in fluid communication with a pump, a magnetic field generator configured to generate a magnetic field, a plurality of hooks for suspending the source bag, the process bag, and the bead addition vessel, each hook of the plurality of hooks is operatively connected to a load cell configured to sense a weight of the bag connected thereto, at least one air bubble sensor, and a pump configured to be in fluid communication with the process loop.

In an embodiment, a method of bioprocessing includes combining a suspension comprising a population of cells with magnetic beads to form a population of bead-bound cells in the suspension, isolating the population of bead-bound cells on a magnetic isolation column, and collecting target cells from the population of cells.

In an embodiment, a non-transitory computer readable medium is provided. The non-transitory computer readable medium includes instructions configured to adapt a controller to maintain a first target environment in a bioreactor vessel containing a population of cells for a first incubation period to produce a population of genetically modified cells from the population of cells, initiate a flow of media to the bioreactor vessel, maintain a second target environment in the bioreactor vessel for a second incubation period to produce an expanded population of genetically modified cells.

In another embodiment, a non-transitory computer readable medium is provided. The non-transitory computer readable medium includes instructions configured to adapt a controller to maintain a first target environment in a first bioreactor vessel for a first incubation period to activate a population of cells in the first bioreactor, and maintain a second target environment in the first bioreactor vessel for a second incubation period to produce a population of genetically modified cells from the population of cells.

In yet another embodiment, a non-transitory computer readable medium is provided. The non-transitory computer readable medium includes instructions configured to adapt a controller to receive data relating to a mass and/or volume of a bioreactor vessel containing a population of cells suspended in a culture medium, actuate a first pump to pump fresh media to the bioreactor vessel, actuate a second pump to pump spent media from the bioreactor vessel to a waste bag, and control an operational setpoint of at least one of the first pump and the second pump in dependence upon the data relating to the mass and/or volume of the bioreactor vessel.

DRAWINGS

The present invention will be better understood from reading the following description of non-limiting embodiments, with reference to the attached drawings, wherein below:

FIG. 29 is a side elevational view of the bioprocessing apparatus of FIG. 12.

DETAILED DESCRIPTION

Figure 1:
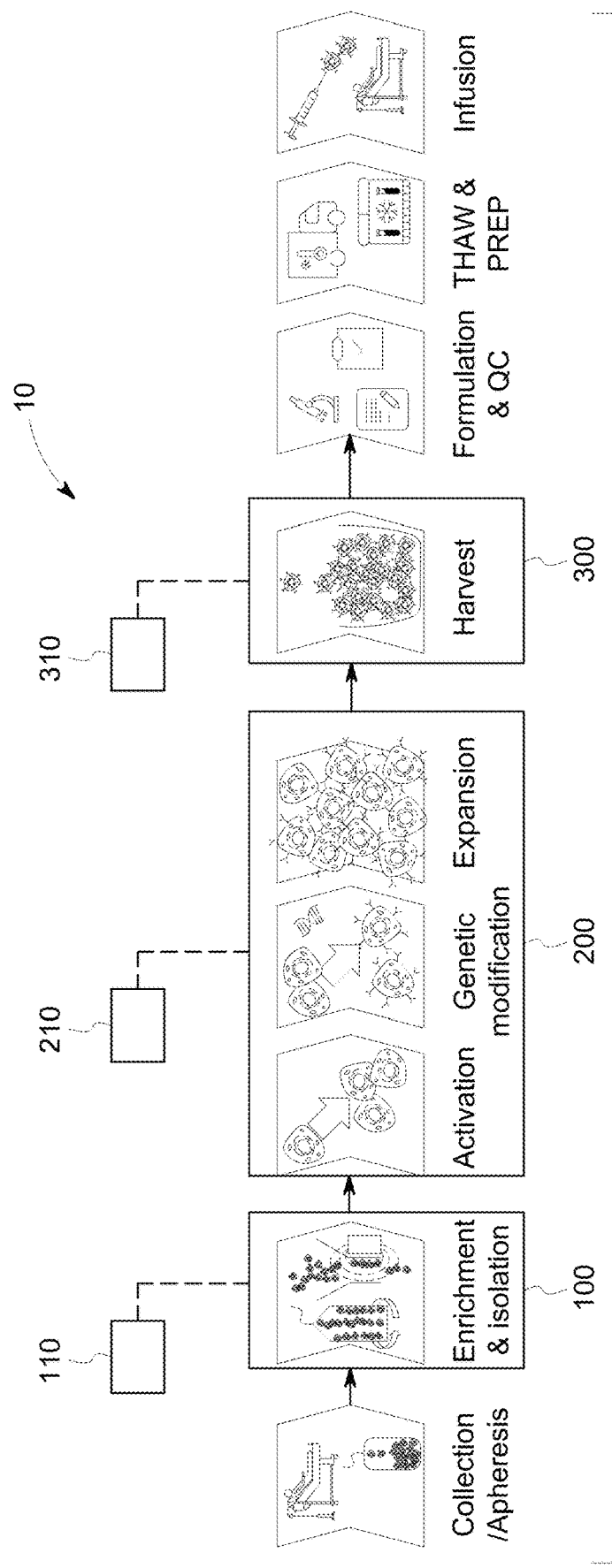
FIG. 1 is a schematic illustration of a bioprocessing system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is semi-rigid or rigid, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container or vessel used, for example, as containment device for various fluids and/or media.

As used herein, "fluidly coupled" or "fluid communication" means that the components of the system are capable of receiving or transferring fluid between the components. The term fluid includes gases, liquids, or combinations thereof. As used herein, "electrical communication" or "electrically coupled" means that certain components are configured to communicate with one another through direct or indirect signaling by way of direct or indirect electrical connections. As used herein, "operatively coupled" refers to a connection, which may be direct or indirect. The connection is not necessarily a mechanical attachment.

As used herein, the term "tray" refers to any object, capable of at least temporarily supporting a plurality of components. The tray may be made of a variety of suitable materials. For example, the tray may be made of cost-effective materials suitable for sterilization and single-use disposable products.

As used herein, the term "functionally-closed system" refers to a plurality of components that make up a closed fluid path that may have inlet and outlet ports, to add or remove fluid or air from the system, without compromising the integrity of the closed fluid path (e.g. to maintain an internally sterile biomedical fluid path), whereby the ports may comprise, for example, filters or membranes at each port to maintain the sterile integrity when fluids or air is added or removed from the system. The components, depending on a given embodiment, may comprise but are not limited to, one or more conduits, valves (e.g. multiport diverters), vessels, receptacles, and ports.

Embodiments of the invention provide systems and methods for manufacturing cellular immunotherapies from a biological sample (e.g., blood, tissue, etc.). In some embodiments, an apparatus for fluid line management in a bioprocessing system is provided. An apparatus for fluid line management may include a first tubing holder block configured to receive at least one pump tube and hold the at least one pump tube in position for selective engagement with a peristaltic pump, and a second tubing holder block configured to receive a plurality of pinch valve tubes and hold each pinch valve tube of the plurality of pinch valve tubes in position for selective engagement with a respective actuator of a pinch valve array. In embodiments, the apparatus may be configured for use with a bioprocessing system having a tray having a plurality of sidewalls and a bottom surface defining an interior compartment, and a generally open top, a pump assembly positioned adjacent to the rear sidewall of the tray, and a pinch valve array positioned adjacent to the rear sidewall of the tray such that the fluid line management apparatus holds the at least one pump tube in position for selective engagement with the pump assembly, and holds the pinch valve tubes in position for selective engagement with actuators of the pinch valve array.

With reference to FIG. 1, a schematic illustration of a bioprocessing system 10 according to an embodiment of the invention is illustrated. The bioprocessing system 10 is configured for use in the manufacture of cellular immunotherapies (e.g., autologous cellular immunotherapies), where, for example, human blood, fluid, tissue, or cell sample is collected, and a cellular therapy is generated from or based on the collected sample. One type of cellular immunotherapy that can be manufactured using the bioprocessing system 10 is chimeric antigen receptor (CAR) T cell therapy, although other cellular therapies may also be produced using the system of the invention or aspects thereof without departing from the broader aspects of the invention. As illustrated in FIG. 1, the manufacture of a CAR T cell therapy generally begins with collection of a patient's blood and separation of the lymphocytes through apheresis. Collection/apheresis may take place in a clinical setting, and the apheresis product is then sent to a laboratory or manufacturing facility for production of CAR T-cells. In particular, once the apheresis product is received for processing, a desired cell population (e.g., white blood cells) is enriched for or separated from the collected blood for manufacturing the cellular therapy, and target cells of interest are isolated from the initial cell mixture. The target cells of interest are then activated, genetically modified to specifically target and destroy tumor cells, and expanded to achieve a desired cell density. After expansion, the cells are harvested, and a dose is formulated. The formulation is often then cryopreserved and delivered to a clinical setting for thawing, preparation and, finally, infusion into the patient.

With further reference to FIG. 1, the bioprocessing system 10 of the invention includes a plurality of distinct modules or subsystems that are each configured to carry out a particular subset of manufacturing steps in a substantially automated, functionally-closed and scalable manner. In particular, the bioprocessing system 10 includes a first module 100 configured to carry out the steps of enrichment and isolation, a second module 200 configured to carry out the steps of activation, genetic modification and expansion, and a third module 300 configured to carry out the step of harvesting the expanded cell population. In an embodiment, each module 100, 200, 300 may be communicatively coupled to a dedicated controller (e.g., first controller 110, second controller 210, and third controller 310, respectively). The controllers 110, 210 and 310 are configured to provide substantially automated control over the manufacturing processes within each module. While the first module 100, second module 200 and third module 300 are illustrated as including dedicated controllers for controlling the operation of each module, it is contemplated that a master control unit may be utilized to provide global control over the three modules. Each module 100, 200, 300 is designed to work in concert with the other modules to form a single, coherent bioprocessing system 10, as discussed in detail below.

By automating the processes within each module, product consistency from each module can be increased and costs associated with extensive manual manipulations reduced. In addition, as discussed in detail hereinafter, each module 100, 200, 300 is substantially closed, which helps ensure patient safety by decreasing the risk of outside contamination, ensures regulatory compliance, and helps avoid the costs associated with open systems. Moreover, each module 100, 200, 300 is scalable, to support both development at low patient numbers and commercial manufacturing at high patient numbers.

With further reference to FIG. 1, the particular manner in which the process steps are compartmentalized in distinct modules that each provide for closed and automated bioprocessing allows for efficient utilization of capital equipment to an extent heretofore not seen in the art. As will be appreciated, the step of expanding the cell population to achieve a desired cell density prior to harvest and formulation is typically the most time-consuming step in the manufacturing process, while the enrichment and isolation steps, and the harvesting and formulation steps, as well as activation and genetic modification steps, are much less time consuming. Accordingly, attempts to automate the entire cell therapy manufacturing process, in addition to being logistically challenging, can exacerbate bottlenecks in the process that hamper workflow and decrease manufacturing efficiency. In particular, in a fully-automated process, while the steps of enrichment, isolation, activation and genetic modification of cells can take place rather quickly, expansion of the genetically modified cells takes place very slowly. Accordingly, manufacture of a cellular therapy from a first sample (e.g., the blood of a first patient) would progress quickly until the expansion step, which requires a substantial amount of time to achieve a desired cell density for harvest. With a fully automated system, the entire process/system would be monopolized by the expansion equipment performing expansion of the cells from the first sample, and processing of a second sample could not begin until the entire system was freed up for use. In this respect, with a fully-automated bioprocessing system, the entire system is essentially offline and unavailable for processing of a second sample until the entire cell therapy manufacturing process, from enrichment to harvest/formulation is completed on the first sample.

Figure 2:
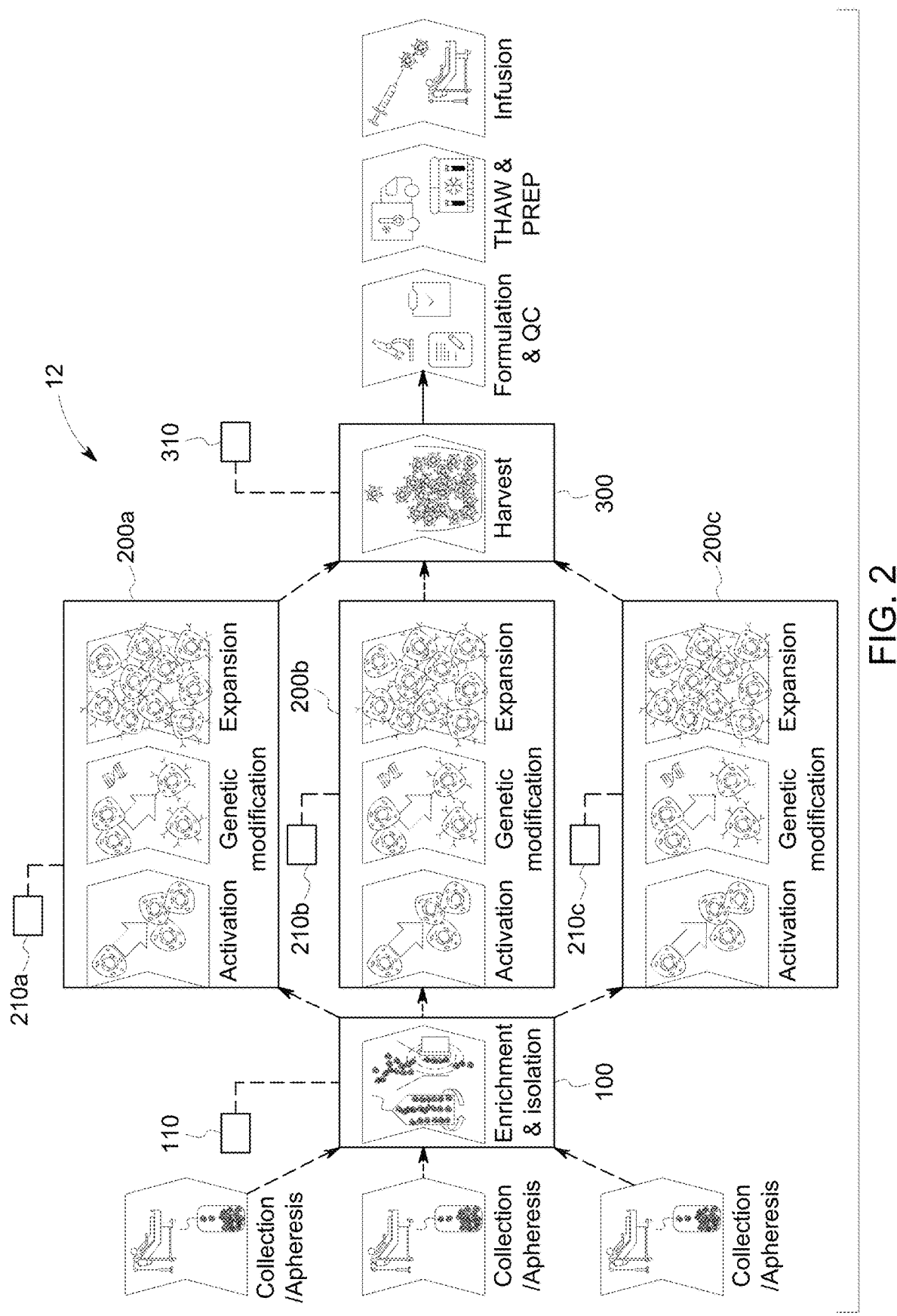
FIG. 2 is a schematic illustration of a bioprocessing system according to another embodiment of the invention.

Embodiments of the invention, however, allow for parallel processing of more than one sample (from the same or different patients) to provide for more efficient utilization of capital resources. This advantage is a direct result of the particular manner in which the process steps are separated into the three modules 100, 200, 300, as alluded to above. With particular reference to FIG. 2, in an embodiment, a single first module 100 and/or a single third module 300 can be utilized in conjunction with multiple second modules, e.g., second modules 200a, 200b, 200c, in a bioprocessing system 12, to provide for parallel and asynchronous processing of multiple samples from the same or different patients. For example, a first apheresis product from a first patient may be enriched and isolated using the first module 100 to produce a first population of isolated target cells, and the first population of target cells may then be transferred to one of the second modules, e.g., module 200a, for activation, genetic modification and expansion under control of controller 210a. Once the first population of target cells is transferred out of the first module 100, the first module is again available for use to process a second apheresis product from, for example, a second patient. A second population of target cells produced in the first module 100 from the sample taken from the second patient can then be transferred to another second module, e.g., second module 200b, for activation, genetic modification and expansion under control of controller 201b.

Similarly, after the second population of target cells is transferred out of the first module 100, the first module is again available for use to process a third apheresis product from, for example, a third patient. A third target population of cells produced in the first module 100 from the sample taken from the third patient can then be transferred to another second module, e.g., second module 200c, for activation, genetic modification and expansion under control of controller 201c. In this respect, expansion of, for example, CAR-T cells for a first patient can occur simultaneously with the expansion of CAR-T cells for a second patient, a third patient, etc.

This approach also allows the post processing to occur asynchronously as needed. In other words, patient cells may not all grow at the same time. The cultures may reach the final density at different times, but the multiple second modules 200 are not linked, and the third module 300 can be used as needed. With the present invention, while samples can be processed in parallel, they do not have to be done in batches.

Harvesting of the expanded populations of cells from the second modules 200a, 200b and 200c can likewise be accomplished using a single third module 300 when each expanded populations of cells are ready for harvest.

Accordingly, by separating the steps of activation, genetic modification and expansion, which is the most time consuming, and which share certain operational requirements and/or require similar culture conditions, into a stand-alone, automated and functionally-closed module, the other system equipment that is utilized for enrichment, isolation, harvest and formulation is not tied up or offline while expansion of one population of cells is carried out. As a result, the manufacture of multiple cell therapies may be carried out simultaneously, maximizing equipment and floorspace usage and increasing overall process and facility efficiency. It is envisioned that additional second modules may be added to the bioprocessing system 10 to provide for the parallel processing of any number of cell populations, as desired. Accordingly, the bioprocessing system of the invention allows for plug-and-play like functionality, which enables a manufacturing facility to scale up or scale down with ease.

In an embodiment, the first module 100 may be any system or device capable of producing, from an apheresis product taken from a patient, a target population of enriched and isolated cells for use in a biological process, such as the manufacture of immunotherapies and regenerative medicines. For example, the first module 100 may be a modified version of a Sefia Cell Processing System, available from GE Healthcare. The configuration of the first module 100 according to some embodiments of the invention is discussed in detail hereinafter.

In an embodiment, the third module 300 may similarly be any system or device capable of harvesting and/or formulating CAR-T cells or other modified cells produced by the second module 200 for infusion into a patient, for use in cellular immunotherapies or regenerative medicine. In some embodiments, the third module 300 may likewise be a Sefia Cell Processing System, available from GE Healthcare. In some embodiments, the first module 100 may first be utilized for enrichment and isolation of cells (which are then transferred to the second module 200 for activation, transduction and expansion (and in some embodiments, harvesting)), and then also used at the end of the process for cell harvesting and/or formulation. In this respect, in some embodiments, the same equipment can be utilized for the front-end cell enrichment and isolation steps, as well as the back-end harvesting and/or formulation steps.

Figure 3:
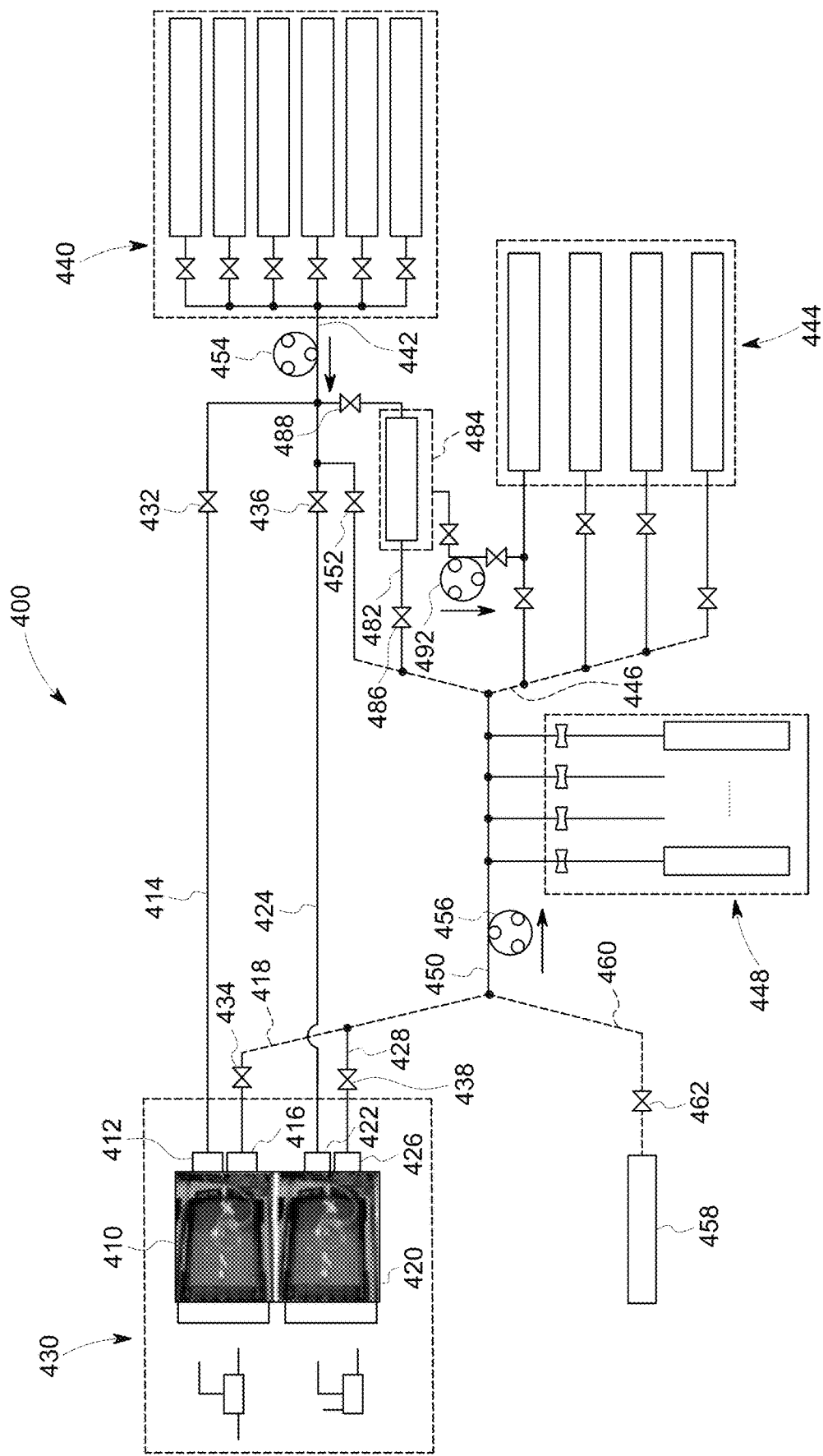
FIG. 3 is a block diagram illustrating the fluid flow configuration/system of a cell activation, genetic modification and expansion subsystem of the bioprocessing system of FIG. 1.
Figure 77:
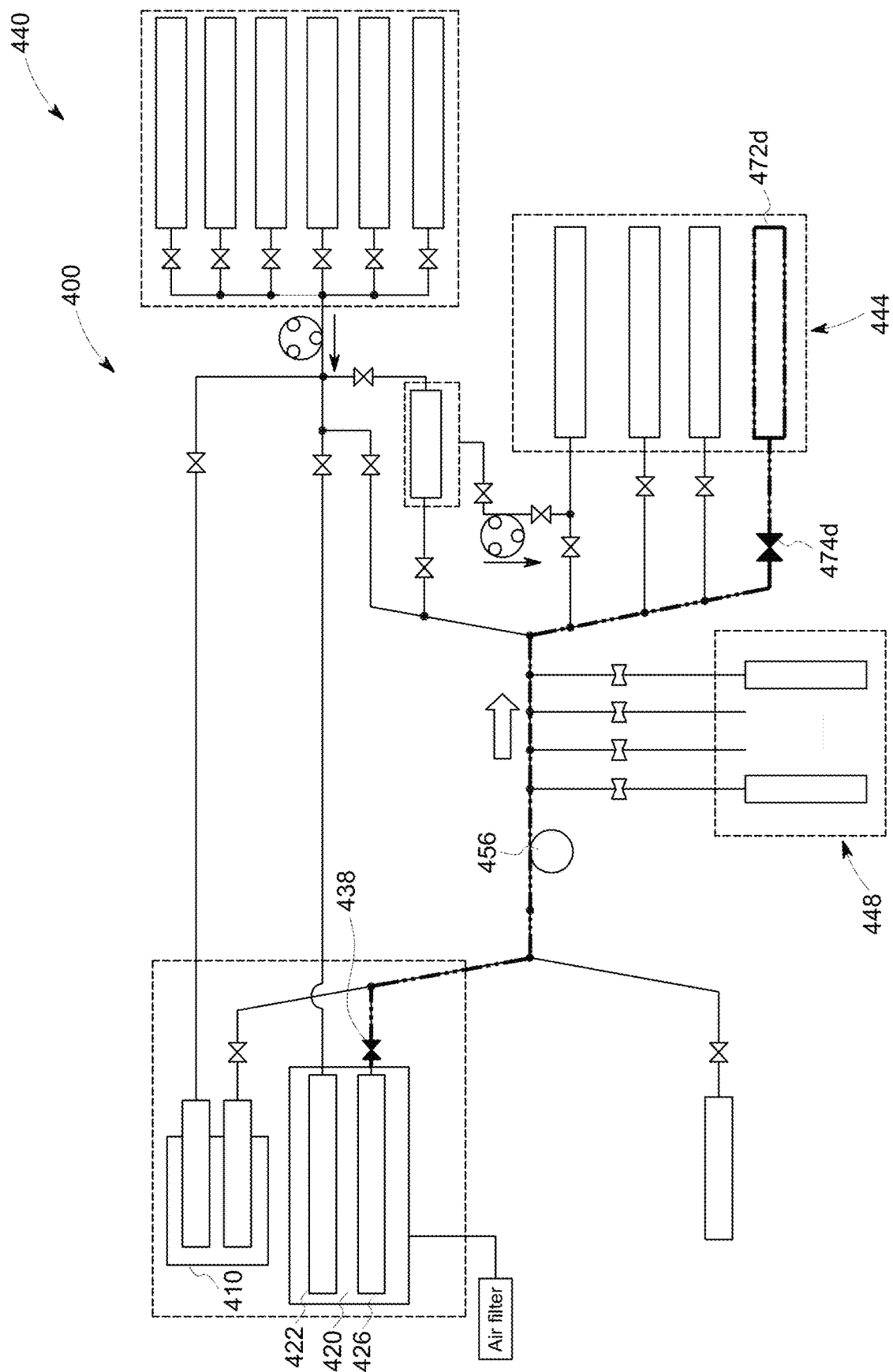

Focusing first on the second module 200, the ability to combine the process steps of cell activation, genetic modification and cell expansion in a single, functionally-closed and automated module 200 that provides for the workflow efficiencies described above is enabled by the specific configuration of components within the second module 200, and a unique flow architecture that provides for a specific interconnectivity between such components. FIGS. 3-77, discussed below, illustrate various aspects of the second module 200 according to various embodiments of the invention. Referring first to FIG. 3, a schematic illustrating the fluid flow architecture 400 (also broadly referred to herein as bioprocessing subsystem 400 or bioprocessing system 400) within the second module 200 that provides for cell activation, genetic modification and expansion (an in some cases, harvesting), is shown. The system 400 includes a first bioreactor vessel 410 and a second bioreactor vessel 420. The first bioreactor vessel includes at least a first port 412 and a first bioreactor line 414 in fluid communication with the first port 412, and a second port 416 and a second bioreactor line 418 in fluid communication with the second port 416. Similarly, the second bioreactor vessel includes at least a first port 422 and a first bioreactor line 424 in fluid communication with the first port 422, and a second port 426 and a second bioreactor line 428 in fluid communication with the second port 426. Together, the first bioreactor vessel 410 and second bioreactor vessel 420 form a bioreactor array 430. While the system 400 is shown as having two bioreactor vessels, embodiments of the invention may include a single bioreactor or more than two bioreactor vessels.

The first and second bioreactor lines 414, 418, 424, 428 of the first and second bioreactor vessels 410, 420 each include a respective valve for controlling a flow of fluid therethrough, as discussed hereinafter. In particular, the first bioreactor line 414 of the first bioreactor vessel 410 includes a first bioreactor line valve 432, while the second bioreactor line 418 of the first bioreactor vessel 410 includes a second bioreactor line valve 424. Similarly, the first bioreactor line 424 of the second bioreactor vessel 420 includes a first bioreactor line valve 436, while the second bioreactor line 428 of the second bioreactor vessel 420 includes a second bioreactor line valve 438.

With further reference to FIG. 3, the system 400 also includes a first fluid assembly 440 having a first fluid assembly line 442, a second fluid assembly 444 having a second fluid assembly line 446, and a sampling assembly 448. An interconnect line 450 having an interconnect line valve 452 provides for fluid communication between the first fluid assembly 440 and the second fluid assembly 444. As shown in FIG. 3, the interconnect line 450 also provides for fluid communication between the second bioreactor line 418 and first bioreactor line 414 of the first bioreactor vessel 410, allowing for circulation of a fluid along a first circulation loop of the first bioreactor vessel. Similarly, the interconnect line also provides for fluid communication between the second bioreactor line 428 and first bioreactor line 424 of the second bioreactor vessel 420, allowing for circulation of a fluid along a second circulation loop of the second bioreactor vessel. Moreover, the interconnect line 450 further provides for fluid communication between the second port 416 and second bioreactor line 418 of the first bioreactor vessel 410, and the first port 422 and first bioreactor line 424 of the second bioreactor vessel 420, allowing for the transfer of contents of the first bioreactor vessel 410 to the second bioreactor vessel 420, as discussed hereinafter. As illustrated in FIG. 3, the interconnect line 450, in an embodiment, extends from the second bioreactor lines 418, 428 to the intersection of the first bioreactor line 414 of the first bioreactor vessel 410 and the first fluid assembly line 442.

As illustrated by FIG. 3, the first and second fluid assemblies 440, 450 are disposed along the interconnect line 450. Additionally, in an embodiment, the first fluid assembly is in fluid communication with the first port 412 of the first bioreactor vessel 410 and the first port of the second bioreactor vessel 420 through the first bioreactor line 414 of the first bioreactor vessel and the first bioreactor line 424 of the second bioreactor vessel 420, respectively. The second fluid assembly 444 is in fluid communication with the second port 416 of the first bioreactor vessel 410 and the second port 426 of the second bioreactor vessel 420 via the interconnect line 450.

A first pump or interconnect line pump 454 capable of providing for bi-directional fluid flow is disposed along the first fluid assembly line 442, and a second pump or circulation line pump 456 capable of providing for bi-directional fluid flow is disposed along the interconnect line 450, the function and purpose of which will be discussed below. In an embodiment, the pumps 454, 456 are high dynamic range pumps. As also shown in FIG. 3, a sterile air source 458 is connected to the interconnect line 450 through a sterile air source line 460. A valve 462 positioned along the sterile air source line 460 provides for selective fluid communication between the sterile air source 458 and the interconnect line 450. While FIG. 3 shows the sterile air source 458 connected to the interconnect line 450, in other embodiments the sterile air source may be connected to the first fluid assembly 440, the second fluid assembly 444, or the fluid flowpath intermediate the second bioreactor line valve and the first bioreactor line valve of either the first bioreactor or the second bioreactor, without departing from the broader aspects of the invention.

Figure 4:
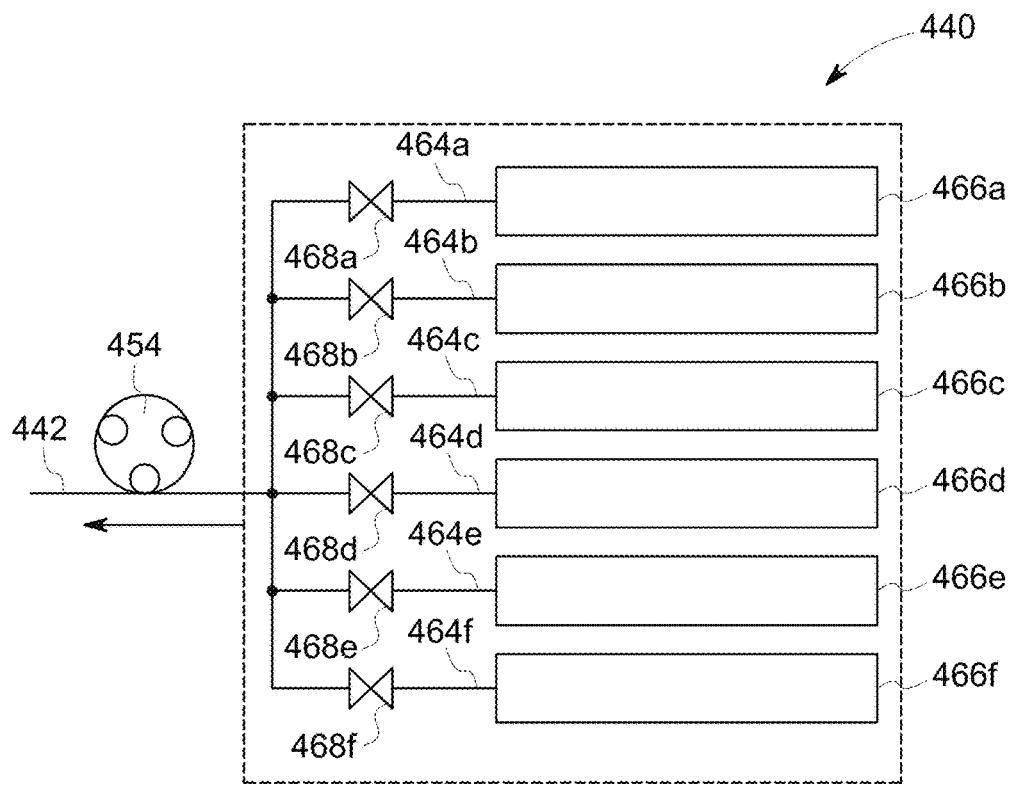
FIG. 4 is a detail view of a portion of the block diagram of FIG. 3, illustrating a first fluid assembly of the fluid flow configuration/system.
Figure 5:
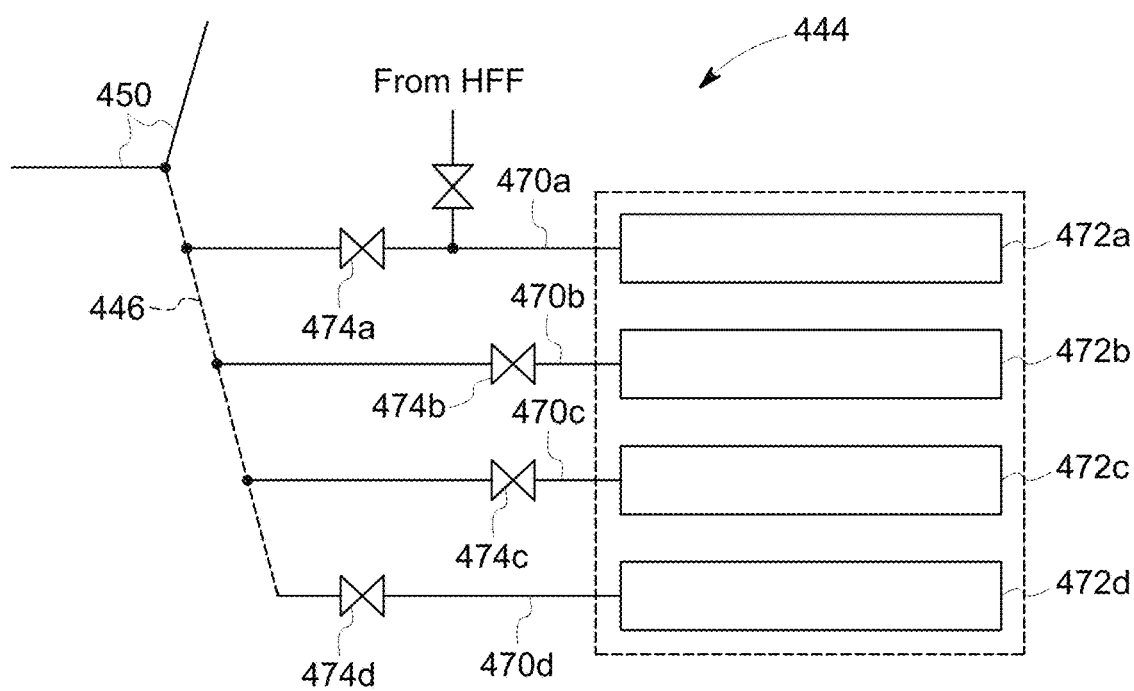
FIG. 5 is a detail view of a portion of the block diagram of FIG. 3, illustrating a second fluid assembly of the fluid flow configuration/system.
Figure 6:
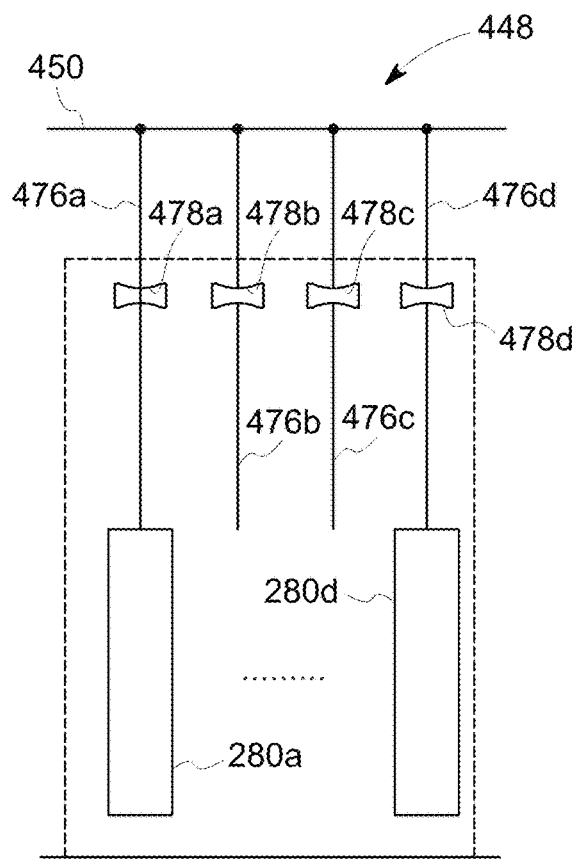
FIG. 6 is a detail view of a portion of the block diagram of FIG. 3, illustrating a sampling assembly of the fluid flow configuration/system.
Figure 7:
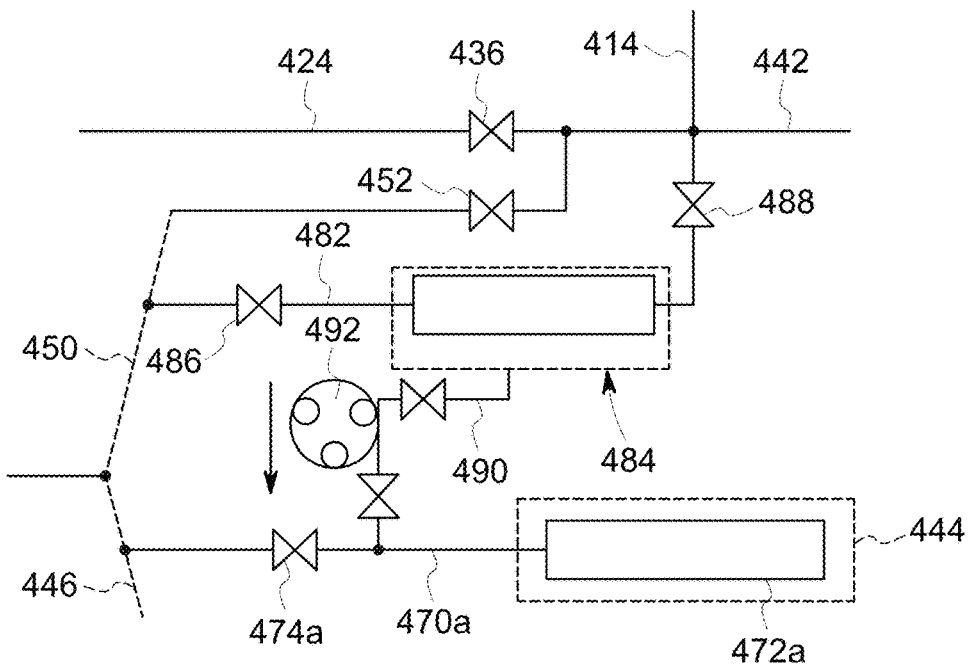
FIG. 7 is a detail view of a portion of the block diagram of FIG. 3 illustrating a filtration flowpath of the fluid flow configuration/system.

With additional reference now to FIGS. 4-6, detailed views of the first fluid assembly 440, second fluid assembly 444 and sampling assembly 448 are shown. With specific reference to FIG. 4, the first fluid assembly 440 includes a plurality of tubing tails 464a-f, each of which is configured for selective/removable connection to one of a plurality of first reservoirs 466a-f. Each tubing tail 464a-f of the first fluid assembly 440 includes a tubing tail valve 468a-f for selectively controlling a flow of fluid to or from a respective one of the plurality of first reservoirs 466a-f of the first fluid assembly 440. While FIG. 4 specifically shows that the first fluid assembly 440 includes six fluid reservoirs, more or fewer reservoirs may be utilized to provide for the input or collection of various processing fluids, as desired. It is contemplated that each tubing tail 464a-f may be individually connected to a reservoir 466a-f, respectively, at a time required during operation of fluid assembly 440, as described below.

With specific reference to FIG. 5, the second fluid assembly 444 includes a plurality of tubing tails 470a-d, each of which is configured for selective/removable connection to one of a plurality of second reservoirs 472a-d Each tubing tail 470a-d of the second fluid assembly 444 includes a tubing tail valve 474a-e for selectively controlling a flow of fluid to or from a respective one of the plurality of second reservoirs 472a-d of the first fluid assembly 444. While FIG. 5 specifically shows that the second fluid assembly 444 includes four fluid reservoirs, more or fewer reservoirs may be utilized to provide for the input or collection of various processing fluids, as desired. In an embodiment, at least one of the second reservoirs, e.g., second reservoir 472d is a collection reservoir for collecting an expanded population of cells, as discussed hereinafter. In an embodiment, the second reservoir 472a is a waste reservoir, the purpose of which is discussed below. The invention further contemplates that one or more reservoirs 472a-d may be pre-connected to their respective tails 470a-d, with each additional reservoir being connected to its respective tail in time for its use within the second fluid assembly 440.

In an embodiment, the first reservoirs 466a-f and the second reservoirs 472a-d are single use/disposable, flexible bags. In an embodiment, the bags are substantially two-dimensional bags having opposing panels welded or secured together about their perimeters and supporting connecting conduit for connection to its respective tail, as is known in the art.

In an embodiment, the reservoirs/bags may be connected to the tubing tails of the first and second tubing assembly using a sterile welding device. In an embodiment, a welding device can be positioned next to the module 200, and the welding device utilized to splice-weld one of the tubing tails to tail to the tube on the bag (while maintaining sterility). Thus the operator can provide the bag at the time it is needed (e.g., by grabbing a tubing tail and inserting its free end into the welding device, laying the bag tube's free end adjacent to the end of the tubing tail, cutting the tubes with a fresh razor blade, and heating the cut ends as the razor is pulled away while the two tube ends are forced together while still melted so that they re-solidify together). Conversely, a bag can be removed by welding the line from the bag and cutting at the weld to separate the two closed lines. Accordingly, the reservoirs/bags may be individually connected when desired, and the present invention does not require that all reservoirs/bags must be connected at the beginning of a protocol, as an operator will have access to the appropriate tubing tails during the entire process to connect a reservoir/bag in time for its use. Indeed, while it is possible that all reservoirs/bags are pre-connected, the invention does not require pre-connection, and one advantage of the second module 200 is that it allows the operator to access the fluid assemblies/lines during operations so that spent bags may be connected in a sterile manner, and disconnected so that other bags can be sterilely connected during a protocol, as discussed below.

As illustrated in FIG. 6, the sampling assembly 448 includes one or more sampling lines, e.g., sampling lines 476a-476d, fluidly connected to the interconnect line 450. Each of the sample lines 476a-476d may include a sample line valve 478a-d that is selectively actuatable to allow fluid to flow from the interconnect line 450 through the sample lines 476a-476d. As also shown therein, a distal end of each sampling line 476a-476d is configured for selective connection to a sample collection device (e.g., sample collection devices 280a and 280d) for collection of the fluid from the interconnect line 450. The sample collection devices may take the form of any sampling device known in the art such as, for example, a syringe, dip tube, bag, etc. While FIG. 6 illustrates the sampling assembly 448 being connected to the interconnect line, in other embodiments the sampling assembly may be fluidly coupled to the first fluid assembly 440, the second fluid assembly 444 a fluid flowpath intermediate the second bioreactor line valve 434 and the first bioreactor line valves 432 of the first bioreactor vessel 410, and/or a fluid flowpath intermediate the second bioreactor line valve 438 and the first bioreactor line valve 436 of the second bioreactor vessel 420. The sampling assembly 448 provides for fully functionally-closed sampling of a fluid at one or more points in the system 400, as desired.

Referring back to FIG. 3, in an embodiment, the system 400 may also include a filtration line 482 that is connected at two points along the interconnect line 450 and defines a filtration loop along the interconnect line 450. A filter 484 is positioned along the filtration line 482 for removing permeate waste from a fluid passing through the filtration line 482. As shown therein, the filtration line 482 includes an upstream filtration line valve 486 and a downstream filtration line valve 488 positioned on the upstream and downstream side of the filter 484, respectively. A waste line 490 provides fluid communication between the filter 484 and the second fluid assembly 444 and, in particular, with tubing tail 470a of the second fluid assembly 444, which is connected to the waste reservoir 472a. In this respect, the waste line 490 conveys waste removed from the fluid passing through the filtration line 482 by the filter 484 to the waste reservoir 472a. As illustrated in FIG. 3, the filtration line 482 surrounds the interconnect line valve 452 so that a flow of fluid through the interconnect line 450 can be forced through the filtration line 482, as discussed hereinafter. A permeate pump 492 positioned along the waste line 490 is operable to pump the waste removed by the filter to the waste reservoir 472a. In an embodiment, the filter 484 is desirably an elongate hollow fiber filter, although other tangential-flow or cross-flow filtration means known in the art such as, for example, a flat sheet membrane filter, may also be utilized without departing from the broader aspects of the invention.

In an embodiment, the valves of the first fluid assembly 440 and second fluid assembly 444, as well as the bioreactor line valves (i.e., valves 432, 434, 436, 438, sterile line valve 462, interconnect line valve 452 and filtration line valves 486, 488 are pinch valves constructed in the manner hereinafter described. In an embodiment, the lines themselves need not include the pinch valves, and the depiction of the pinch valves in FIGS. 3-8 may simply denote locates where pinch valves can operate on the lines so as to prevent fluid flow. In particular, as discussed below the pinch valves of the flow architecture 400 may be provided by respective actuators (e.g., solenoids) that operate/act against a corresponding anvil while the fluid path/line is in between to "pinch off" the line to prevent fluid flow therethrough.

In an embodiment, the pumps 454, 456 and 492 are peristaltic pumps, and the pumps are integrated into a single assembly, as discussed hereinafter. Desirably, operation of these valves and pumps are automatically directed according to a programmed protocol so as to enable proper operation of module 200. It is contemplated that second controller 210 may direct the operation of these valves and pumps by module 200.

Turning now to FIGS. 8-11, the configuration of the first bioreactor vessel 410 according to an embodiment of the invention is illustrated. As the second bioreactor vessel 420 is desirably, although not required to be, identical in configuration to the first bioreactor vessel 410, for simplicity, only first bioreactor vessel 410 will be described below. In an embodiment, the bioreactor vessels 410, 420 are perfusion-enabled, silicone membrane-based bioreactor vessels that support activation, transduction and expansion of a population of cells therein. The bioreactor vessels 410, 420 may be used for cell culture, cell processing, and/or cell expansion to increase cell density for use in medical therapeutics or other processes. While the bioreactor vessel may be disclosed herein as being used in conjunction with particular cell types, it should be understood that the bioreactor vessel may be used for activation, genetic modification and/or expansion of any suitable cell type. Further, the disclosed techniques may be used in conjunction with adherent cells, i.e., cells that adhere to and/or proliferate on a cell expansion surface. In an embodiment, the first and second bioreactor vessels 410, 420 may be constructed and function as disclosed in U.S. patent Ser. No. 15/893,336, filed on Feb. 9, 2018, which is incorporated by reference herein in its entirety.

Figure 8:
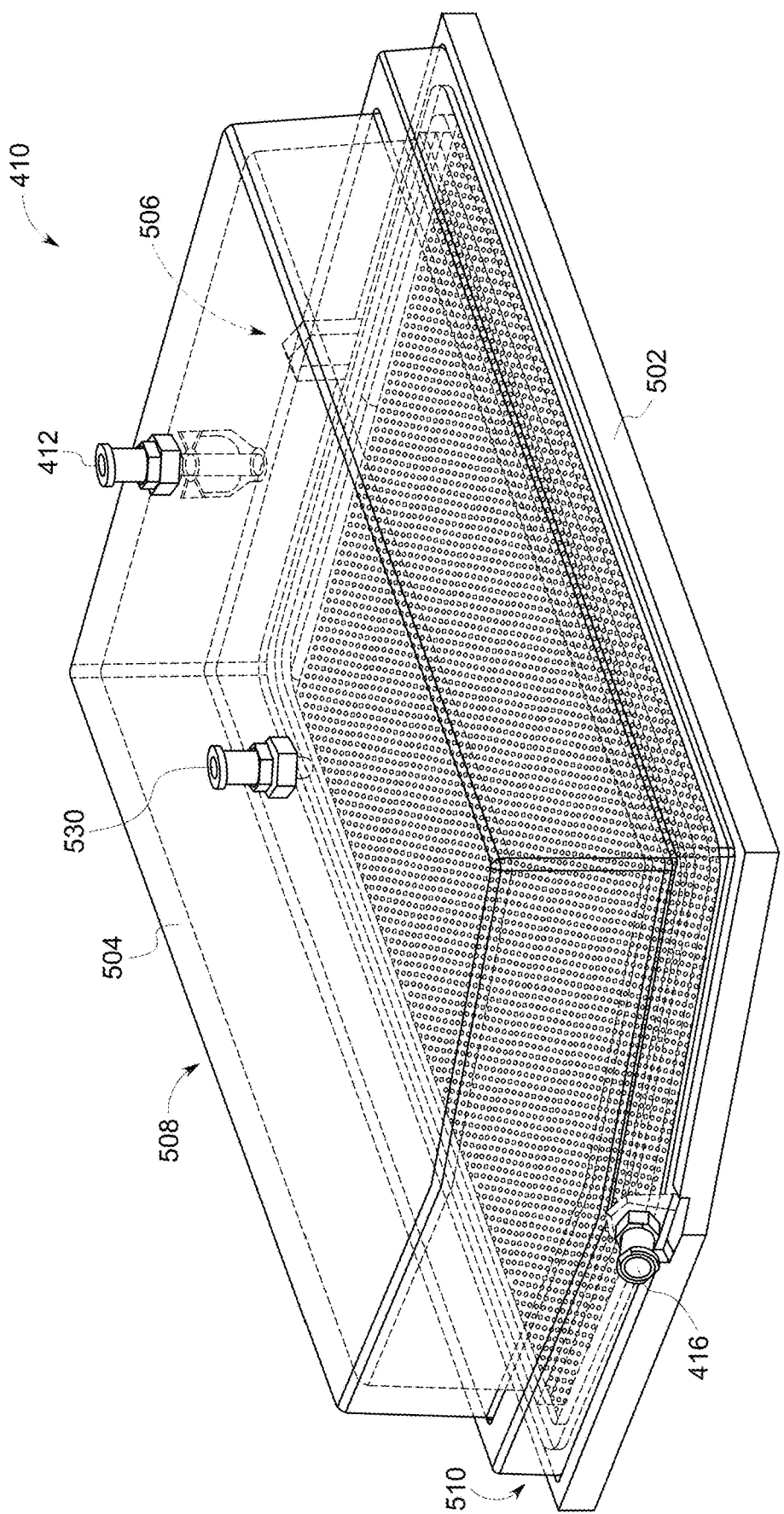
FIG. 8 is a perspective view of a bioreactor vessel according to an embodiment of the invention.
Figure 9:
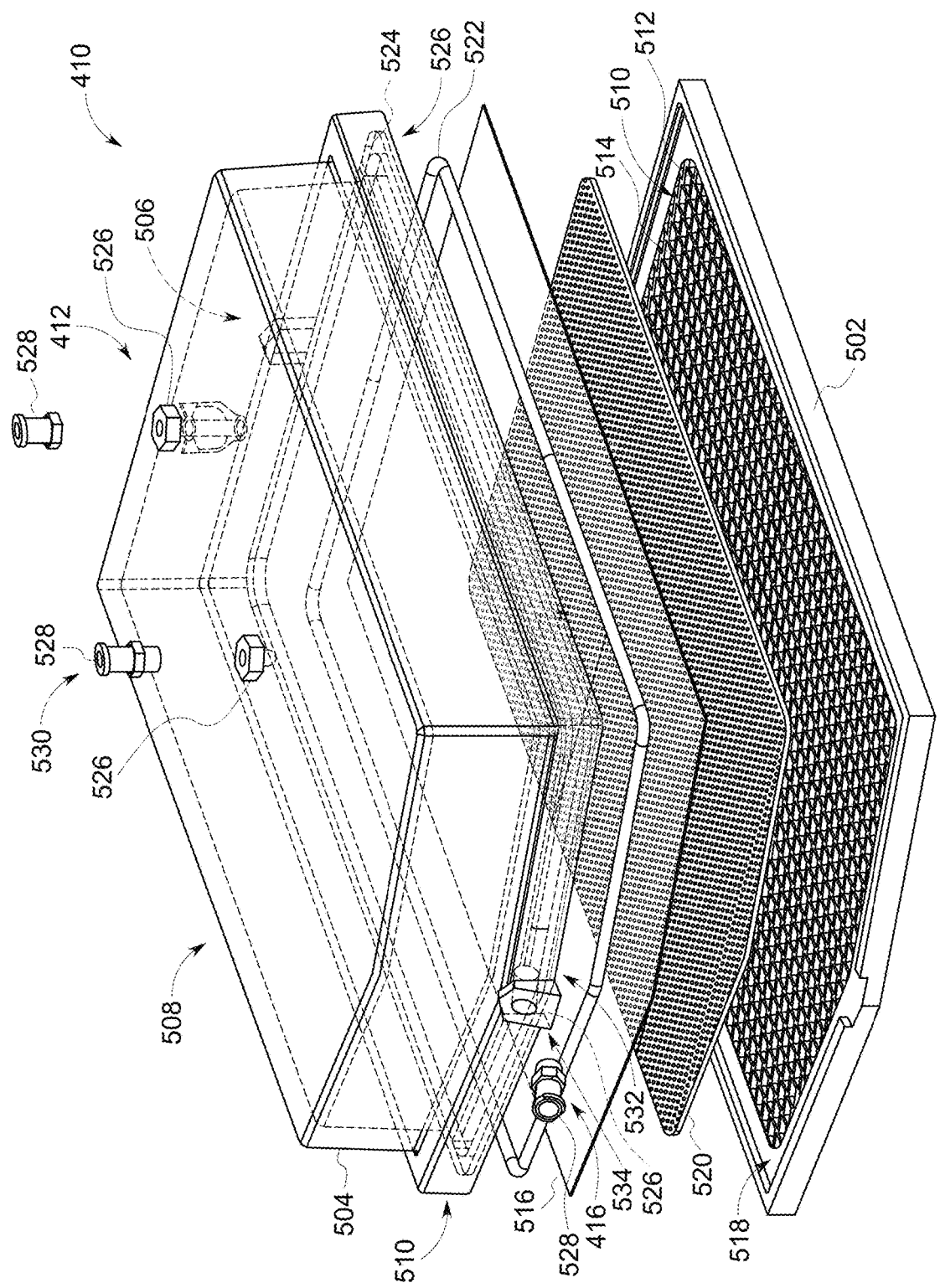
FIG. 9 is an exploded view of the bioreactor vessel of FIG. 8.

As shown in FIGS. 8 and 9, the first bioreactor vessel 410 may include a bottom plate 502 and a vessel body 504 coupled to the bottom plate 502. The bottom plate 502 may be a rigid structure to support a cell culture. However, the bottom plate may be a non-solid plate (e.g., may be open and/or porous) to permit oxygen to be provided to the cell culture, as discussed in greater detail with reference to FIG. 9. In the illustrated embodiment, the bottom plate 502 is rectangular, or almost rectangular, in shape. In other embodiments, the bottom plate 502 may be any other shape that may enable a low-profile vessel and/or may maximize space in the location that the first bioreactor vessel may be utilized or stored.

In an embodiment, the vessel body 504 includes a rigid, generally concave structure that, when coupled to the bottom plate 502, forms a cavity or interior compartment 506 of the first bioreactor vessel 410. As shown therein, the vessel body 504 may have a perimeter shape that is similar to the perimeter shape of the bottom plate 502 such that the vessel body 504 and the bottom plate 502 may be coupled to one another. Additionally, as in the illustrated embodiment, the vessel body 504 may be made of a transparent or translucent material that may enable visual inspection of the contents of the first bioreactor vessel 410 and/or may enable light to enter the first bioreactor vessel 410. The interior compartment 506 formed by the bottom plate 502 and the vessel body 504 may contain a cell medium and the cell culture during use of the first bioreactor vessel for cell activation, genetic modification (i.e., transduction), and/or cell expansion.

As best shown in FIGS. 8-11, the first bioreactor vessel 410 may include multiple ports through the vessel body 504 that may enable fluid communication between the interior compartment 506 and the outside of the first bioreactor vessel 410 for certain processes related to activation, transduction/genetic modification and expansion of cells, such as media input and waste removal. The ports may include, for example, first port 412 and second port 416. The ports 416 may be disposed at any location in the vessel body 504, including through a top surface 508 and/or any of the sides 510 of the vessel body 504, as in the illustrated embodiment. As will be discussed in greater detail herein, the specific structure of the first bioreactor vessel 410, including the particular quantity and position of the ports 412, 416, enables the first bioreactor vessel 410 to be used to support activation of cells, genetic modification of cells, and high cell density expansion.

FIG. 9 is an exploded view of an embodiment of the first bioreactor vessel 410. The bottom plate 502 of the first bioreactor vessel 410 may be the bottom or support of the first bioreactor vessel 410. As previously discussed, the bottom plate 502 may be formed of a non-solid structure. In the illustrated embodiment, the bottom plate 502 contains a grid 510 that may be structurally rigid while further providing opening to enable free gas exchange through the bottom plate 502 to the interior compartment 506 containing the cell culture. The grid 510 may include multiple holes 512 defined between solid areas or crossbars 514 between each hole 512 of the grid 510. Thus, the holes 512 may provide openings for gas exchange, and the crossbars 514 may provide structural support for other structures and the cell culture within the interior compartment 506 of the first bioreactor vessel 410.

To provide further support for the cell culture within the interior compartment 506 of the first bioreactor vessel 410, the first bioreactor vessel 410 may include a membrane 516 that may be disposed above a top surface 518 of the bottom plate 502. The membrane 516 may be a gas permeable, liquid impermeable membrane. The membrane 516 may also be selected having properties enabling high gas permeability, high gas transfer rates, and/or high permeability to oxygen and carbon dioxide. Therefore, the membrane 516 may support high cell densities (e.g., up to about 35 $MM/cm^2$) within the interior compartment 506. The gas permeability feature of the membrane 516 may enable the free gas exchange to support the cell culture and/or cell expansion. As such, the membrane 516 may be a cell culture surface and/or cell expansion surface. The membrane 516 may have a relatively small thickness (e.g., 0.010 inches or 0.02 cm), which may permit the membrane 516 to be gas permeable. Further, the membrane 516 may be formed from a gas permeable material, such as silicone or other gas permeable material.

Flatness of the membrane 516 may increase the surface area for the cell culture to settle on for activation, transduction and/or expansion. To enable the membrane 516 to remain flat during use of the first bioreactor vessel 410, a mesh sheet 520 may be disposed between the bottom plate 502 and the membrane 516. The mesh sheet 520 may provide structural support to the membrane 516, such that the membrane 516 may remain planar and may not sag or distort under the weight of the cell culture and/or any cell medium added to the first bioreactor vessel 410 for cell culture and/or cell expansion. Further, the mesh characteristic of the mesh sheet 520 may enable support of the membrane 516, while its porosity still enables free gas exchange between the interior compartment 506 of the first bioreactor vessel 410 and the environment immediately outside of the first bioreactor vessel 410. The mesh sheet may be a polyester mesh, or any other suitable mesh material that may provide support to the membrane and enable free gas exchange.

As previously discussed, the vessel body 504 may be coupled to the bottom plate 502 to form the interior compartment 506 of the first bioreactor vessel 410. As such, the mesh sheet 520 and the membrane 516 may be disposed within, or at least partially within, the interior compartment 506. An O-ring 522 may be used to seal the first bioreactor vessel 410 when the vessel body 504 is coupled to the bottom plate 502. In an embodiment, the O-ring 522 may be a biocompatible O-Ring (Size 173, Soft Viton® Fluoroelastomer O-Ring). The O-ring 522 may fit within a groove 524 formed in a perimetrical surface 526 of the vessel body 504. Perimetrical surface 526 faces top surface 518 of plate 502 when body 504 is mated to plate 502. As such, the O-ring 522 may be compressed within the groove 524 and against the top surface 518 of the plate 516 and/or the bottom plate 502. Such compression of the O-ring 522 desirably seals the first bioreactor vessel 410 without any chemical or epoxy bonding. As the first bioreactor vessel 410 may be used for activation, transduction and expansion of biological cells, the O-ring 522 is desirably formed from a suitably biocompatible, autoclavable, gamma radiation stable and/or ETO sterilization stable material.

As discussed above, the first bioreactor vessel 410 may include multiple ports, such as first port 412 and second port 416. The ports 412, 416 may be disposed through the vessel body 504 and may enable communication between the interior compartment 506 and the outside of the first bioreactor vessel 410 for certain processes related to the cell culture, cell activation, cell transduction, and/or cell expansion, such as fluid or media input, waste removal, collection and sampling. Each port 416 may include an opening 526 and a respective fitting or tubing 528 (e.g., a luer fitting, barb fitting, etc.). In some embodiments, the opening 526 may be configured so as to allow for tubing to be bonded directly and obviate the need for a fitting (e.g., a counterbore).

In an embodiment, in addition to the first port 412 and second port 416, the first bioreactor vessel 410 may further include an air balance port 530 disposed in the top surface 508 of the vessel body 504. The air balance port 530 may be constructed similarly to first port 412 and second port 416, where like reference numerals denote like parts. The air balance port 530 may further provide gas exchange between the interior compartment 506 and outside of the first bioreactor vessel 410 for use by the cell culture for expansion. Further, the air balance port 530 may help maintain atmospheric pressure within the interior compartment 506 to provide an environment within the interior compartment 506 for cell culture and/or cell expansion. The air balance port 530 may be disposed through the top surface 508 of the vessel body 504, as in the illustrated embodiment, or at any other position about the vessel body 504. A central position through the top surface 508 of the vessel body 504 may help prevent wetting of the air balance port 530 during mixing of the cell culture through tilting of the first bioreactor vessel 410, as discussed in greater detail below.

Each element of the first bioreactor vessel 410, including the bottom plate 502, the vessel body 504, the ports 412, 416 and 530, the membrane 516, the mesh sheet 520, and the O-ring 522, may be made from material that are biocompatible, autoclavable, and gamma radiation, and/or ETO sterilization stable. As such, each element, and the first bioreactor vessel 410 as a whole unit, may be used for activation, transduction and expansion of biological cells, and/or for other processes of the cell manufacturing process.

The first bioreactor vessel 410 may enable cell culture and/or cell expansion via perfusion, which may provide nutrients necessary for supporting cell growth and may reduce impurities in the cell culture. Continuous perfusion is the addition of a fresh media supply to the growing cell culture with simultaneous removal of spent media (e.g., used media). First port 412 and second port 416 may be used for the perfusion process, as discussed below. The first port 412 may enable communication between the interior compartment 506 and the outside of the first bioreactor vessel 410 and may be used to add a fresh medium into the first bioreactor vessel 410 (such as from a culture medium reservoir of the first fluid assembly 440). In some embodiments, the first port 412 may be disposed in and extend through the vessel body 504 at any location above the surface of the cell culture and medium within the first bioreactor vessel 410. In some embodiments, the first port 412 may be disposed such that it contacts or extends through the surface of the cell culture and medium within the first bioreactor vessel 410.

The second port 416 may be disposed at any location that is fully or partially submerged under the surface of the cell culture and the medium within the first bioreactor vessel 410. For example, the second port 416 may be a nearly lateral port disposed through one of the sides 510 of the vessel body 504. In some embodiments, the second port 416 may be disposed such that the second port 416 does not reach to the bottom of the interior compartment 506 (e.g., the membrane 516). In some embodiments, the second port 416 may reach the bottom of the interior compartment 506. The second port 416 may be a dual functionality port. As such, the second port may be used to pull the perfusion media out of the interior compartment 506 of the first bioreactor vessel 410 to facilitate perfusion of the cell culture. Further, the second port 416 may also be used to remove the cells of the cell culture. As noted above, in some embodiments, the second port may not reach the bottom surface of the interior compartment 506 of the first bioreactor vessel 410. For example, the second port 416 may be located approximately 0.5 cm away from the membrane 516. Therefore, in a static planar position, the second port 416 may be used to remove the spent cell culture medium without pulling out the cells of the cell culture because the cells may settle to the membrane 516 (e.g., the cell expansion surface) via gravity. Thus, in the static planar position, the second port 416 may facilitate the perfusion process and may enable an increase in the cell density of the growing cell culture within the first bioreactor vessel 410. When cells are desired to be removed from the interior compartment 506, for example during harvest of the cell culture, to minimize the hold-up volume, the first bioreactor vessel 410 may be tilted toward the second port 416 providing access to the cells for cell removal, in the manner described hereinafter.

Additionally, in an embodiment, the second port 416 may not include a filter and thus, the perfusion process may be filter-free. As such, there may be no physical blockage of the cells from entering the second port 416 when the second port 416 is used for media removal. Further, the second port 416 may be slanted such that although the second port 416 is disposed laterally through the side 22 of the vessel body 504, the second port 416 may be slanted toward the membrane 516 and the bottom plate 502. The slanted feature of the second port 416 may enable the second port 416 to be positioned relatively low on the vessel body 504 closer to the membrane surface 36, while minimizing interference with the O-ring 522 and the groove 524 to help maintain sealing of the first bioreactor vessel 410 when in use. Further, in some embodiments, the slanted feature of the second port 416 may lower the velocity of the fluid flow through the second port 416 when used medium is removed. Additionally, the port diameter in conjunction with fluid flow rate out of the second port 416 may be such that an inhaling velocity through the second port 416 used to pull the media out of the interior compartment 506 may minimize suction force on individual cells adjacent to the second port 416 such that the force is lower than the gravitational force pulling the cells toward the membrane 516. Therefore, as discussed above, the second port 416 may be used to remove the perfusion medium to facilitate perfusion of the cell culture without substantially removing the cells of the cell culture. As the settling time of the cells increases, a cell concentration of the removed media may decrease into an immeasurable range facilitated by the position of the second port 416. Further, the position of the interior opening 540 may be changed to change the recommended cell settling time. Positions closer to the membrane 516 may be associated with longer settling times, while positions at or nearer to a top of the medium are associated with shorter settling times, because cells will settle and be first depleted from the top of the growth medium.

In an embodiment, the second port 416 may therefore be used not only for removal of the used media during the perfusion process, but may also be used to remove cells of the cell culture from the interior compartment 506, for example during harvest of the cell culture. To facilitate greater removal of the used perfusion medium and removal of cells, the vessel body 504 may include an angled or chevron-shaped sidewall 532. The chevron-shaped sidewall 532 thus includes an apex, or point, 534. Apex 534 of sidewall 532 may further include second port 416 therethrough the vessel body 504 is disposed near the point 534 when the vessel body 504 coupled to the bottom plate 502. The angled side 532 and the point 534 may enable greater drainage of the media and/or the cells of the cell culture when the first bioreactor vessel 410 is tilted toward the second port 416, e.g., at a 5-degree angle.

Figure 10:
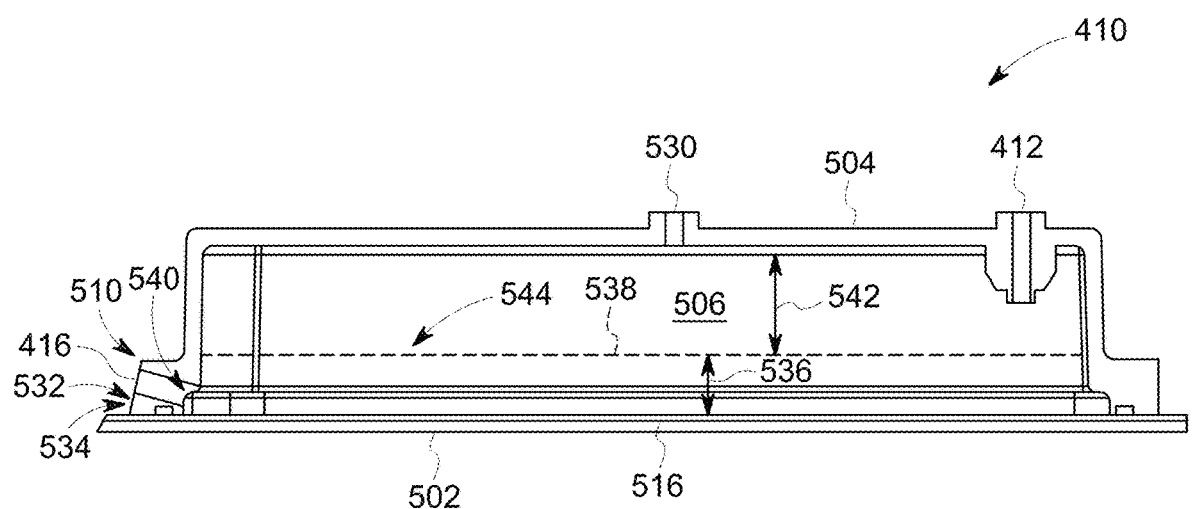
FIG. 10 is an exploded, cross-sectional view of the bioreactor vessel of FIG. 8.

The use of perfusion to grow the cells facilitated by the positions of the first port 412 and the second port 416 may enable a low media height (e.g., 0.3-2.0 cm) within the interior compartment 506, as discussed in greater detail with reference to FIG. 10. A relatively low media height within the interior compartment 506 may enable the first bioreactor vessel 410 to be a relatively low-profile vessel, while enabling an increase in the maximum achievable cell density. Further, the use of perfusion with the first bioreactor vessel 410 may support cell growth by providing fresh medium to the cells within the interior compartment 506, but also enable removal of impurities in the cell culture, such that additional cell washing in a separate device may not be needed once a particular cell density goal is reached within the first bioreactor vessel 410. For example, through the filter-free perfusion, the first bioreactor vessel 410 may provide fresh medium and reduce impurities within the cell culture at a rate of a full volume exchange per day (e.g., resulting in an impurity reduction at a rate of approximately 1 log per 2.3 days). Therefore, the structure of the first bioreactor vessel 410 may enable the use of perfusion for growing the cell culture within the first bioreactor vessel 410, which may thus enable expansion of the cell culture to a high target density with a reduced impurity level. As also discussed hereinafter, through the filter-free perfusion, the first bioreactor vessel 410 may provide fresh medium at a rate of a substantially more volumes per day (e.g., greater than 2 volumes per day) for seeding, rinsing, washing/residual reduction, and/or draining/harvesting of the cells after expansion.

To facilitate a low-profile structure of the first bioreactor vessel 410, a relatively low media height within the interior compartment 506 may be maintained. FIG. 10 is a cross-sectional view of the first bioreactor vessel 410 illustrating a height 536 of cell media 538 within the first bioreactor vessel 410. As previously discussed, the vessel body 504 may be coupled to the bottom plate 502 to form the interior compartment 506 within which expansion of the cell culture may be achieved through perfusion. As such, replacement or fresh medium 538 may be provided for cell growth through the first port 412 disposed through the vessel body 504, and existing or used medium 538 may be removed through the second port 416 disposed through the side 510 of the vessel body 504. The perfusion process may facilitate relatively low medium height 536 of the medium 538 within the interior compartment 506 of the first bioreactor vessel 410. The relatively low height 536 of the perfusion medium 538 within the interior compartment 506 may enable the first bioreactor vessel 410 to be a low-profile structure, which thus, may enable a compact cell manufacturing system as a whole.

The height 536 of the perfusion medium 538 within the interior compartment 506 of the first bioreactor vessel 410 may be between 0.3 cm and 2 cm, and the height of the head room 542, i.e., a gap formed between the medium 538 and the top surface 508 of the vessel body 504 in the interior compartment 506, may be approximately 2 cm. Thus, there may be less than 2 mL of media per $cm^2$ and less than 4 mL of total volume per $cm^2$, including the media, the cell culture, and headspace. A relatively low media height 536 may enable a ratio of media volume to surface area of the membrane 516 to be below a certain value. As such, the ratio of the medium volume to the membrane surface area may be below a threshold level, or within a desirable range, facilitated by the use of perfusion to grow the cells of the cell culture. For example, the threshold level may be a ratio between 0.3-2.0. The low ratio medium volume to membrane surface area may enable the first bioreactor vessel 410 to have a low-profile or compact structure, while still permitting a high cell density cell culture to be achieved.

As previously discussed, the dual functionality second port 416 may be disposed through the vessel body 504 such that it is fully or partially submerged under a surface 544 of the medium 538 within the first bioreactor vessel 410. In some embodiments, the second port 416 may be disposed such that the second port 416 reaches to the bottom of the interior compartment 506 (e.g., the membrane 516). Positioning of the second port 416 may facilitate media and impurity removal from the cell culture within the interior compartment 506, without removal of the cells until such removal is desired, for example harvesting. The filter-free second port 416, along with the first port 412, may permit the use of perfusion to provide the growth medium 538 to the cells for cell expansion, and to remove the used medium 538 and other impurities or byproducts. The position of the first port 412 and the dual functioning second port 416 about the vessel body 504 facilitates a configuration in which the height 536 of the medium within the interior compartment 506 to be maintained at a relatively low level and thus, permit the first bioreactor vessel 410 to be a relatively low-profile vessel, while still permitting generation of a high-density cell culture.

Figure 11:
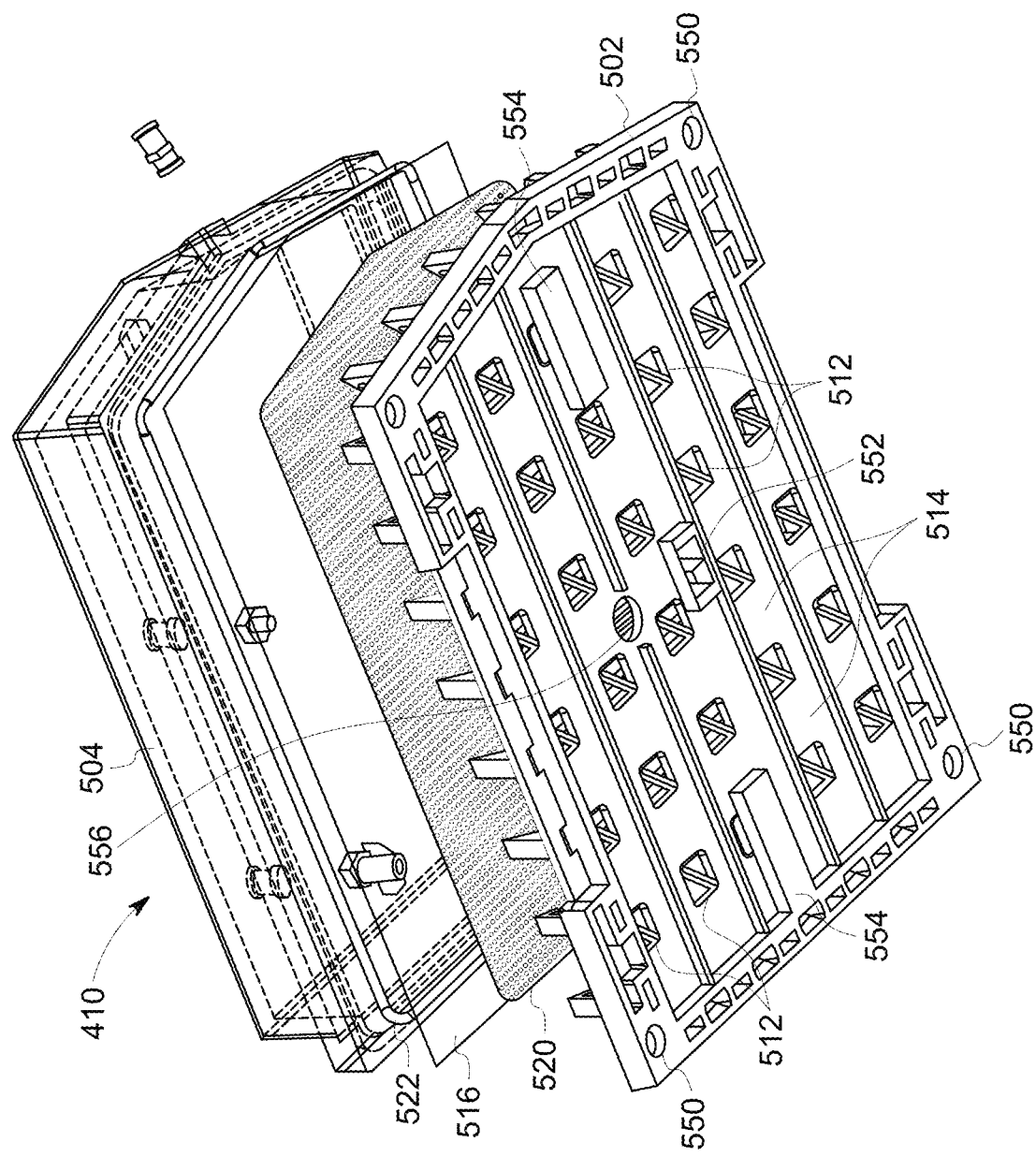
FIG. 11 is an exploded bottom, perspective view of the bioreactor vessel of FIG. 8.

With specific reference to FIG. 11, the bottom plate 502 of the bioreactor vessel 410 includes a variety of features that enable use of the bioreactor vessel as part of the broader bioprocessing system 10 and in particular, the second module 200 of the bioprocessing system 10. As shown therein, the bottom plate 502 includes a plurality of recesses 550 formed in a bottom surface of the bottom plate 502, the purpose of which will be described hereinafter. In an embodiment, the recesses may be located adjacent to the corners of the bottom plate 502. The recesses 550 may each be generally cylindrical in shape and terminate at a dome-like or hemispherical-like interior surface. As also shown in FIG. 11, the bottom plate 502 may include a position verification structure 552 that is configured to interact with a sensor of the second module 200 to ensure proper positioning of the first bioreactor vessel 410 within the second module 200. In an embodiment, the position verification structure may be a beam break that is configured to interrupt an optical beam of the second module 200 when the first bioreactor vessel 410 is properly seated therein.

The bottom plate 502 also includes a pair of flat engagement surfaces 554 formed on the bottom surface adjacent, which are offset from a center line of the bottom plate (that extends across the width of the bottom plate). Desirably, the engagement surfaces 554 are spaced-apart along a longitudinal centerline of bottom plate 502 so as to be positioned adjacent to opposed ends of the bottom plate 502. The bottom plate 502 may further include at least one aperture or opening 556 to allow for sensing of the contents of the first bioreactor vessel 410 by a bioprocessing apparatus which engages and operates the bioreactor vessel.

Figure 12:
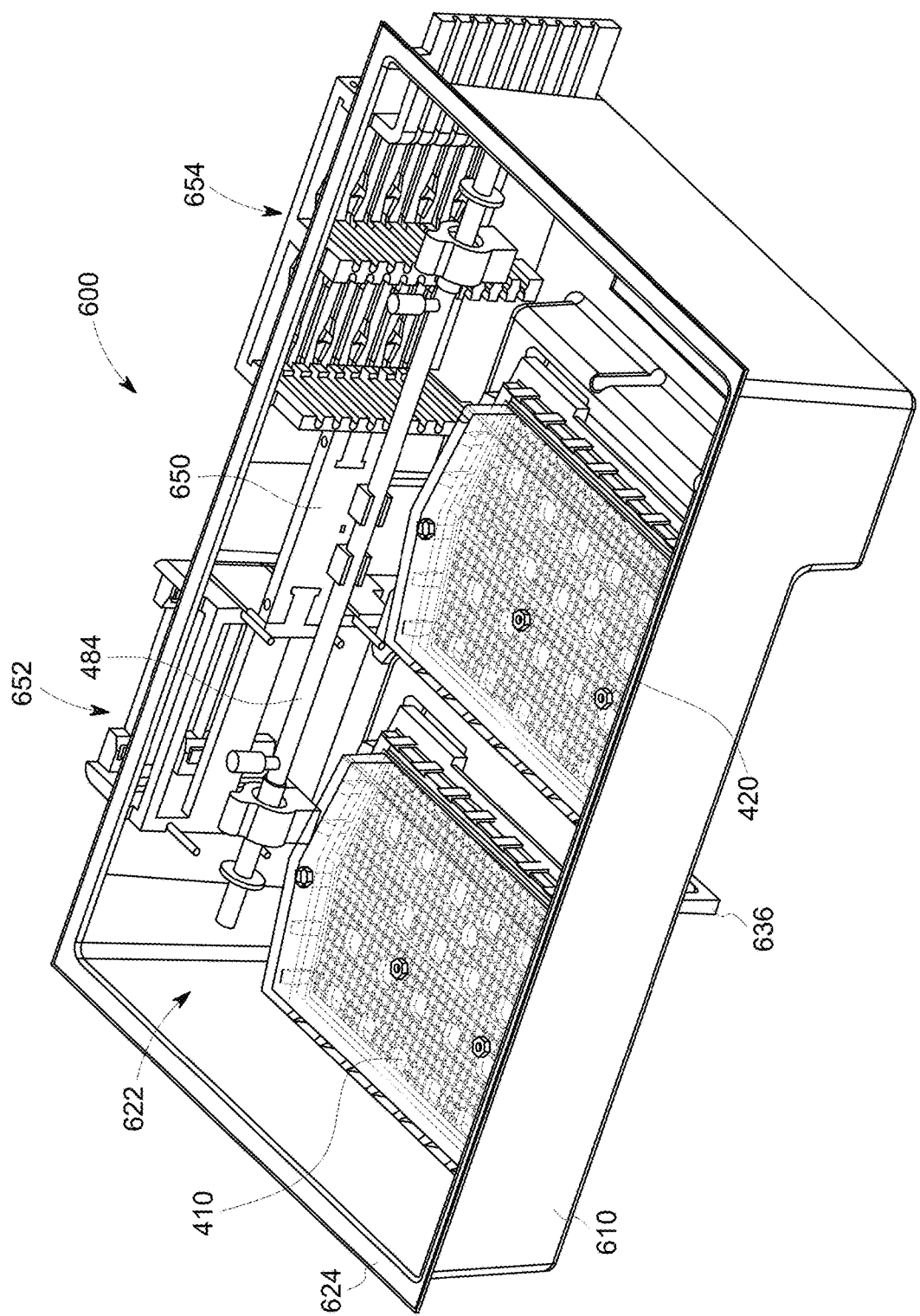
FIG. 12 is a perspective top and front view of a disposable drop-in kit of the bioprocessing system of FIG. 1, according to an embodiment of the invention.
Figure 13:
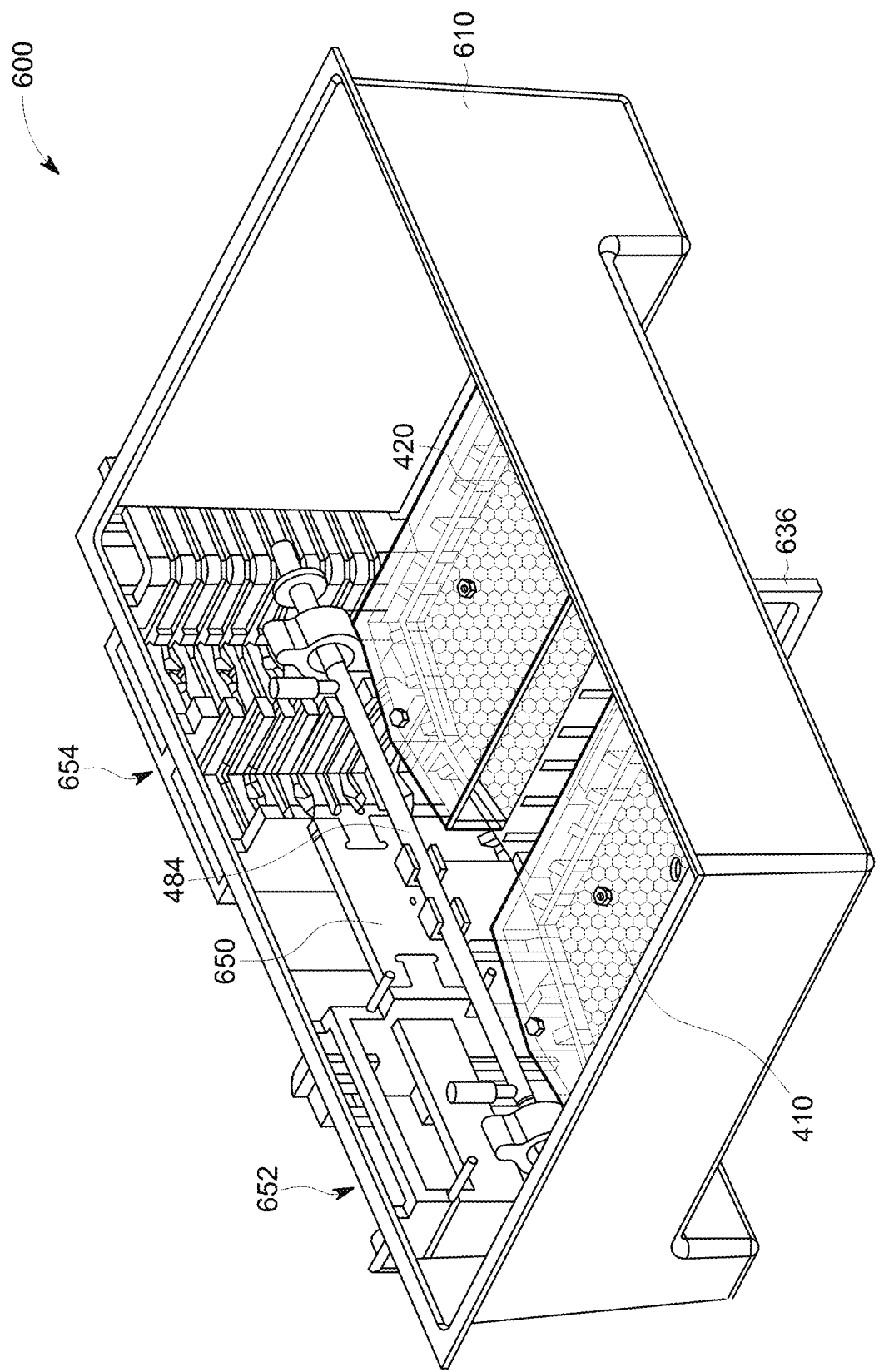
FIG. 13 is another perspective top and front view of the disposable drop-in kit of FIG. 12.
Figure 14:
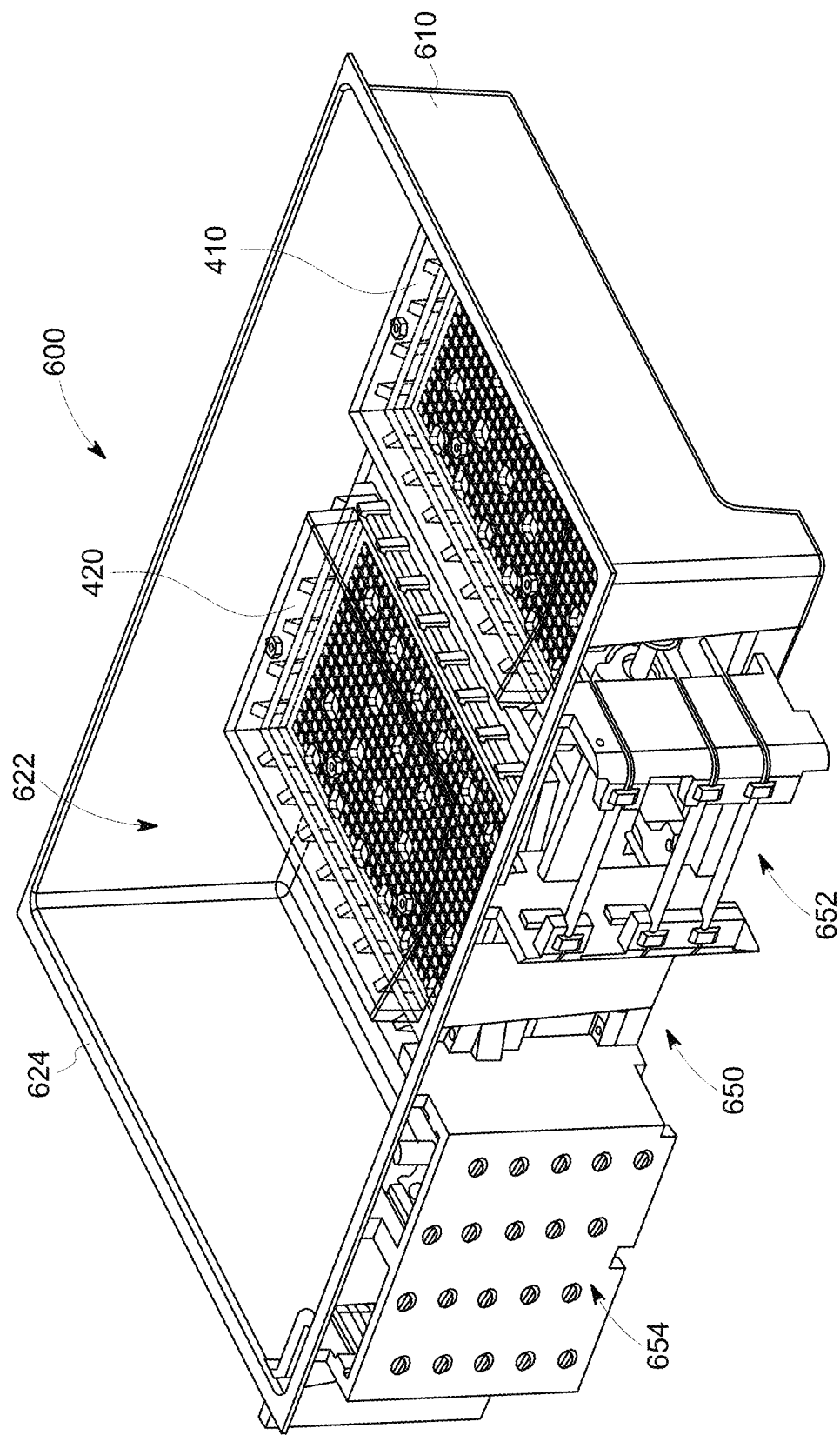
FIG. 14 is a perspective top and rear view of the disposable drop-in kit of FIG. 12.

In an embodiment, the first and second bioreactor vessels 410, 420 and the fluid architecture 400 may be integrated into an assembly or kit 600 in the manner disclosed below. In an embodiment, the kit 600 is a single-use, disposable kit. As best shown in FIGS. 12-14, the first bioprocessing vessel 410 and the second bioprocessing vessel 420 are received side-by-side within a tray 610 of the disposable kit 600, and the various tubes of the flow architecture 400 arranged within the tray 610 in the manner described hereinafter.

Figure 15:
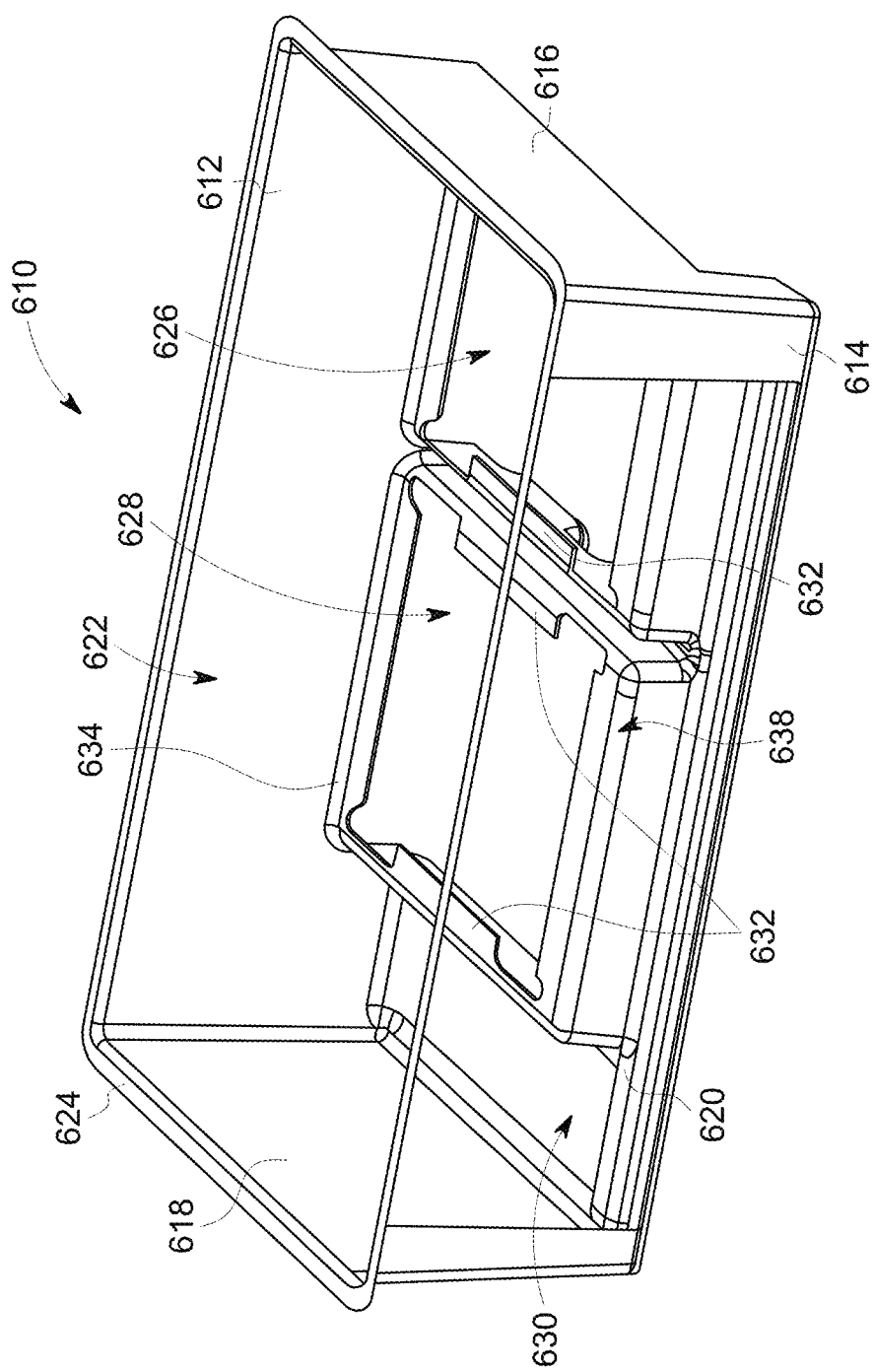
FIG. 15 is a perspective view of a tray of the disposable drop-in kit of FIG. 12, according to an embodiment of the invention.

With additional reference to FIG. 15, the tray 610 includes a plurality of generally thin, rigid or semi-rigid sidewalls including a front wall 612, a rear wall 614, and opposed lateral sides 616, 618 perimetrically bounding a bottom surface 620 and a generally open top. The sidewalls and bottom surface 620 define an interior compartment 622 of the tray 610. In an embodiment, the open top of the tray 610 is bounded by a peripheral flange 624 that presents a surface for receiving removable cover (not shown) that encloses the interior compartment 622 as well as for desirably seating on an upper rim of a drawer of a bioprocessing apparatus, as indicated below. The bottom surface 620 of the tray 610 includes a number of openings corresponding to the number of bioreactor vessels in the bioprocessing system. For example, the tray 610 may include a first opening 626 and a second opening 628. The bottom surface 620 may also include an additional opening 630 adjacent to the first and second openings 626, 628 for the purpose described below. In an embodiment, the tray 610 may be thermoformed, 3D printed, or injection molded, although other manufacturing techniques and processes may also be utilized without departing from the broader-aspects of the invention.

As best shown in FIG. 15, each of the first and second opening 626, 628 has a perimeter that is shaped and/or dimensioned such that the first and second bioreactor vessels 410, 420 can be positioned above the respective openings 626, 628 and supported by the bottom surface 620 of the tray 610 within the interior compartment 622, while still allowing for a portion of the bioreactor vessels 610, 620 to accessible from the bottom of the tray 610 through the respective openings 626, 628. In an embodiment, the perimeter of the openings include at least one tab or projection for supporting the bioreactor vessels above the respective openings. For example, the perimeter of each opening 626, 628 may include tabs 632 that project inwardly towards the center of the openings 626, 628 for supporting the bioreactor vessels 410, 420 placed thereon. As shown in FIGS. 12 and 15, the tray 610 may also include one or more bosses extending upwardly above the openings 626, 628 for inhibiting lateral movement of the bioreactor vessels when they are received above the respective openings 626, 628. The bosses therefore serve as alignment devices that facilitate proper positioning of the bioreactor vessels 410, 420 within the tray 610, and help to prevent inadvertent movement of the bioreactor vessels 410, 420 during loading or positioning of the kit 600 in the second module 200, as discussed below.

With further reference to FIGS. 12 and 13, the tray 610 may include one or more support ribs 636 formed on the bottom surface of the tray 610. The support ribs 636 may extend across the width and/or length of the tray 610 and impart rigidity and strength to the tray 610, facilitating movement and manipulation of the kit 600. The ribs 636 may be integrally formed with the tray or may be added as an auxiliary component via attachment means known in the art. (See FIG. 13). In an embodiment, the tray 610 includes an opening 638 for receiving an engagement plate, also referred to herein as tubing module 650, therethrough, which retains the fluid flow lines in an organized manner and holds them in position for engagement by the pumps and pinch valves. In other embodiments, the tubing module 650 may be integrally formed with the rear wall 614 of the tray 610.

Figure 16:
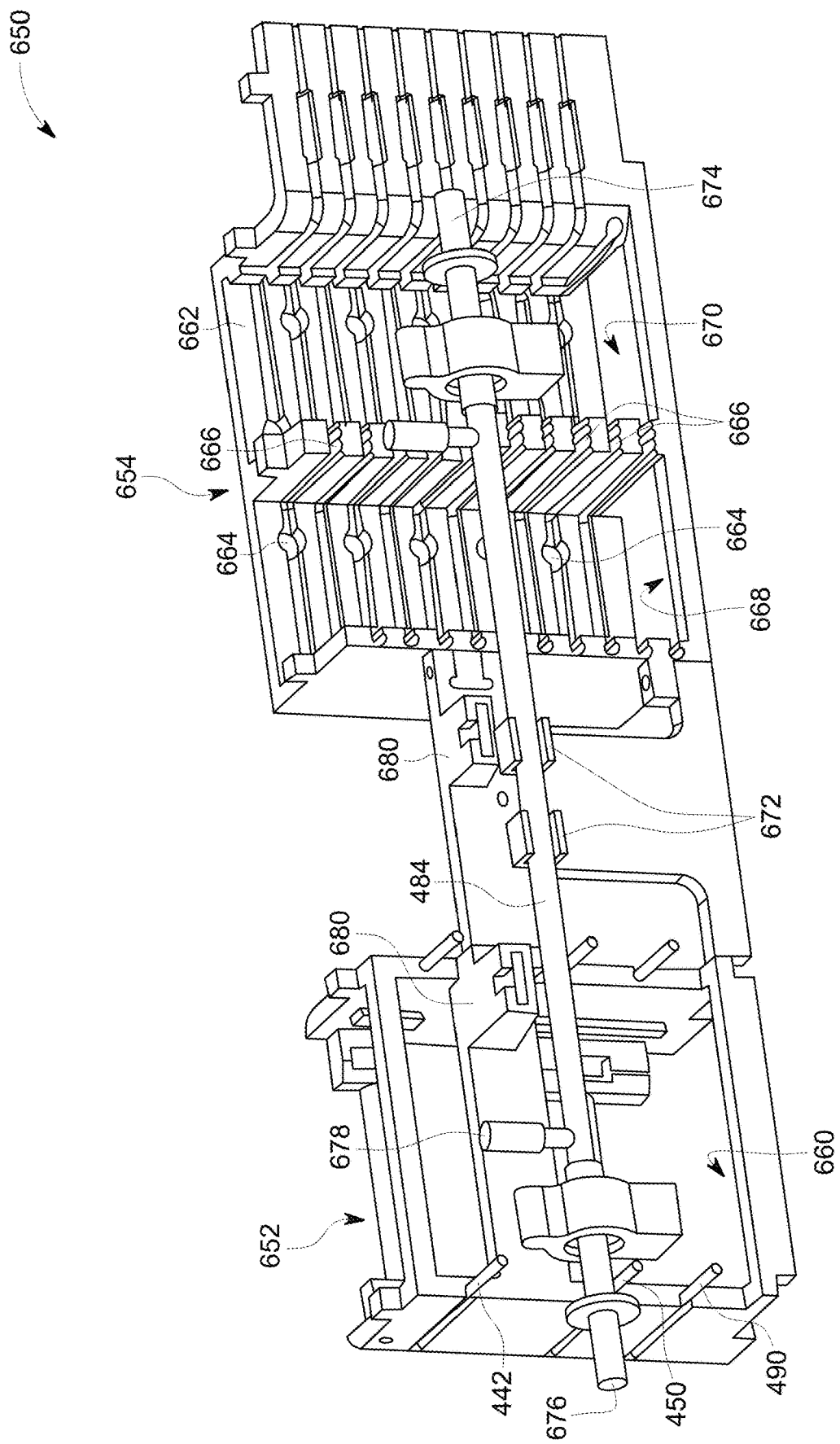
FIG. 16 is a front perspective view of a tubing module of the disposable drop-in kit of FIG. 12, according to an embodiment of the invention.
Figure 17:
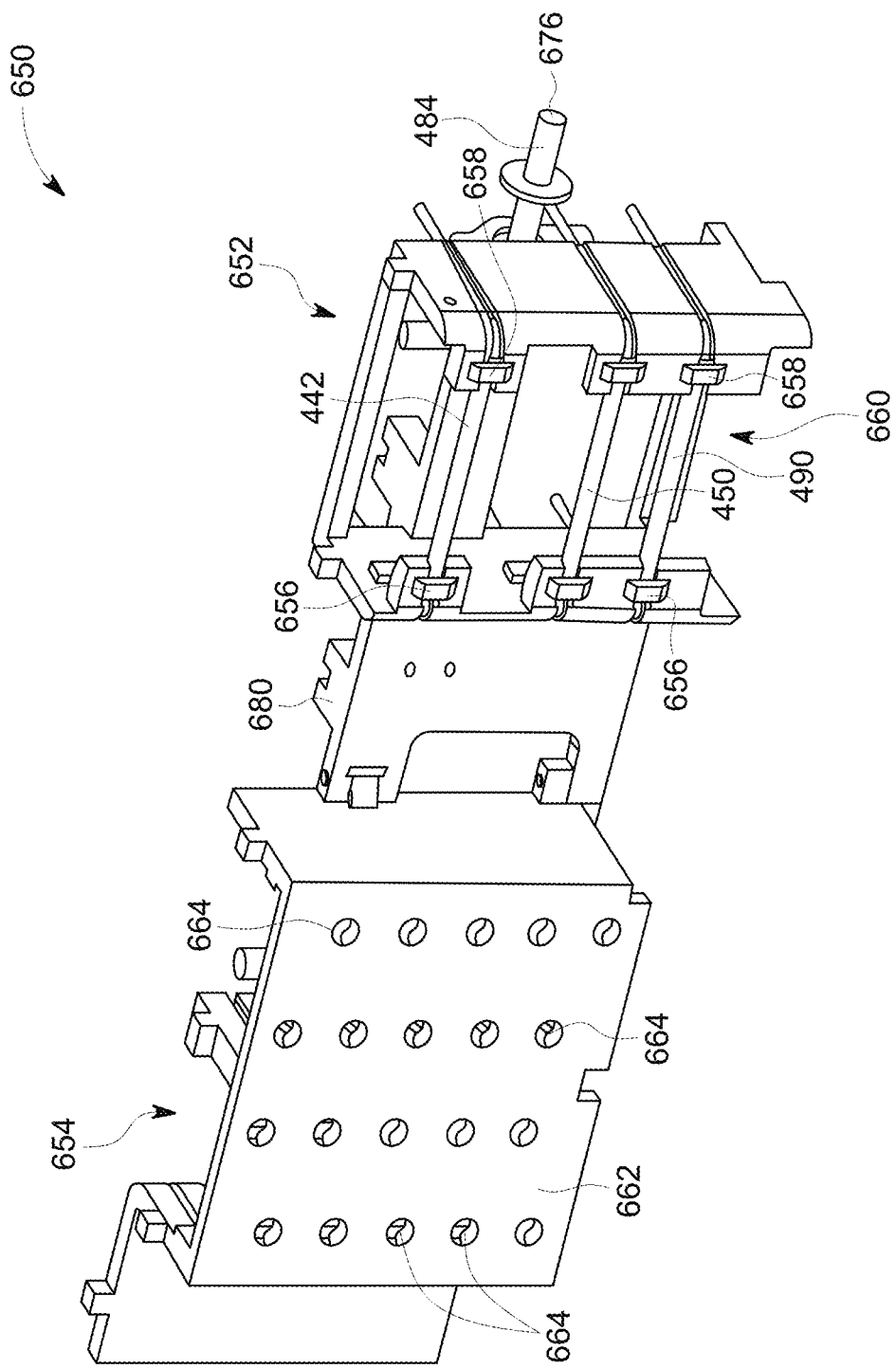
FIG. 17 is a rear perspective view of the tubing module of FIG. 16.

FIGS. 16 and 17 illustrate the configuration of the tubing module 650 according to an embodiment of the invention. As shown therein, the tubing module 650 includes a first tubing holder block 652 configured to receive the first fluid assembly line 442, the interconnect line 450 and the waste line 490 of the fluid flow system 400, and hold the first fluid assembly line 442, the interconnect line 450 and the permeate waste line 490 in position for selective engagement with respective pump heads 454, 456, 492 of a peristaltic pump assembly described below in connection with FIGS. 35 and 36. In an embodiment, the fluid assembly line 442, interconnect line 450 and waste line 490 are maintained in horizontally-extending and vertically-spaced orientation by the first tubing holder block 652. In particular, as best shown in FIG. 17, the first tubing holder block 652 engages each the lines 442, 450, 490 at two spaced-apart locations 656, 658 (such as through clips or simple interference between the tubes and slots in the tubing holder block 652) that define a void therebetween. As also shown in FIG. 17, the first tubing holder block 652 includes a clearance opening 660 that is configured to receive a shoe (not shown) of the peristaltic pump assembly. This configuration allows for peristaltic compression of the lines 442, 450, 490 against the shoe by the respective pump heads of the peristaltic pump(s) so as to provide a respective motive force of fluid through the lines, as discussed below.

Figure 18:
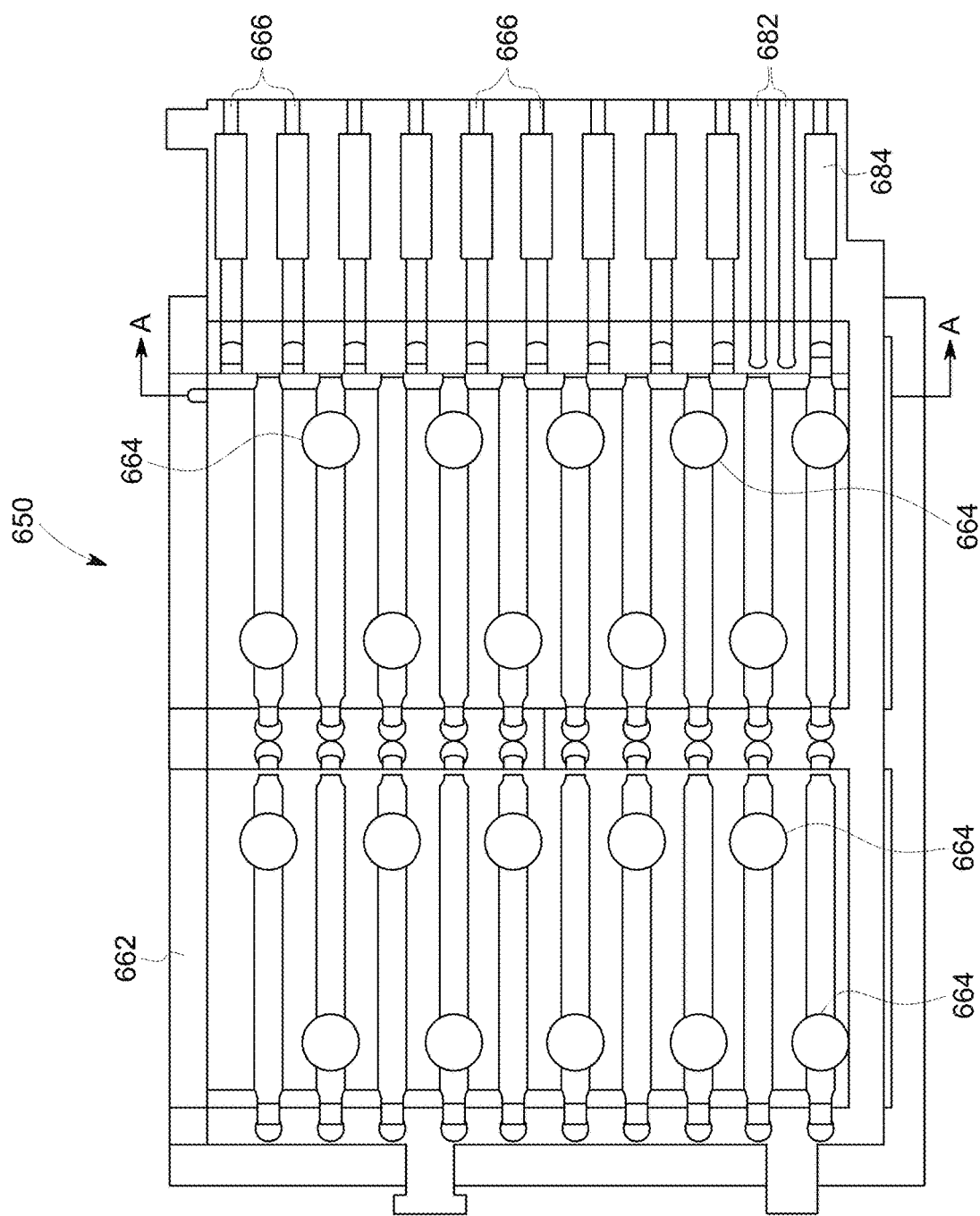
FIG. 18 is an elevational view of a second tubing holder block of the tubing module, according to an embodiment of the invention.
Figure 19:
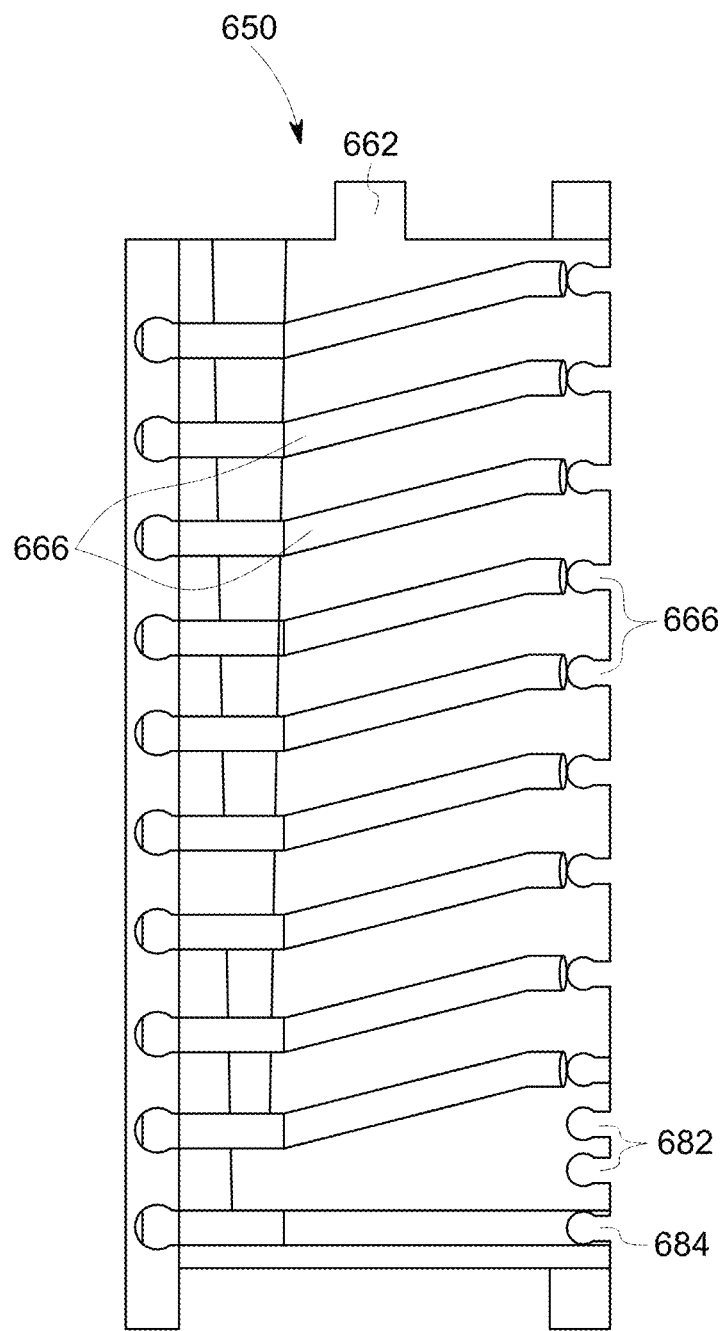
FIG. 19 is a cross-sectional view of the second tubing holder block of FIG. 18.

With further reference to FIGS. 16-18, the tubing module 650 further includes a second tubing holder block 654 integrally formed with (or otherwise coupled to) the first tubing holder block 652. The second tubing holder block 654 is configured to receive all of the fluid flow lines of the fluid flow system 400 with which pinch valves are associated. For example, the second tubing holder block 654 is configured to retain the tubing tails 464*a-f* of the first fluid assembly 440, the tubing tails 470*a-d* of the second fluid assembly 444, the first bioreactor line 414 and second bioreactor line 418 of the first bioreactor vessel 410, the first bioreactor line 424 and the second bioreactor line 428 of the second bioreactor vessel 420, the sterile air source line 460, the interconnect line 450 and the filtration line 482 (and in some embodiment, the sampling lines 476*a-476d*). Similar to the first tubing holder block 652, the second tubing holder block 654 may maintain these tubes in horizontally-extending and vertically-spaced orientation. In particular, the second tubing holder block 654 may include a plurality or vertically-spaced and horizontally-extending slots 666 that are configured to receive the lines therein. FIGS. 18 and 19 also best illustrate the configuration of the slots 666 that retain all of the flow lines that are acted upon by/interface with the pinch valves. Desirably, slots 666 follow the contour of block 654 but particularly extends across planar back plate so as to open towards filter 484. As shown in FIG. 18, in an embodiment, the second tubing holder block 654 may have one or more narrow tubing slots 682 at the bottom of the second tubing holder block 654 for holding a loop of the interconnect line 450, from which the sampling lines extend, and a waste line tubing slot 684 for receiving the tubing tail 470 that is connected to the waste reservoir 472*a*.

The second tubing holder block 654 may include a planar back plate 662 having a plurality of apertures 664 corresponding to the plurality of fluid flow lines retained by the second tubing holder block 654. In particular, at least one aperture 664 is horizontally aligned with each slot 666 and flow line retained therein. As best shown in FIG. 16, the second tubing holder block 654 includes two clearance openings 668, 670 that are configured to receive an anvil (not shown) of a pinch valve assembly therethrough. This configuration allows for selective compression of the tubing tails 464*a-f* of the first fluid assembly 440, the tubing tails 470*a-d* of the second fluid assembly 444, the first bioreactor line 414 and second bioreactor line 418 of the first bioreactor vessel 410, the first bioreactor line 424 and the second bioreactor line 428 of the second bioreactor vessel 420, the sterile air source line 460, the interconnect line 450 and the filtration line 482 against the anvil by a respective piston of an actuator of the pinch valve array, to selectively prevent or allow fluid flow, as discussed below. As shown in FIGS. 18 and 19, the apertures 664 may be arranged in first and second columns positioned side by side, wherein the apertures in the first column of apertures are offset in a vertical direction with respect to the apertures on the second column of apertures so that the apertures in the first column of apertures are not in horizontal alignment with the apertures in the second column of apertures. This configuration allows for the tubing module 650, tray 610 and kit 600, as a whole, to have a low profile.

In an embodiment, the filter 484 (shown in FIG. 16 as an elongate hollow fiber filter module) may be integrated with the tubing module 650, such as by mounting the filter 484 to the tubing module 650 through the use of retaining clips 672. Where the filter 484 is a hollow fiber filter, the filter 484 may extend substantially the entire length of the tubing module 650 and may include a first, input end 674 for receiving an input flow of fluid from the filtration line 482, and a second, output end 676 for conveying the retentate, after removal of permeate/waste, back to the filtration line 482 and interconnect line 450 for circulation to one of the first bioreactor vessel 410 or second bioreactor vessel 420. The filter 484 may also include a permeate port 678 adjacent to the second, output end 676 for connection to the waste line 490 for conveying the waste/permeate to permeate/waste reservoir 472*a*. Finally, the tubing module 650 may include a plurality of features 680 for receiving clips and organizing the bioreactor lines (e.g., first and second bioreactor lines 414, 418 of the first bioreactor vessel 410 and/or first and second bioreactor lines 424, 428 of the second bioreactor vessel 420).

Similar to the tray 610, the tubing module 650 may be thermoformed, 3D printed, or injection molded, although other manufacturing techniques and processes may also be utilized without departing from the broader-aspects of the invention. As discussed above, in an embodiment, the tubing module 650 may be integrally formed with the tray 610. In other embodiments, the tubing module 650 may be a separate component that is removably received by the tray 610.

Figure 20:
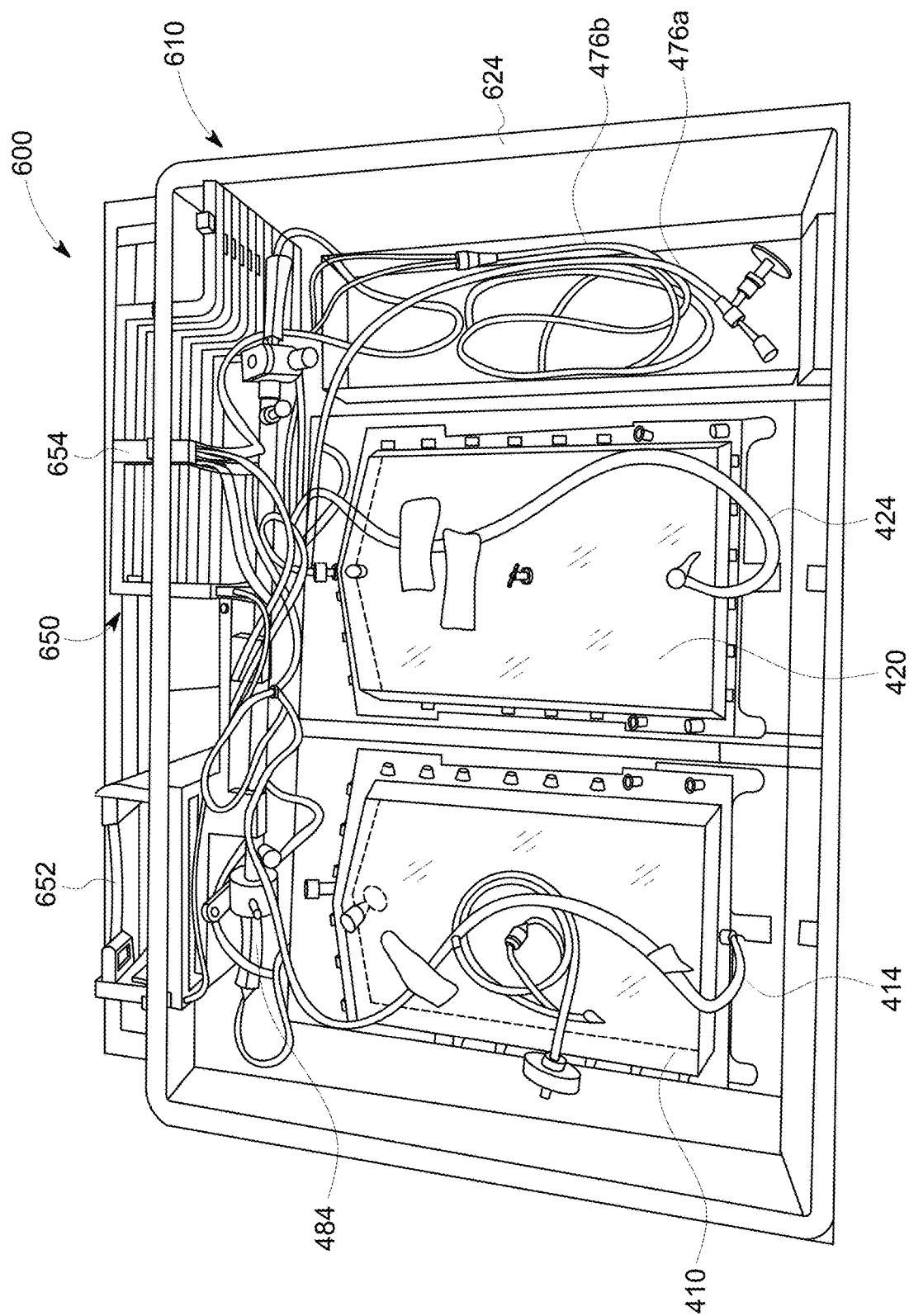
FIG. 20 is another perspective front view of the drop-in kit of FIG. 12, showing the flow architecture integrated therein.
Figure 21:
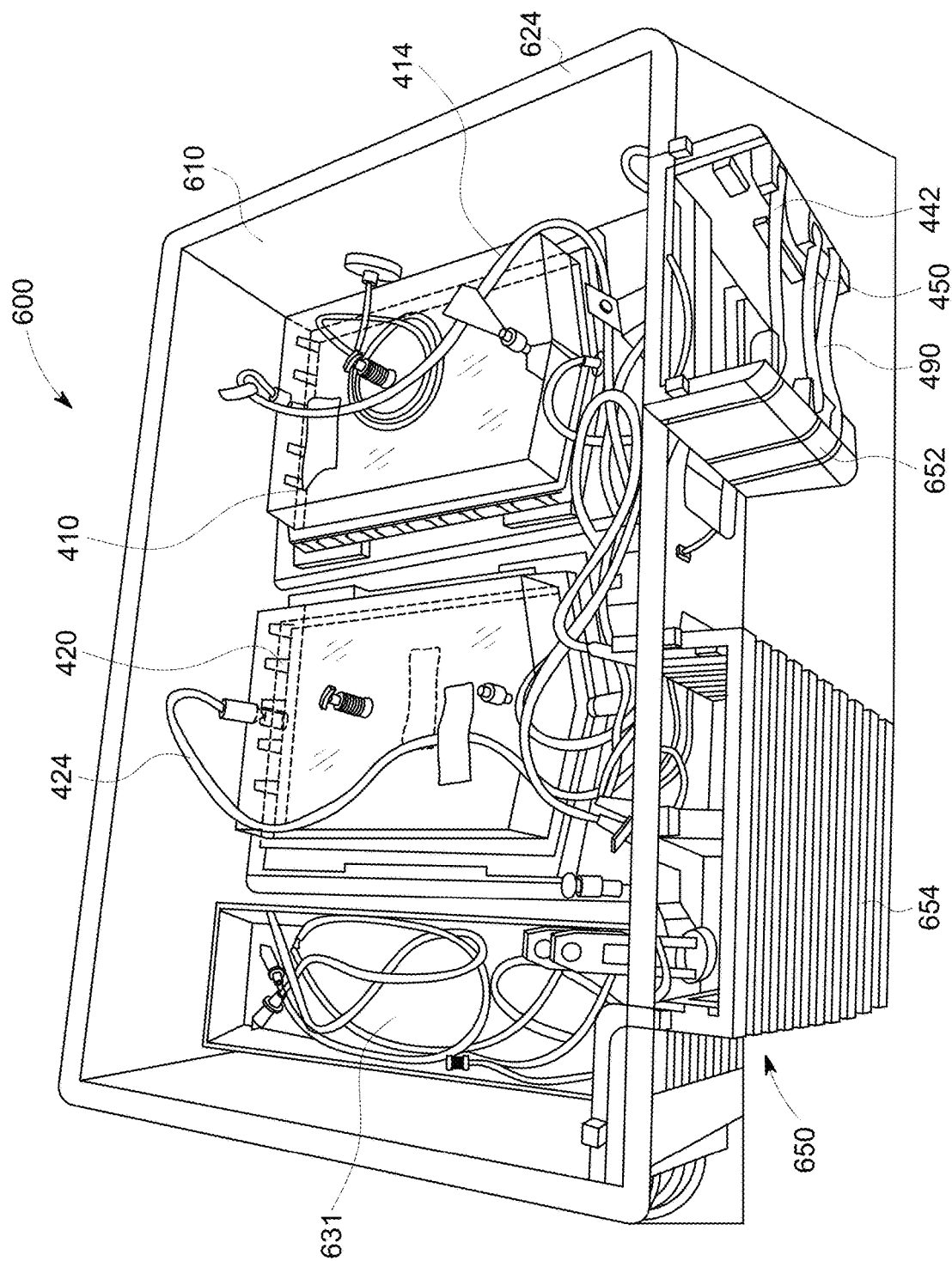
FIG. 21 is a perspective rear view of the drop-in kit of FIG. 12, showing the flow architecture integrated therein.
Figure 22:
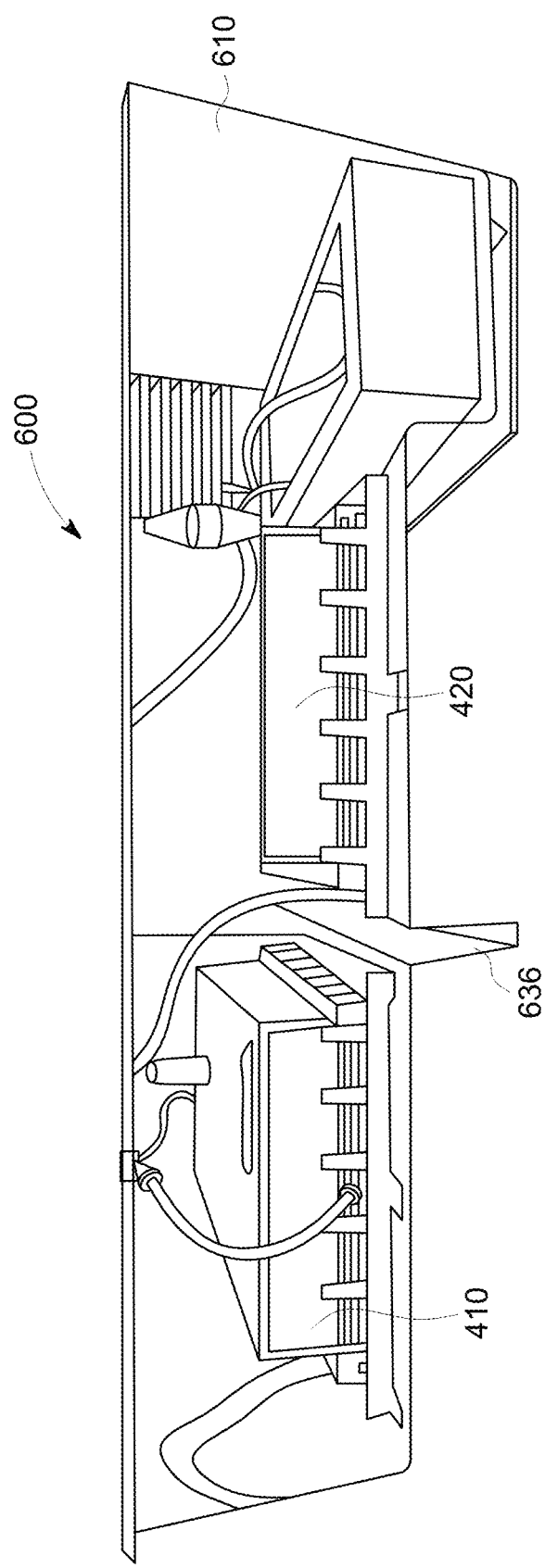
FIG. 22 is a front elevational view of the drop-in kit of FIG. 12, showing the flow architecture integrated therein.

FIGS. 20-22 show various views of an embodiment of the kit 600, illustrating the first bioreactor vessel 410 and the second bioreactor vessel 420 received within the tray 610 and the fluid lines of the flow architecture 400 received by the tubing module 650. As shown therein, rather than having an opening 630, the kit 600 as shown in FIGS. 20-22 includes a solid floor there so as to provide a sampling space 631 in tray 610 for receiving a container that holds the sampling lines (e.g., sampling lines 476*a*, 476*b*). The kit 600 provides for a modular platform for cell processing that can be easily set up and discarded after use. The tubing tails of the first and second fluid assemblies 440, 444 allow for plug-and-play functionality, enabling the quick and easy connection of various media, reagent, waste, sampling and collection bags to allow for a variety of processes using to be carried out on a single platform. In an embodiment, connection and disconnection can accomplished by sterile cutting and welding of tube segments, as discussed above, such as with a TERUMO device, or by pinching, welding, and cutting the tail segment as is known in the art.

Figure 23:
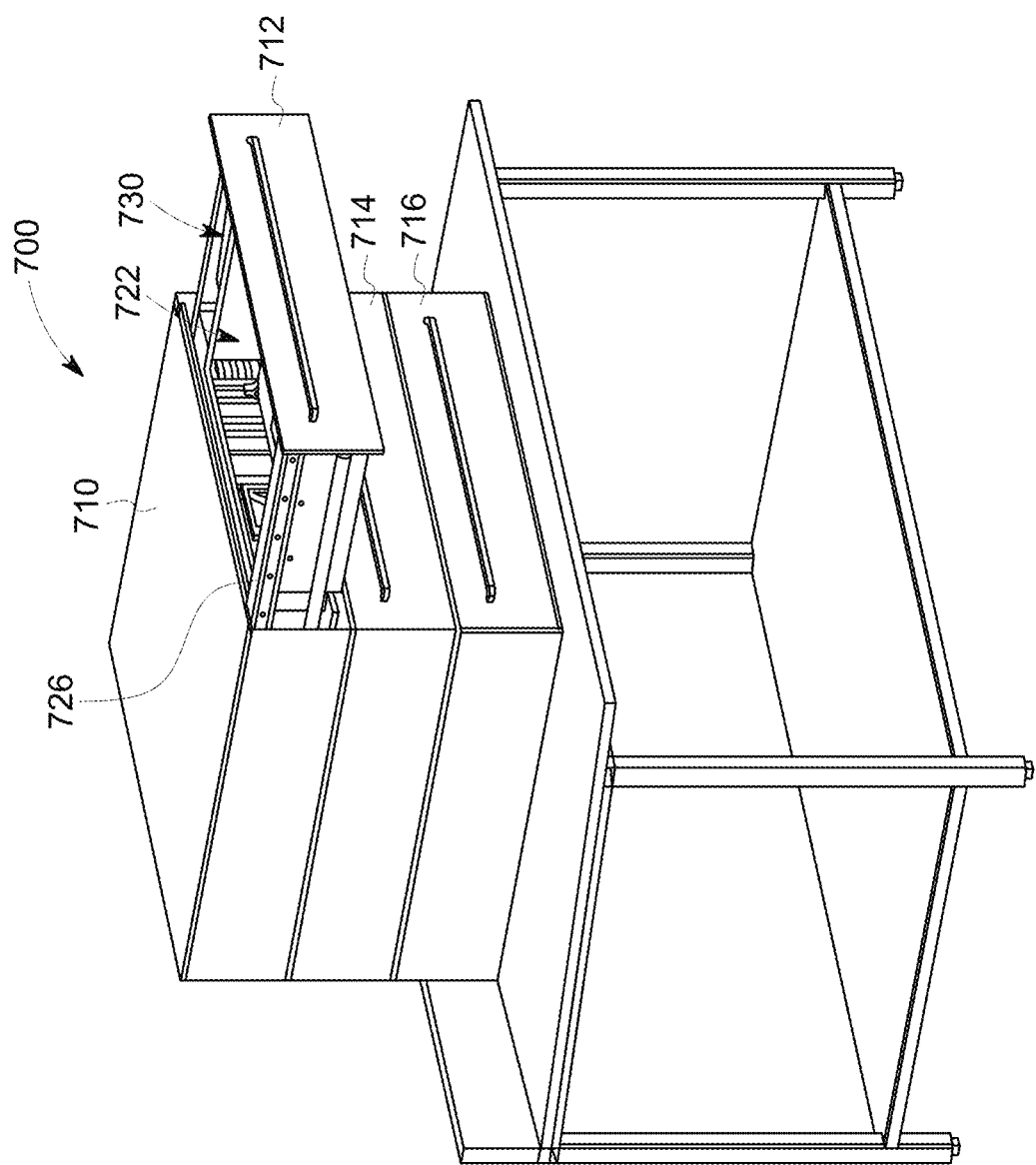
FIG. 23 is a perspective view of a bioprocessing apparatus, according to an embodiment of the invention.
Figure 24:
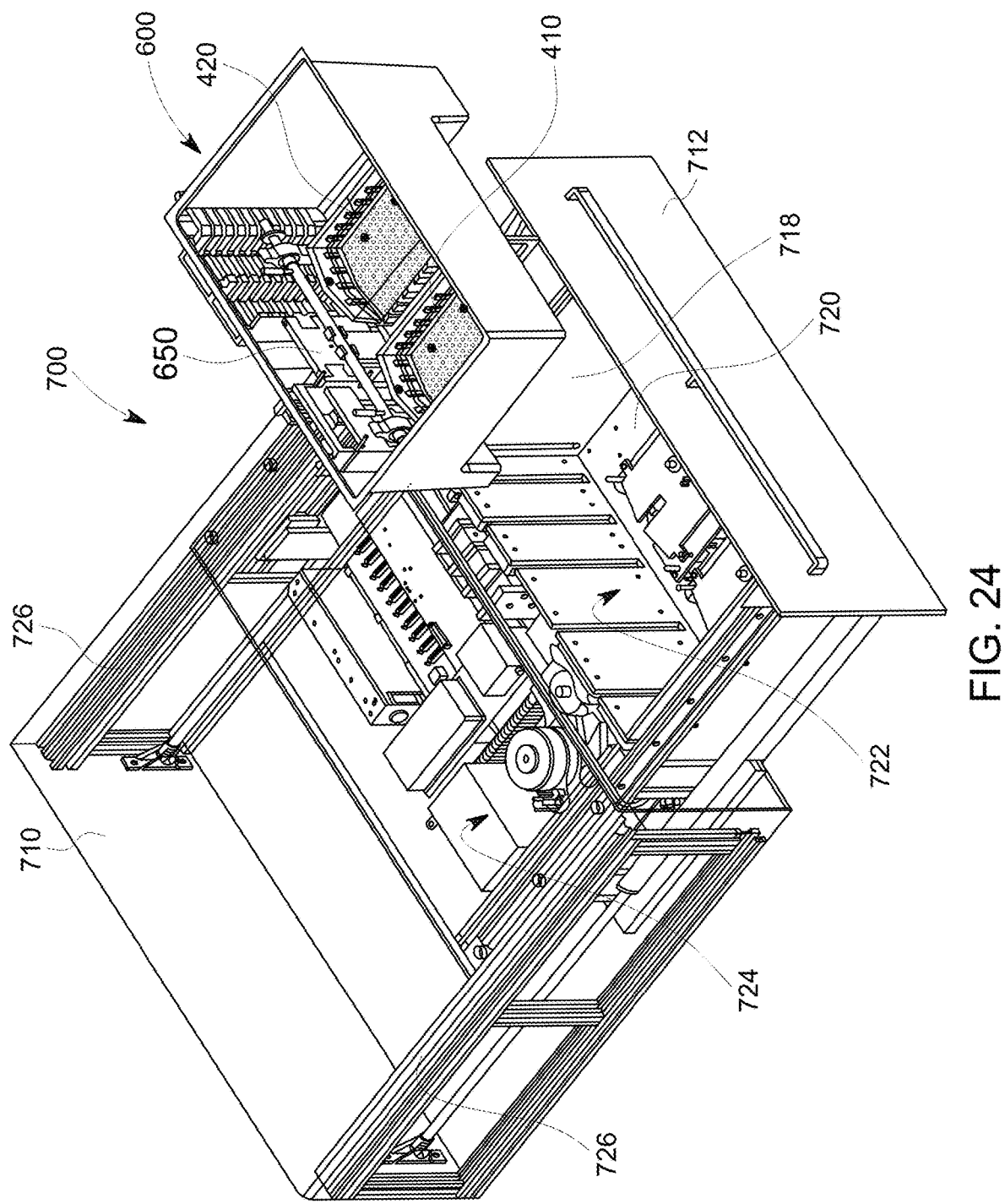
FIG. 24 is a perspective view of a drawer of the bioprocessing apparatus for receiving the drop-in kit of FIG. 12, according to an embodiment of the invention.
Figure 25:
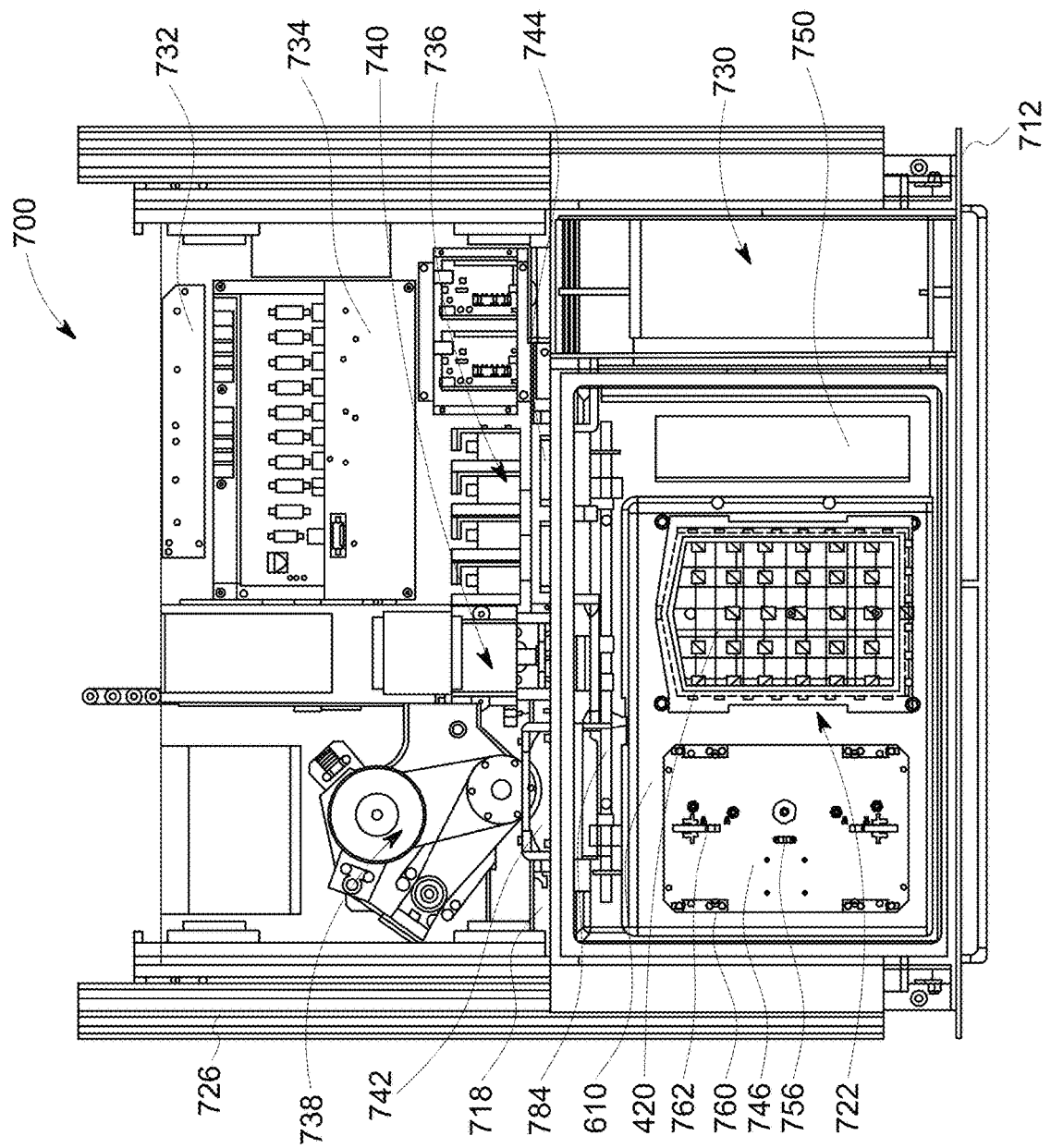
FIG. 25 is a top plan view of the drawer of FIG. 24.
Figure 26:
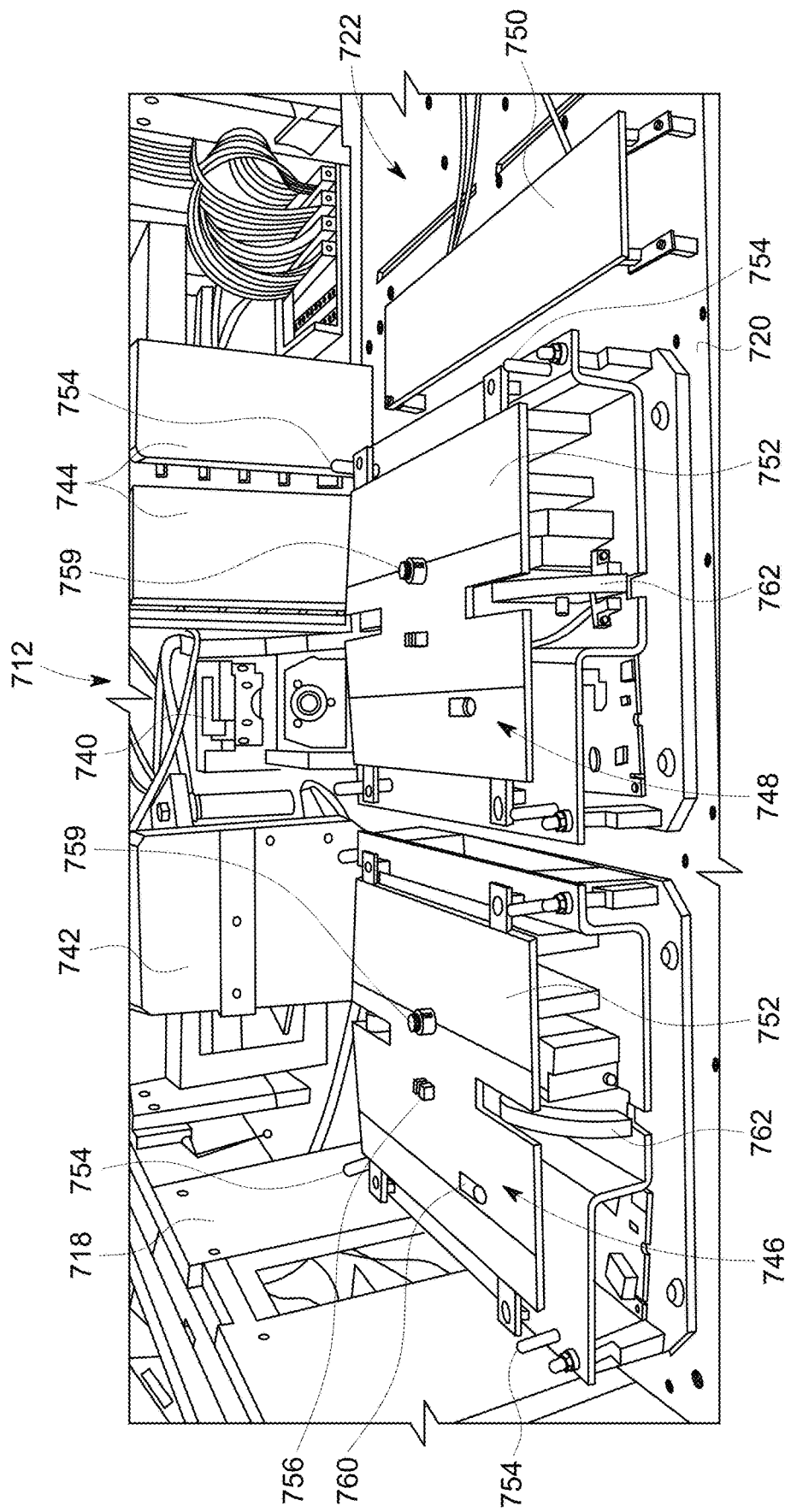
FIG. 26 is a front, perspective view of a processing chamber of the drawer of FIG. 24.
Figure 27:
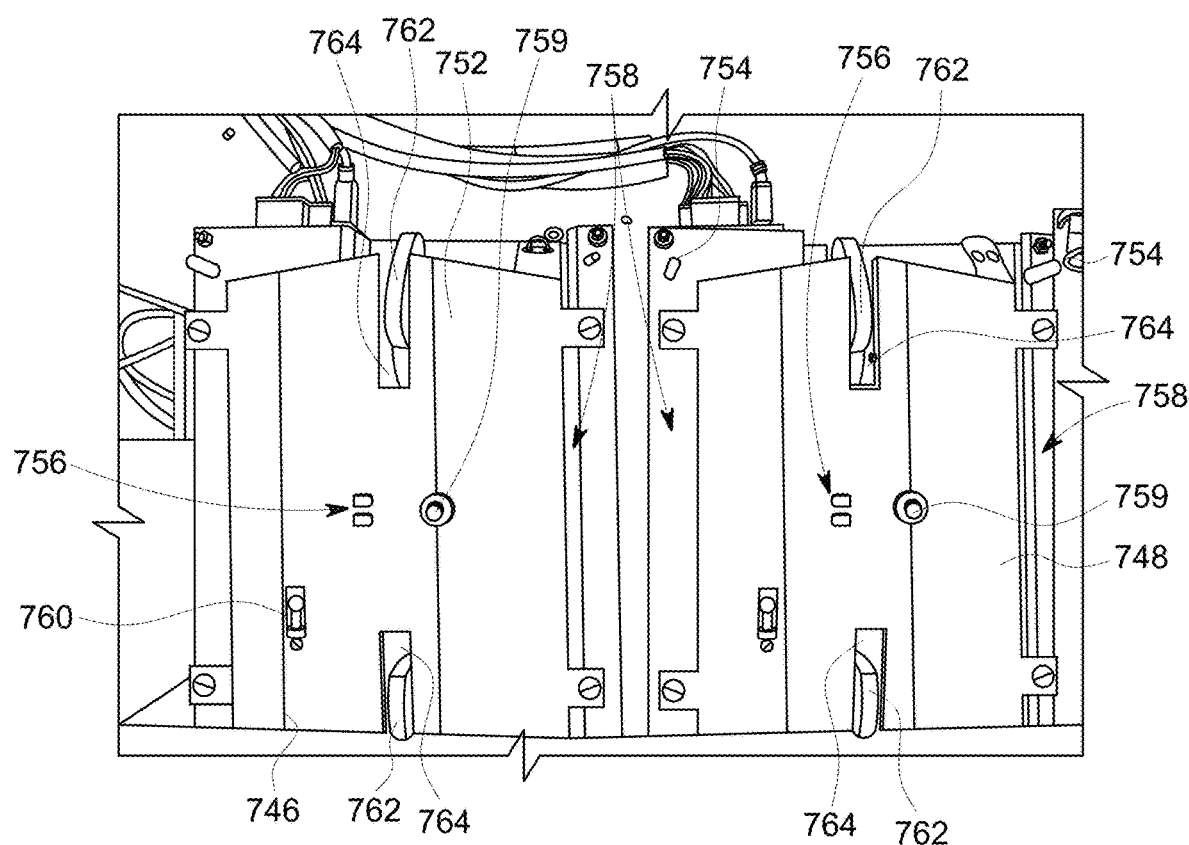
FIG. 27 is a top plan view of the processing chamber of the drawer.

Turning now to FIGS. 23-25, the kit 600 is specifically configured to be received by a bioprocessing apparatus 700 that contains all of the hardware (i.e., controllers, pumps, pinch valve actuators, etc.) required for actuating kit 600 as part of a bioprocessing method. In an embodiment, the bioprocessing apparatus 700 and kit 600 (containing the flow architecture 400 and bioreactor vessels 410, 420) together form the second bioprocessing module 200 described above in connection with FIGS. 1 and 2. The bioprocessing apparatus 700 includes a housing 710 having a plurality of drawers 712, 714, 716 receivable within the housing 710. While FIG. 23 depicts an apparatus 700 containing three drawers, the apparatus may have as few as a single drawer, two drawers, or more than three drawers to provide for simultaneous bioprocessing operations to be carried out within each drawer. In particular, in an embodiment, each drawer 712, 714, 716 may be a stand-alone bioprocessing module for carrying out the processes of cell activation, genetic modification and/or expansion (i.e., equivalent to the second modules 200a, 200b and 200c described above in connection with FIG. 2). In this respect, any number of drawers may be added to the apparatus 700 to provide for parallel processing of multiple samples from the same or different patients. In an embodiment, rather than each drawer sharing a common housing, in an embodiment, each drawer may be received within a dedicated housing, and the housings can be stacked atop one another.

As shown in FIGS. 23 and 24, each drawer, e.g. drawer 712, includes a plurality of sidewalls 718 and a bottom surface 720 defining a processing chamber 722, and a generally open top. The drawer 712 is movable between a closed position in which the drawer is fully received within the housing 710, as shown for drawers 714 and 716 in FIG. 23, and an open position, as shown for drawer 712 in FIGS. 23 and 24, in which the drawer 712 extends from the housing 710 enabling access to the processing chamber 722 through the open top. In an embodiment, one or more of the sidewalls 718 are temperature-controlled for controlling a temperature within the processing chamber 722. For example, one or more of the sidewalls 718 may include an embedded heating element (not shown), or be in thermal communication with a heating element, so that the sidewalls 718 and/or processing chamber 722 may be heated to a desired temperature for maintaining the processing chamber 722 at a desired temperature (e.g., 37 degrees Celsius) as optimized for process steps to be performed by module 200. In some embodiments, the bottom surface 720 and the underside of the top surface of the housing (above the processing chamber when the drawer is closed) may be temperature-controlled in a similar manner (e.g., an embedded heating element). A hardware compartment 724 of the drawer 712 behind the processing chamber 722 may house all of the hardware components of the apparatus 700, as discussed in detail hereinafter. In an embodiment, the drawer 712 may further include an auxiliary compartment 730 adjacent to the processing chamber 722 for housing the reservoirs containing media, reagents, etc. that are connected to the first fluid assembly 440 and second fluid assembly 444. In an embodiment, the auxiliary compartment 730 may be refrigerated.

Each drawer, e.g., drawer 712, may be slidably received on opposed guide rails 726 mounted to the interior of the housing 710. A linear actuator may be operatively connected to the drawer 712 to selectively move the drawer 712 between the open and closed positions. The linear actuator is operable to provide smooth and controlled movement of the drawer 712 between the open and closed positions. In particular, the linear actuator is configured to open and close the drawer 712 at a substantially constant speed (and minimal acceleration and deceleration at the stop and start of the motion) to minimize disturbance to the contents of the bioreactor vessels(s).

FIG. 25 is a top plan view of the interior of the drawer showing the processing chamber 722, the hardware compartment 724 and the auxiliary compartment 730 of the drawer 712. As illustrated therein, the hardware compartment 724 is located rearward of the processing chamber 722 includes a power supply 732, a motion control board and drive electronics 734 that are integrated with or otherwise in communication with the second module controller 210, a low-power solenoid array 736, the pump assembly 738 (which includes pump heads for the pumps 454, 456, 492) and a drawer engagement actuator 740. The hardware compartment 724 of the drawer 712 further includes a pump shoe 742 and a pair of pinch valve anvils 744 for interfacing with the pump assembly 738 and the solenoid array 736, respectively, as described hereinafter. In an embodiment, the pump shoe 742 and the solenoid anvil 744 are fixed to the front base plate of the processing chamber (the front plate). The hardware compartment (and the components described) are all mounted to the back base plate. Both the plates are slidably mounted to the rails. Further, the drawer engagement actuator 740 couples the two plates and is used to bring the two plates (and the components carried on the plates to an engagement position (bringing the pump roller heads into the pump shoe and thereby squeezing the pump tubing if inserted between). As is further described herein, pump assembly provides selective operation on lines 442, 450 and 490 of fluidpath 400 to provide independent respective peristaltic motive forces therefor. Similarly, tubing holder block 654 of tray 600 will be positioned between the solenoid array 736 and the anvils 744 as will be described further.

As also illustrated in FIG. 25, two bed plates, e.g., first and second bed plates 746, 748, are located within the processing chamber 722 on the bottom surface 720 and extend upwardly or stand proud therefrom. In an embodiment, the processing chamber 722 may house a single bed plate, or more than two bed plates. The bed plates 746, 748 are configured to receive or otherwise engage the first bioreactor vessel 410 and second bioreactor vessel 420 thereon. As also shown in FIG. 25, the drawer 712 also includes a plate 750 configured with load cells positioned adjacent to the bed plates 746, 748 within the processing chamber 722 for sensing a weight of a reservoir, e.g., waste reservoir 472a positioned thereon.

Figure 28A:
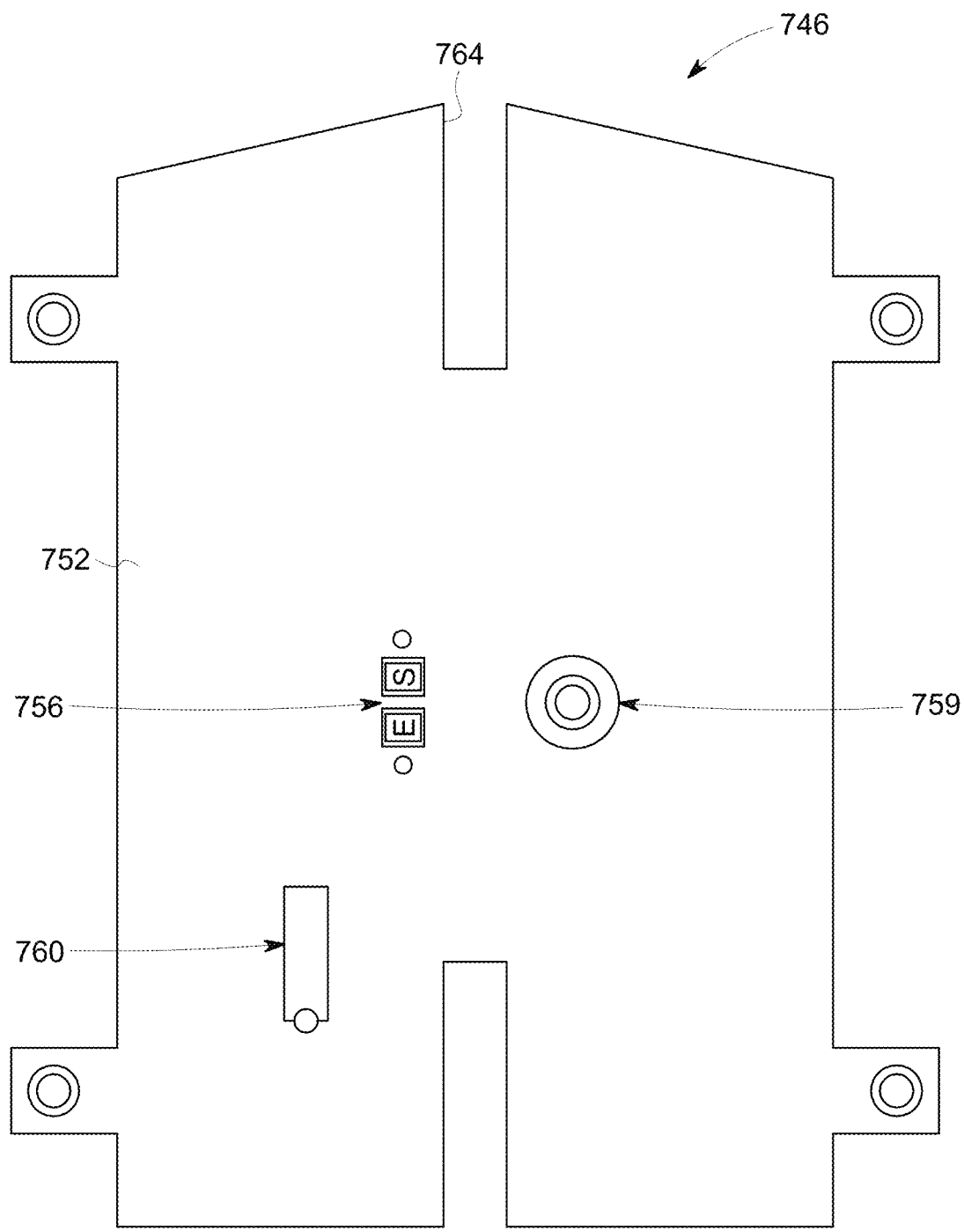
FIG. 28A is a top plan view of a bed plate of the bioprocessing apparatus of FIG. 23.
Figure 28B:
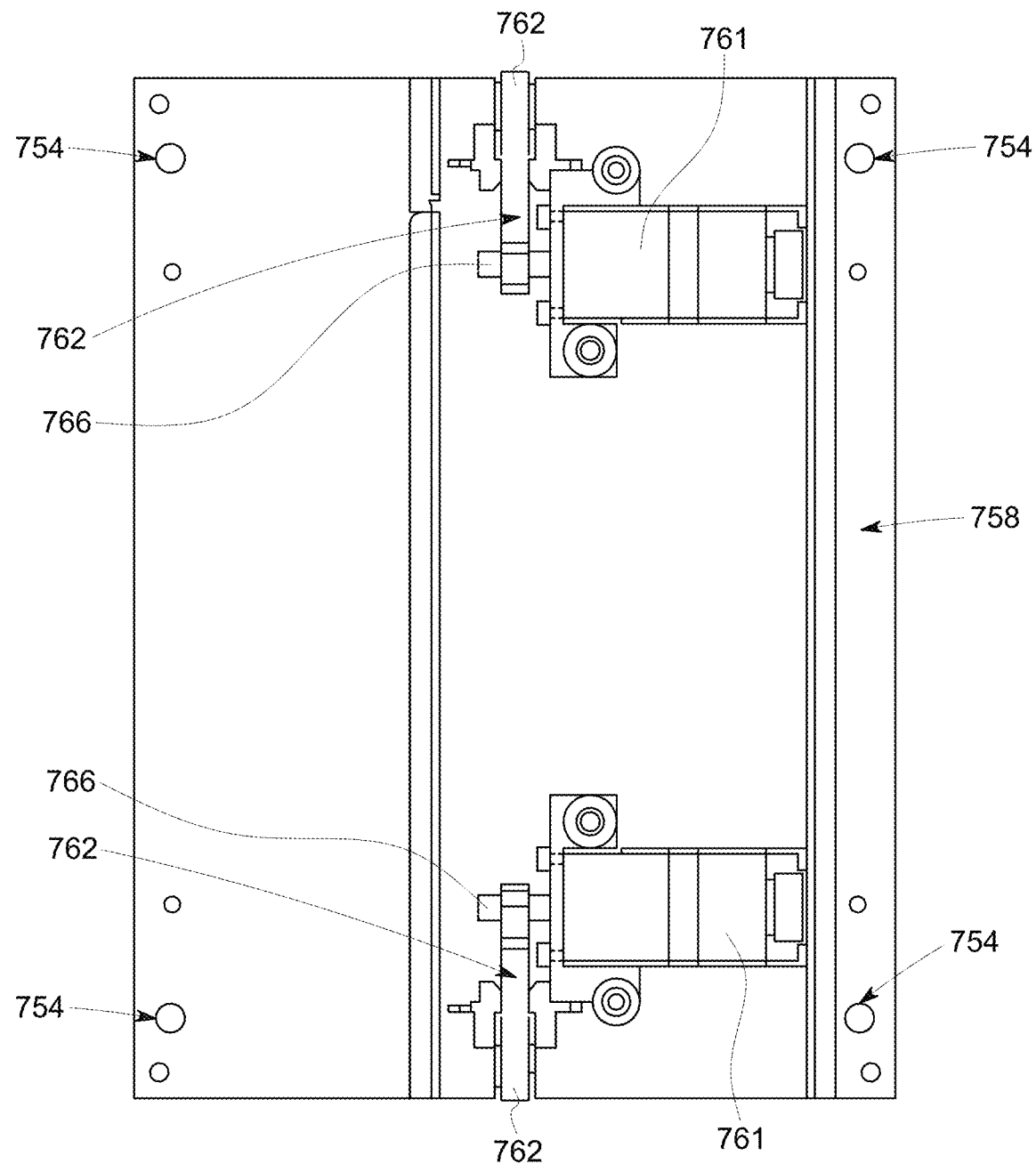
FIG. 28B is a top plan view of the hardware components housed beneath the bed plate of FIG. 28A.

FIGS. 26-28B best illustrate the configuration of the bed plates 746, 748, with FIG. 28B showing the hardware components positioned beneath the bed plate. A used herein, the bed plates 746, 748 and the hardware components (i.e., sensors, motors, actuators, etc. integrated therewith or positioned therebeneath as shown in FIG. 28B) may collectively be referred to as the bed plate. The first and second bed plates 746, 748 are substantially identical in configuration and operation, but for simplicity, the following description of the bed plates 746, 748 makes references only to the first bed plate 746. The bed plates 746, 748 have a substantially planar top surface 752 having a shape and surface area that generally corresponds to the shape and area of the bottom plate 502 of the first bioreactor vessel 410. For example, the bed plate may be generally rectangular in shape. The bed plates 746, 748 may also include relief or clearance areas 758, that generally correspond to the position of the projections or tabs 632 of the tray 610, the purpose of which will be described below. The bed plates 746, 748 are supported by a plurality of load cells 760 (e.g., four load cells 760 positioned beneath each corner of the bed plate 746). The load cells 760 are configured to sense the weight of the first bioreactor vessel 410 during bioprocessing, for use by the controller 210.

In an embodiment, the bed plate 746 may include an embedded heating element or be in thermal communication with a heating element so that the processing chamber 722 and/or the contents of the first bioreactor vessel 410 placed thereon can be maintained at a desired temperature. In an embodiment, the heating element may be the same or different than the heating element that heats the sidewalls 718, top wall and bottom surface.

As illustrated, the bed plate 746 includes plurality of locating or alignment pins 754 that protrude above the top surface 452 of the bed plate 746. The number of locating pins 754 and the position and spacing of the locating pins 754 may correspond to the number, position and spacing of the recesses 550 in the bottom surface of the bottom plate 502 of the bioreactor vessels 410, 420. As indicated below, the locating pins 754 are receivable within the recesses 550 in the bottom plate 502 of the first bioreactor vessel 410 when the first bioreactor vessel 410 is positioned within the processing chamber 722 to ensure proper alignment of the first bioreactor vessel 410 on the first bed plate 746.

With further reference to FIGS. 26-28B, the bed plate 746 may further include an integrated sensor 756 for detecting proper alignment (or misalignment) of the first bioreactor vessel 410 on the first bed plate 746. In an embodiment, the sensor 756 is an infrared optical beam, although other sensor types such as a lever switch may also be utilized without departing from the broader aspects of the invention. The sensor is configured to interact with the position verification structure 552 on the bottom plate 502 when the first bioreactor vessel 410 is properly seated on the first bed plate 746. For example, where the sensor 756 is an infrared optical beam and the position verification structure 552 is a beam break (i.e., a flat tab), with a substantially IR-opaque position verification structure 552, when the first bioreactor vessel 410 is fully seated on the bed plate 746, the beam break will interrupt the infrared optical beam (i.e., break the beam). This will signal to the controller 210 that the first bioreactor vessel 410 is properly seated. If, after positioning the first bioreactor vessel 410 on the first bed plate 746, the controller does not detect that the infrared optical beam of the sensor 756 is broken, this indicates that the first bioreactor vessel 410 is not fully or properly seated on the bed plate 746 and that adjustment is needed. The sensor 756 on the bed plate 746 and position verification structure 552 on the bottom plate 502 of the first bioreactor vessel 410 therefore ensure that the first bioreactor vessel 410 is seated in level position on the bed plate 746 (as determined by the alignment pins) prior to commencing bioprocessing.

Referring still further to FIGS. 26-28B, the bed plate 746 additionally includes an embedded temperature sensor 759 that is positioned so as to be in alignment with the aperture 556 in the bottom plate 502 of the first bioreactor vessel 410. The temperature sensor 759 is configured to measure or sense one or more parameters within the bioreactor vessel 410 such as, for example, a temperature level within the bioreactor vessel 410. In an embodiment, the bed plate 746 may additionally include a resistance temperature detector 760 configured to measure a temperature of the top surface 752, and a carbon dioxide sensor (located under the bed plate) for measuring a carbon dioxide level within the bioreactor vessel.

As further shown in FIGS. 26-28B, each bed plate 746, 748 includes an actuator mechanism 761 (e.g., a motor) that includes, for example, a pair of opposed cam arms 762. The cam arms 762 are received within slots 764 in the bed plates 746, 748, and are rotatable about cam pin 766 between a clearance position where the cam arms 762 are positioned beneath the top surface 752 of the bed plate 746, and an engagement position where the cam arms 762 extend above the top surface 752 of the bed plate and contact the opposed flat engagement surfaces 554 of the bottom plate 502 of the first bioreactor vessel 410 when the first bioreactor vessel 410 is received atop the first bed plate 746. As discussed in detail below, the actuator mechanism is operable to tilt the bioreactor vessel atop the bed plate to provide for agitation and/or to assist draining of the bioreactor vessel.

Referring to FIGS. 29-32, more detailed views of the linear actuator 768 and drawer engagement actuator 740 in the hardware compartment 724 of the drawer 712 are shown. With reference to FIG. 29, and as indicated above, the linear actuator 768 is operable to move the drawer 712 between the open and closed positions. In an embodiment, the linear actuator 768 is electrically connected to a rocker switch 770 on the exterior of the housing 710 which allows for user control of the movement of the drawer. The linear actuator 770 provides controlled movement of the drawer 712 to prevent disturbance of the contents of the bioreactor vessel(s) within the drawer 712. In an embodiment, the linear actuator 768 has a stroke of approximately 16" and has a maximum speed of approximately 2 inches per second.

Figure 30:
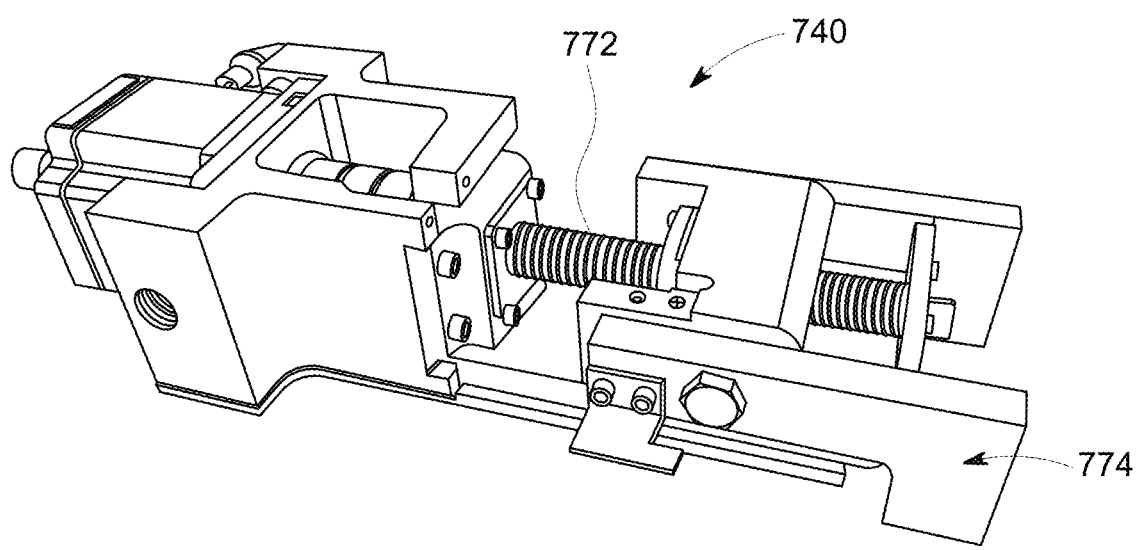
FIG. 30 is a perspective view of a drawer engagement actuator of the bioprocessing apparatus of FIG. 12.

Turning now to FIG. 30, the drawer engagement actuator 740 includes a lead screw 772 and a clevis arm 774 that attaches to a front plate 751 within the drawer 712. The drawer engagement actuator is operatively connected to the pump assembly 738 and the solenoid array 736 and is operable to move the pump assembly 738 and the solenoid array 736 between a first, clearance position and an engagement position.

Figure 31:
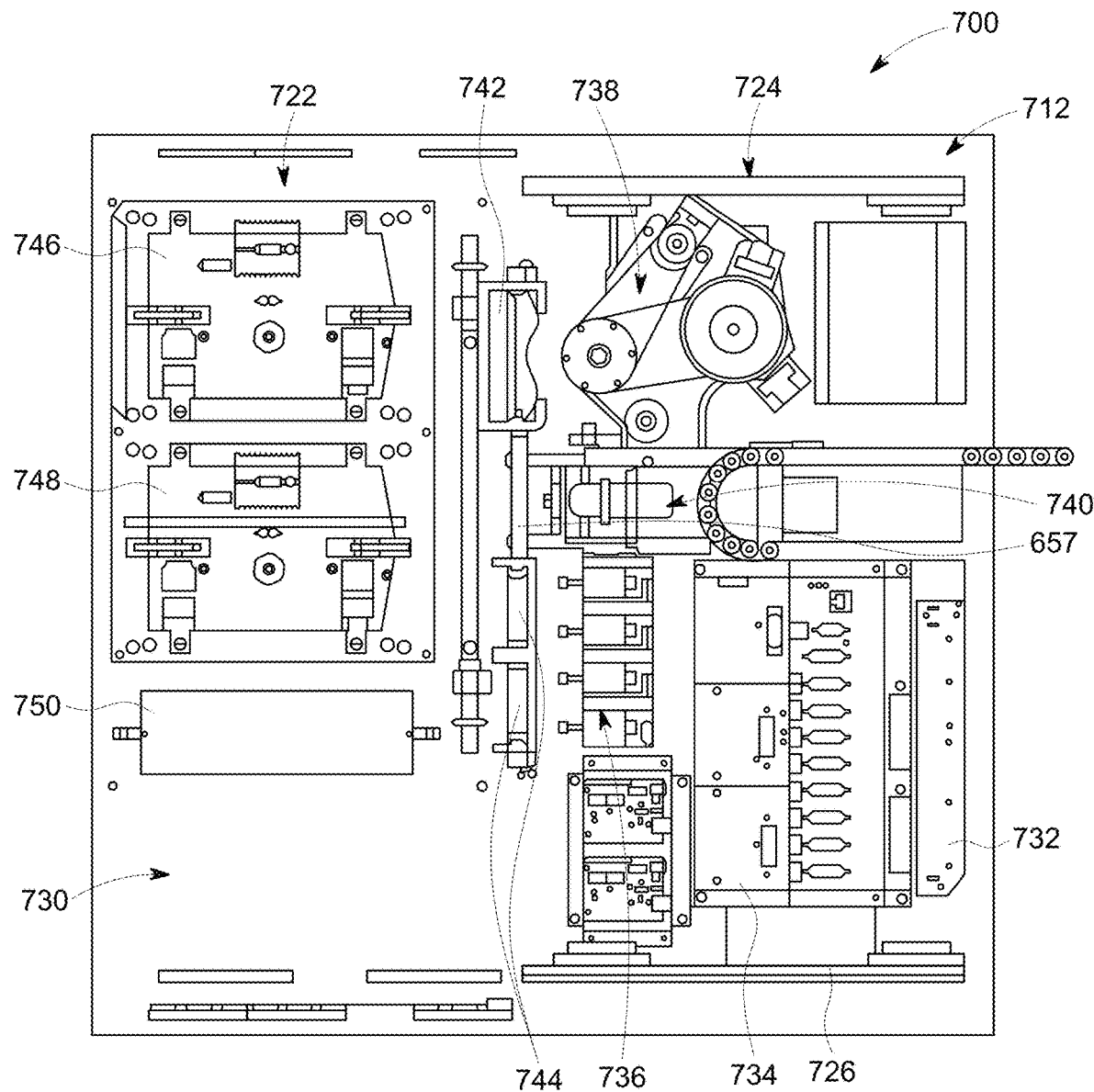
FIG. 31 is a top plan view of the drawer of the bioprocessing apparatus, illustrating a clearance position of a drawer engagement actuator, pump assembly and solenoid array.
Figure 32:
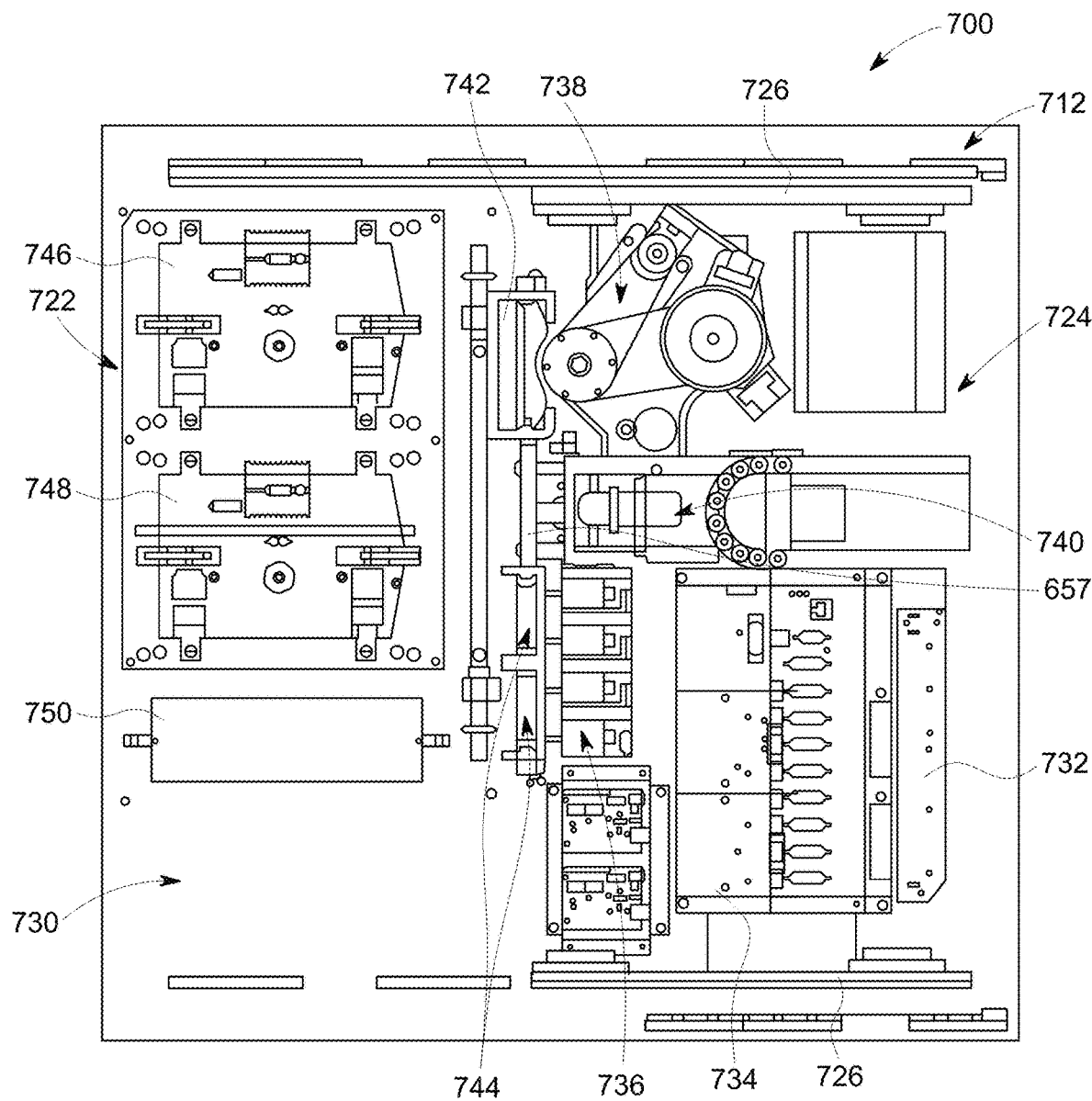
FIG. 32 is a top plan view of the drawer of the bioprocessing apparatus, illustrating an engagement position of the drawer engagement actuator, pump assembly and solenoid array.

FIGS. 31 and 32 better illustrate the clearance position and engagement position of the pump assembly 738 and solenoid array 736. As illustrated in FIG. 31, in the clearance position, the pump assembly 738 and solenoid array 736 are spaced from the pump shoe 742 and pinch valve anvils 744, respectively. Upon actuation of the lead screw 772, the drawer engagement mechanism 740 moves the pump assembly 738 and solenoid array linearly forward to the position shown in FIG. 32. In this position, the pump heads of the pump assembly 738 engage the lines 442, 450, 490 in the first tubing holder block 652 and the solenoid array 736 is positioned close enough to the pinch valve anvils 744 that a piston/actuator of the solenoid array 736 can pinch/clamp its respective fluid flow lines of the second tubing holder block 654 against the pinch valve anvil(s) 744, thereby preventing flow through that fluid flow line.

Figure 33:
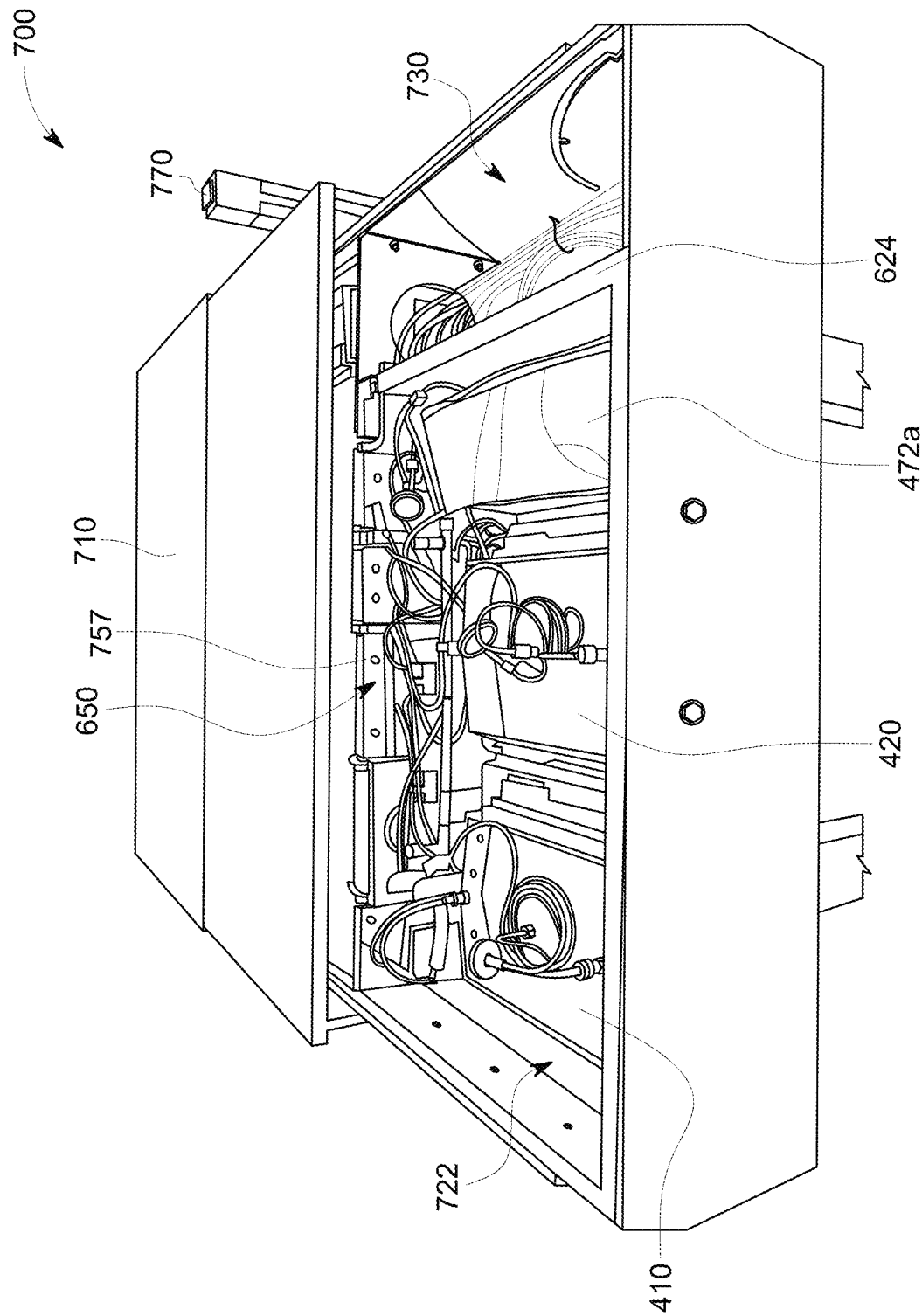
FIG. 33 is a perspective view of the bioprocessing apparatus, illustrating the drop-in kit in position within the processing chamber of the drawer.
Figure 34:
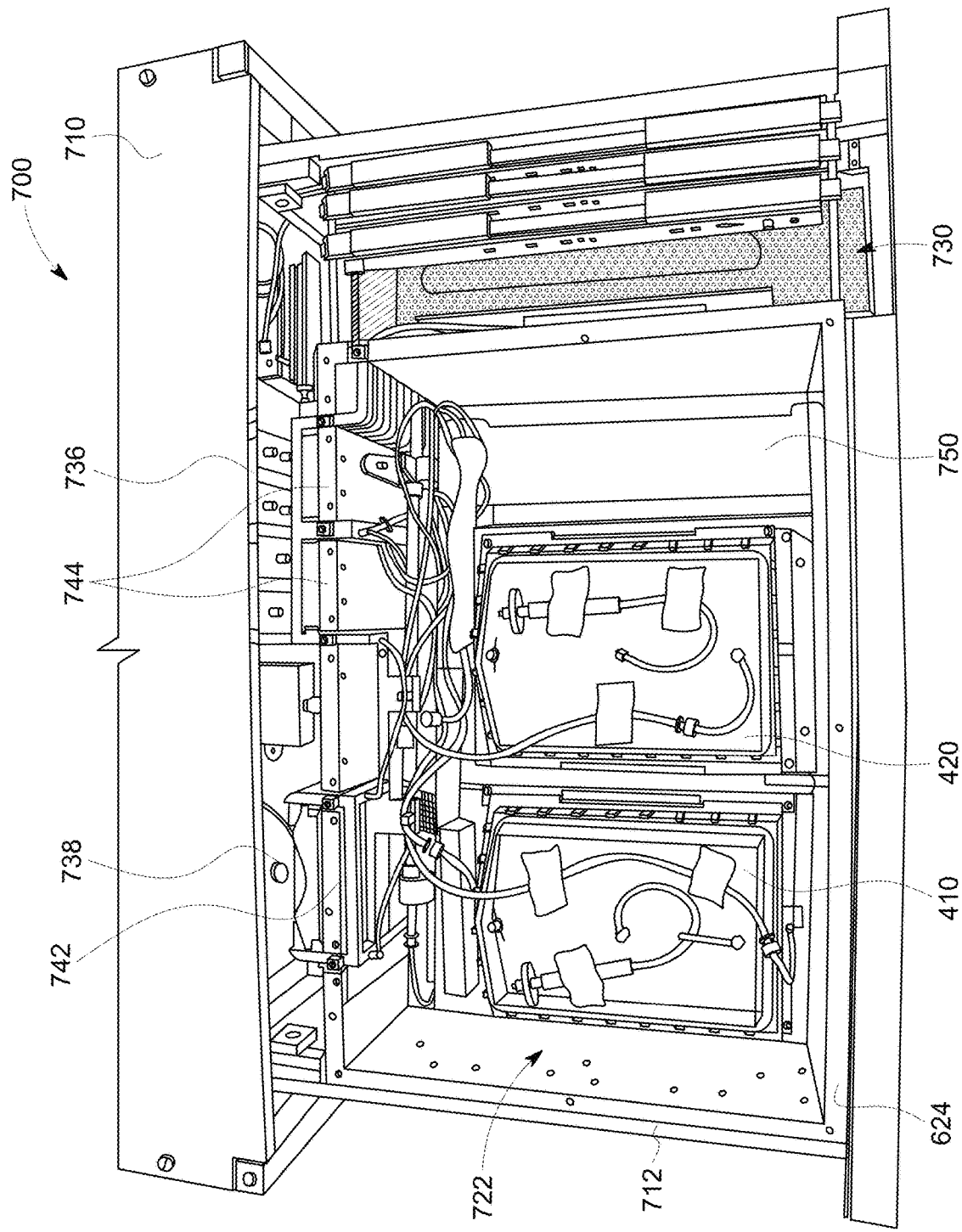
FIG. 34 is a top plan view of the bioprocessing apparatus, illustrating the drop-in kit in position within the processing chamber of the drawer.
Figure 35:
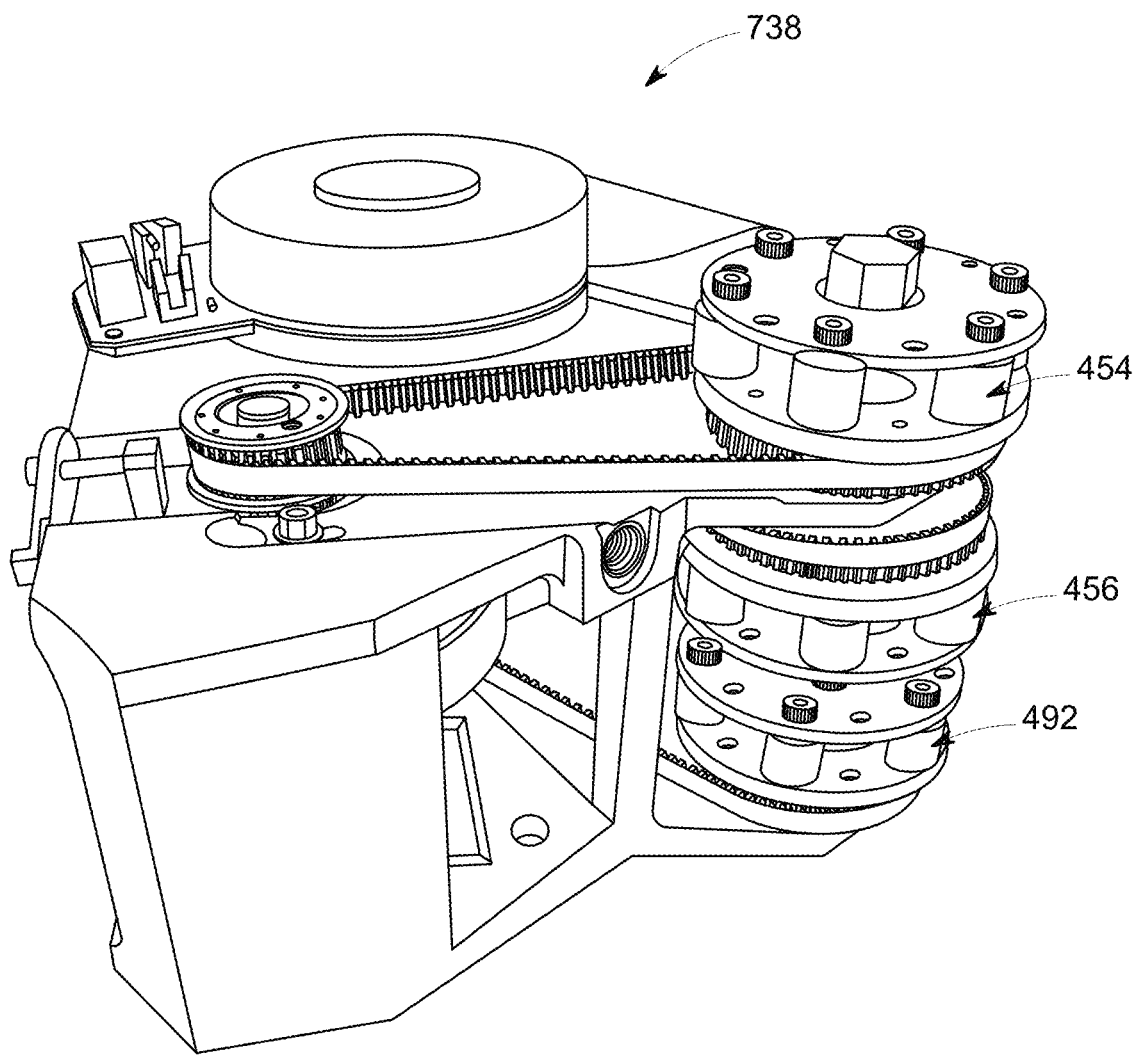
FIG. 35 is a perspective view of a peristaltic pump assembly of the bioprocessing apparatus.
Figure 36:
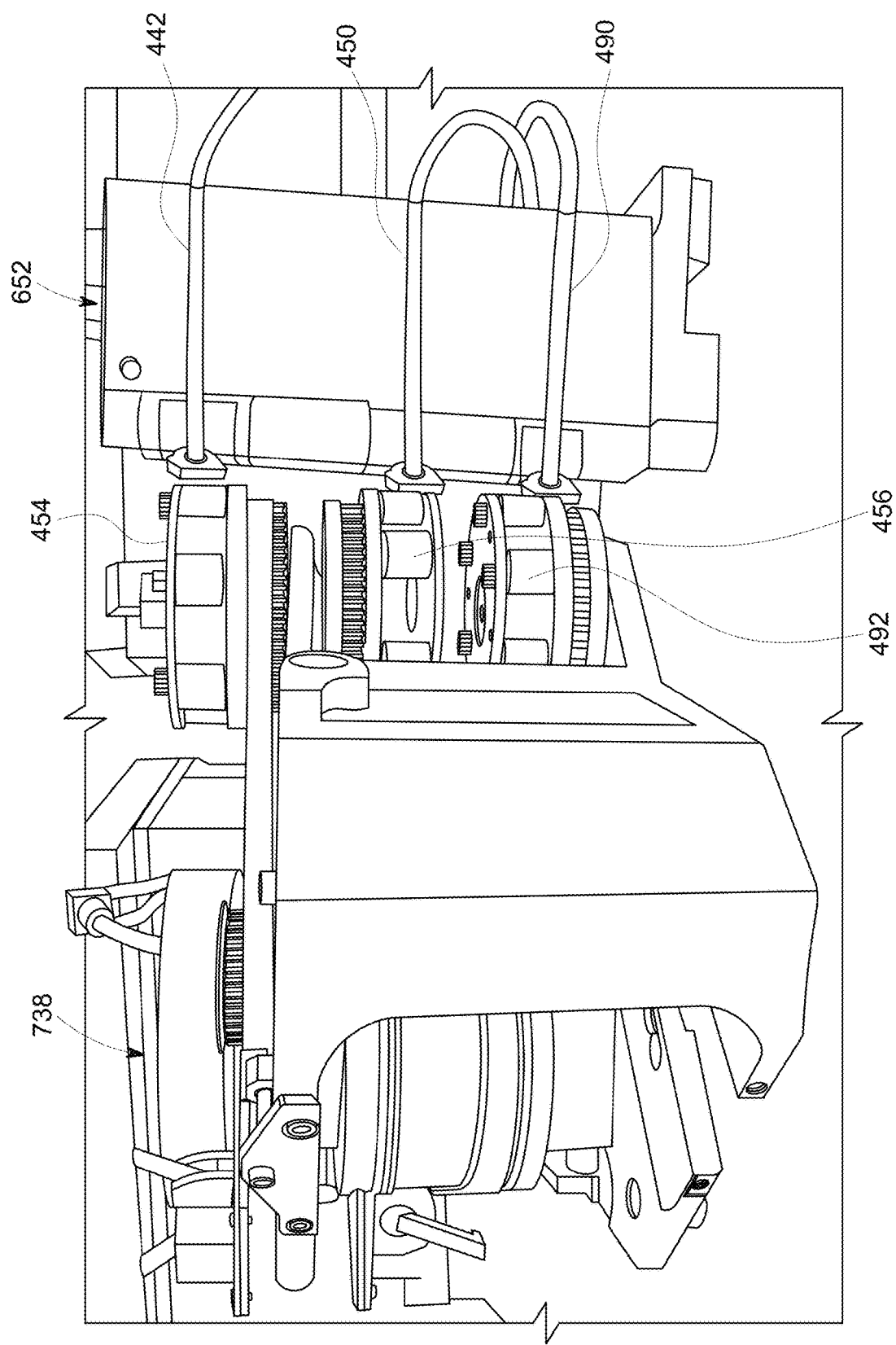
FIG. 36 is a side elevational view of the peristaltic pump assembly and a tubing holder module of the drop-in kit, illustrating the relationship between components.

Referring back to FIG. 24, and with additional reference to FIGS. 33-39, in operation, the drawer 712 may be controllably moved to the open position by actuating the rocker switch 770 on the outside of the housing 710. The disposable drop in kit 600 containing the tubing module 650 (which holds all the tubes and tubing tails of the flow architecture 400) and first and second bioreactor vessels 410, 420 is then lowered into position within the processing chamber 722. As the kit 600 is lowered into the processing chamber 722, the pump shoe 742 is received through the clearance opening 660 of the first tubing holder block 652 so that the pump tubes 442, 450, 490 are positioned between the pump shoe 742 and the pump heads 454, 456, 492 of the peristaltic pump assembly 738. FIG. 35 is a perspective view of the peristaltic pump assembly 738, showing the positioning of the pump heads 454, 456, 492 in relation to one another. FIG. 36 illustrates the positioning of the pump heads 454, 456, 492 in relation to the pump tubes 442, 450, 490 when the kit 600 is received within the processing chamber 722. As shown therein, the pump tubes 442, 450, 490 are positioned between the pump shoe 742 and the pump heads 454, 456, 492. In operation, when the drawer engagement actuator 740 positions the pump assembly 738 in the engagement position, the pump heads 454, 456, 492 are selectively actuatable under control of the controller 210 to initiate, maintain and cease a flow of fluid through the tubes 442, 450, 490.

Figure 37:
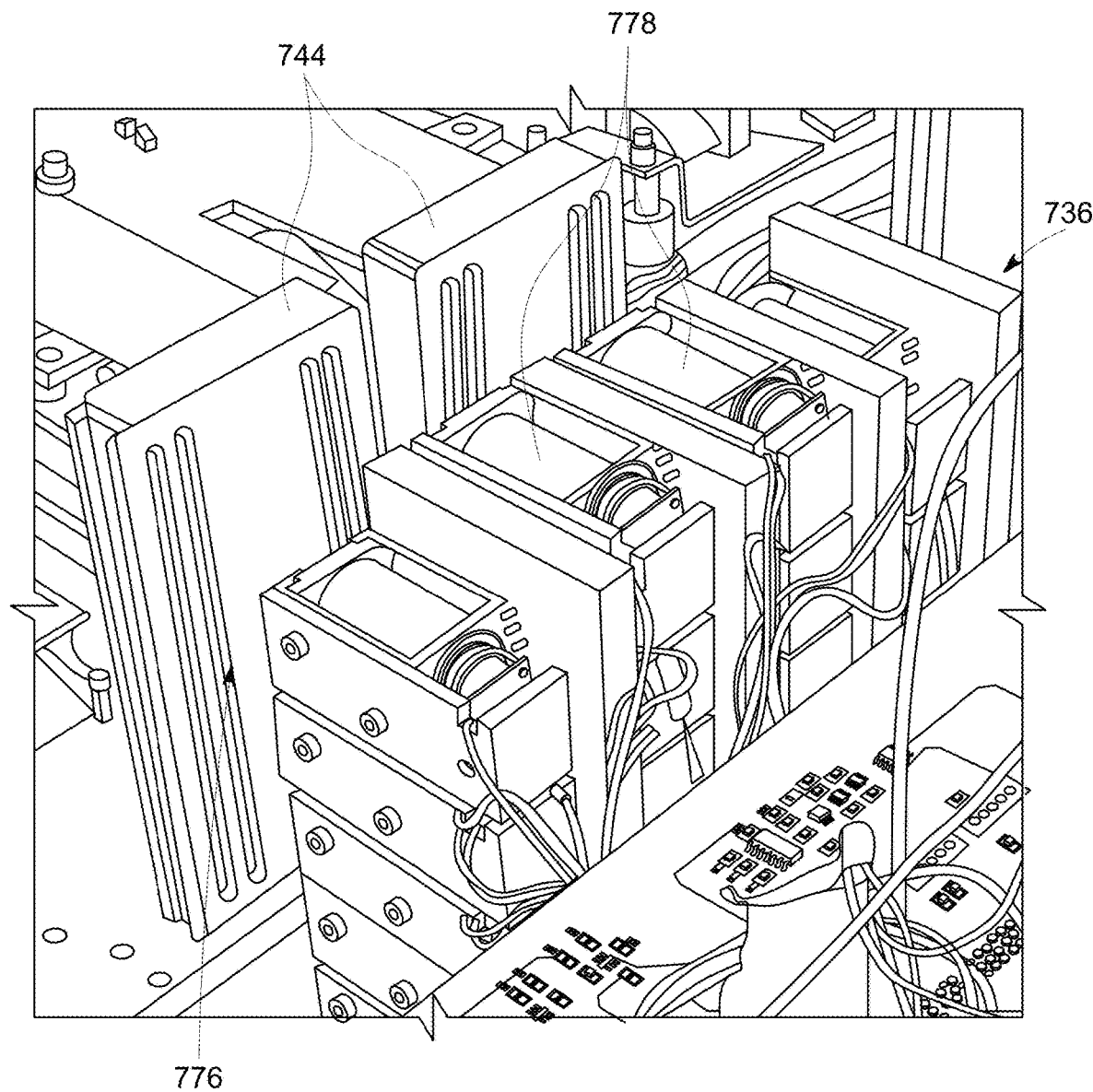
FIG. 37 is a perspective view of a solenoid array and pinch valve anvils which form a pinch valve array of the bioprocessing apparatus.
Figure 38:
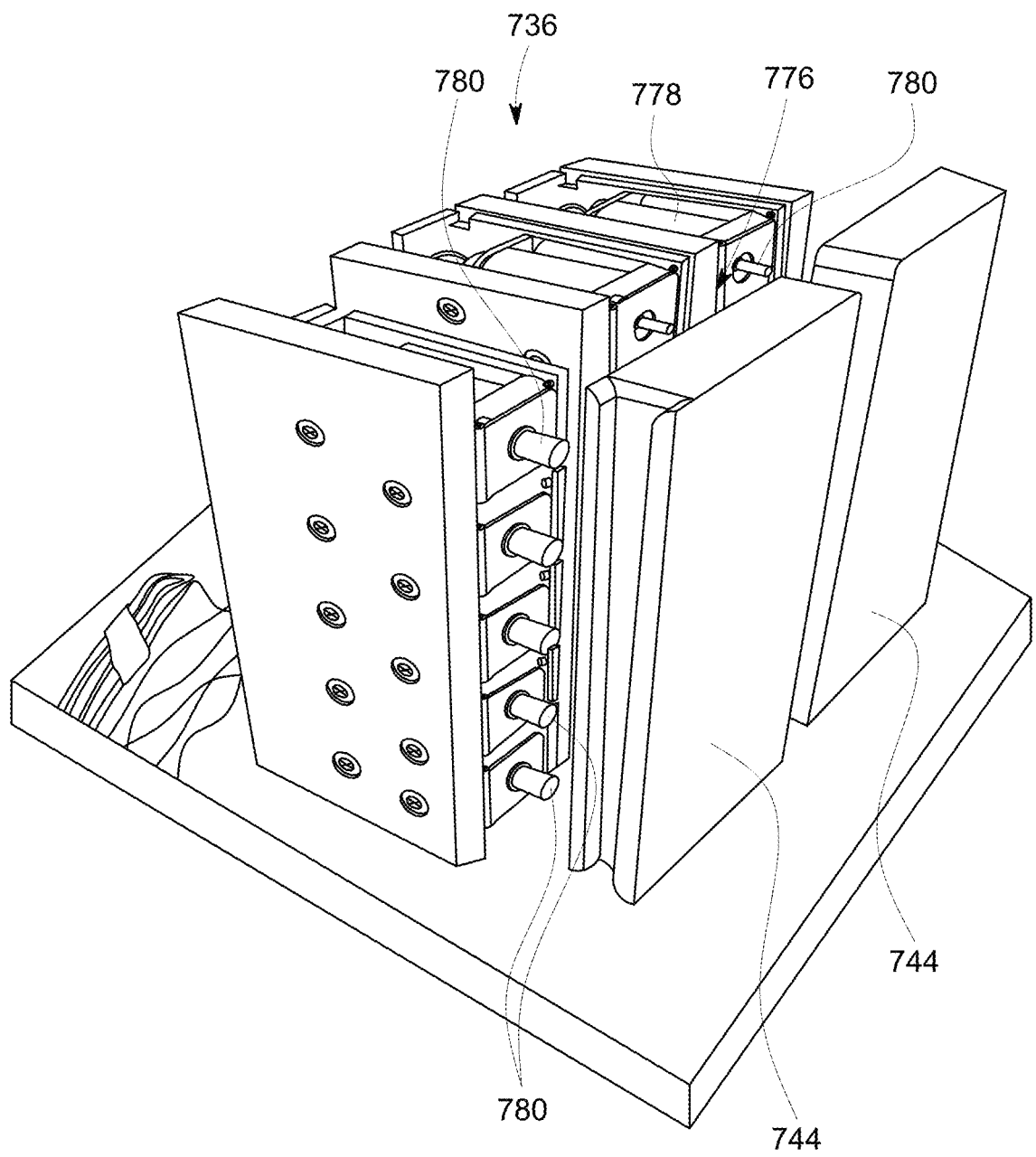
FIG. 38 is another perspective view of the pinch valve array of the bioprocessing apparatus.
Figure 39:
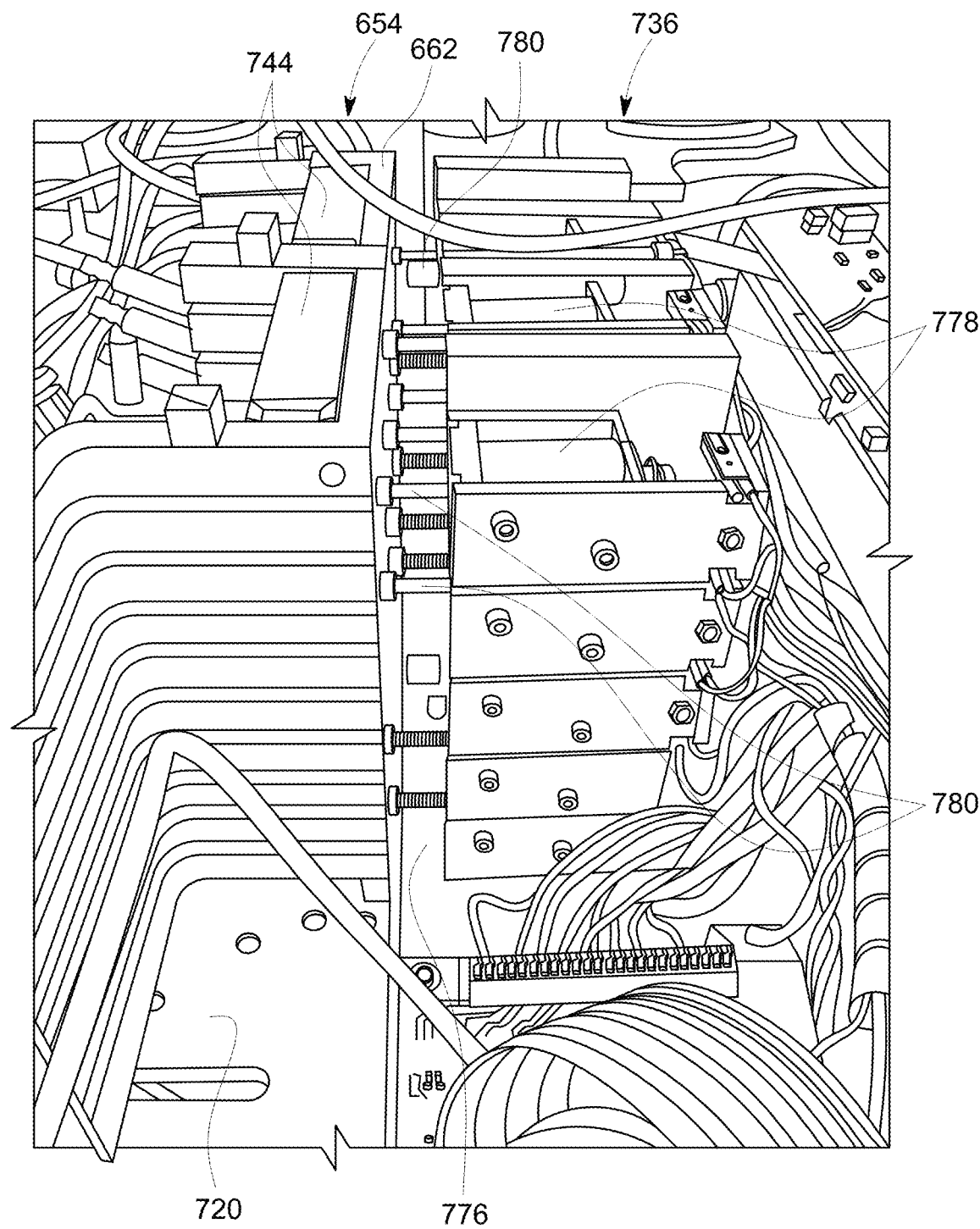
FIG. 39 is another perspective view of the pinch valve array, illustrating positioning of the tubing holder module of the drop-in kit with respect to the pinch valve array, in an engaged position.

Similarly, as the kit 600 is lowered into the processing chamber 722, the pinch valve anvils 744 are received through the clearance openings 668, 670 of the second tubing holder block 654 so that the tubing tails 464a-f of the first fluid assembly 440, the tubing tails 470a-d of the second fluid assembly 444, the first bioreactor line 414 and second bioreactor line 418 of the first bioreactor vessel 410, the first bioreactor line 424 and the second bioreactor line 428 of the second bioreactor vessel 420, the sterile air source line 460, the interconnect line 450 and the filtration line 482 that are retained by the second tubing holder block 654 are positioned between the solenoid array 736 and the pinch valve anvils 744. This configuration is best illustrated in FIGS. 37-39 (FIGS. 37 and 38 illustrating the relationship between the solenoid array 736 and the pinch valve anvils 744 prior to receiving the back plate 662 of the second tubing holder block 654 within space 776).

As shown therein, each solenoid 778 of the solenoid array 736 includes a piston 780 that is extendable linearly through an associated aperture (of apertures 664) in the back plate 662 of the second tubing holder block 654 to clamp an associated tube against the pinch valve anvil 744. In this respect, the solenoid array 736 and the anvil 744 together form a pinch valve array (which includes the valves of the first fluid assembly 440 and second fluid assembly 444, as well as the bioreactor line valves, i.e., valves 432, 434, 436, 438, sterile line valve 462, interconnect line valve 452 and filtration line valves 486, 488). In particular, the pinch valves of the flow architecture 400 are provided by the respective solenoids 778 (i.e., pistons of the solenoids) of the solenoid array 736 operating/acting against its respective anvil 744 while the fluid path/line is in between. In particular, in operation, when the drawer engagement actuator 740 positions the solenoid array 736 in the engagement position, each solenoid 778 is selectively actuatable under control of the controller 210 to clamp an associated fluid flow line against the anvil 744 to prevent a flow of fluid therethrough. The present invention contemplates that each fluid line is positioned between a planar anvil face and a planar solenoid actuator head. Alternatively, the solenoid actuator head may include a shaped head, such as a two tapering surfaces meeting at an elongate edge akin to a Phillips-head screwdriver, that is optimized to provide a desired pinching force on the resiliently-flexible fluid line. Alternatively still, the anvil face may include an elongate ridge or projection extending towards each fluid line such that a planar solenoid head may compress the fluid line against this transversely-extending ridge so as to close the line to fluid flow therethrough.

Figure 40:
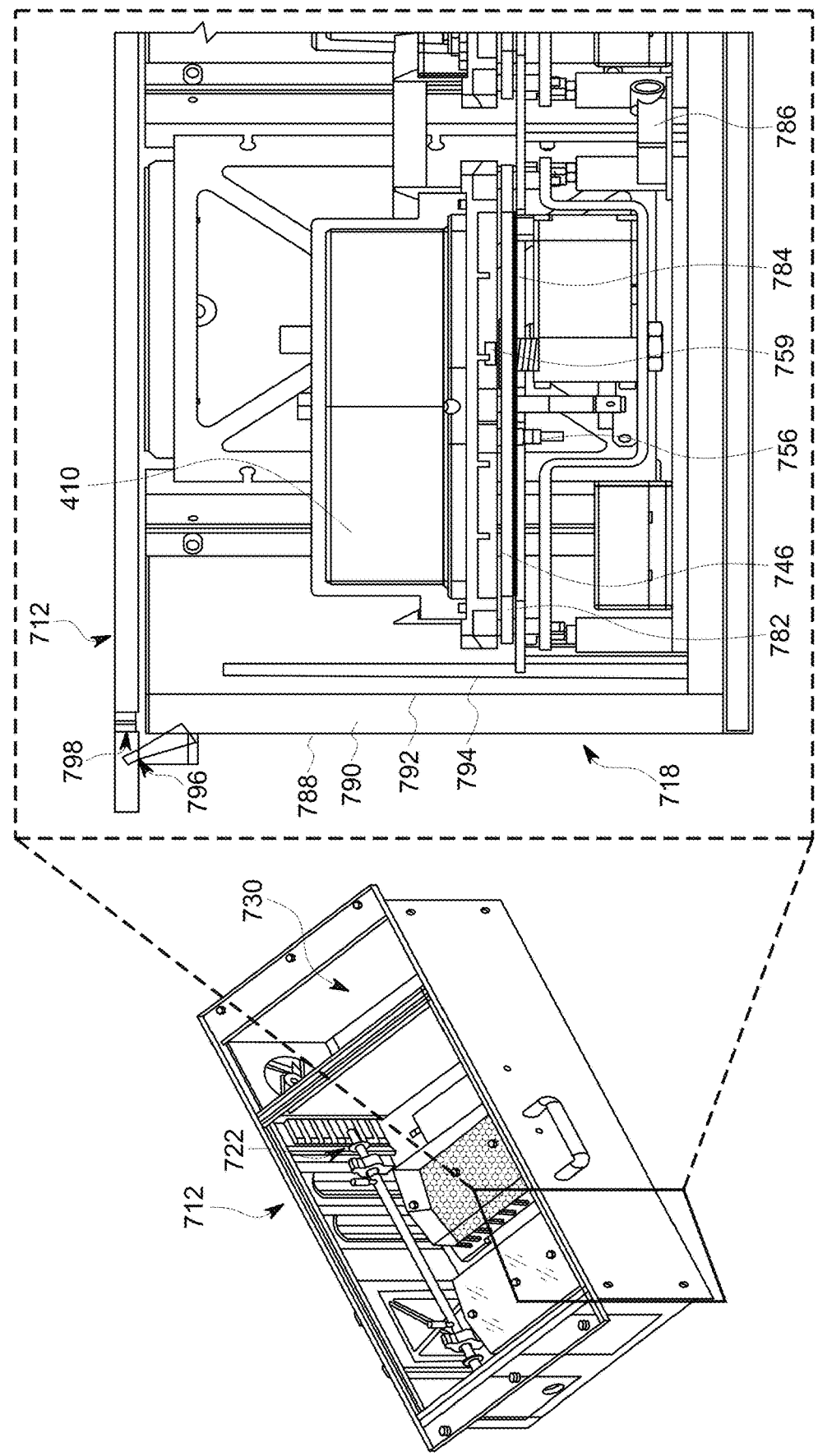
FIG. 40 is a cross-sectional view of the drawer of the bioprocessing apparatus, illustrating a seated position of the bioreactor vessel on the bed plate.

With reference to FIGS. 33, 34 and 40, as the kit 600 is lowered into the processing chamber of the drawer, the first bioreactor vessel 410 and the second bioreactor vessel 420 are supported above the openings 626, 628 by the perimeter of the openings and, in particular, by the tabs/projections 632. As the kit is lowered further, the bed plates 746, 748 extend through the openings 626, 628 and receive or otherwise engage the bioreactor vessels 410, 420. The shape of the openings 626, 628 and the top surface 752 of the bed plates 746, 748 (e.g., relieved areas 758 of the bed plates 746, 748 that correspond to the tabs/projections 632 of the tray 610) allow the tray 610 to continue downward travel once the bioreactor vessels 410, 420 are received by the bed plates 746, 748 such that the bottom surface of the tray 610 and the tabs/projections 632 are seated at a location lower than the top surface 752 of the bed plates 746, 748 so that the bioreactor vessels 410, 420 can be supported by the bed plates 746, 748 in spaced relationship to the bottom surface 620 of the tray 610. This ensures that the tray 610 does not interfere with the level seating of the bioreactor vessels 410, 420 on the bed plates 746, 748.

As the bed plates 746, 748 extend through the openings 726, 728 in the tray 610, the locating pins 754 on the bed plates 746, 748 are received in the corresponding recesses 550 in the bottom plate 502 of the bioreactor vessels 410, 420, ensuring that the bioreactor vessels 410, 420 will be properly aligned with the bed plates 410, 420. When properly seated on the bed plates 746, 748, the beam break 552 breaks the optical beam of the sensor 756 in the bed plates, indicating to the controller that the bioreactor vessels 410, 420 are in proper position. Because the bed plates 746, 748 and the alignment pin heights are level, interruption of the optical beam of the sensor 756 by the beam break 552 likewise ensures that the bioreactor vessels 410, 420 are level. In this properly seated position, sensor 759 on the bed plates 746, 748 is aligned with the aperture 556 in the bottom plate 502 to allow for sensing of processing parameters within the interior compartment of the bioreactor vessels 410, 420, respectively. In addition, in the fully seated position, the cam arms 762 of the bed plates 746, 748 are aligned with the flat engagement surfaces 554 on the bottom plate 502 of the bioreactor vessels 410, 420, respectively.

FIG. 40 is a cross-sectional, front view illustrating this fully seated position of the first bioreactor vessel 410 on the bed plate 746. As shown in FIG. 40, a heating element in the form of a heating pad 782 and heating module 784 may be positioned below the bed plate 746 for heating the bed plate 746. As shown in FIG. 40, a carbon dioxide sensing module 786 may also be positioned beneath the bed plate for sensing a carbon dioxide content within the processing chamber 722.

As further shown in FIG. 40, in an embodiment, the sidewalls 718 and bottom, of the drawer 712 (and the top wall of the housing) may comprise a cover 788, an insulative foam layer 790 to help minimize heat loss from the processing chamber 722, a film heater 792 for heating the walls as described above, and an inner metal plate 794. In an embodiment, the inner metal plate 794 may be formed from aluminum, although other thermally conductive materials may also be utilized without departing from the broader aspects of the invention. The drawer 712 may further include one or more brush seals 796 to help minimize heat loss from the processing chamber 722, and a thermal break 798 to minimize or prevent the flow of thermal energy from the drawer 712 to other components of the apparatus 700 (such as housing 710 or other drawers (e.g., drawers 714, 716)).

Referring once again to FIG. 34, when the kit 600 is received in the processing chamber 722, the load cell 750 in the bottom of the processing chamber 722 adjacent to the second bed plate 748 extends through the opening 730 in the tray 610 so that a waste bag 472a may be connected to the tubing tail 470a and positioned on the load cell 750. As shown therein, when the kit 600 is received within the drawer 712, the second tubing holder block 654 retains the tubing such that the tubing tails 464a-f of the first fluid assembly 440 and the tubing tails 470b-d of the second fluid assembly 444 extend into the auxiliary compartment 730 for the connection of the reservoirs thereto. In an embodiment, the sampling lines 476a-476d likewise extend into the auxiliary compartment 730.

Turning now to FIGS. 41-44, operation of the cam arms 762 of the bed plates 746, 748 is illustrated. As shown therein, the cam arms 762 are movable between a retracted position where they are positioned beneath the top surface of the bed plates 746, 748 and an engagement position where they are rotated about cam pin 766 and extend above the bed plates 746, 748 to engage the flat engagement surfaces 554 of the bioreactor vessels 410, 420 to lift the bioreactor vessels 410, 420 off of the bed plates 746, 748. Because the cam arms 762 are retracted beneath the top surface of the bed plates 746, 748 in a default state and the bioreactor vessels 410, 420 are supported on the level bed plates 746, 748 (and, particularly, the level alignment pins 754, no power is needed to maintain the bioreactor vessels in a level position. In particular, when the bioreactor vessels 410, 420 are received on the bed plates 746, 748, they are in level position. In the event of a power interruption, the bioreactor vessels 410, 420 remain seated on the level bed plates 746, 748 and do not require any continual adjustment using the cam arms 762 to maintain the level position. This is in contrast to some systems which may require constant adjustment of the bioreactor using servomotors to maintain a level position. Indeed, with configuration of the cam arms 762 of the invention, the actuator need only be energized when tilting the bioreactor vessels for agitation/mixing, as discussed below, which minimizes heat contribution to the processing chamber 722.

Figure 41:
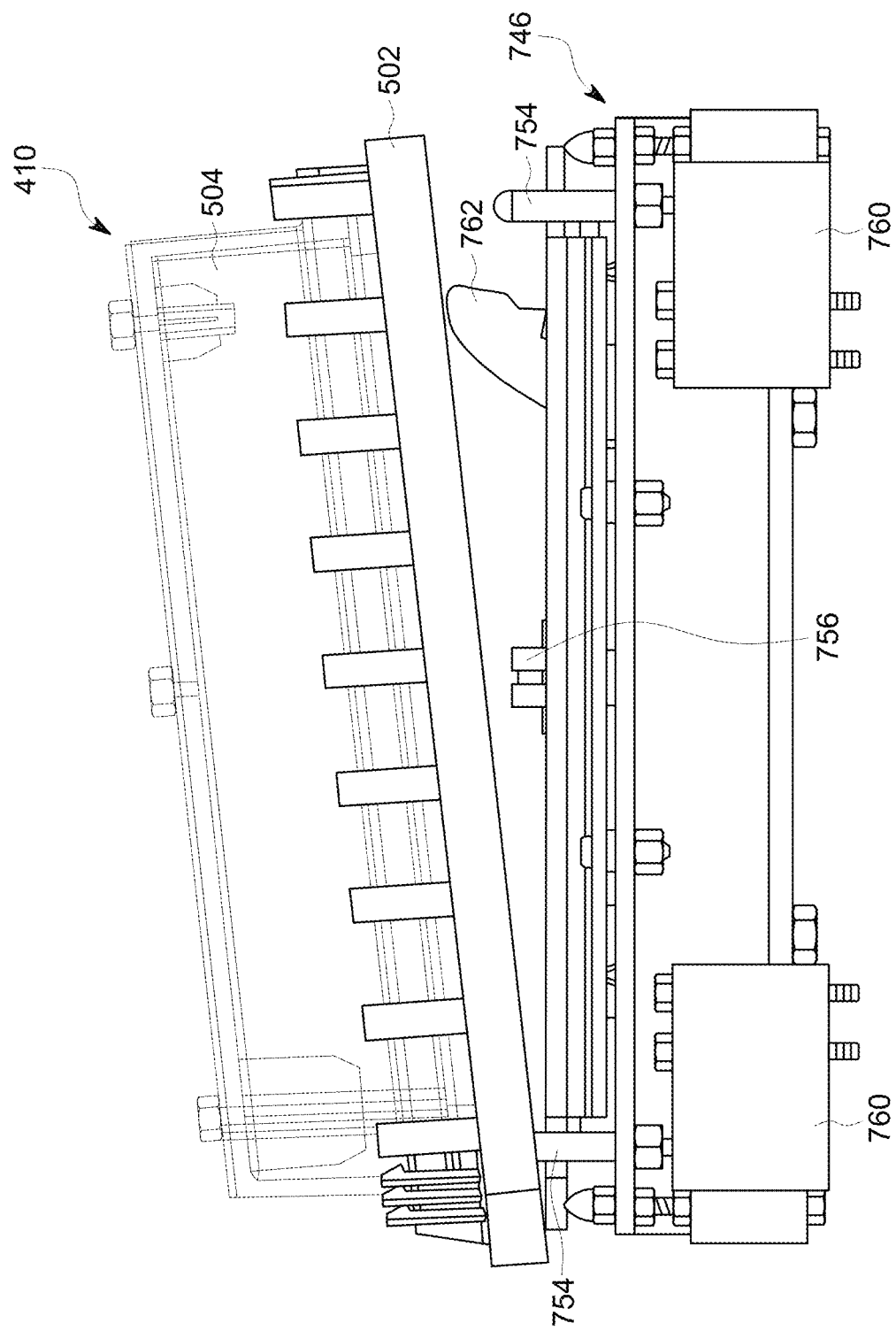
FIG. 41 is a side elevational view of a bioreactor received on a bed plate, illustrating an agitation/mixing mode of operation of the bioreactor system.
Figure 42:
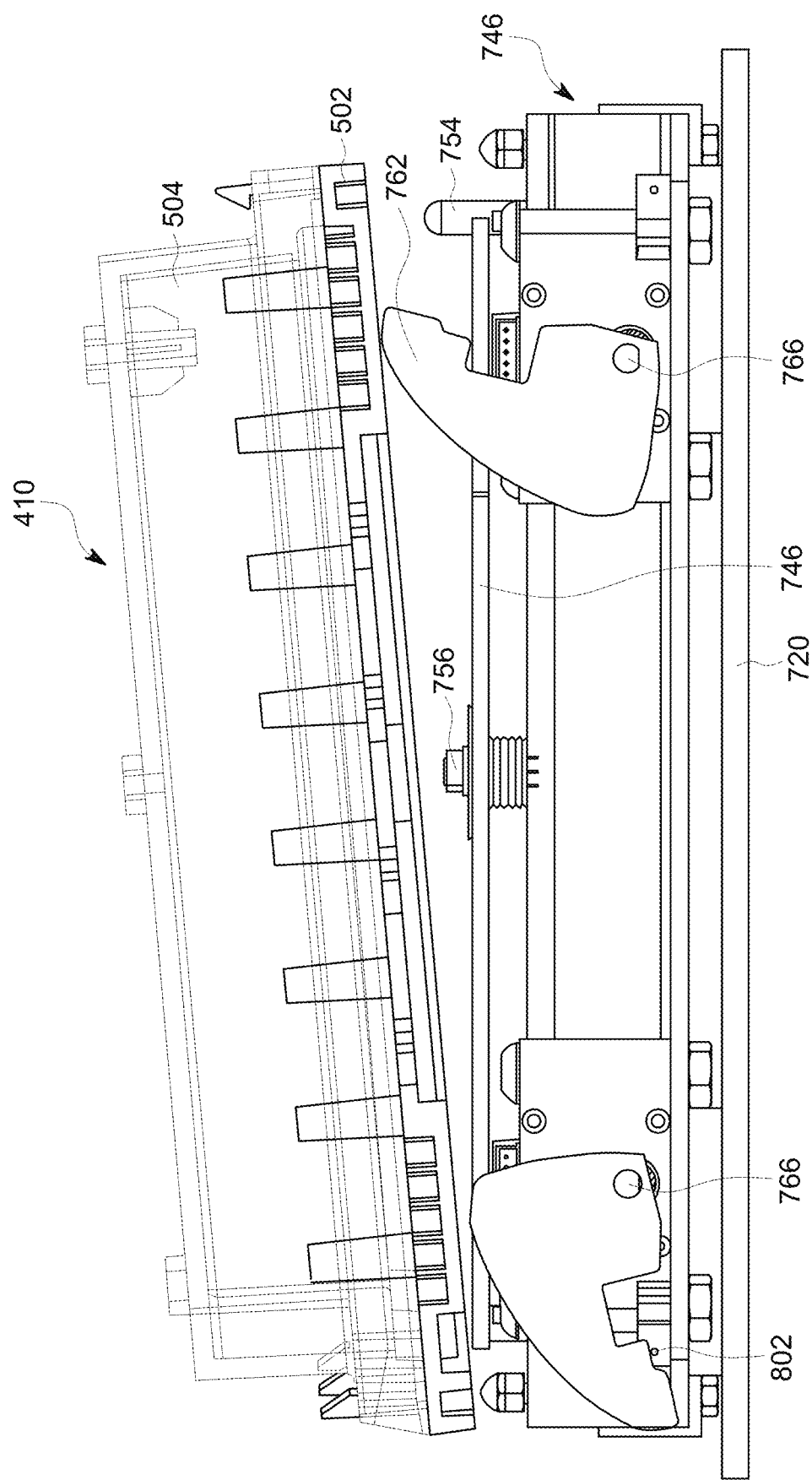
FIG. 42 is a side, cross sectional view of the bioreactor received on the bed plate, illustrating the agitation/mixing mode of operation of the bioreactor system.
Figure 43:
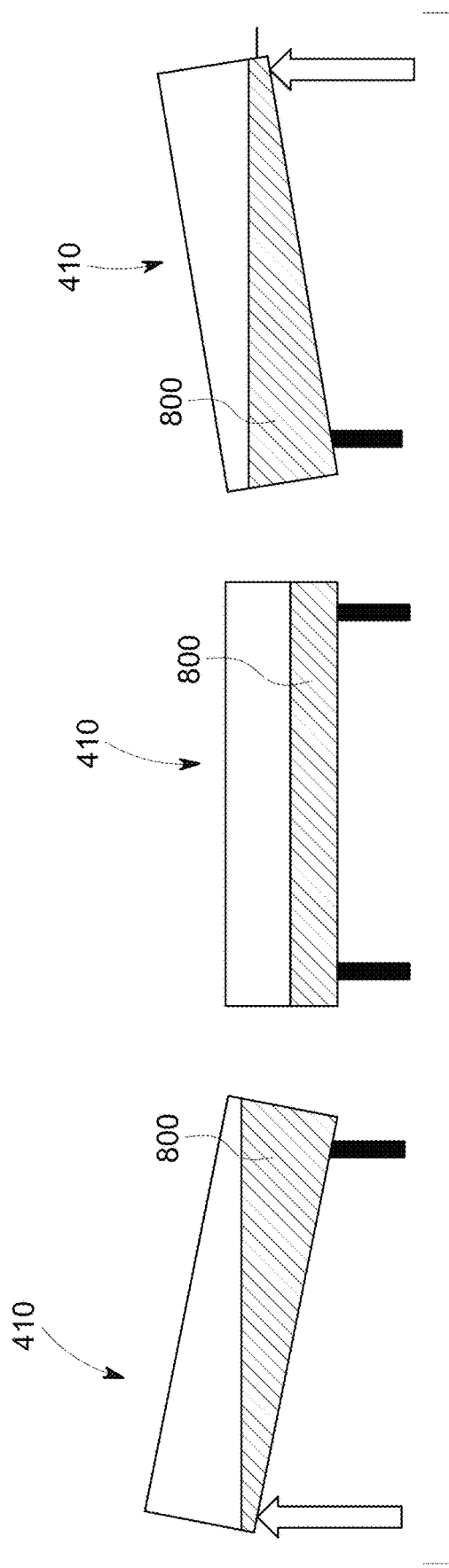
FIG. 43 is a schematic illustration of the bioreactor vessel shown a fluid level within the bioreactor vessel during the agitation/mixing mode of operation.

As shown in FIGS. 41-43, the cam arms 762 may be operable sequentially to agitate the contents of the bioreactor vessels 410, 420. For example, when it is desired to agitate the contents of the bioreactor vessel 410, one of the cam arms will be actuated to lift one end of the bioreactor vessel 410 off of the bed plate 746 (and out of engagement with the locating pins 754 on the bed plate 746, while the opposing end remains seated on the bed plate and the locating pins 754 on the non-raised end remain received in the corresponding recesses 550 in the bottom plate 502. The raised cam arm will then be rotated back to the clearance position beneath the bed plate and the opposing cam arm will be rotated to the engagement position to raise the opposing end of the bioreactor vessel off of the bed plate and locating pins.

In an embodiment, the cam actuation system may be designed such that the cam arms 762 can be homed without touching the bioreactor vessel, preventing disruption to the culture and allowing the cam arms 762 to be homed (or tested) at any point during the long cell processing periods. Thus while the present invention contemplates that other rocking or agitations means may be provided for the bioreactor vessels, by having two cam arms 762 on opposite sides of the bed plate, the overall height of the mixing mechanism can be minimized. For example a +/−5-degree motion could be achieved with a central actuator (located centrally on the bed plate), but nearly the same motion of a vessel can be achieved with the 0-5-degree motion of the vessel driven by a cam arm on both sides of the vessel, effectively giving the vessel a +/−5 degrees motion in half the height. Further, the motion of the cam arms 762 (e.g., speed of cam arm rotation and timing between opposing cam arms) can be adjusted to maximize the wave formation in the vessel to maximize wave amplitude and thus (ideally) maximize homogeneity of vessel contents and time to achieve homogeneity. The timing can also be adjusted based on volume in a vessel with a given geometry to maximize the mixing efficiency.

In an embodiment, the optical sensor 756 can be used to confirm that the first bioreactor vessel 410 has been correctly re-positioned after each cam agitation motion. It is further contemplated that correct re-positioning of the bioreactor vessel can be checked and verified even between alternating cam motions. This enables quick detection of misalignment, in substantially real time, allowing for an operator to intervene to reseat the bioreactor vessel without substantial deviation from the bioprocessing operation/protocol.

FIG. 43 is a schematic illustration showing the position of a fluid 800 within the bioreactor vessel during this agitating process. As shown in FIG. 42, in an embodiment, a homing sensor 802 integrated with the bed plate 746 may be utilized by the controller to determine when the cam arms 762 have returned to the clearance position beneath the top surface of the bed plate 746. This is useful in coordinating the motion of the cam arms 762 to provide a desired mixing frequency in the bioreactor vessels. In an embodiment, the cam arms 762 are configured to provide a maximum 5 degree tilting angle with respect to the bed plate 746.

Figure 44:
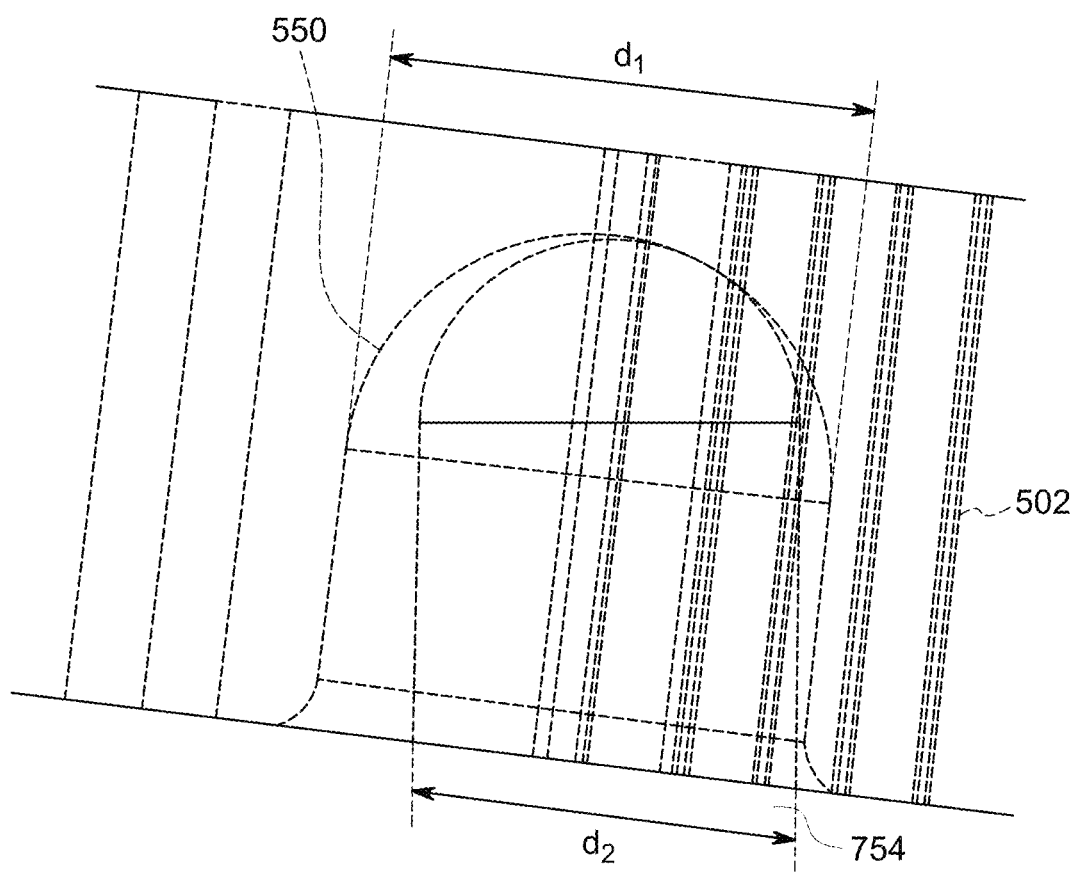
FIG. 44 is a cross-sectional, detail view of an interface between locating pins on the bed plate and receiving recesses on a bioreactor vessel during agitation/mixing mode of operation.

With reference to FIG. 44, the interface between the locating pins 754 of the bed plate and the recesses 550 in the bottom plate 502 of the bioreactor vessel 410 during mixing/agitation is illustrated. In an embodiment, the recesses 550 have a dome-like or hemispherical-like interior surface and a diameter, d1, that is greater than a diameter, d2, of the locating pins 754. As illustrated in FIG. 44, this configuration provides for clearance between the locating pins 754 and recesses 550, which allows for tilting of the bioreactor vessel 410 when the locating pins 554 are received in the recesses 550.

Figure 45:
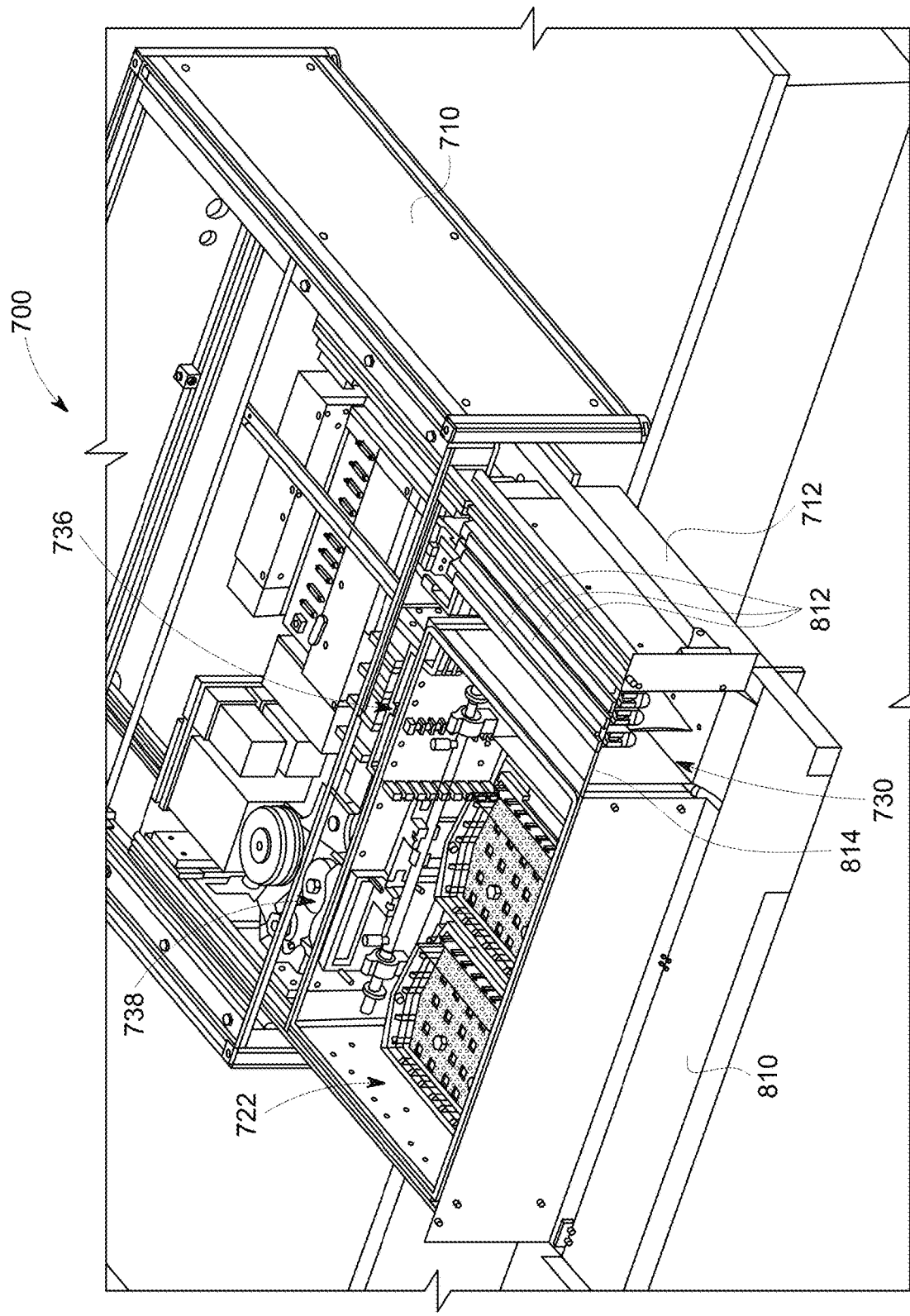
FIG. 45 is a perspective view of a bioprocessing apparatus having a flip-down front panel according to an embodiment of the invention, showing the processing drawer thereof in an open position.
Figure 46:
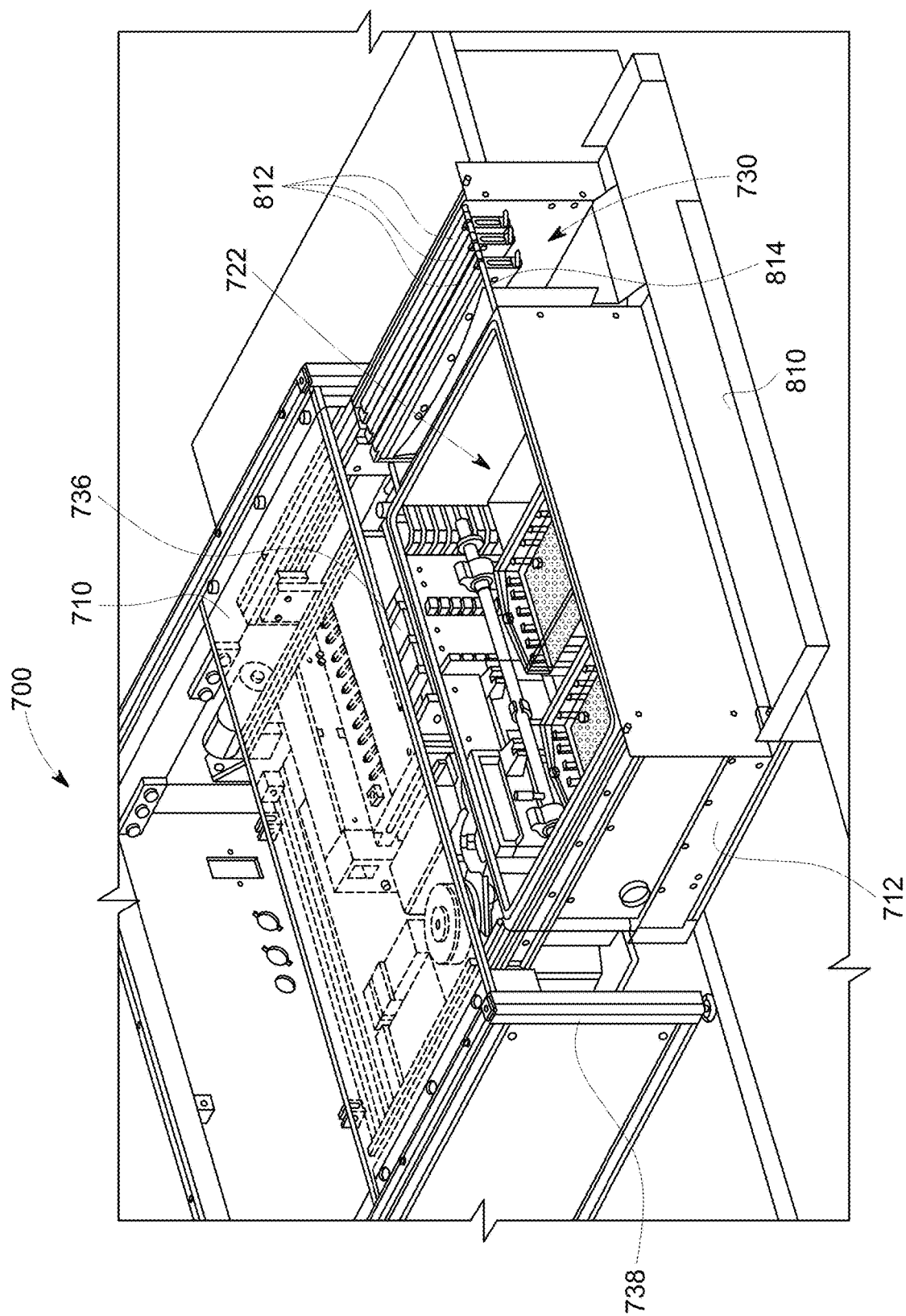
FIG. 46 is another perspective view of the bioprocessing apparatus of FIG. 45, showing the processing drawer thereof in an open position.
Figure 47:
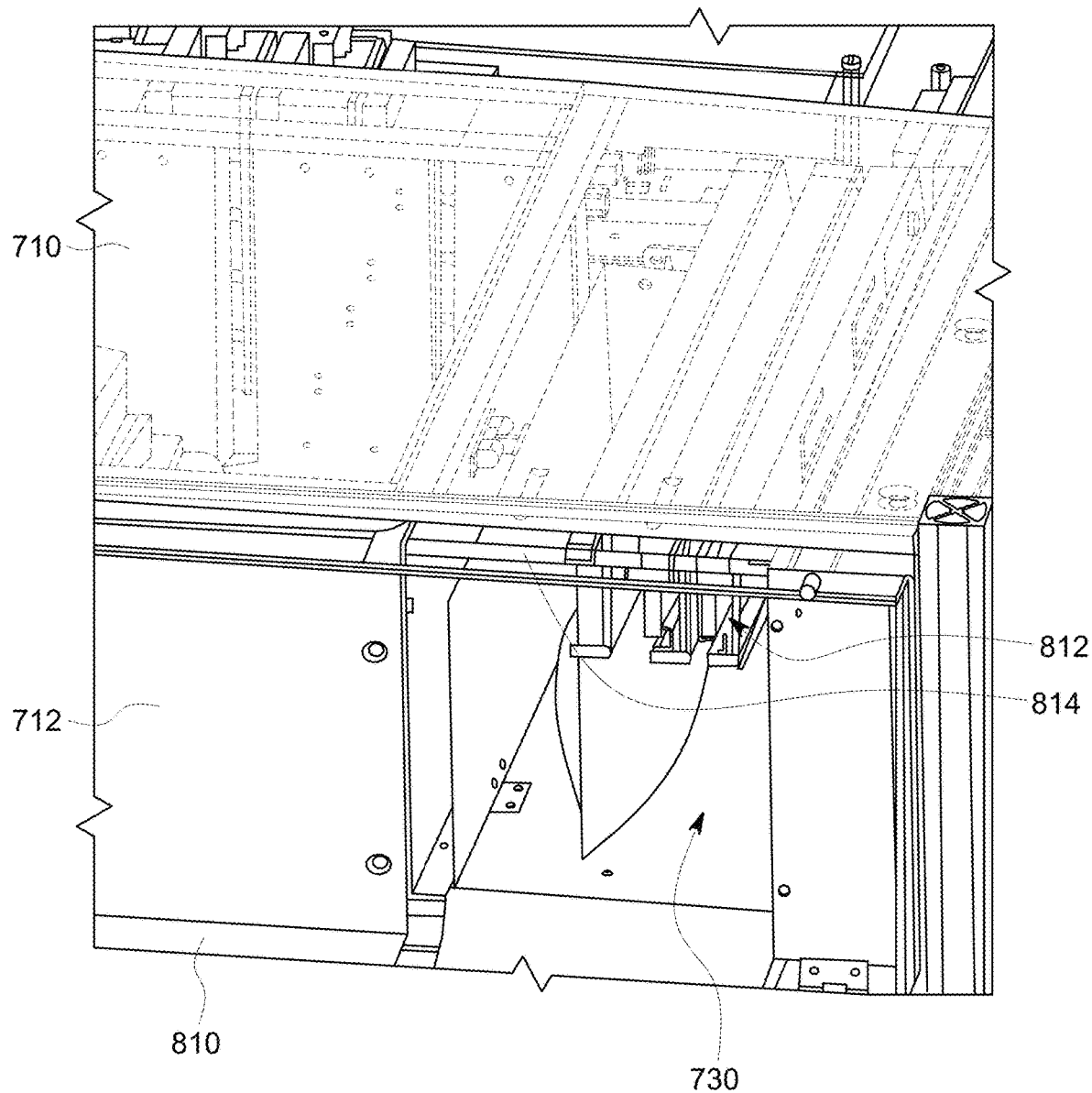
FIG. 47 is an enlarged, perspective view of an auxiliary compartment of the bioprocessing apparatus of FIG. 45, showing the processing drawer in a closed position with access to the auxiliary compartment.
Figure 48:
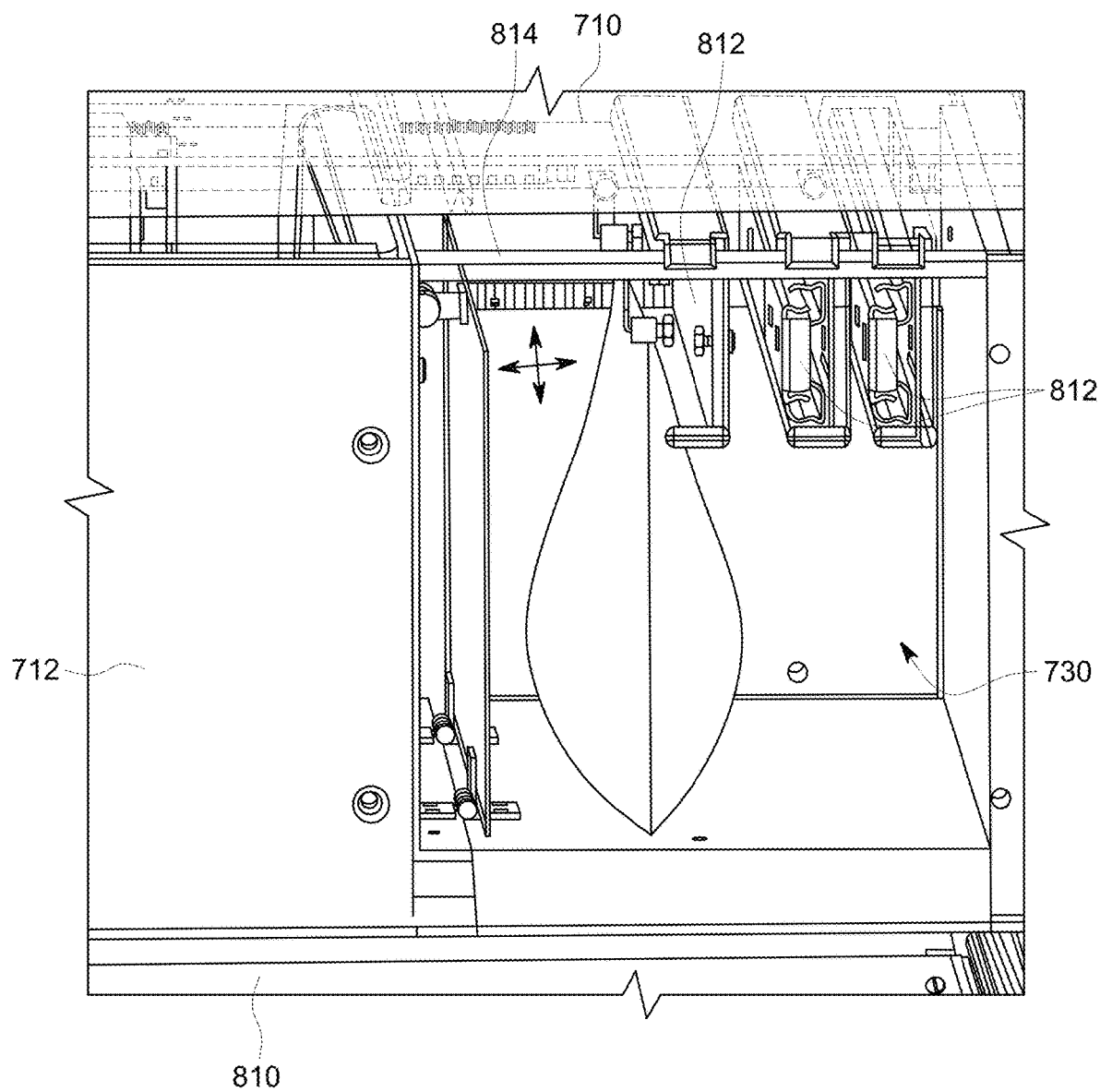
FIG. 48 is another enlarged, perspective view of the auxiliary compartment of the bioprocessing apparatus of FIG. 45, showing the processing drawer in the closed position with access to the auxiliary compartment.
Figure 49:
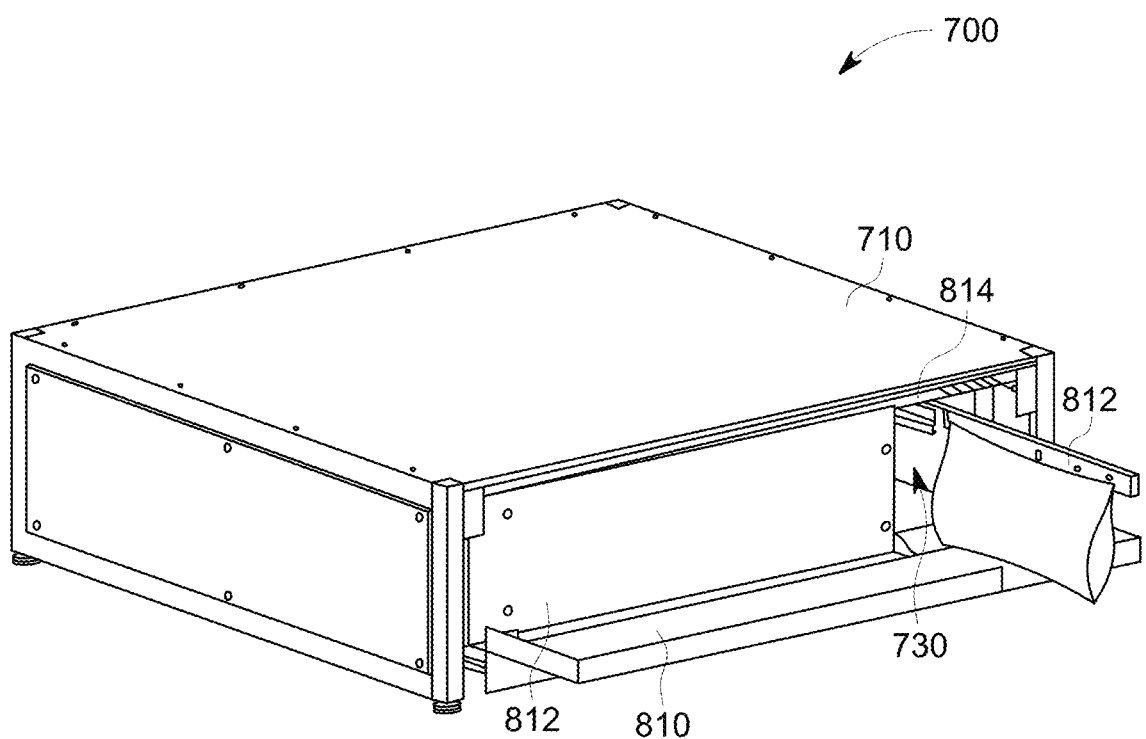
FIG. 49 is a perspective view of the bioprocessing apparatus of FIG. 45, showing the processing drawer thereof in the closed position with access to the auxiliary compartment.
Figure 50:
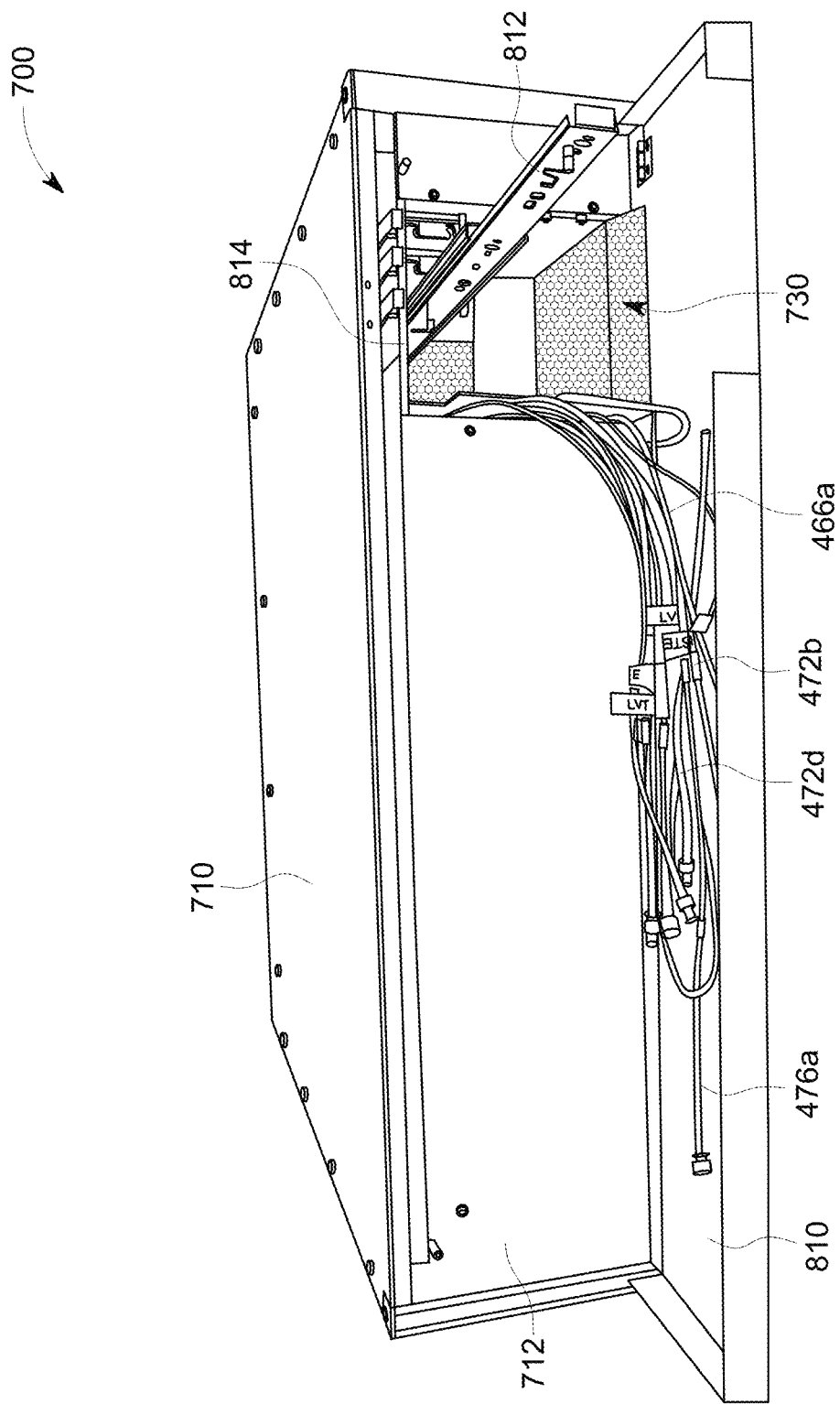
FIG. 50 is another perspective view of the bioprocessing apparatus of FIG. 45, showing the processing drawer thereof in the closed position with access to the auxiliary compartment.

In an embodiment, each drawer of the bioprocessing apparatus 700, e.g., drawer 712, desirably includes have a flip-down front panel 810 hingedly-mounted thereto, as shown in FIGS. 45-50. The flip-down front panel 810 allows access to the auxiliary compartment 730 without having to open the drawer 712, as best shown in FIGS. 45, 49 and 50. As will be appreciated, this configuration allows for in-process sampling and exchange of media bags. In connection with the above, in an embodiment, the auxiliary compartment 730 may be configured with a plurality of telescoping sliding rails 812 providing attachment means 815 from which the various reservoirs/media bags can be suspended. Rails 812 are movable between a retracted position within compartment 730, as depicted in FIG. 48, to an extended position out from compartment 730, as depicted in FIG. 49. When a collection bag is full, or a media/fluid bag needs replacement, the rails 812 can simply be extended outward and the bag unclipped. A new bag can be connected to its respective tail and then be suspended from a rail and slid back into the auxiliary compartment 730 without having to open the drawer 712 or pause processing. In an embodiment, the rails 812 may be mounted on transversely-extending cross rods 814. The rails 812 may thus be laterally slidable on the rods 814, and extendable from and retractable into the auxiliary compartment. In addition, the when the drawer is open (FIG. 46) the rails 812 can rotate about the rear cross rod so that it clears the compartment 730 to allow a user to thread the tubing tails towards the front of the 730 compartment, providing for a third degree of freedom.

Figure 51:
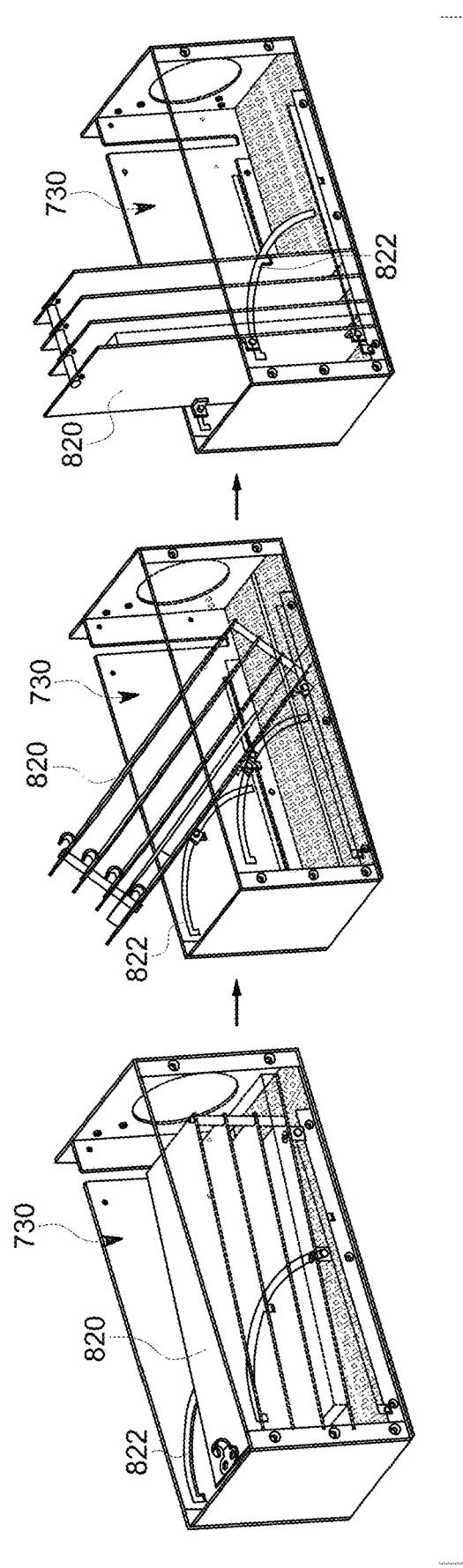
FIG. 51 is a perspective view of the auxiliary compartment of the bioprocessing apparatus, according to another embodiment of the invention.

As illustrated in FIG. 51, in another embodiment, the media/fluid bags may be mounted on a platform 820 that is rotatable out of the auxiliary compartment 730 from a stowed position to an access position. For example the platform 820 may be mounted for movement along a guide track 822 formed in the sidewalls of the auxiliary compartment 730.

Figure 52:
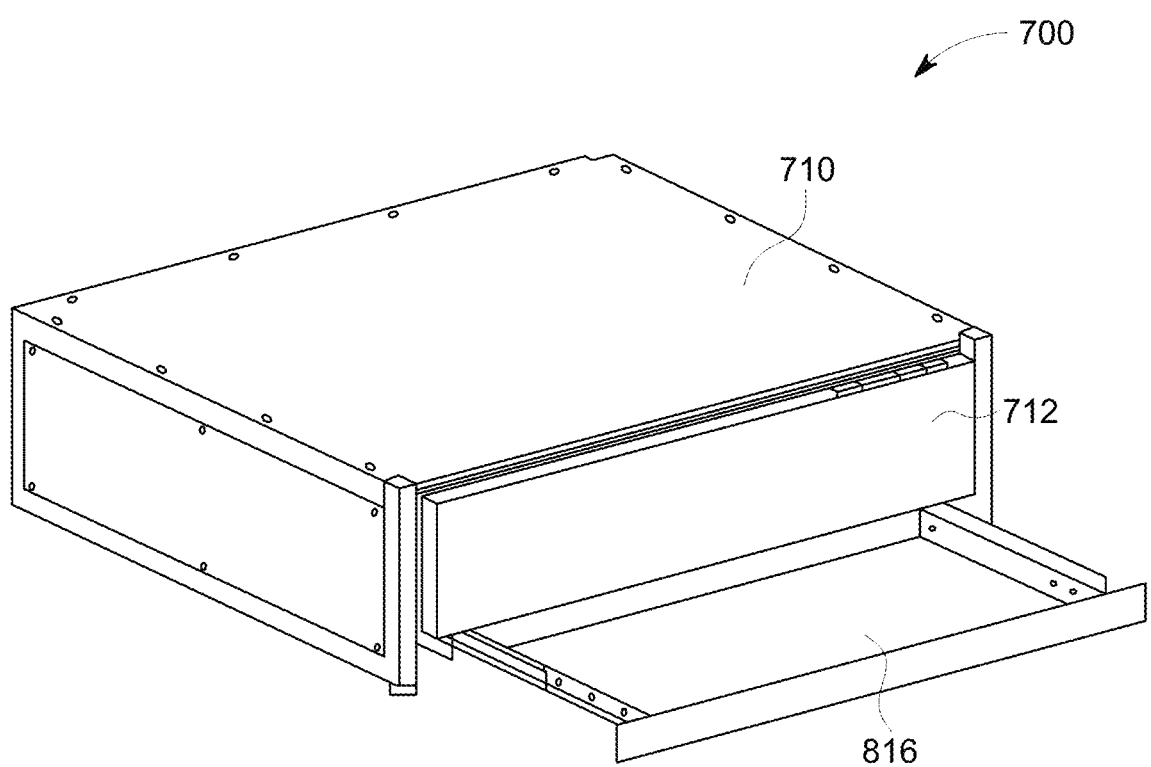
FIG. 52 is a perspective view of a bioprocessing system having a waste tray, according to an embodiment of the invention.

With reference to FIG. 52, in an embodiment, the bioprocessing apparatus 700 may further include a low-profile waste tray 816 received within the housing 710 beneath each drawer, e.g., drawer 712. Waste tray 816 is independently mounted on its drawer to be moveable between a closed and open position. In the closed position, tray 816 desirably extends flush with the front surface of the drawer while in the open position tray 816 exposes its own chamber 819 to be accessible to an operator. Chamber 819 provides for easy storage of large waste bags connected to the fluid path of its overlying tray 600 and provides access thereto without having to open the drawer 712. In addition, in the closed position, the waste tray 816 positions chamber 819 in underlying registry with its drawer and is sized and shaped so as to be operable to contain any leaks from the processing chamber 722 or auxiliary compartment 730.

In an embodiment, each drawer may include a camera positioned above processing chamber (e.g., above each bioreactor vessel 410, 420) to allow for visual monitoring of the interior of the drawer 712 without having to open the drawer 712. In an embodiment, the camera (or an additional camera) can be integrated with the bed plate assembly, or on a sidewall looking laterally into the bioreactor vessel(s).

The second module 200 of the invention therefore provides for the automation of cell processing to an extent heretofore not seen in the art. In particular, the fluid flow architecture 400, pump assembly 738 and pinch valve array 736 allows for automated fluid manipulation between the bioreactor vessels 410, 420 and the bags connected to the first and second fluid assemblies 740, 744 (e.g., fluid addition, transfer, draining, rinsing, etc.). As discussed below, this configuration also permits hollow-fiber filer concentration and wash, filterless perfusion and line priming. The use of the drawer engagement actuator 740 also for automatic engagement and disengagement of the drop-in kit 600, further minimizing human touchpoints. Indeed, human touchpoints may only be required for source/media bag addition and removal, sampling and data input (e.g., sample volume, cell density, etc.).

Referring to FIGS. 53-77, an automated, generic protocol for a workflow with immobilized Ab coating, soluble Ab addition, gamma-retroviral vector with expansion in the same vessel, using the second module 200 and fluid flow architecture 400 thereof, is illustrated. This generic protocol provides for activation (illustrated in FIG. 53-59), pre-transduction preparation and transduction (illustrated in FIGS. 60-71), expansion (FIGS. 72-76), and, for some embodiments, harvesting (FIG. 77) of a population of cells in an automated and functionally-closed manner. In describing operation of the pinch valves, below, when a valve is not used for a particular operation, the valve is in its closed state/position. Accordingly, after a valve is opened to allow for a particular operation, and once that operation is completed, the valve is closed before proceeding to the next operation/step.

Figure 53:
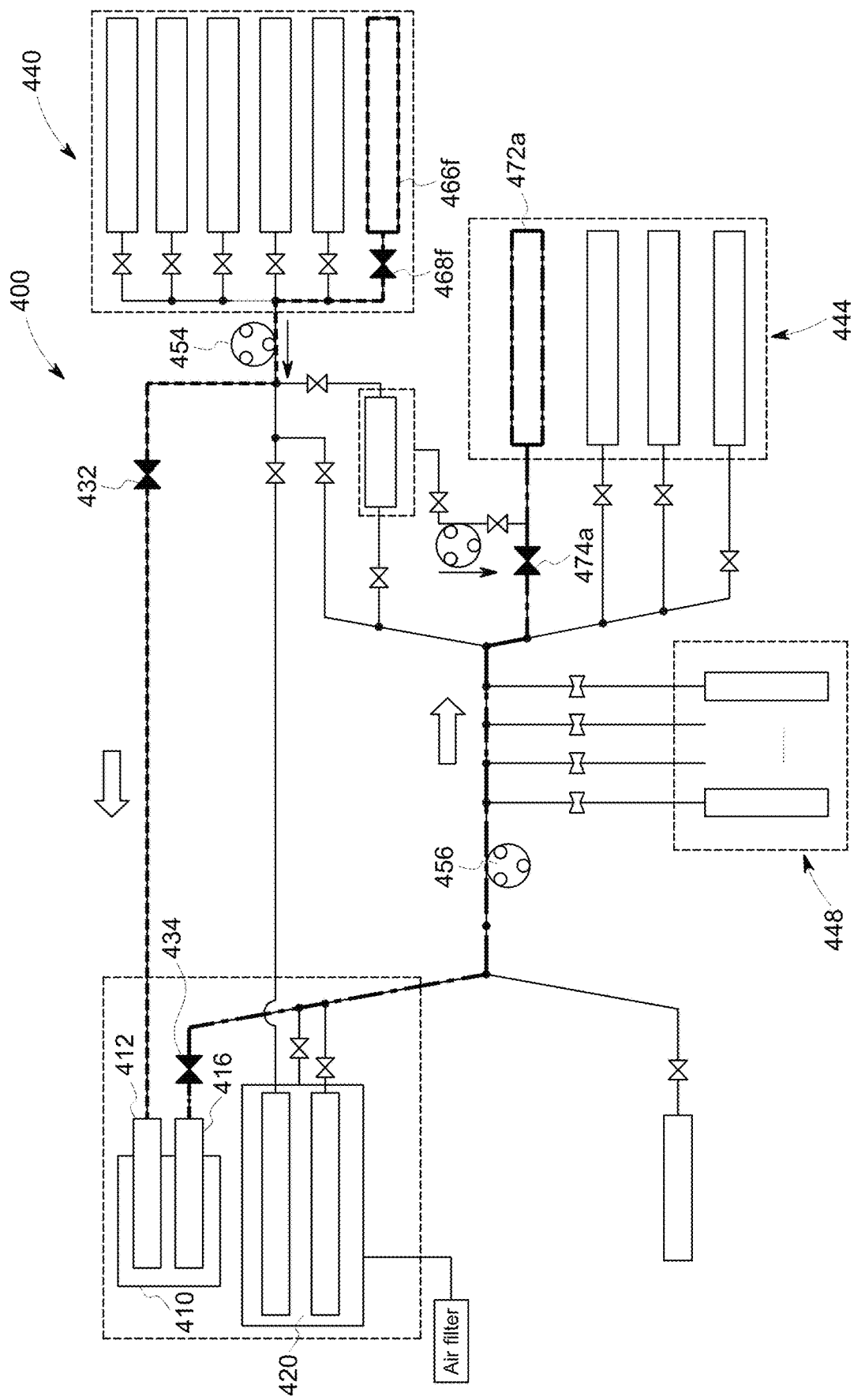
FIGS. 53-77 are schematic illustrations of an automated, generic protocol of the bioprocessing system utilizing the fluid flow architecture of FIG. 3, according to an embodiment of the invention.
Figure 54:
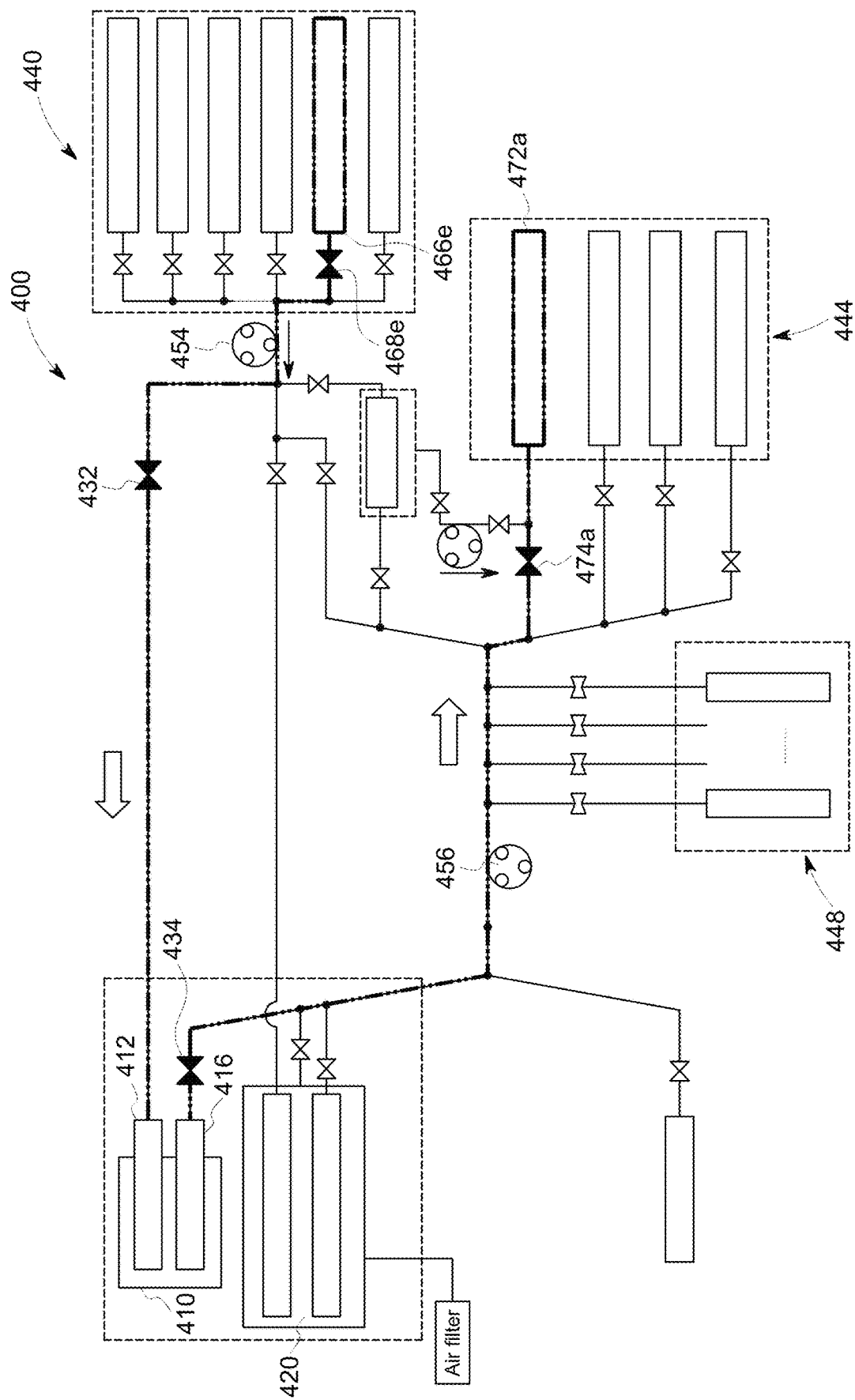

As shown in FIG. 53, in a first step, valves 432 and 468/are opened and first fluid assembly line pump 454 is actuated to pump an antibody (Ab) coating solution from reservoir 466f connected to the first fluid assembly 440 to the first bioreactor vessel 410 through the first port 412 thereof. The antibody coating solution is incubated for a period of time, and then drained through the interconnect line to a waste reservoir 472a of the first fluid assembly 440 by opening valves 434, 474a and activating the circulation line pump 456. As described herein, draining of the bioreactor vessel 410 may be facilitated by tilting the bioreactor vessel 410 using the cam arms 462.

After draining the antibody coating solution, valves 432 and 468e are opened and pump 454 is actuated to pump a rinse buffer from reservoir 466e connected to the first fluid assembly 440 to the first bioreactor vessel 410 through the first bioreactor line. The rinse buffer is then drained through interconnect line 450 to the waste reservoir 472a by actuating the circulation line pump 456 and opening valve 474a. In an embodiment, this rinse and draining procedure may be repeated multiple times to adequately rinse the first bioreactor vessel 410.

Figure 55:
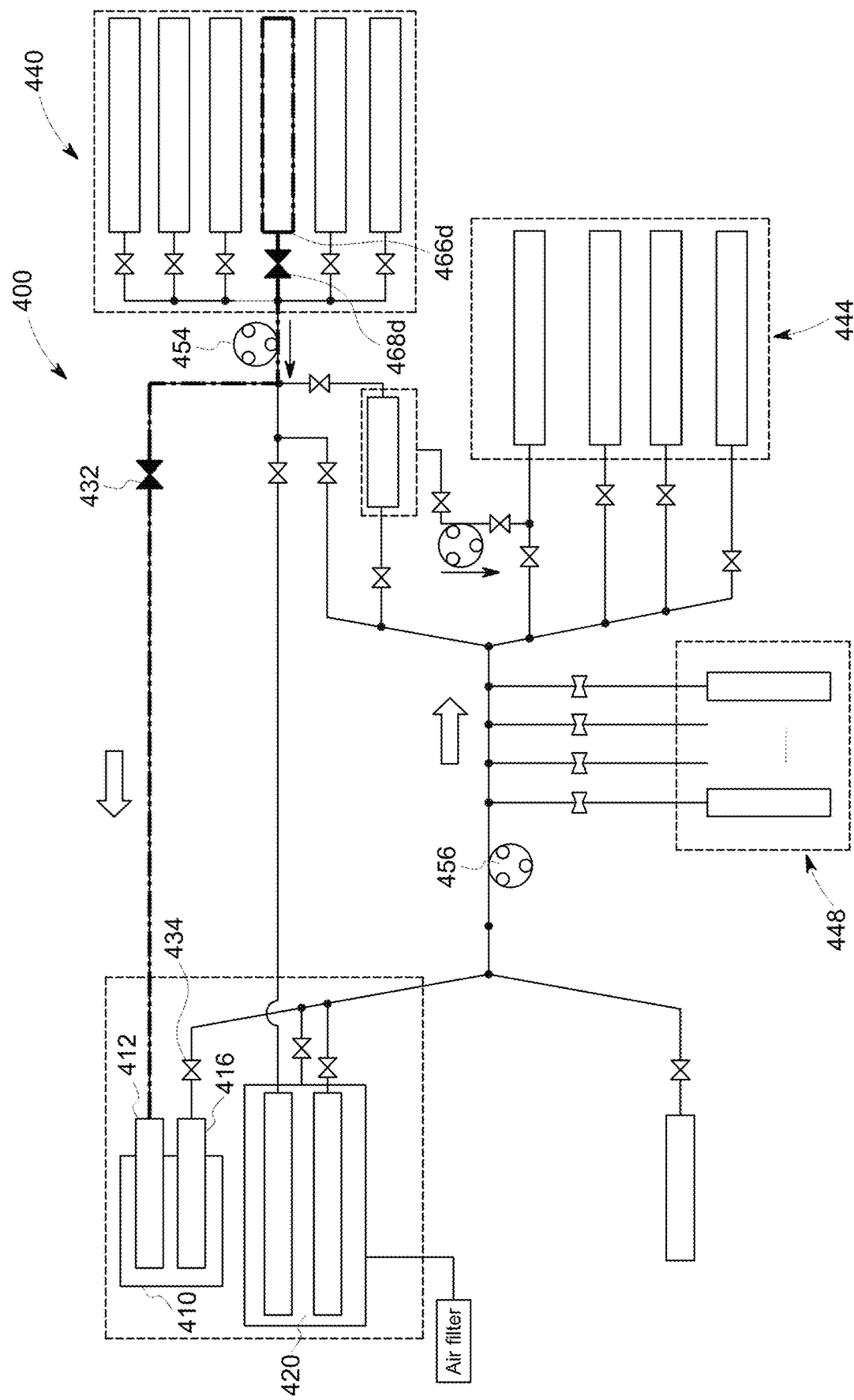
Figure 56:
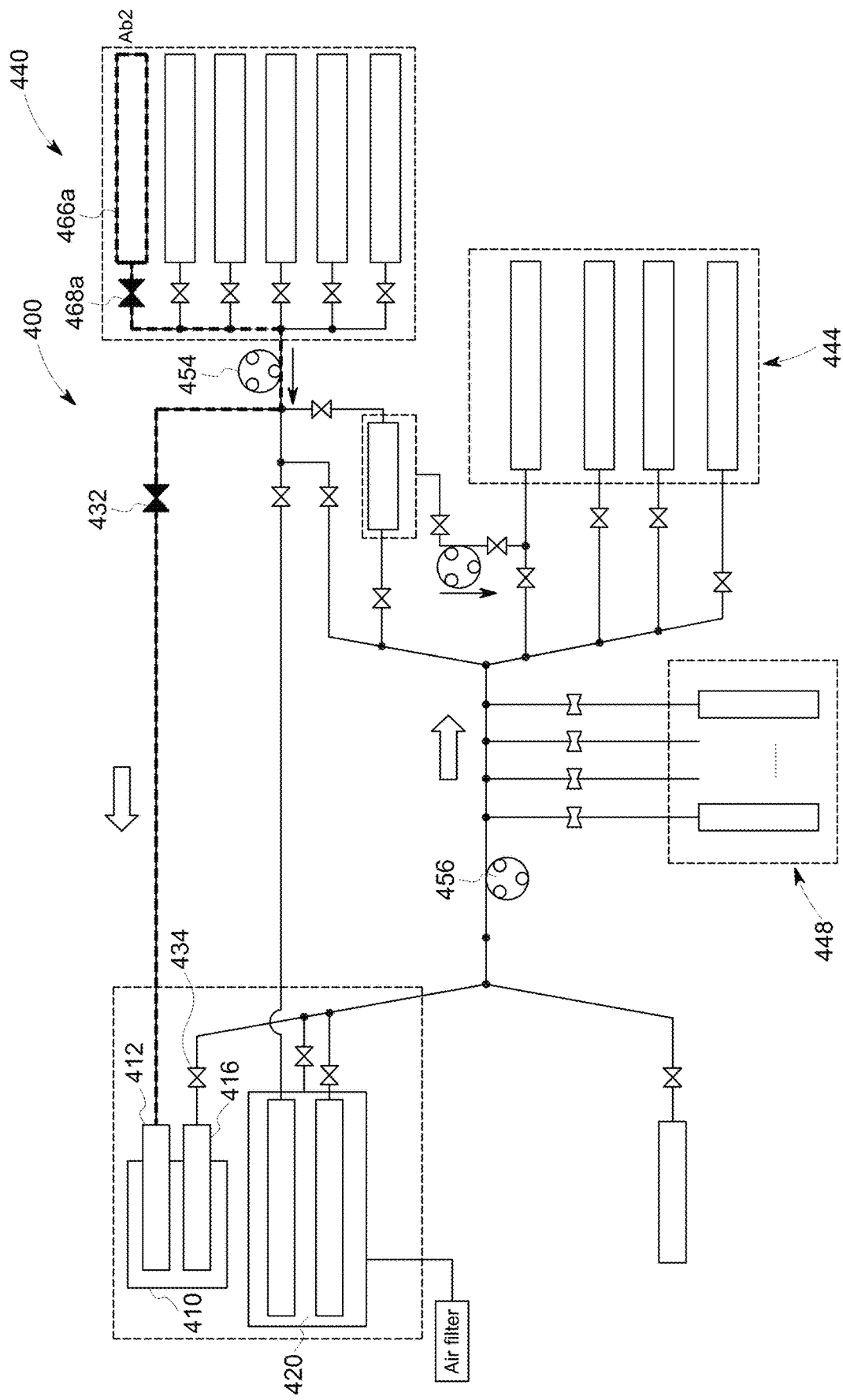

Turning to FIG. 55, after rinsing the first bioreactor vessel 410 with the buffer, cells in a seed bag 466d (which have been previously enriched and isolated using the first module 100) are transferred to the first bioreactor vessel by opening valves 468d and 432, and actuating the pump 454. The cells are pumped through the first bioreactor line 414 of the first bioreactor vessel 410 and enter the bioreactor vessel 410 through first port 412. As shown in FIG. 56, valves 432 and 468a are then opened and pump 454 is actuated to pump a second antibody (Ab) solution from reservoir 466a connected to the first fluid assembly 440 to the first bioreactor vessel 410 through the first port 412.

Figure 57:
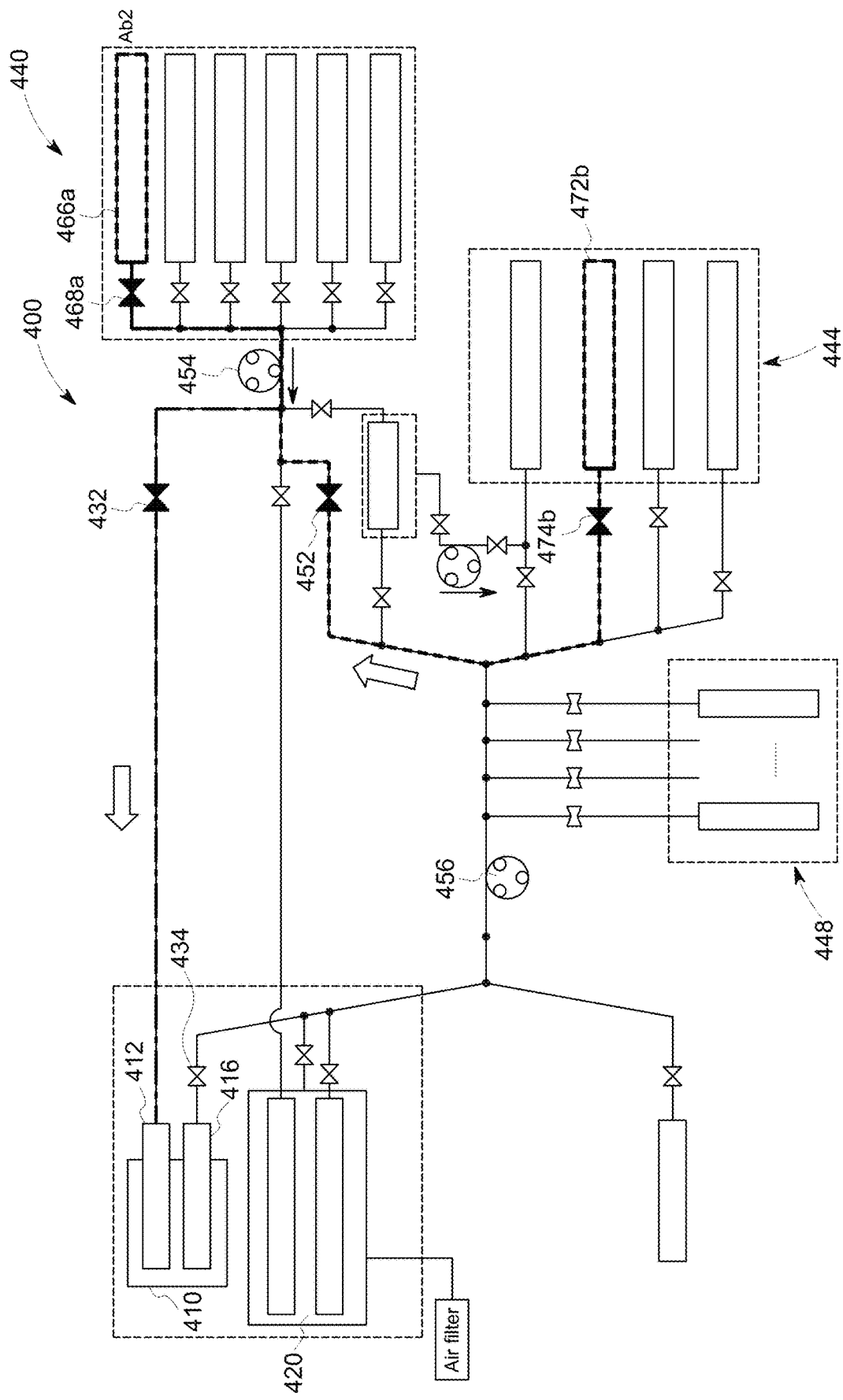

After pumping the second antibody solution into the first bioreactor vessel, the second antibody solution reservoir 466a is then rinsed and the rinse media is pumped to the first bioreactor vessel. In particular, as shown in FIG. 57, valves 474b, 452 and 468a are opened and rinse media from a rinse media reservoir/bag 472b of the second fluid assembly 444 is pumped using pump 454 into the second antibody solution reservoir 466a to rinse the reservoir. After rinsing, valve 432 is opened and the rinse media is pumped from the reservoir 466a to the first bioreactor vessel 410. In an embodiment, second antibody solution reservoir 466a may be rinsed multiple times using this procedure.

Figure 58:
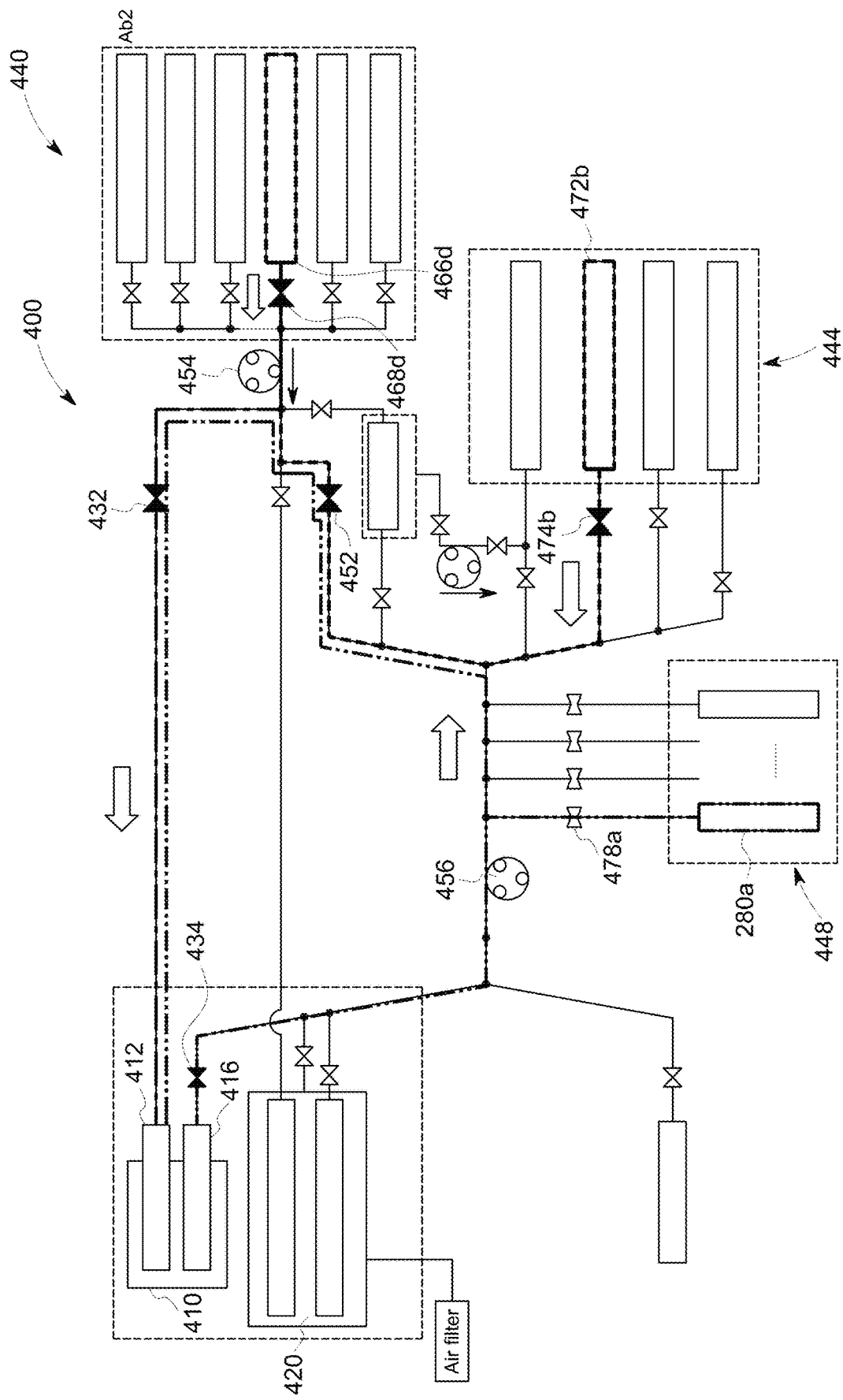

After rinsing the second antibody solution reservoir 466a, the inoculum/seed cell bag 466d may also be optionally rinsed. In particular, as shown in FIG. 58, valves 474b, 452 and 468d are opened and rinse media from a rinse media reservoir/bag 472b of the second fluid assembly 444 is pumped into the inoculum/seed cell bag 466d to rinse the bag using pump 454. After rinsing, valve 432 is opened and the rinse media is pumped from the bag 466d to the first bioreactor vessel 410 using pump 454. By pumping the rinse media to the first bioreactor vessel 410 after rinsing the inoculum/seed cell bag 466d, the cell density in the first bioreactor vessel 410 is reduced. At this time, a sample may be taken to measure one or more parameters of the solution in the first bioreactor vessel prior to activation (e.g., to ensure a desired cell density is present prior to activation. In particular, as shown in FIG. 58, valves 434, 452 and 432 are opened and pump 456 is actuated to pump the contents of the first bioreactor vessel 410 along a first circulation loop of the first bioreactor vessel (i.e., out of the second port 416, through the interconnect line 450, and back to the first bioreactor vessel 410 through the first bioreactor line 414 and first port 412 of the first bioreactor vessel 410). To take a sample, a first sample vessel 280a (e.g., a dip tube, syringe, etc.) is connected to the first sample tubing tail 476a and valve 478*a* is opened to divert some of the flow through the interconnect line 450 to the first sample vessel 280*a* for analysis.

Figure 59:
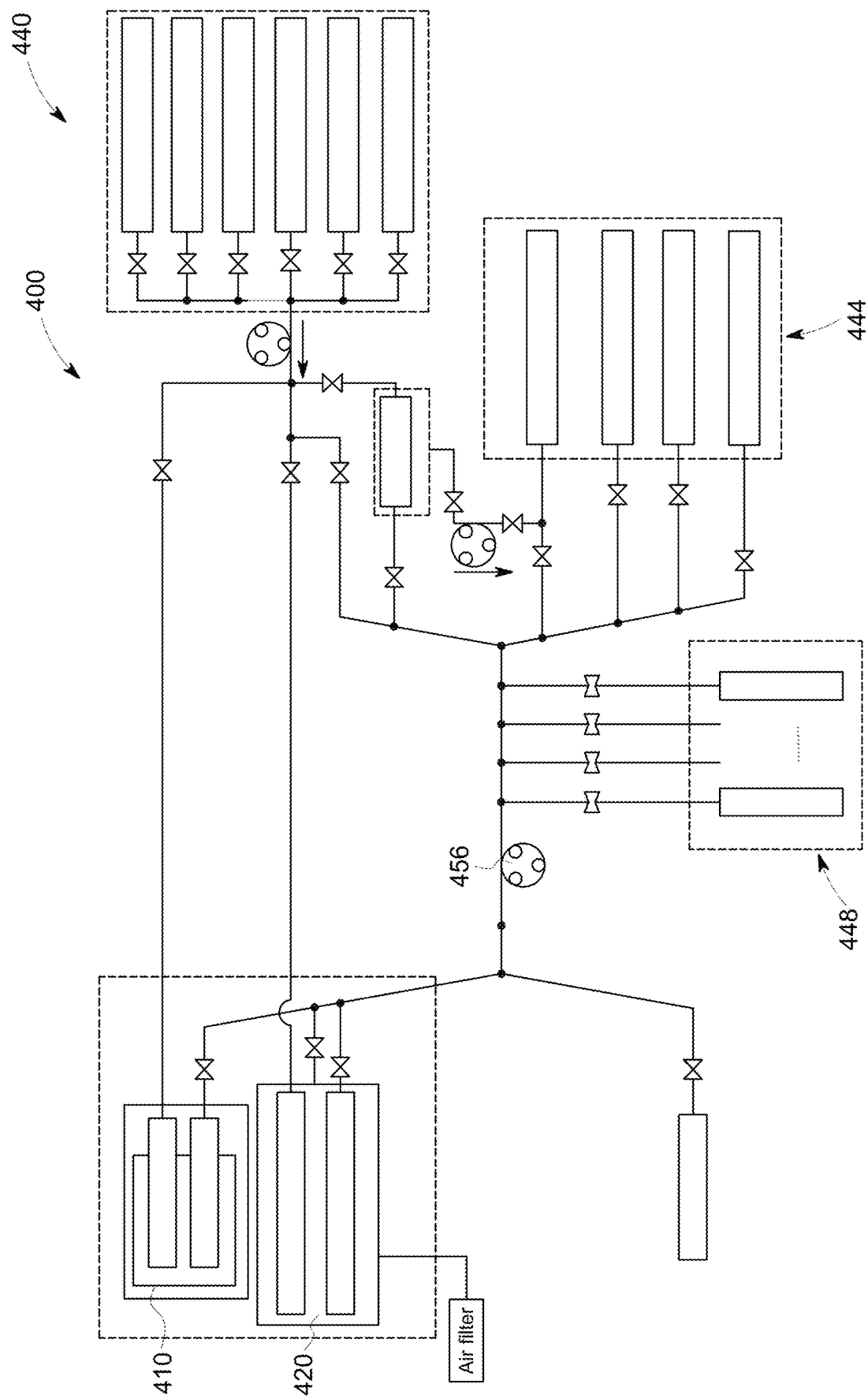

If analysis of the sample taken indicates that all solution parameters are within predetermined ranges, then the solution within the first bioreactor vessel 410 is incubated for a predetermined period of time for activation of the population of cells in solution, as illustrated in FIG. 59. For example, in an embodiment, the population of cells in the first bioreactor vessel 410 may be incubated for approximately 24-48 hours.

Figure 60:
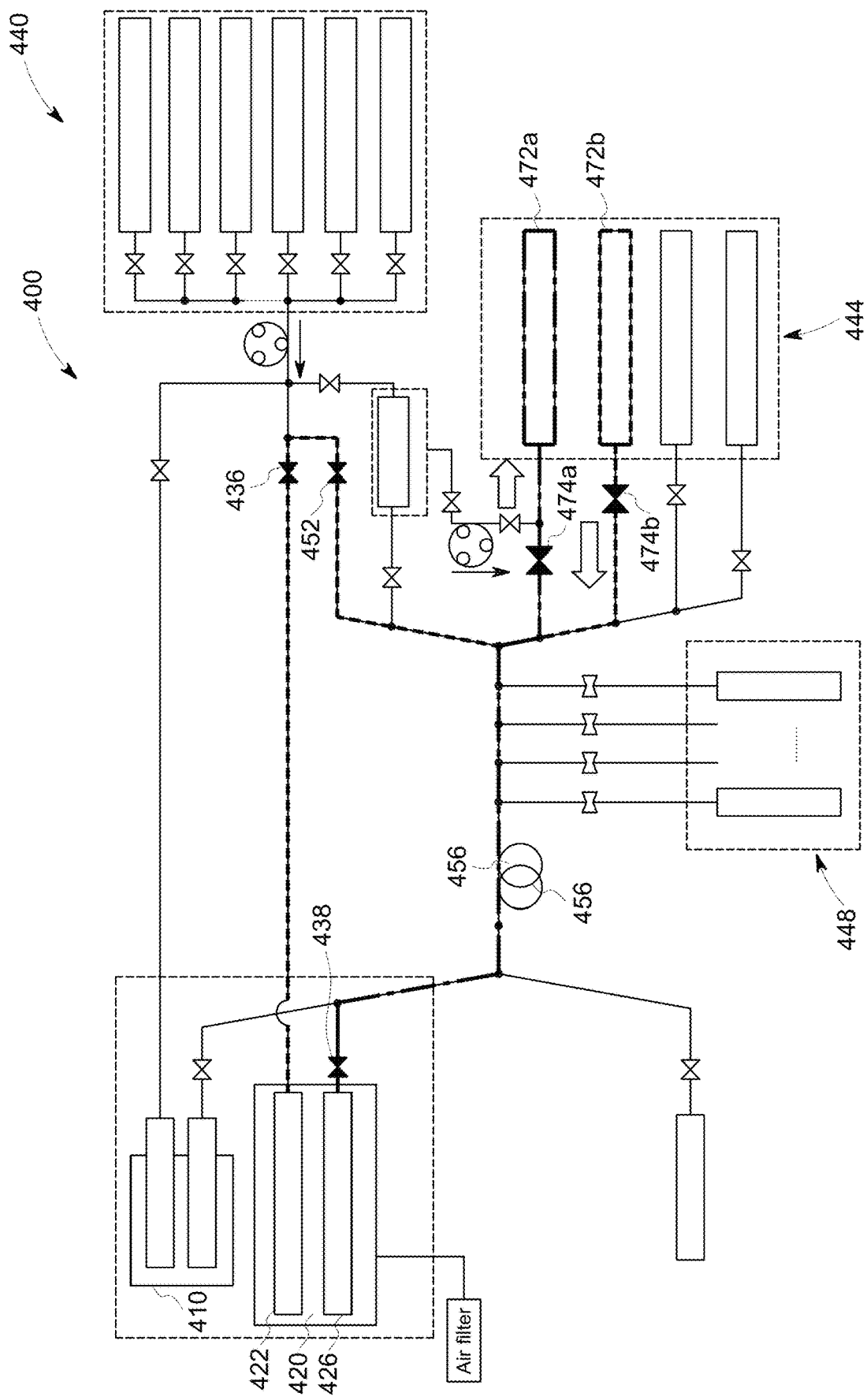

Referring now to FIG. 60, after activation, to prepare for transduction, valves 438 and 474*b* may be opened and pump 456 operated to pump the RetroNectin solution from reservoir 472*b* to the second bioreactor vessel 420 through the second port 426 of the second bioreactor vessel 420. After pumping the RetroNectin solution to the second bioreactor vessel 420 for RetroNectin coating of the second bioreactor vessel 420, the solution is incubated in the second bioreactor vessel 420 for a predetermined time period. As further shown in FIG. 60, after incubation, all RetroNectin solution is then drained from the second bioreactor vessel 420 to the waste reservoir 472*a* by opening valves 438 and 474*a* and actuating the circulation line pump 456. During these RetroNectin coating, incubation and draining steps (relating to the second bioreactor vessel 420), it should be noted that the activated cell population remains in the first bioreactor vessel 410. It should be noted that it is not necessary that RetroNectin or other reagents for enhancing the efficiency of genetic modification be utilized in all processes.

Figure 61:
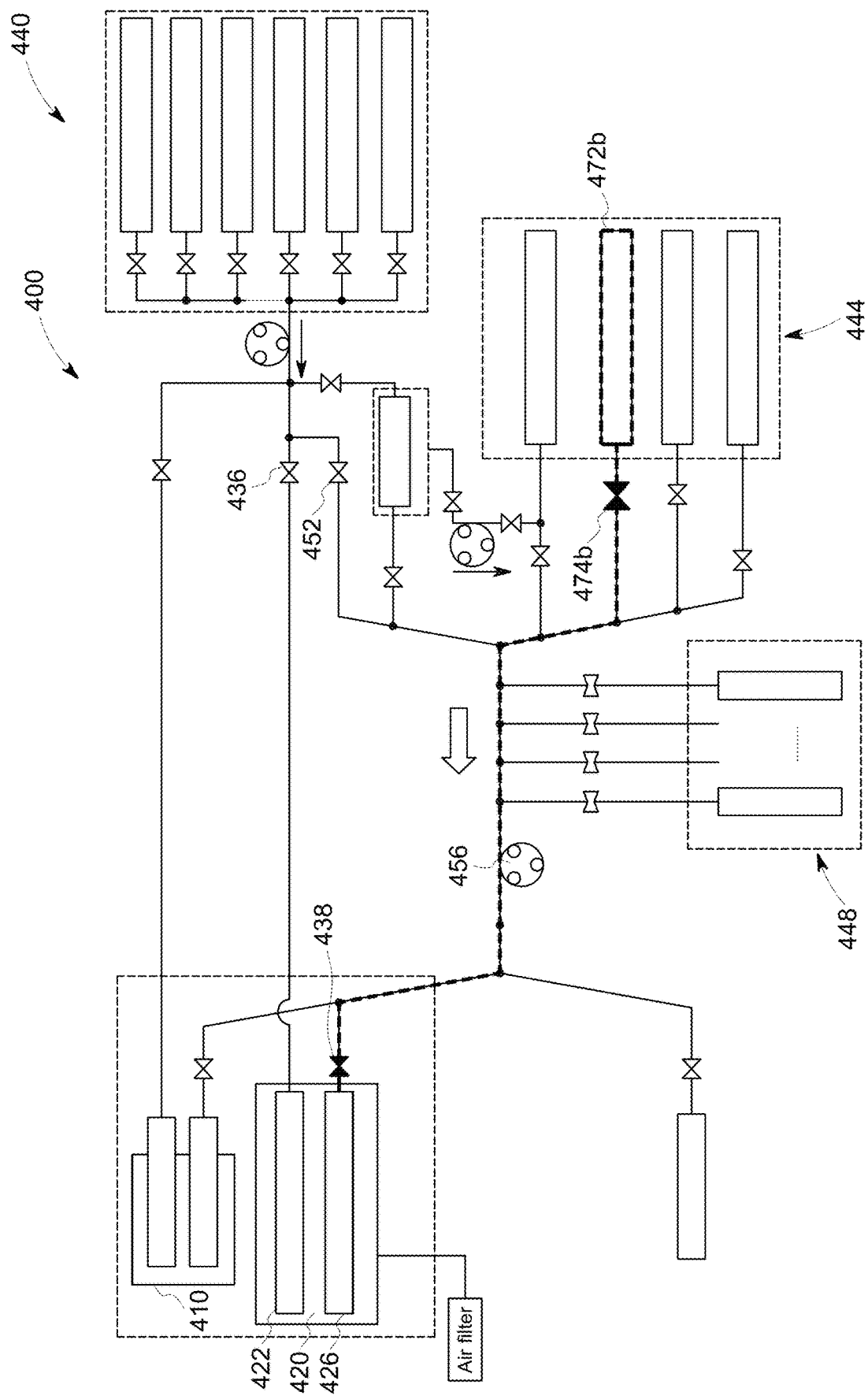

As shown in FIG. 61, after RetroNectin coating, a rinse buffer bag 472*b* is connected to the second fluid assembly 444 (or it may already be present and connected to one of the tubing tails), and valves 474*b* and 438 are opened and pump 456 is actuated to pump buffer from the bag 472*b* to the second bioreactor vessel 420. As discussed above, alternatively, the buffer may be pumped through the first port 422 of the second bioreactor vessel 420 by instead opening valves 452 and 436.

Figure 62:
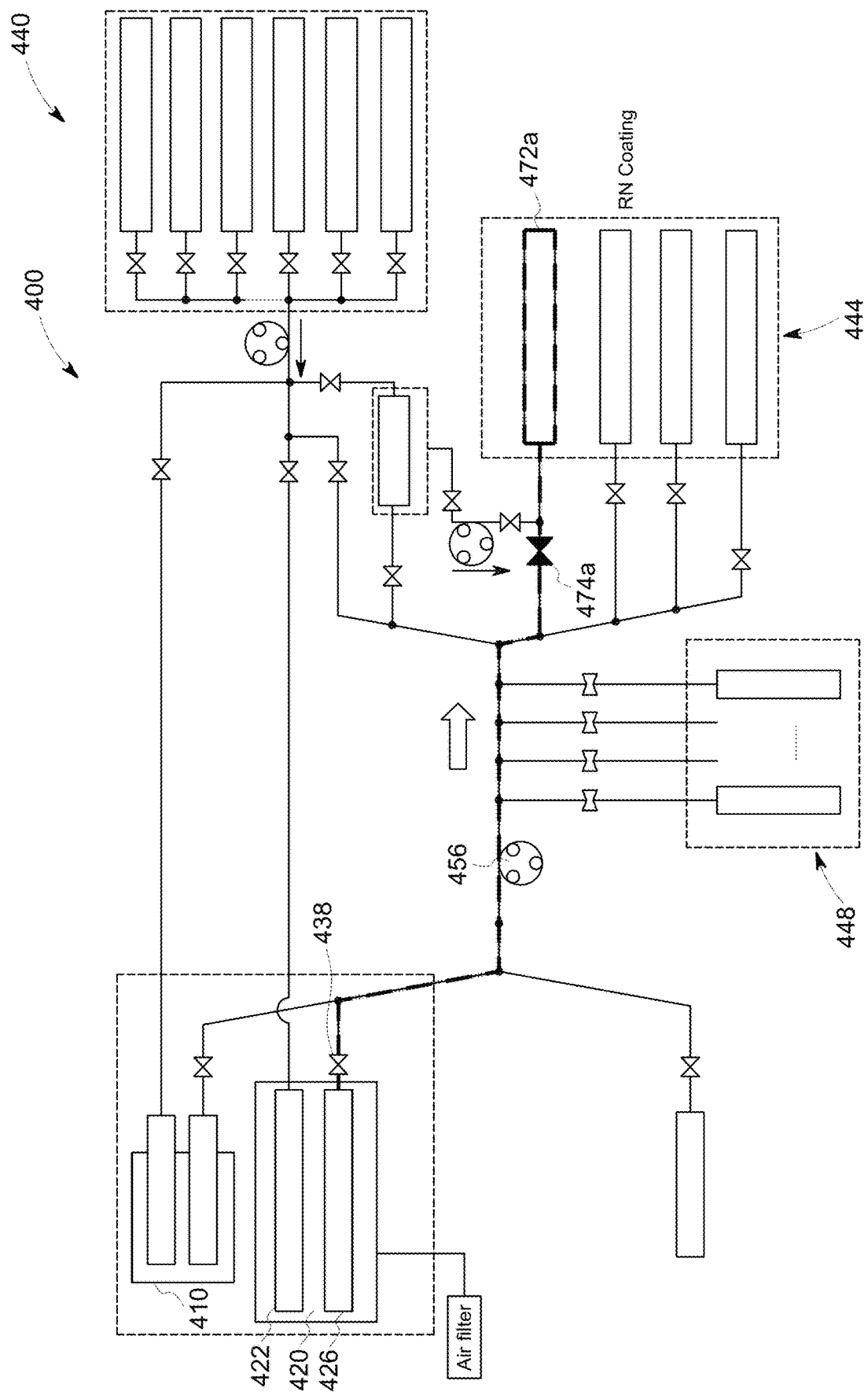

Turning now to FIG. 62 after a defined period of time, all buffer in the second bioreactor vessel 420, is drained to the waste reservoir 472*a* of the second fluid assembly 444 by opening valves 438 and 474*a* and actuating the interconnect line pump 456.

Figure 63:
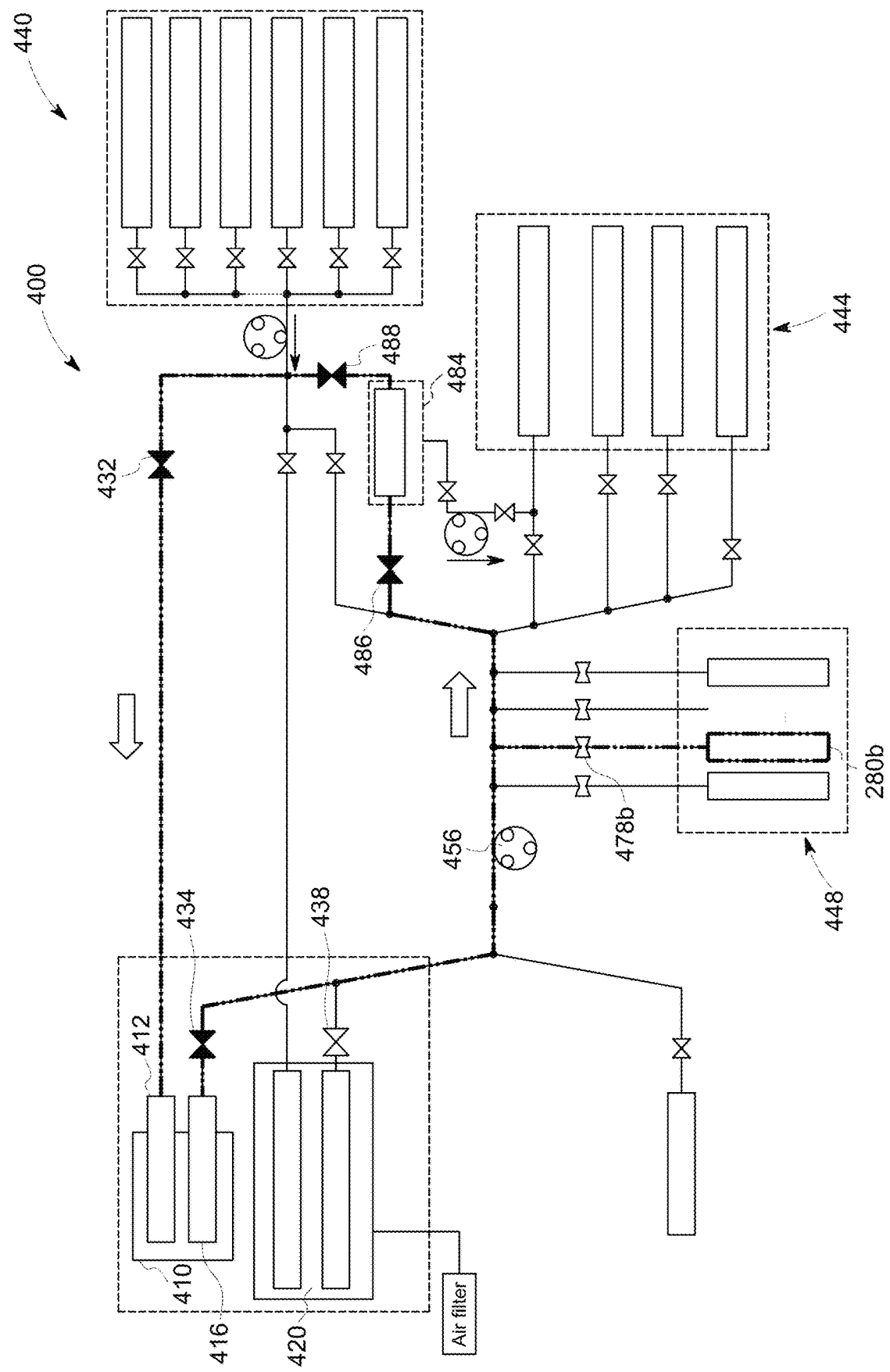

At this point, as shown in FIG. 63, a post-activation pre-concentration sample may be taken of the cells in the first bioreactor vessel 410. As shown therein, valves 434, 486, 488 and 432 are opened and pump 456 actuated to circulate the solution in the first bioreactor vessel 410 out of the second port 434, through the interconnect line, through the filtration line 48 and filter 484, through the first bioreactor line 414 of the first bioreactor vessel 410, and back to the first bioreactor vessel 410 through the first port 412. To take a sample, a second sample vessel 280*b* (e.g., a dip tube, syringe, etc.) is connected to the second sample tubing tail 476*b* and valve 478*b* is opened to divert some of the flow through the interconnect line 450 to the second sample vessel 280*b* for analysis.

Figure 64:
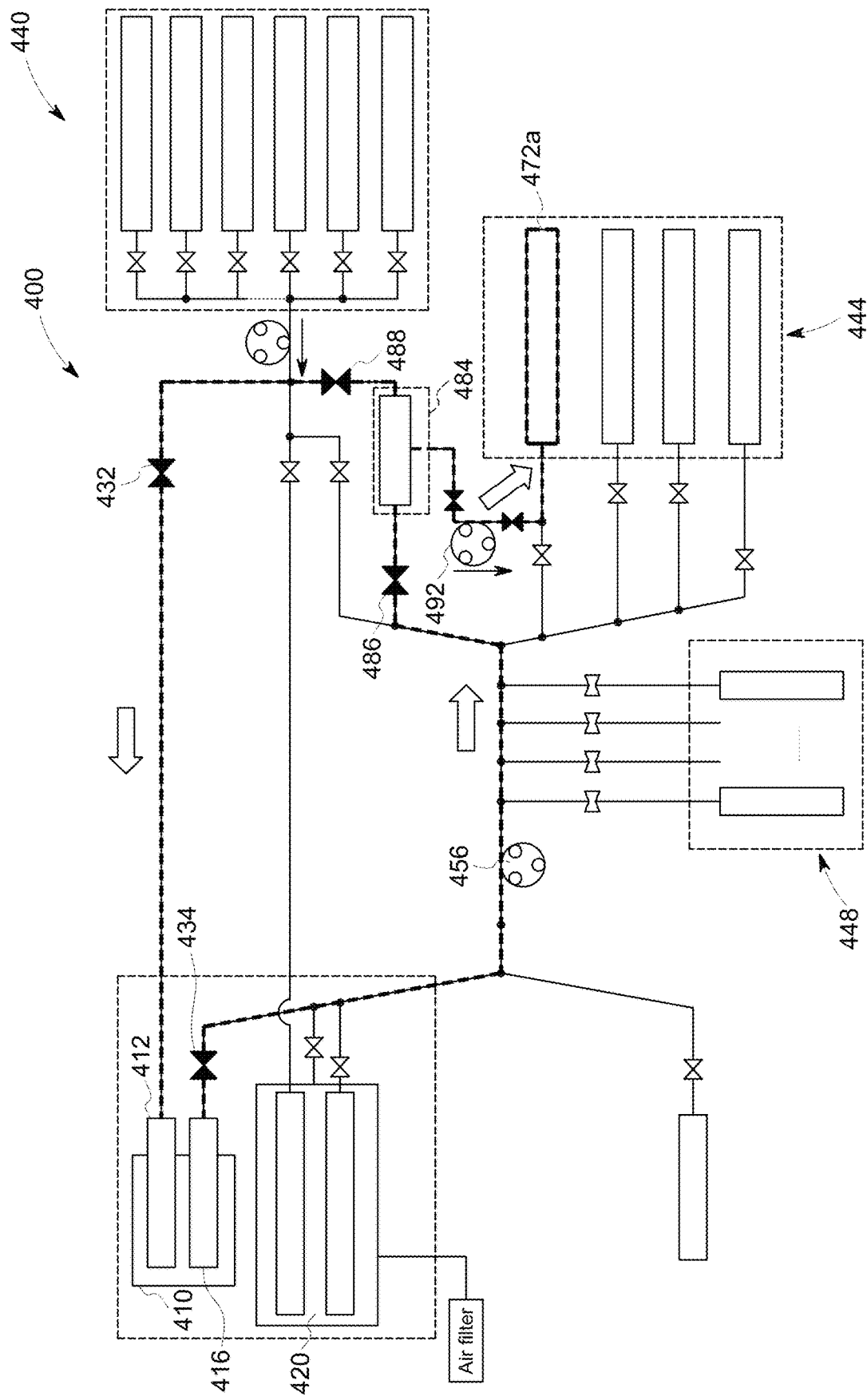

Referring now to FIG. 64, and depending on the concentration obtained from the sample, concentration may be carried out by circulating the contents of the first bioreactor vessel 410 trough the filter 484. As discussed above, this is accomplished by opening valves 434, 486, 488 and 432 and actuating pump 456, which causes circulation of the solution in the first bioreactor vessel 410 out of the second port 416, through the second bioreactor line 418, through the interconnect line 450, through the filtration line 482 and filter 484, through the first bioreactor line 414 of the first bioreactor vessel 410, and back to the first bioreactor vessel 410 through the first port 412. As the fluid passes through the filter 484, waste is removed and permeate pump 492 pumps such waste to the waste reservoir 472*a* of the second fluid assembly 444 through waste line 490. In an embodiment, this procedure is repeated until the volume in the first bioreactor vessel 410 is concentrated to a predetermined volume.

Figure 65:
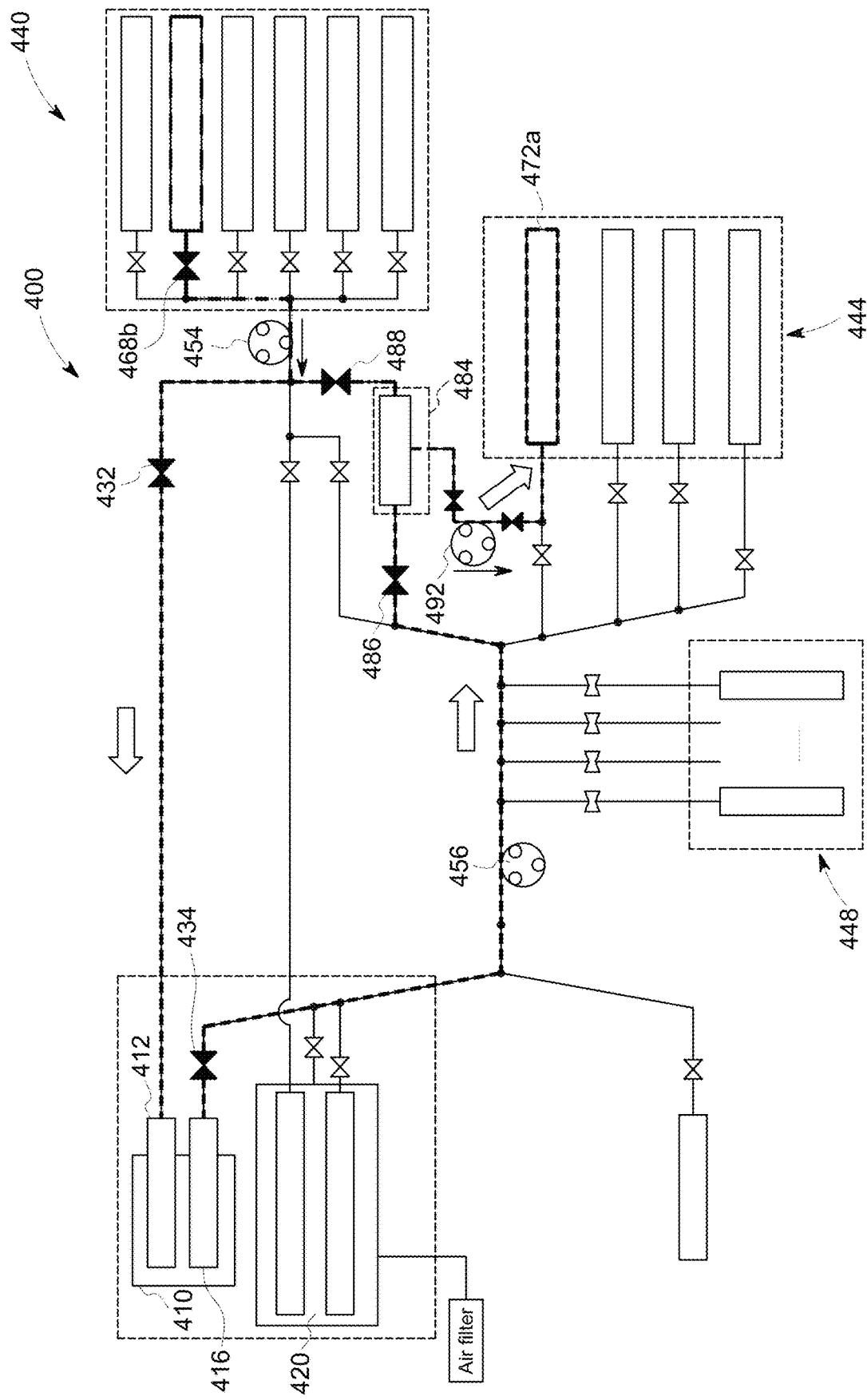

Turning to FIG. 65 after concentration, the concentrated cell population in the activation vessel (i.e., first vessel 410 containing a concentrated cell population) is washed at constant volume through perfusion. In particular, as shown therein, media from a media bag 466*b* of the first fluid assembly 440 is pumped into the first bioreactor vessel 410 through first port 412 through the interconnect line 450 at the same time as media is pumped out of the first bioreactor vessel 410 though the second port 416 such that a constant volume is maintained in the first bioreactor vessel 410. As the media is added and removed from the vessel 410, waste may be filtered out by filter 484 and directed to the waste reservoir 472*a*.

Figure 66:
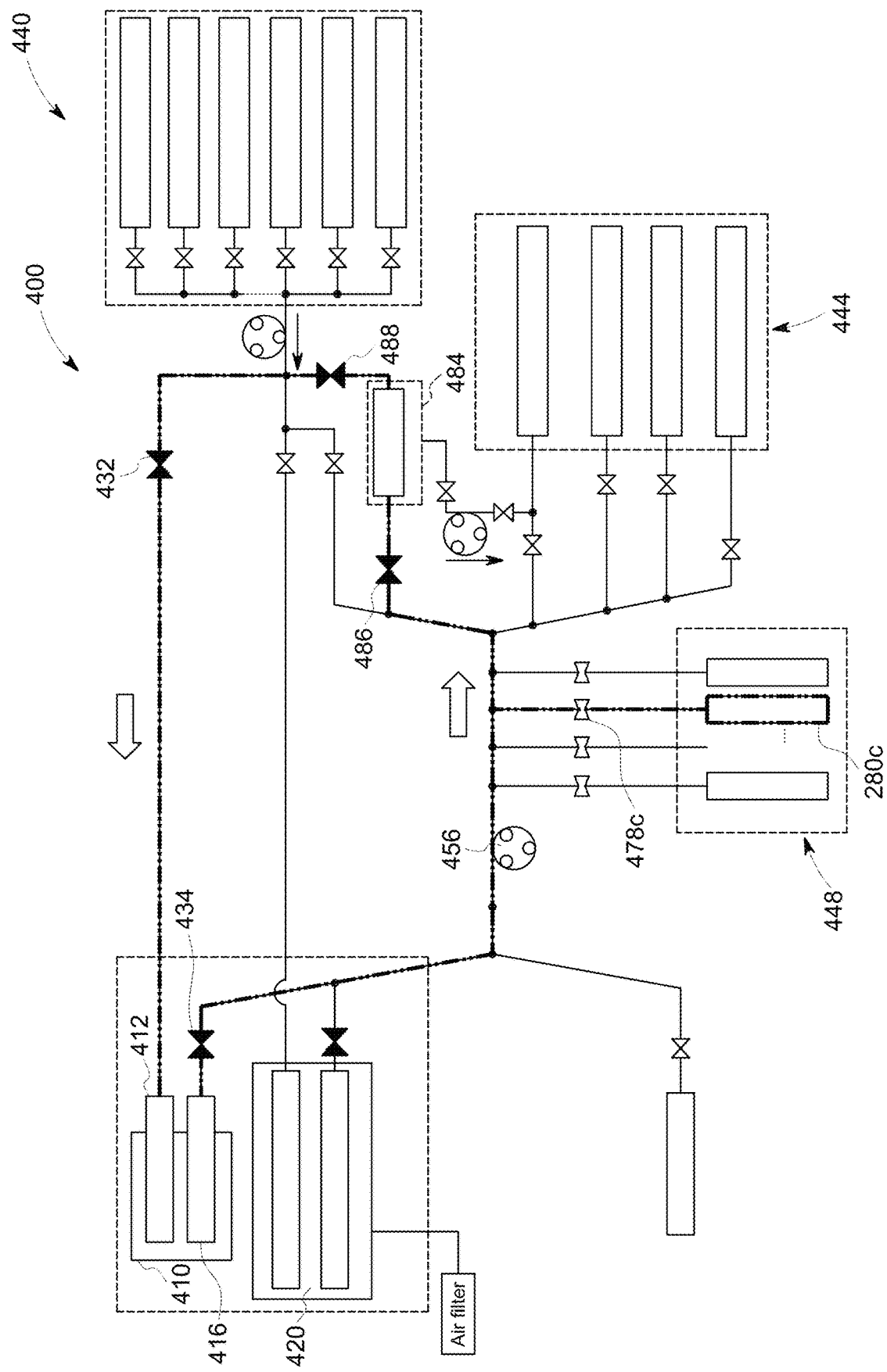

A post-wash sample may be taken of the cells in the first bioreactor vessel 410 in a manner similar to that previously described for pre-concentration sampling. In particular, as shown in FIG. 66, valves 434, 486, 488 and 432 are opened and pump 456 actuated to circulate the fluid in the first bioreactor vessel 410 out of the second port 434, through the interconnect line, through the filtration line 48 and filter 484, through the first bioreactor line 414 of the first bioreactor vessel 410, and back to the first bioreactor vessel 410 through the first port 412. To take a sample, a third sample vessel 280*c* (e.g., a dip tube, syringe, etc.) is connected to the third sample tubing tail 476*c* and valve 478*c* is opened to divert some of the flow through the interconnect line 450 to the third sample vessel 280*c* for analysis.

Figure 67:
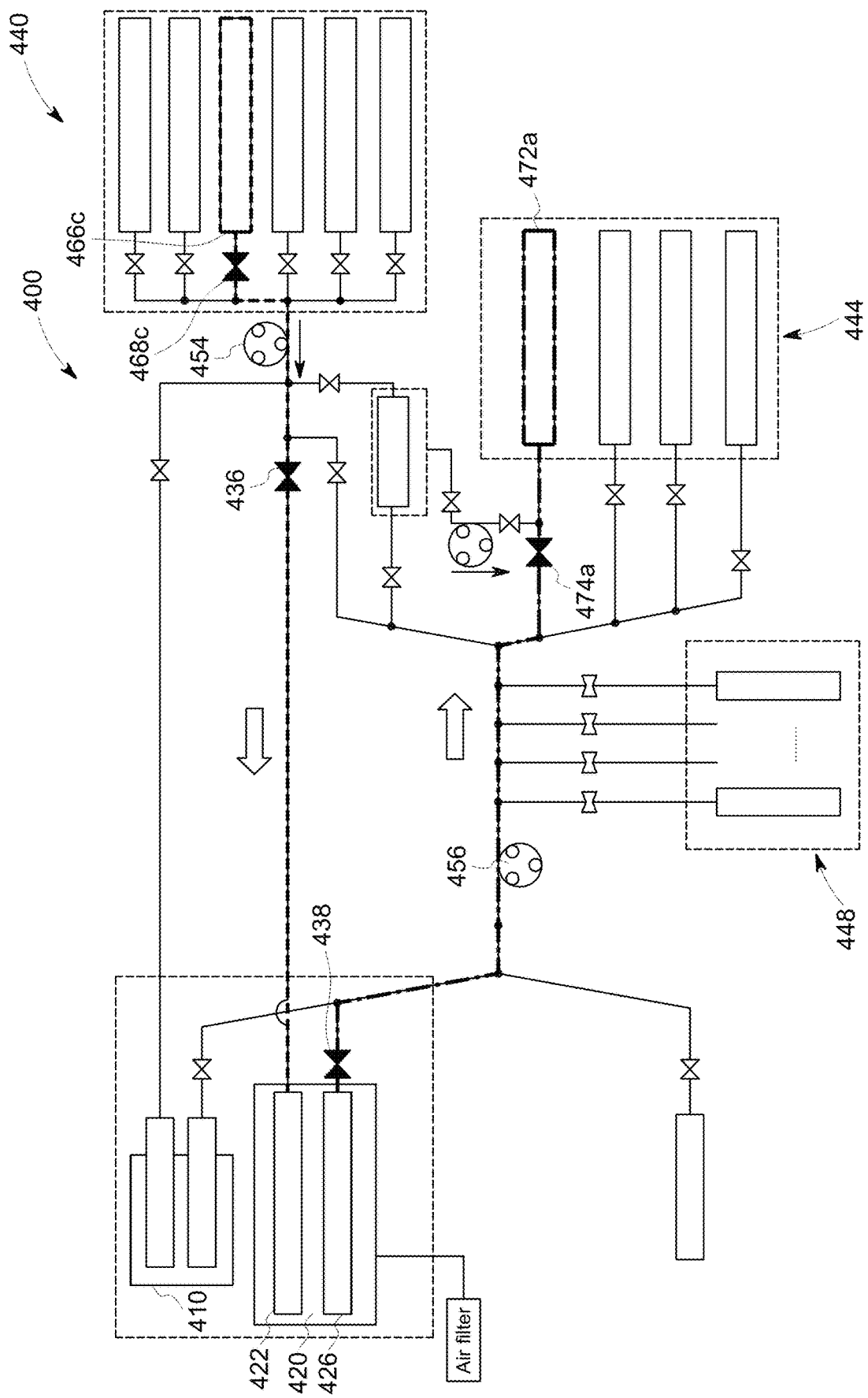

As shown in FIG. 67, a bag containing a thawed viral vector is connected to the first fluid assembly 440, such as through tubing tail 464*c*. Valves 468*c* and 436 are then opened and pump 454 actuated to transfer the viral vector coating solution from the bag 466*c* to the second bioreactor vessel 420 through first port 422. Incubation is then carried out for a predetermined period of time, for virus coating of the second bioreactor vessel 420. Subsequent to incubation, the viral vector coating solution is drained from the second bioreactor vessel 420 to the waste reservoir 472*a* by opening valves 438 and 474*a* and actuating the circulation line pump 456. In embodiments, viral and non-viral vectors can be utilized as agents for transduction/genetic modification.

Figure 68:
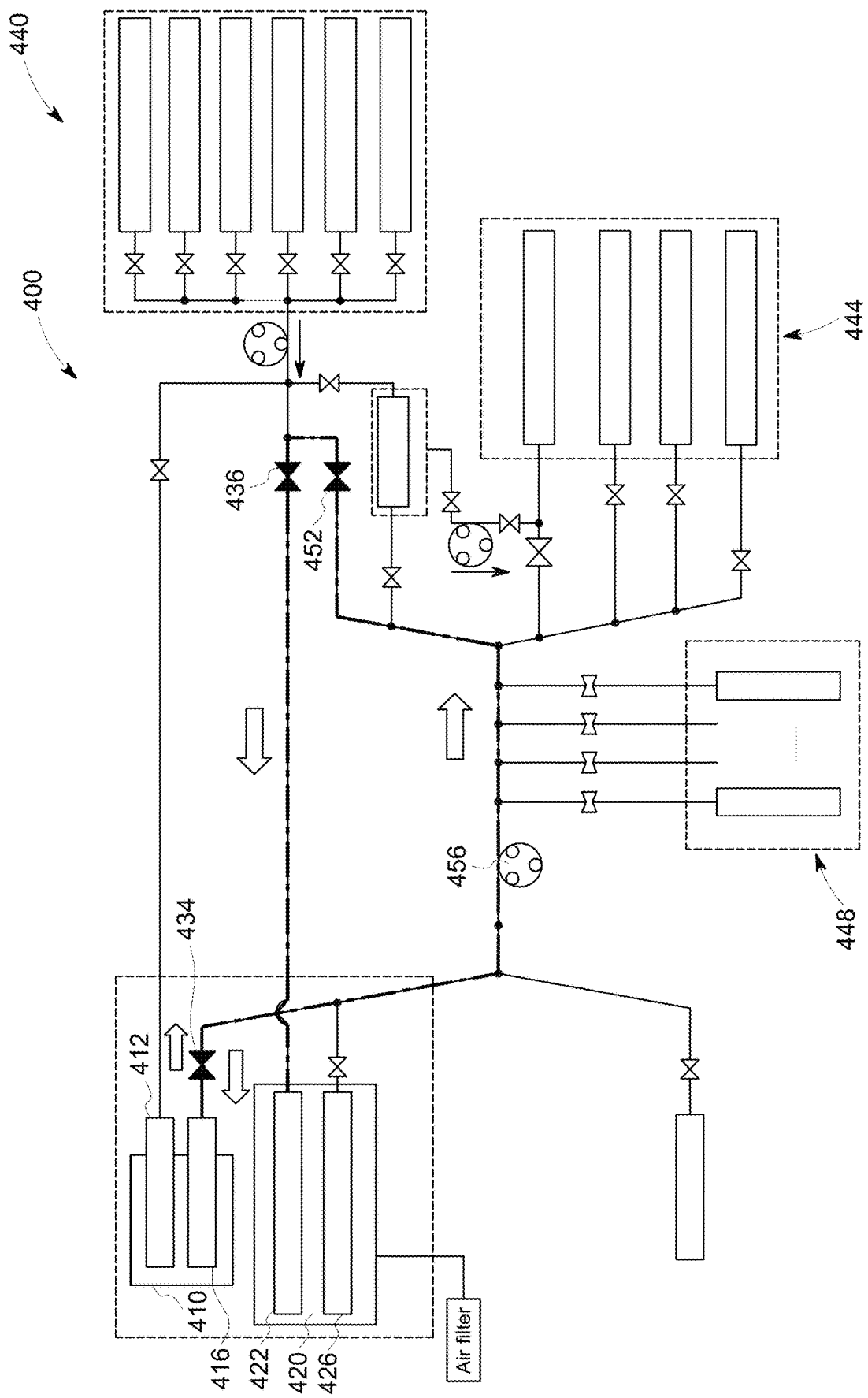

As illustrated in FIG. 68, after the second bioreactor vessel 420 is coated with the viral vector, the post-wash cells from the first bioreactor vessel 410 are transferred to the second bioreactor vessel 420 for transduction/genetic modification. In particular, valves 434, 452 and 436 are opened and the circulation line pump 456 is actuated to pump the cells out of the first bioreactor vessel 420 through the second port 416 of the first bioreactor vessel 410, through interconnect line 450, to the first bioreactor line 424 of the second bioreactor vessel 420, and into the second bioreactor vessel 420 through the first port 422 of the second bioreactor vessel 420.

Figure 69:
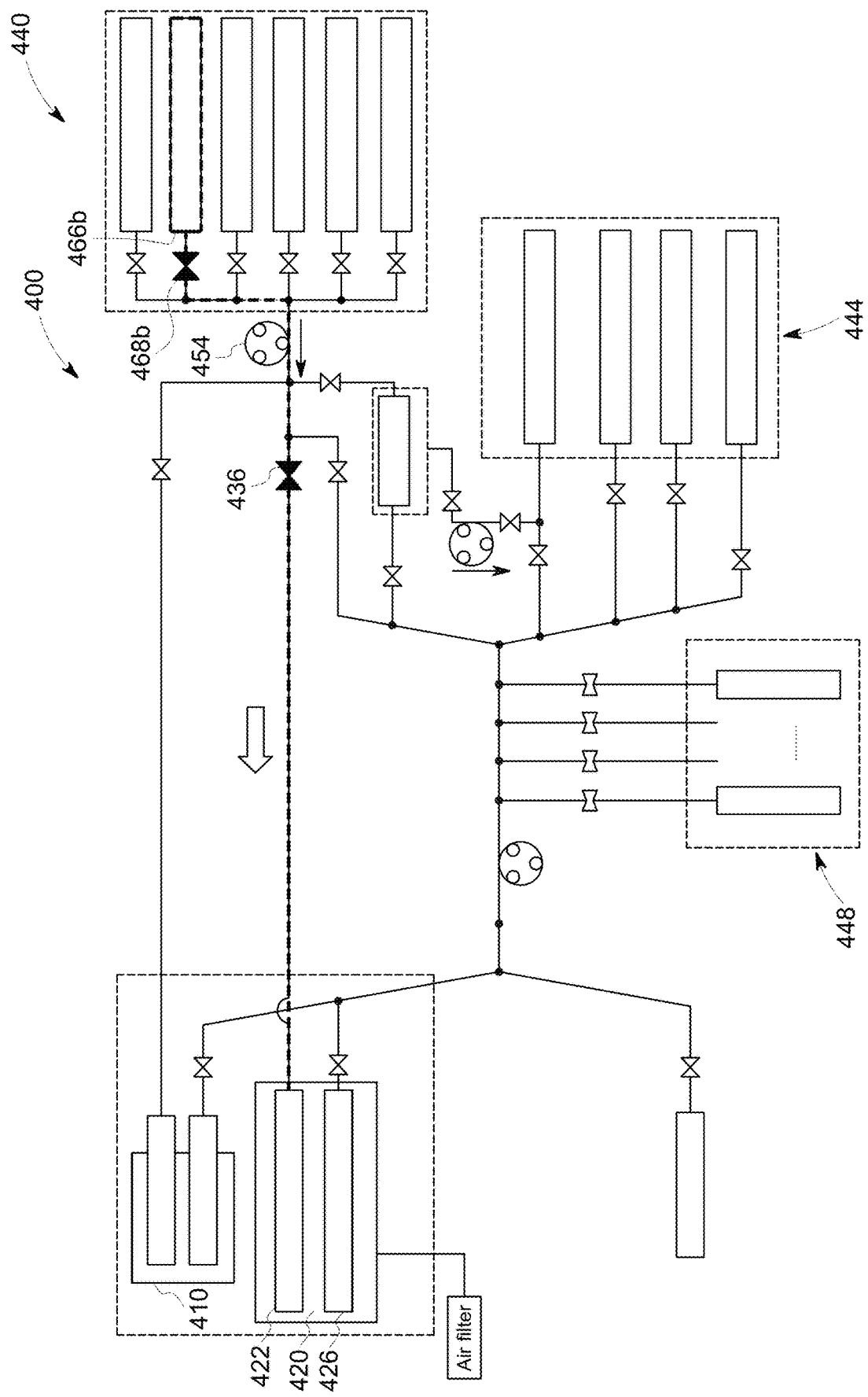
Figure 70:
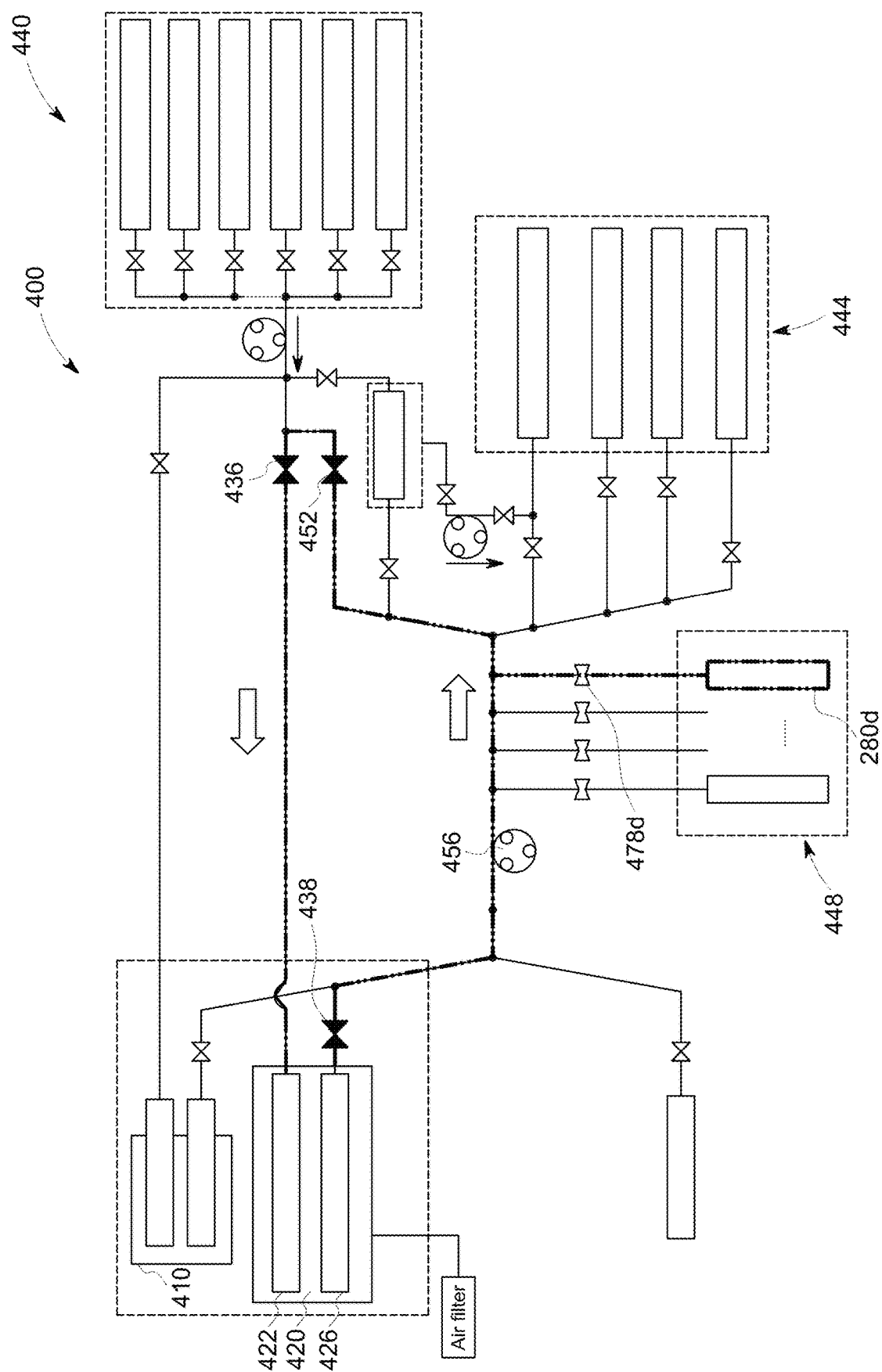

Media from media bag 466*b* is then added to the second bioreactor vessel 420 by opening valves 468*b* and 436 and actuating pump 454 to increase the total volume of the solution in the second bioreactor vessel 420 to a predetermined volume, as illustrated in FIG. 69. With reference to FIG. 70, a pre-transduction sample may then be taken by opening valves 438, 452 and 436 and actuating the circulation line pump 456 to pump the solution in the second bioreactor vessel 420 along a circulation loop of the second bioreactor vessel (i.e., out of the second port 426, through the interconnect line 450, and back to the second bioreactor vessel 420 through the first bioreactor line 414 and first port 422 of the second bioreactor vessel 420). To take a sample, a fourth sample vessel 280d (e.g., a dip tube, syringe, etc.) is connected to the fourth sample tubing tail 476d and valve 478d is opened to divert some of the flow through the interconnect line 450 to the fourth sample vessel 280d for analysis.

Figure 71:
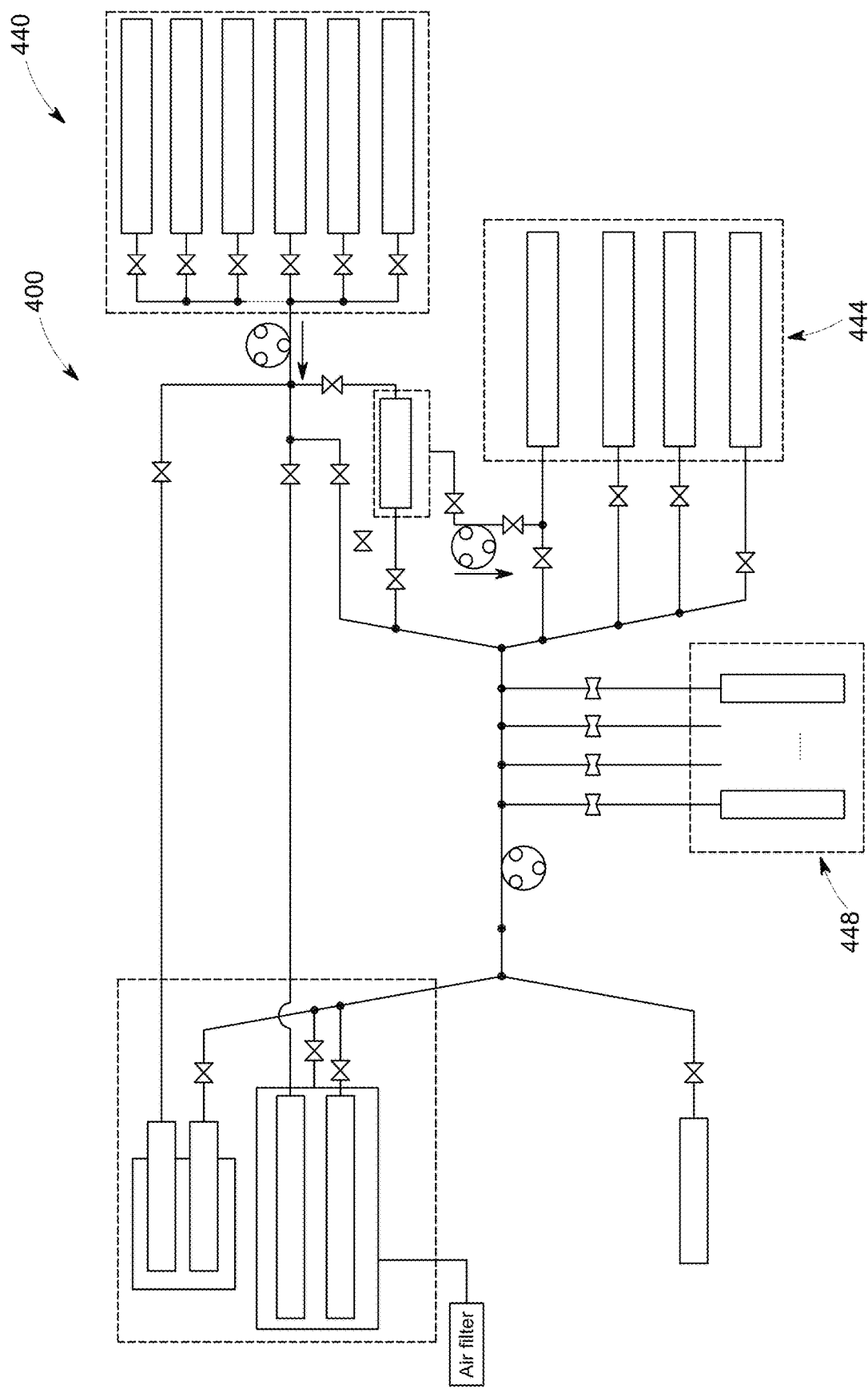

If analysis of the fourth sample taken indicates that all parameters are within predetermined ranges required for successful transduction, then the population of cells within the second bioreactor vessel 420 is incubated for a predetermined period of time for transduction of the population of cells in solution, as illustrated in FIG. 71. For example, in an embodiment, the population of cells in the second bioreactor vessel 420 may be incubated for 24 hours for transduction.

Figure 72:
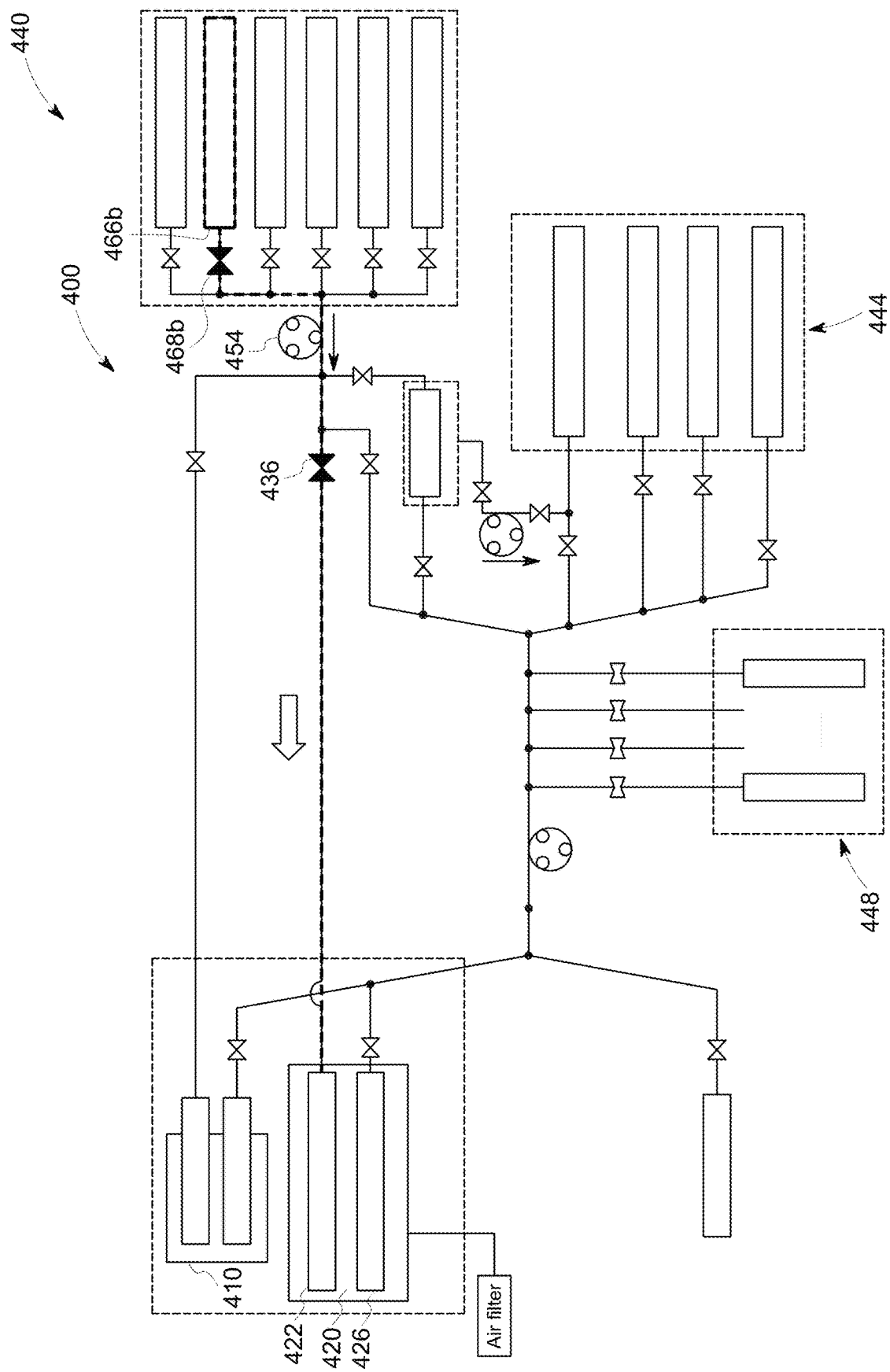

With reference to FIG. 72, after transduction, media is added to the second bioreactor vessel 420 to achieve a predetermined expansion volume in the second bioreactor vessel 420. As shown therein, to add media, valves 468b and 436 are opened and pump 454 is actuated to pump growth/perfusion media from media bag 466b to the second bioreactor vessel 420 through the first port 422 of the second bioreactor vessel until the predetermined expansion volume is reached.

Figure 73:
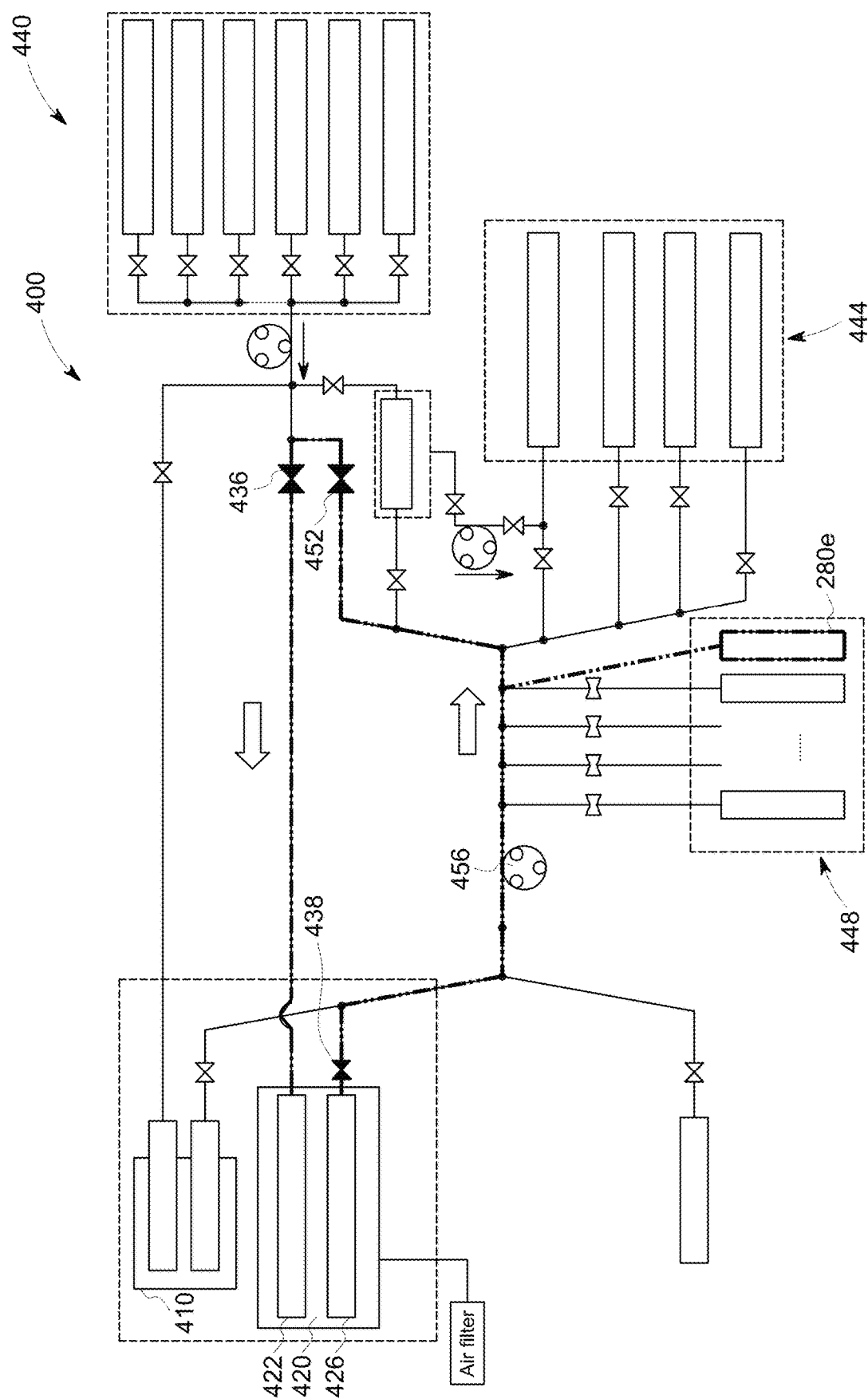

As illustrated in FIG. 73, a pre-expansion sample may then be taken by opening valves 438, 452 and 436 and actuating the circulation line pump 456 to pump the solution in the second bioreactor vessel 420 along the circulation loop of the second bioreactor vessel 420, as indicated above (i.e., out of the second port 426, through the interconnect line 450, and back to the second bioreactor vessel 420 through the first bioreactor line 414 and first port 422 of the second bioreactor vessel 420). To take a sample, a fifth sample vessel 280e (e.g., a dip tube, syringe, etc.) is connected to the fifth sample tubing tail 476e and valve 478e is opened to divert some of the flow through the interconnect line 450 to the fifth sample vessel 280e for analysis.

If analysis of the fifth sample taken indicates that all parameters are within predetermined ranges required for successful expansion of the population of cells, then the population of cells within the second bioreactor vessel 420 is incubated for a predetermined period of time, e.g., 4 hours, to let the cells settle.

Figure 74:
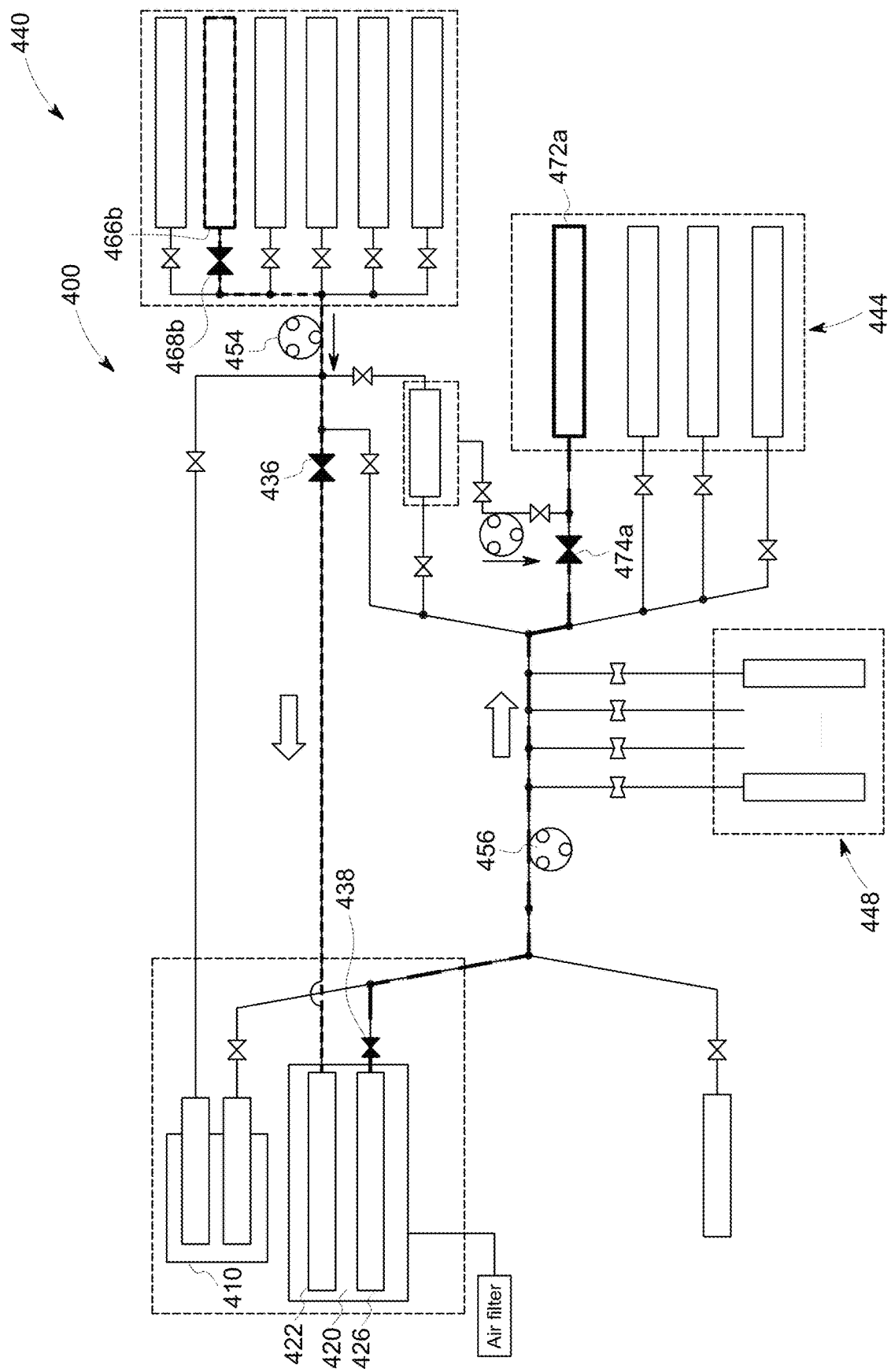

Subsequent to this incubation period or at a later predetermined time, perfusion at a rate of 1 volume per day (1× perfusion) is carried out by pumping media from media bag 466b into the second bioreactor vessel 420 through first port 422 at the same time as spent/used media is pumped out of the second bioreactor vessel 420 though the second port 426 (and through interconnect line 450 to the waste reservoir 472a), as shown in FIG. 74. This perfusion is accomplished by opening valves 468b, 436, 438 and 474a, and actuating the first pump 454 and circulation line pump 456. During this 1× perfusion, the media from media bag 466b is introduced into the second bioreactor vessel 420 at substantially the same rate as used media is removed from the second bioreactor vessel 420 and sent to waste, to maintain a substantially constant volume within the second bioreactor vessel 420.

Figure 75:
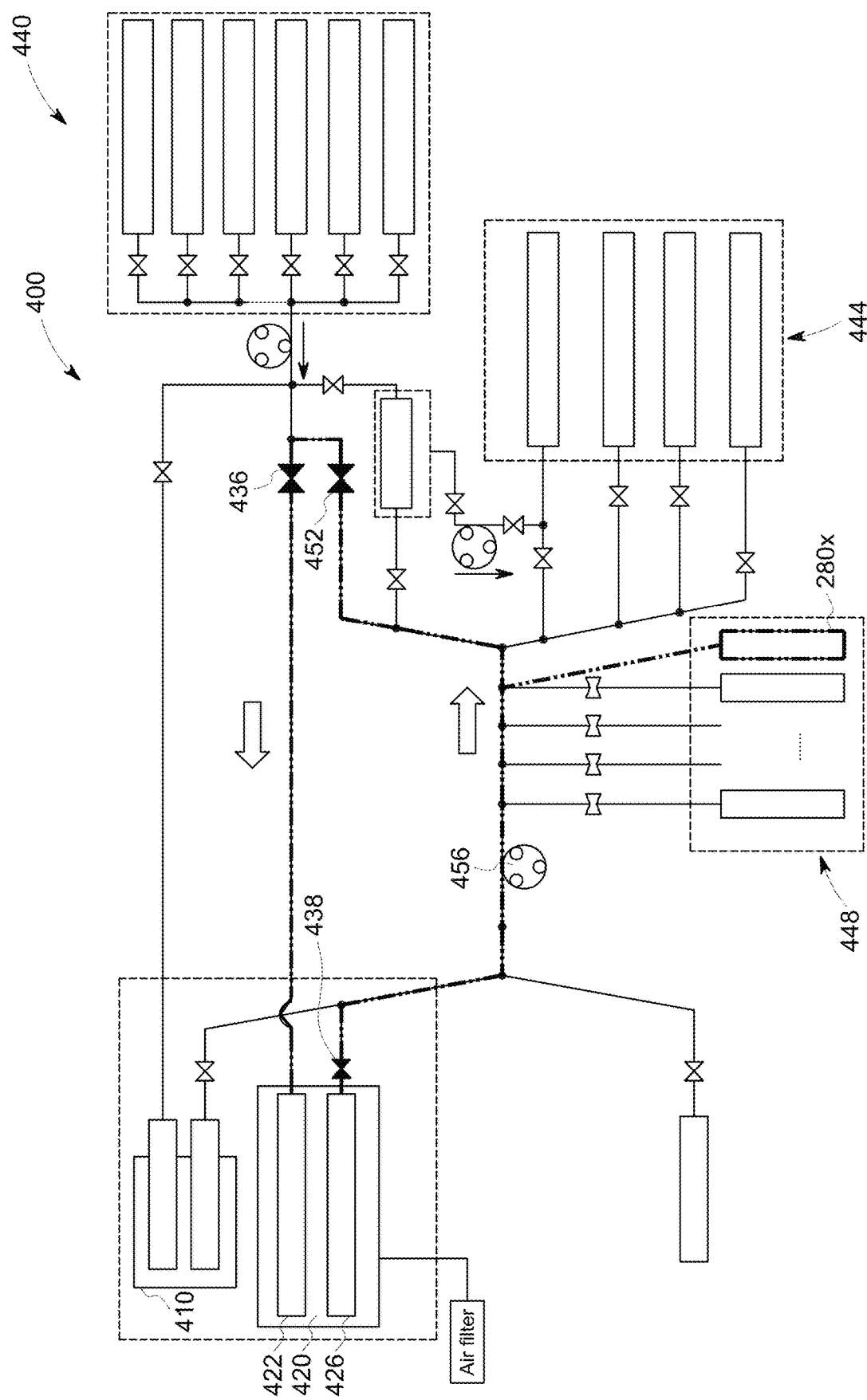

Sampling may then be carried out as needed/desired to monitor the expansion process and/or to determine when a desired cell density is reached. As discussed above, samples may be taken by opening valves 438, 452 and 436 and actuating the circulation line pump 456 to pump the solution in the second bioreactor vessel 420 along the circulation loop of the second bioreactor vessel 420, as indicated above (i.e., out of the second port 426, through the second bioreactor line 428, through the interconnect line 450, and back to the second bioreactor vessel 420 through the first bioreactor line 424 and first port 422 of the second bioreactor vessel 420). To take a sample, another sample vessel 280x (e.g., a dip tube, syringe, etc.) is connected to a sample tubing tail of the sample assembly 448 and a valve of the tubing tail is opened to divert some of the flow through the interconnect line 450 to the sample vessel 280x for analysis, as shown in FIG. 75. After each sampling operation, incubation without perfusion is carried out for a predetermined time period, e.g., four hours, to allow the cells to settle before restarting perfusion.

Figure 76:
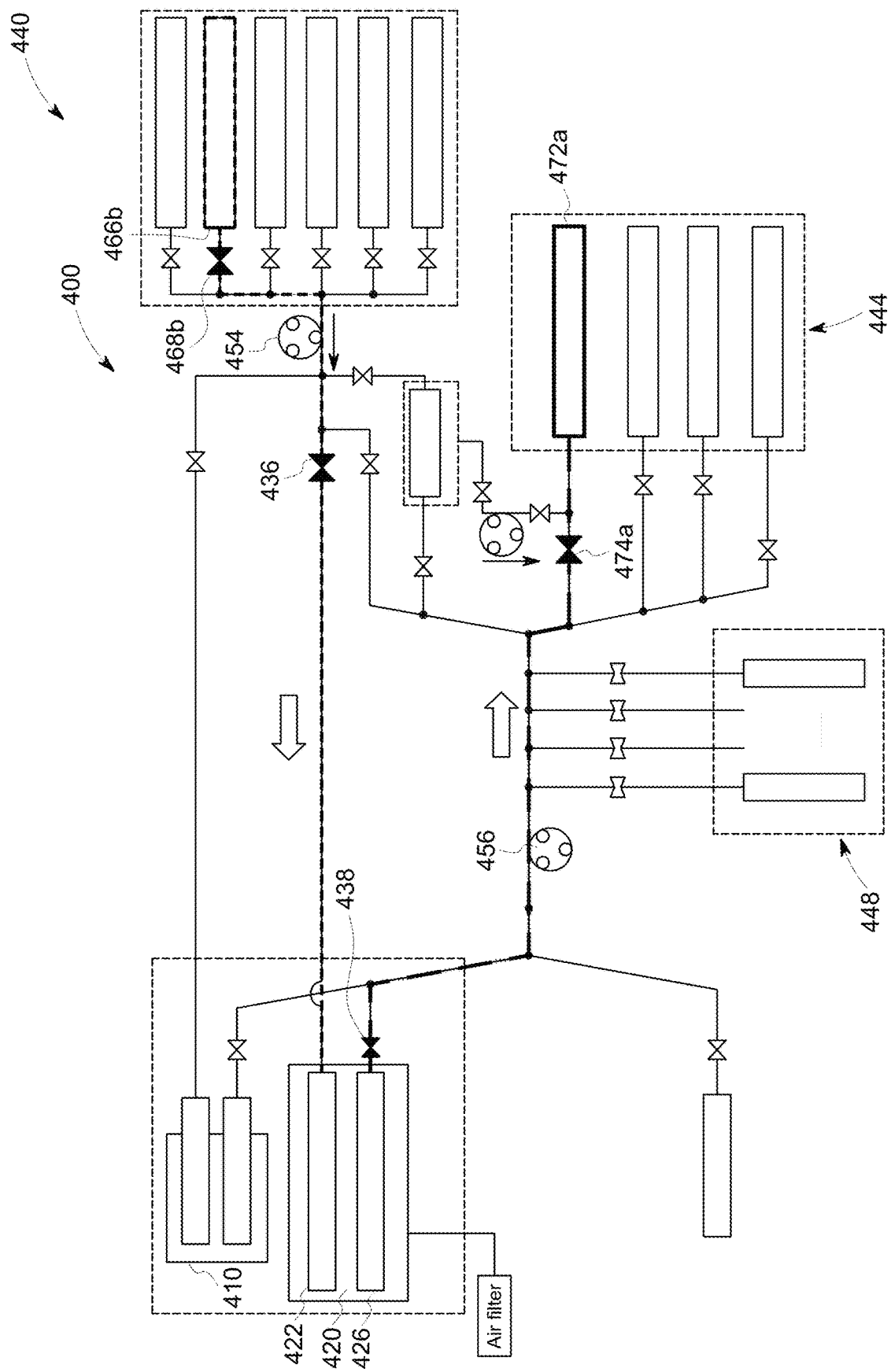

As shown in FIG. 76, Subsequent to this incubation period, perfusion at a rate of 1 volume per day (1× perfusion) is carried out by pumping media from media bag 466b into the second bioreactor vessel 420 through first port 422 at the same time as spent/used media is pumped out of the second bioreactor vessel 420 though the second port 426 (and through interconnect line 450 to the waste reservoir 472a), as shown in FIG. 74. This perfusion is accomplished by opening valves 468b, 436, 438 and 474a, and actuating the first pump 454 and circulation line pump 456.

When sampling indicates a viable cell density (VCD) of a predetermined threshold value (e.g., 5 MM/mL), perfusion at a rate of 2 volumes per day (2× perfusion) is carried out by pumping media from media bag 466b into the second bioreactor vessel 420 through first port 422 at the same time as spent/used media is pumped out of the second bioreactor vessel 420 though the second port 426 (and through interconnect line 450 to the waste reservoir 472a), as shown in FIG. 76. This perfusion is accomplished by opening valves 468b, 436, 438 and 474a, and actuating the first pump 454 and circulation line pump 456. During this 2× perfusion, the media from media bag 466b is introduced into the second bioreactor vessel 420 at substantially the same rate as used media is removed from the second bioreactor vessel 420 and sent to waste, to maintain a substantially constant volume within the second bioreactor vessel 420.

Finally, with reference to FIG. 77, after a desired, viable cell density is achieved, the cells may be harvested by opening valves 438 and 474d and actuating the circulation line pump 456. The expanded population of cells is then pumped out of the second bioreactor vessel 420 through the second port 426, through interconnect line 450, and to a collection bag 472d connected to the tubing tail 470d of the second tubing assembly 444. These cells can then be formulated in a manner heretofore known in the art for delivery and infusion into a patient.

The second module 200 of the bioprocessing system 10, and the flow architecture 400 and bioreactor vessels 410, 420 thereof, therefore provides for a flexible platform on which a variety of bioprocessing operations may be carried out in a substantially automated and functionally closed manner. In particular, while FIGS. 53-77 illustrate an exemplary generic protocol that can be carried out using the bioprocessing system 10 of the invention (particularly, using the second module 200 thereof), the system is not so limited in this regard. Indeed, various automated protocols can be enabled by the system of the invention, including a number of customer-specific protocols.

In contrast to existing systems, the second module 200 of the bioprocessing system 10 is a functionally-closed, automated system that houses the first and second bioreactor vessel 410, 420 and the fluid handling and fluid containment systems, which are all maintained at cell-culture friendly environmental conditions (i.e., within a temperature and gas-controlled environment) to enable cell activation, transduction and expansion. As discussed above, the system includes automated kit loading and closed sampling capability. In this configuration, the system enables all steps of immune cell activation, transduction, expansion, sampling, perfusion and washing in a single system. It also provides the user the flexibility of combining all steps in a single bioreactor vessel (e.g., first bioreactor vessel 410) or using both of the bioreactor vessels 410, 420 for end-to-end activation and washing. In an embodiment, a single expansion bioreactor vessel (e.g., bioreactor vessel 420) is capable of robustly generating a dose of billions of T cells. Either single or multiple doses can be generated in situ with high recovery and high viability. In addition, the system is designed to give the end-user the flexibility of running different protocols for the manufacture of genetically modified immune cells.

Some of the commercial advantages provided by the bioprocessing system of the invention include robust and scalable manufacturing technology for product commercialization by simplifying workflows, reducing labor intensity, reducing the burden on clean room infrastructure, reducing failure nodes, reducing costs and the ability to increase scale of operations.

As discussed above in connection with the generic workflow, the system of the invention, the bioprocessing system 10, and the flow architecture 400 and bioreactor vessels 410, 420 of the second module 200 provide for culture concentration, washing, slow perfusion, fast perfusion, and 'round robin' perfusion processes to be carried out in an automated and functionally-closed manner. For example, as discussed above, the pump 456 on the interconnect line 450 can be used to circulate the fluid from one of the ports of the bioreactor through the filtration line 482 and filter 484 and then back to another port on the bioreactor, while running the permeate pump 492 (typically at a percentage of the circulation pump 456, such as for example, about 10%], in a concentration step. The concentration can be run open loop, or can be stopped based on a measured volume removed from the bioreactor or a measured volume accumulated in the waste. In an embodiment, the filter, pump speeds, filter area, number of lumens, etc. are all sized appropriately for total number of cells and target cell density to limit fouling and excessive cell loss due to shear.

In an embodiment, and as discussed above, the system of the invention can also be used for washing, e.g., to remove residuals such as remaining viral vector after incubation. Washing involves the same steps described above for concentration, except the pump 454 on the first fluid assembly line 442 is used to pump in additional culture media to replace the fluid pumped from the permeate waste pump 492. The rate of introduction of new medium can correspond to the rate of removal of fluid by the permeate pump 492. This allows for a constant volume to be maintained in the bioreactor vessel, and residuals can be removed exponentially with time so long as the contents in the bioreactor are well mixed (circulation may suffice). In embodiments, this same process can be utilized post activation for the in-situ hollow fiber filtration-based washing of the cell suspension to remove residuals. For coated and non-coated surfaces, the soluble activation reagent washout can also be done via filter-based perfusion.

As also discussed above, the pump 454 on the first fluid assembly line 442 can be used to add media to a given bioreactor vessel while the pump 456 on the interconnect line 450 is used to move spent media to the waste bag in the second fluid assembly, in a perfusion process. In an embodiment, gravity can be used to settle the cells, and the spent media can be pumped out at such a rate so as not to significantly disturb the cells within the bioreactor vessel. This process may involve running the pumps 454 and 456 open loop at the same rate. In an embodiment, one pump (454 or 456) may be run at a set rate, and the rate of the other pump may be adjusted based on the mass/volume of the bioreactor vessel or the mass/volume of the waste bag (or the mass/volume of a measured source bag).

In connection with the above, it is contemplated that pump control may be based on a weight measurement of the bioreactor vessels (using the feedback from the load cells 760). For example, the configuration of the system enables on-the-fly pump calibration based on load cell readings, allowing the system to automatically accommodate changes in the tube/pump performance over time. Further, this method can be used for closed loop control on a mass (volume) rate of change when emptying or filling a bioreactor vessel.

Figure 81:
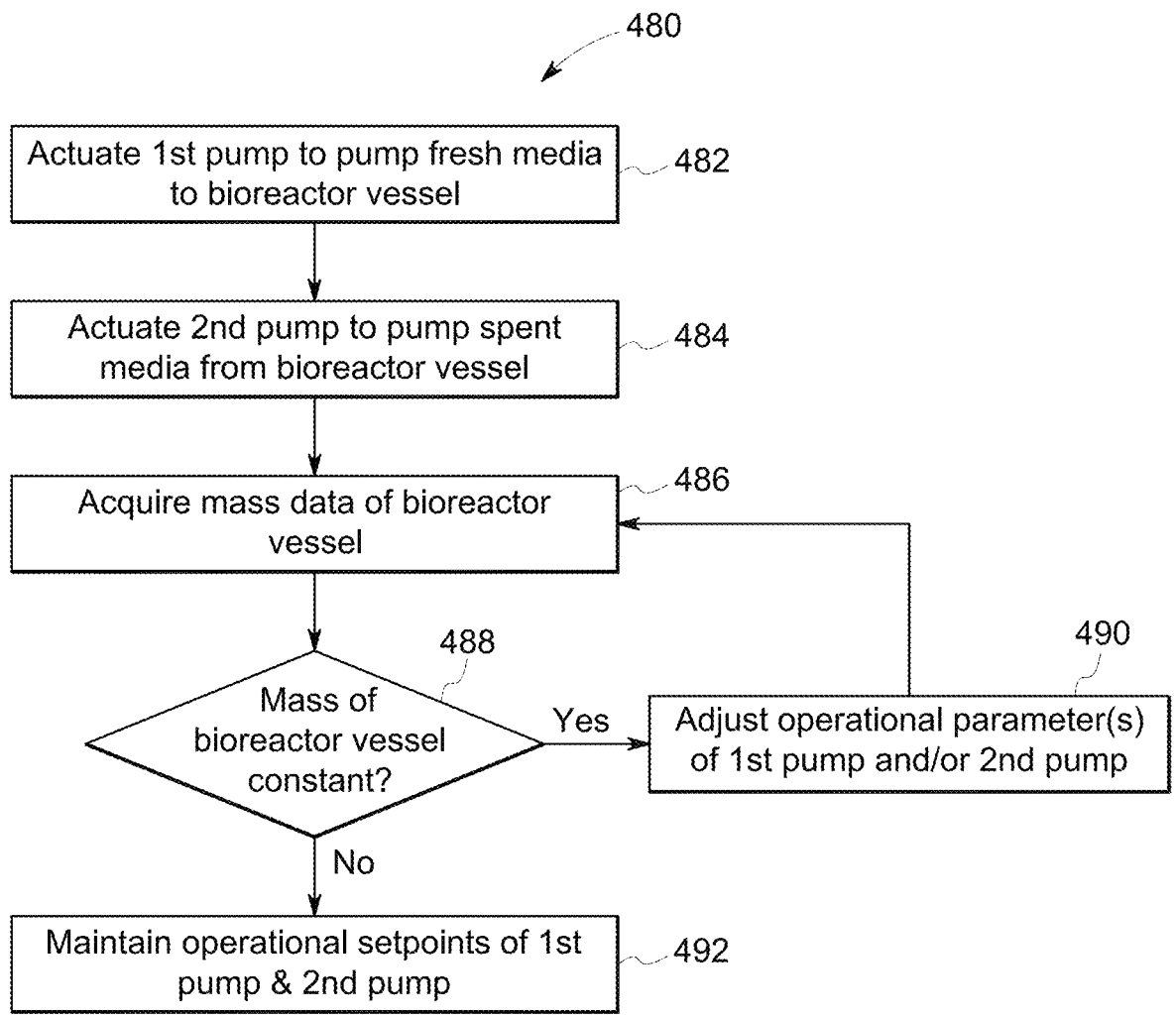
FIG. 81 is a flowchart of a method of bioprocessing using the system of FIG. 1, in accordance with an embodiment of the present invention.

FIG. 81 illustrates one exemplary embodiment of a method 480 of utilizing the second module 200 in a perfusion process. The method 480 includes activating a first pump 454 to pump fresh media to the bioreactor vessel 410 containing a genetically modified population of cells, at 482, activating a second pump 456 to pump spent media from the bioreactor vessel 410 to a waste bag 472*a*, at 484, acquiring mass data relating to a mass of the bioreactor vessel (e.g., bioreactor vessel 410) using the load cells associated with the bed plate, at 486, determining whether or not the mass of bioreactor vessel 410 has changed or remains substantially constant, at 488, and if the mass of the bioreactor vessel has changed, adjusting an operational parameter of at least one of the first pump and the second pump to maintain a substantially constant mass of the bioreactor vessel 410, at 490. For example, if it is determined that the mass of the bioreactor vessel 410 has decreased, this indicates that the spent media is being removed from the bioreactor vessel at a rate greater than the rate of addition of fresh media to the bioreactor vessel. Accordingly, and in response, the flow rate of the first pump may be increased and/or the flow rate of the second pump may be decreased to maintain a substantially constant mass (and volume) in the bioreactor vessel 410. Further mass data may then be acquired and further adjustments to pump operation made, if necessary, to maintain a substantially constant mass/volume in the bioreactor vessel 410. If the mass is determined to be substantially constant after some period of time of operation of the first and second pumps, the pumps may be maintained at their current operational setpoints (e.g., flow rates), as shown at 492.

In another embodiment, the bioprocessing system allows for round-robin perfusion of the various bioreactor vessels in the system using the flow architecture 400. For example, the circulation pump 456 and the pump 545 along the first fluid assembly line 442 are used to perfuse cells within the first bioreactor vessel 410 in conjunction with the appropriate pinch valve states, as described above. Perfusion of the cells within the first bioreactor vessel 410 may then be ceased or paused, and then the circulation pump 456 and the pump 454 and appropriate pinch valves may be actuated to perfuse cells within the second bioreactor vessel 420. In this respect, perfusion of the various bioreactors can be performed sequentially (i.e., perfusion of the first bioreactor vessel 410 for a period of time, then perfusion of the second bioreactor vessel 420 for period of time, in a repeating and alternating manner). This allows for perfusion of any number of bioreactor vessels in the system without requiring the use of more pumps, media bags or waste bags.

With round-robin perfusion, the pumps could run continuously, could be run intermittently together (duty cycle), or could be run sequentially (source, then waste, repeat), so as still maintain the volume/mass in the various bioreactor vessels at about the same level. Round robin perfusion (intermittently running the set of pumps together and waiting an interval of time) would also allow for perfusion of multiple vessels using the same two pumps, as indicated. Further, round robin perfusion allows for a lower effective exchange rate (such as about 1 Vol/day) even if the pumps don't have a great low-end dynamic range. Further, round-robin perfusion also allows each vessel to be perfused with different medium as controlled by the valves in the first fluid assembly 440.

In addition, in an embodiment, fast perfusion can be used for residual removal (e.g., for post activation Ab removal and/or post transduction residual removal). In a fast-perfusion process, the perfusion process described above may be run much faster than the typical 1-5 volumes/day, such as, for example, between about 8-20 volumes/day, or greater than about 20 volumes/day to achieve 1 log reduction in a matter of minutes to hours. In an embodiment, the perfusion rate is balanced against cell loss. In some embodiment, fast perfusion may allow for the elimination of the hollow filter 484 and still meet biological imperatives of quickly removing residuals after certain steps.

As further described above, the system of the invention facilitates rinsing a bag/reservoir connected to the first fluid assembly 440 using a rinse buffer or fluid from another bag/reservoir connected to the second fluid assembly 444 using the pump 454 on the first fluid assembly line 442. In addition, the fluid lines of the flow architecture/system 400 can be cleared with sterile air from the sterile air source 458 to prevent cells from sitting in the lines and dying or to prevent medium or reagents from sitting in the lines and degrade or go unused. The sterile air source 458 can also be used to clear out reagents from the lines so as to ensure that no more reagent is pumped to the bioreactor vessels 410, 420 than intended. The sterile air source 458 can likewise be used to clear lines all the way to the connected bag (of the first or second fluid assembly 440, 444) to clear for sterile tube welding to limit carryover. Alternatively, or in addition to clearing lines using the sterile air source 458, lines may be cleared using air pulled from one of the bioreactor vessels so long as the port through which the air is pulled is not immersed and the bioreactor vessel has an air balance port 530.

As discussed above, the system allows for closed-drawer, in process sampling of the contents of the bioreactor vessel(s). During sampling, the vessel from which the sample is to be pulled may be agitated using the cam arms 762, circulating the contents of the vessel using the circulation line pump 456, and using the sampling assembly 448 to withdraw a sample from the interconnect line 450. In an embodiment, only non-bead bound cells may be agitated.

As also discussed above, the system of the invention allows for the population of cells to be collected after a target cell density is achieved. In an embodiment, collecting the expanded population of transduced cells may include moving cells to one of the bags connected to the second fluid assembly 444 using the pump 456 on the interconnect line 450, or circulating the cells with interconnect pump 456 to move the cells to a bag connected to the first fluid assembly 440. This process could be used for final collection or for a large sample volume, or could be used to fully automate the sampling process (i.e., by connecting a syringe or bag to the first fluid assembly 440, circulating contents of the bioreactor vessel, and pulling in a portion of a desired sample volume from the circulated contents with fluid assembly pump 454 and moving towards syringe/bag). In such a case, the circulation pump 456 and valves can then be used to clear circulation lines of fluid/cells. In addition, the pump 454 on the first fluid assembly line 442 can be used to continue to push all of the aliquoted sample volume to the sample container, using the air in the line to complete to sample transfer to the container without an appreciable amount of cells remaining in the lines.

While the embodiments described above disclose a workflow where activation of cells is carried out in a first bioreactor vessel and the activated cells are transferred to the second bioreactor vessel for transduction and expansion, in an embodiment, the system of the invention may allow for activation and transduction operations to be carried out in a first bioreactor vessel, and expansion of the genetically modified cells carried out in a second bioreactor vessel. Moreover, in an embodiment, the system of the invention may allow for the in-situ processing of isolated T cells wherein the activation, transduction and expansion unit operations are all performed within a single bioreactor vessel. In an embodiment, the invention therefor simplifies existing protocol by enabling a simplified and automation-friendly 'one-pot' activation, transduction and expansion vessel.

In such an embodiment, the T-cell activator may be micron-sized Dynabeads and a lentiviral vector is used for transduction. In particular, as disclosed therein, micron-sized Dynabeads serve the dual purpose of isolating and activating T cells. In an embodiment, activation (and isolation) of the T cells may be carried out in one of the bioreactor vessels 410 using Dynabeads in the manner indicated above. Subsequently, the activated cells are transduced by viruses for genetic modification, such as in the manner described above in connection with FIGS. 60-71. Post-activation and viral transduction, the virus may then be washed out of the bioreactor vessel 410 using the filterless perfusion method described above that retains the cells and the micron-sized Dynabeads in the bioreactor vessel 410. This enables cell expansion in the same bioreactor vessel 410 that is used for activation and transduction. The filterless perfusion method additionally enables the culture wash to take place without the need for first immobilizing the activation beads that need to be retained along with the cells during expansion. In particular, when the virus is washed out, the micron size Dynabeads are not fluidized in the slow perfusion rate and are retained in the vessel. Nanometer sized viral particles and residual macromolecules are fluidized during the slow perfusion and are washed out.

In an embodiment, after expansion, the cells may be harvested in the manner described above in connection with FIG. 77. After harvest, a magnetic debeading process may be utilized to remove the Dynabeads from the collected cells. In other embodiments, the steps of harvesting the expanded population of cells and debeading the cells are carried out simultaneously using perfusion, whereby culture media is introduced through a feed port in the bioreactor vessel while cell culture medium including the expanded population of cells is removed from the bioreactor vessel through a drain port in the bioreactor vessel. In particular, when final debeading of the culture is required, filterless perfusion can be used to debead the micron-sized beads by taking advantage of the difference in weight of the cells and that of the cell-Dynabead complexes. In order to debead the culture, the entire contents of the bioreactor vessel would be mixed (using, for exampling the cam arms 762 of the actuator mechanism in the manner hereinbefore described). After mixing/agitation, the heavy Dynabeads would sink and settle on the silicon membrane 516 within 10-15 minutes. In contrast, the cells need over 4 hours to settle down over the membrane 516. After a hold period of 10-15 minutes post mixing/agitation, the cell suspension can be slowly pulled out using perfusion without disturbing the settled Dynabeads. The incoming medium line may be used to maintain the medium bed height within the bioreactor vessel. Thus invention described herein simplifies the current Dynabeads protocol by eliminating the need for several mid-process cell transfers and discreet washing and debeading steps, and minimizes costs and potential risks. By debeading the culture at the same time as harvesting the cells, the need of additional magnetic devices or disposables, which have typically been necessary, can be eliminated.

In contrast to other static, perfusion-free culture systems, the gas-permeable membrane-based bioreactor vessel 410 of the invention supports high density cell culture (e.g., up to 35 mm/cm$^2$). Thus, all four unit processes of activation using Dynabeads, transduction, washing and expansion can be performed in the same bioreactor vessel, in a fully automated and functionally-closed manner. The bioprocessing system of the invention therefore simplifies current protocol by eliminating the need for mid-process cell transfer and discreet washing steps, and minimizes costs and potential risks resulting from multiple human touchpoints.

In an embodiment, the two bioreactor vessels 410, 420 of the system can be run with either the same starting culture or two simultaneous split cultures, e.g., CD4+ cells in one bioreactor vessel 410, and CD8+ cells in the other bioreactor vessel 420. A split culture allows the parallel independent processing and expansion of two cell types that can be combined prior to infusion into the patient.

While a number of possible CAR-T workflows for the generation and expansion of genetically modified cells using the bioprocessing system of the invention have been described above, the workflows described herein are not intended to be comprehensive, as other CAR-T workflows are also enabled by the system of the invention. In addition, while the system of the invention and, in particular, the second module 200 of the system, has been described in connection with the manufacture of CAR-T cells, the system of the invention is also is compatible with the manufacture of other immune cells, such TCR-T cells and NK cells. Moreover, while embodiments of the invention, disclose the use of the two bioreactor vessels 410, 420 in a two-step, sequential process where the output of the first bioreactor vessel 410 is added to the second bioreactor vessel 420 for additional processing steps (e.g., activation in the first bioreactor vessel and transduction and expansion in the second bioreactor vessel), in some embodiments, the two bioreactor vessels can be used for identical workflows in duplicate. Example reasons for using a second bioreactor vessel sequentially can include residual chemical modifications (e.g., coatings or immobilized reagents) that cannot be washed out of the first bioreactor that are detrimental in later steps or if overexposure of cells occurs in earlier steps, or a need to pre-coat a bioreactor surface prior to the addition of cells (e.g., RetroNectin coating).

Additional examples of potential single bioreactor vessel workflows that are enabled by the system of the invention include (1) soluble activator activation, viral transduction, filterless perfusion and expansion in a single bioreactor vessel, (2) Dynabead-based activation, viral transduction, filterless perfusion and expansion in a single bioreactor vessel and (3) TransAct bead-based activation, viral transduction, filterless perfusion and expansion in a single vessel.

Moreover, further examples of potential multiple bioreactor vessel workflows that are enabled by the system of the invention include (1) soluble activator activation, viral transduction, filterless perfusion and expansion in the first bioreactor vessel 410, and soluble activator activation, Lentiviral transduction, filterless perfusion and expansion in the second bioreactor vessel 420, using identical cell types or split cultures in the two bioreactor vessels; (2) Dynabead-based activation, viral transduction, filterless perfusion and expansion in the first bioreactor vessel 410, and Dynabead-based activation, Lentiviral transduction, filterless perfusion and expansion in the second bioreactor vessel 420, using identical cell types or split cultures in the two bioreactor vessels; (3) TransAct bead-based activation, viral transduction, filterless perfusion and expansion in the first bioreactor vessel 410, and TransAct-based activation, Lentiviral transduction, filterless perfusion and expansion in the second bioreactor vessel 420, using identical cell types or split cultures in the two bioreactor vessels; (4) soluble activator activation in the first bioreactor vessel 410, and RetroNectin coating, transduction and expansion in the second bioreactor vessel 420; (5) immobilized activator activation in the first bioreactor vessel 410, and RetroNectin coating, transduction and expansion in the second bioreactor vessel 420; (6) Dynabead activation in the first bioreactor vessel 410, and RetroNectin coating, transduction and expansion in the second bioreactor vessel 420; (7) Dynabead activation and Lentiviral transduction in the first bioreactor vessel 410, and expansion in the second bioreactor vessel 420; (8) TransAct activation in the first bioreactor vessel 410, and RetroNectin coating, transduction and expansion in the second bioreactor vessel 420; (9) soluble activator activation in the first bioreactor vessel 410, and expansion of ex-situ electroporated cells or other non-viral modified cells in the second bioreactor vessel 420; (10) TransAct activation in the first bioreactor vessel 410, and expansion of ex-situ electroporated cells or other non-viral modified cells in the second bioreactor vessel 420; (11) Dynabead activation in the first bioreactor vessel 410, and expansion of ex-situ electroporated cells or other non-viral modified cells in the second bioreactor vessel 420; (12) expansion of allogenic NK cells in the first bioreactor vessel 410, and expansion of allogenic NK cells in the second bioreactor vessel 420 (small molecule-based expansion, with no genetic modification; (13) expansion of allogenic NK cells in the first bioreactor vessel 410, and expansion of allogenic NK cells in the second bioreactor vessel 420 (feeder cell-based expansion, with no genetic modification); and (14) soluble activator activation, viral transduction, filterless perfusion and expansion of allogenic CAR-NK or CAR-NK 92 cells in the first bioreactor vessel 410 and/or the first and second bioreactor vessels 410,420 (with no RetroNectin coating, and where Polybrene is used to assist in transduction).

While the embodiments described above illustrate process monitoring sensors that are integrated with the bioreactor vessels and/or the bed plate (e.g., on the membrane, integrated in the membrane, on the vessel sidewall, etc.), in other embodiments it is contemplated that additional sensor may be added to the fluid architecture 400, e.g., along the fluid flow lines themselves). These sensors may be disposable-compatible sensors for monitoring parameters such as pH, dissolved oxygen, density/turbidity (optical sensor) conductivity and viability within the circulated fluids. By arranging the sensors in the circulation loop (e.g., the circulation loop of the first bioreactor vessel and/or the circulation loop of the second bioreactor vessel), the vessel construction can be simplified. Additionally, in some embodiments, the sensors along the circulation loop may provide more accurate representation of vessel contents when circulated (rather than measuring when the cells are static within the vessel). Still further, a flow rate sensor (e.g., ultrasound based) may be added to the flow loop to measure pumping performance and used in conjunction with an algorithm to correct pumping parameters, as necessary.

Figure 78:
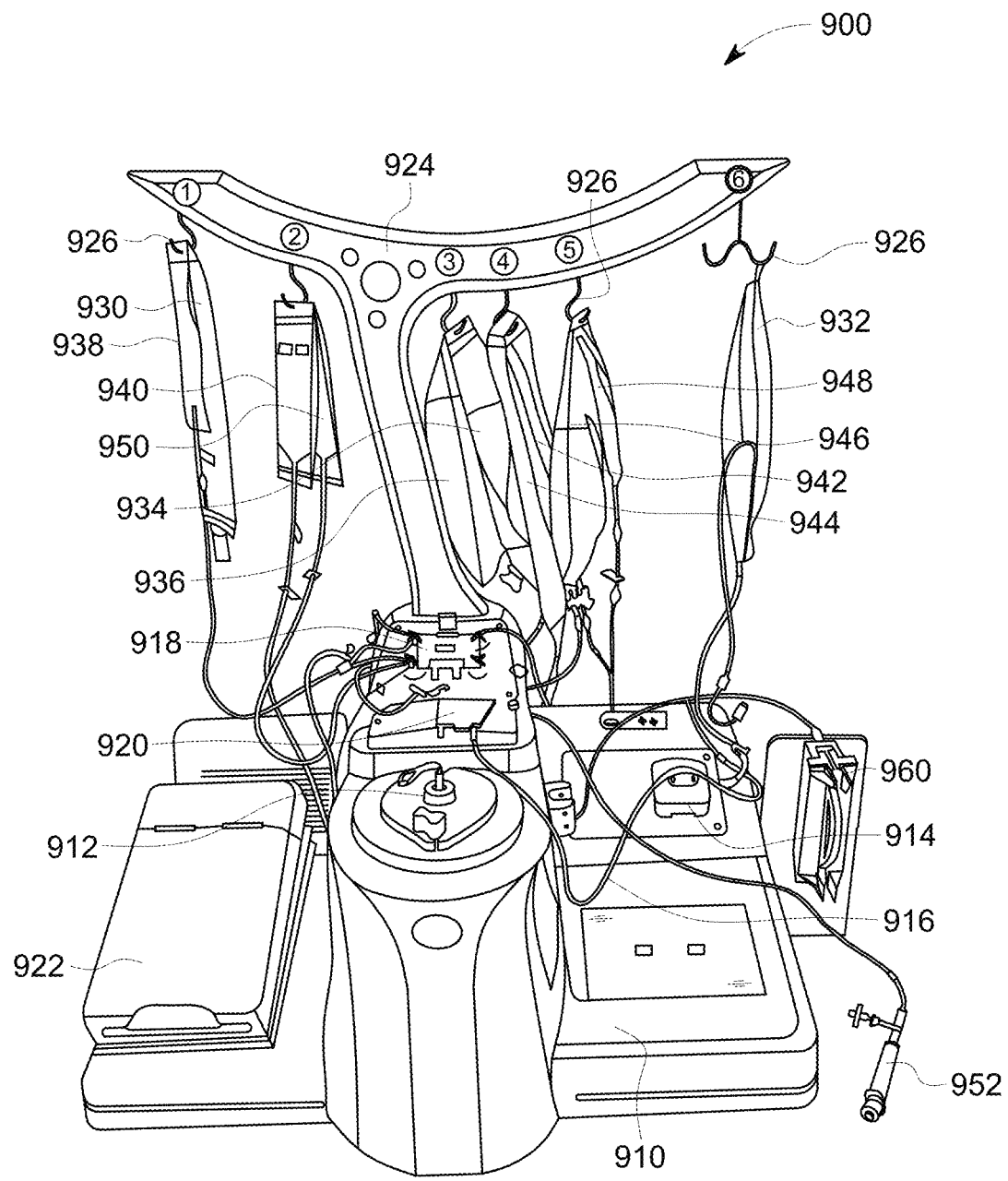
FIG. 78 is perspective view of an enrichment and isolation apparatus according to an embodiment of the invention.

As indicated above, the first and third modules 100, 300 may take any form of any system or device(s) known in the art that is capable of cell enrichment and isolation, and harvesting and/or formulation. FIG. 78 illustrates one possible configuration of a device/apparatus 900 which may be used in the bioprocessing system 10 as the first module 100, for cell enrichment and isolation using various magnetic isolation bead types (including, for example, Miltenyi beads, Dynabeads and StemCell EasySep beads). As shown therein, the apparatus 900 includes a base 910 that houses a centrifugal processing chamber 912, a high dynamic range peristaltic pump assembly 914, a small internal diameter pump tube 916 received by the peristaltic pump assembly, a stopcock manifold 918, optical sensors 920, and a heating-cooling-mixing chamber 922. As indicated below, the stopcock manifold 918 provides a simple and reliable means of interfacing multiple fluid or gas lines together using, for example, luer fittings. In an embodiment, the pump 914 is rated to provide flow rates as low as about 3 mL/min and as high as about 150 ml/min).

As further shown in FIG. 78, the apparatus 900 may include a generally T-shaped hanger assembly 924 that extends from the base 910 and includes a plurality of hooks 926 for suspending a plurality of processing and/or source vessels or bags. In an embodiment, there may be six hooks. Each hook may include an integrated weight sensor for detecting a weight of each vessel/bag. In an embodiment, the bags may include a sample source bag 930, a process bag 932, an isolation buffer bag 934, a washing bag 936, a first storage bag 938, a second storage bag 940, a post-isolation waste bag 942, a washing waste bag 944, a media bag 946, a release bag 948 and a collection bag 950.

The apparatus 900 is configured to be used with, or include, a magnetic cell isolation holder 960, as provided herein. The magnetic cell isolation holder 960 may be removable coupled to a magnetic field generator 962 (e.g., magnetic field plates 964, 966). The magnetic cell isolation holder 960 accommodates a magnetic retention element or material 968, such as a separation column, matrix or tube. In an embodiment, the magnetic cell isolation holder 960 may be constructed as disclosed in U.S. patent application Ser. No. 15/829,615, filed on Dec. 1, 2017, which is hereby incorporated by reference herein in its entirety. The apparatus 900 may be under control of a controller (e.g., controller 110), operating according to instructions executed by a processor and stored in memory. Such instructions may include the magnetic field parameters. In an embodiment, the apparatus 900 may further include a syringe 952 that can be utilized for bead addition, as discussed hereinafter.

Figure 79:
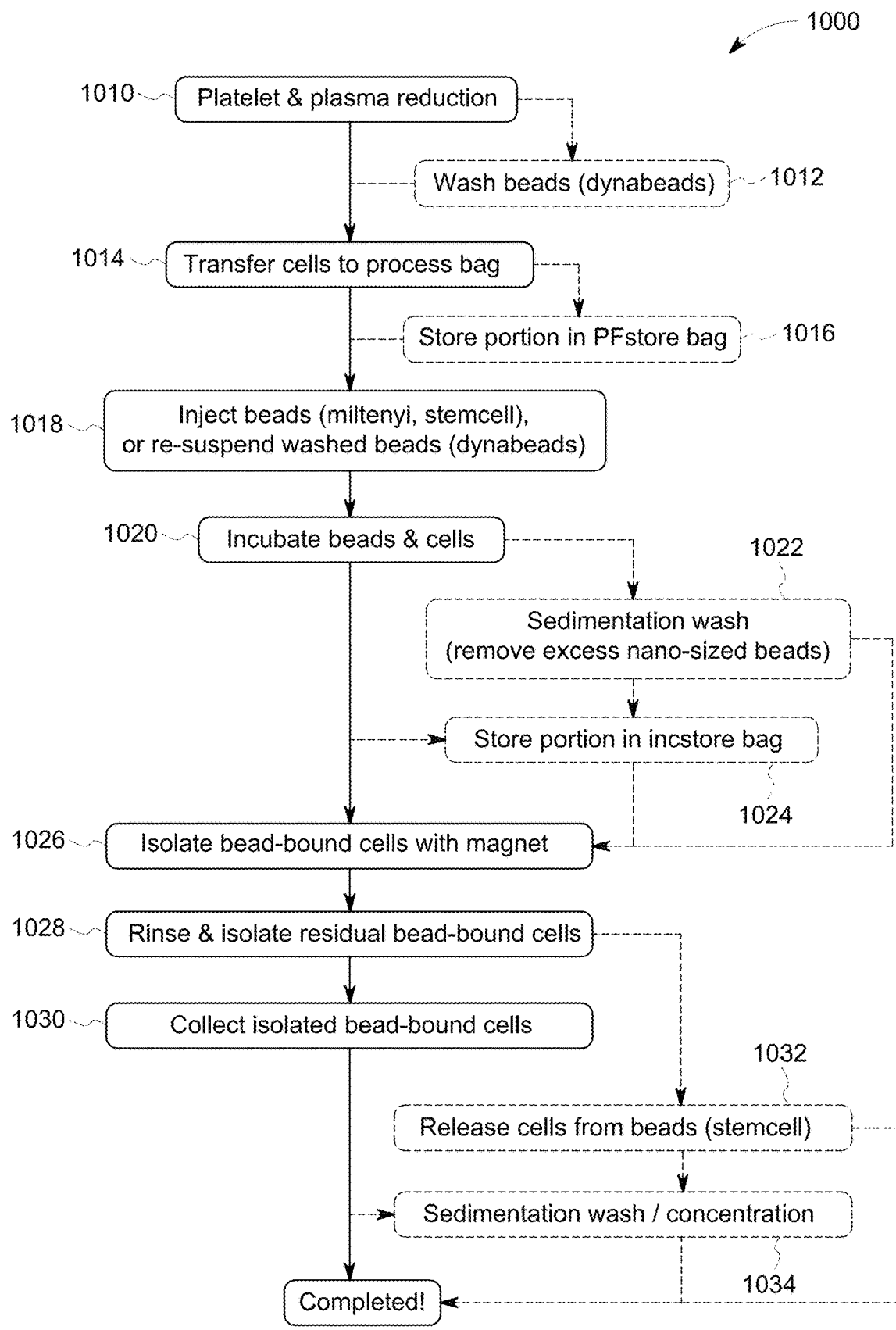
FIG. 79 is a process flow diagram of the enrichment and isolation apparatus of FIG. 78.

Turning now to FIG. 79, a generic protocol 1000 of the apparatus 700 is shown. As illustrated therein, in a first step 1010, enrichment is carried out by reducing platelets and plasma in a sample. In embodiments where Dynabeads are utilized as magnetic isolation beads, a washing step 1012 to remove the residuals in the Dynabead suspension may then be carried out. After enrichment, the cells are then transferred to the process bag 932, at step 1014. In some embodiments, a portion of the enriched cells may be stored in a first storage bag 938, at step 1016, prior to transfer into the process bag 932. At step 1018, magnetic isolation beads are injected into the process bag, such as by using the syringe 952, at step 1020. In an embodiment, the magnetic isolation beads are Miltenyi beads or StemCell EasySep beads. Where Dynabeads are utilized, the washed Dynabeads from step 1012 are resuspended in the process bag 932. In an embodiment, rather than utilizing a syringe, the magnetic isolation beads may be housed in a bag or vessel that is connected to the system, and the beads may be drawn into the system by the pump 914.

The beads and cells in the process bag 932 are then incubated for a period of time, at step 1020. In embodiments where the magnetic isolation beads are Miltenyi nano-sized beads, a sedimentation wash is carried out at step 1022 to remove the excess nano-sized beads, and a portion of the incubated bead-bound cells is stored in the second storage bag 940, at step 1024. After incubation, the bead-bound cells are isolated using a magnet, e.g., magnetic field plates 964, 966 of magnetic cell isolation holder 960, at step 1026. Residual bead-bound cells are then rinsed and isolated, at step 1028. Finally, in embodiments where Miltenyi or Dynabeads are utilized, at step 1030, the isolated bead-bound cells are collected in collection bag 950. In embodiments where StemCell EasySep beads are utilized, the additional step 1032 of releasing the cells from the beads to remove the beads, and the optional step 1034 of washing/concentrating the collected cells are carried out.

Figure 80:
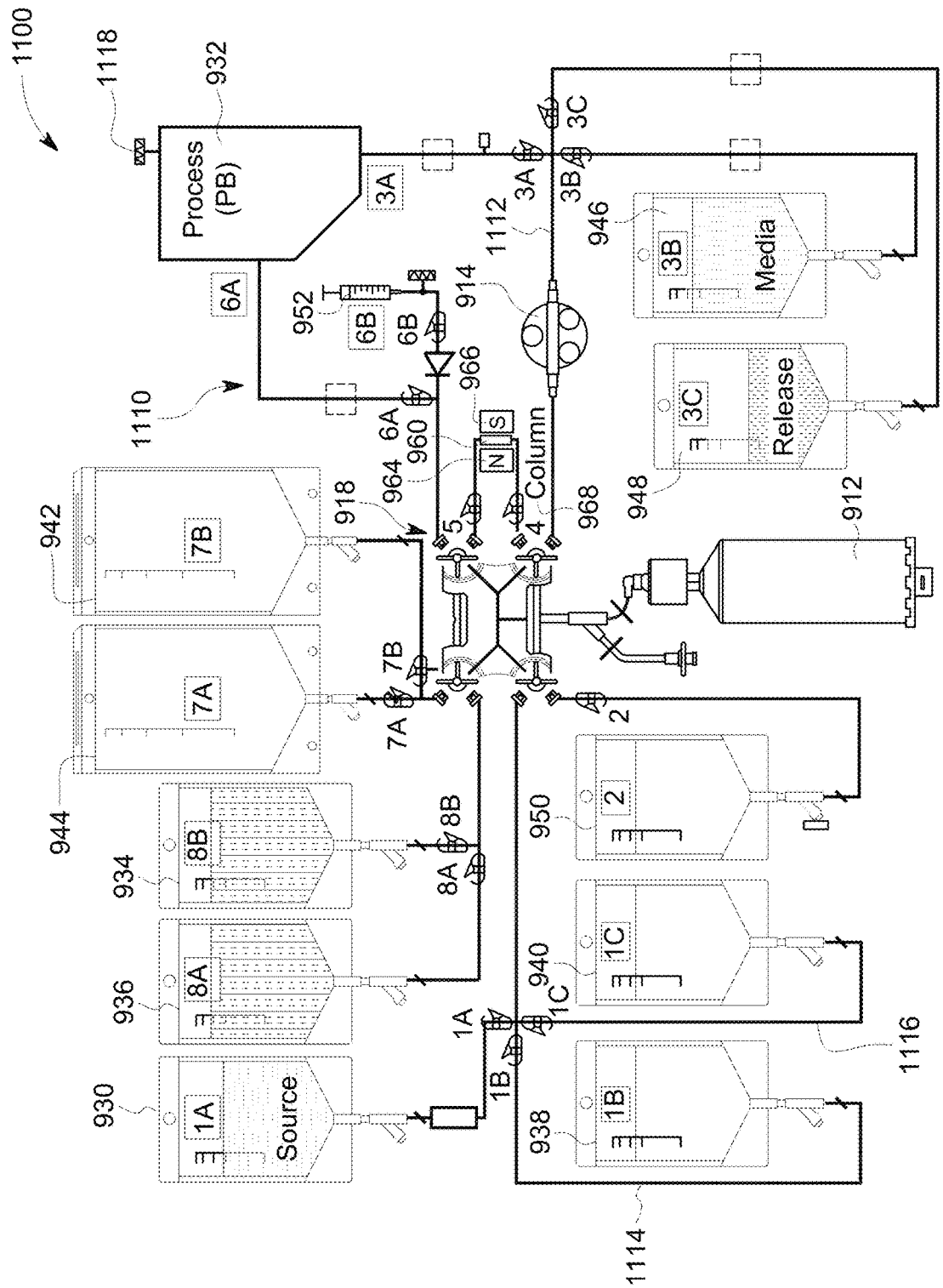
FIG. 80 is a schematic illustration of the fluid flow architecture of the apparatus of FIG. 78, for carrying out enrichment and isolation of a population of cells.

A more detailed description of the generic protocol of FIG. 79 using the apparatus 900 is described in more detail below, with specific reference to FIG. 80, which is a schematic illustration of the flow architecture 1100 of the apparatus 900. To begin, the process of enrichment (step 1010) is commenced by transferring the apheresis product contained within the source bag 930 and washing buffer from washing buffer bag 936 to the chamber 912 for washing using washing buffer, in order to reduce the amount of platelets and serum. At this point, the enriched source material is located in the chamber 912. To begin the isolation process, a separation column received by the magnet cell isolation holder 960 is primed by initiating a flow of a buffer from isolation buffer bag 934 to the process bag 932 through the manifold 918 and through the column to prime the column.

As disclosed above, in certain embodiments, such as where Dynabeads are utilized as magnetic isolation beads, a washing step (step 1012) is carried out to remove any residuals in the bead suspension buffer. The washing step includes injecting the beads using the syringe 952 while circulating in a process loop 1110 (e.g., from the process bag 932, through the peristaltic pump tubing 914, through the manifold 918, and back to the process bag 932), clearing the process loop 1110, and then capturing the beads by flowing the process bag 932 to the isolation waste bag 942 while the magnetic field generator 962 in 'ON'. In embodiments where no washing is desired, the process bag 932 is flowed to the isolation waste bag 942 to ensure that the process bag 932 is clear. As used herein, in the case of a permanent magnet, ON means that the magnetic retention element or material 968 (e.g., the separation column, matrix or tube) is in the appropriate position within the magnetic field. OFF means that the tubing section is removed from the magnetic field.

Next, the enriched cells in the processing chamber 912 are transferred to the process bag 932 (step 1014), and an isolation buffer from the isolation buffer bag 934 is drawn into the processing chamber 912 to rinse the chamber 912 of any remaining cells. After rinsing, the fluid is expelled to the process bag 932. This rinsing process may be repeated, as desired. After all of the cells have been transferred to the process bag 932, the chamber 912 is cleaned by drawing buffer from the isolation buffer bag 934 into the chamber 912 and expelling the fluid to the source bag 930. This cleaning process may be repeated, as desired.

The contents of the process bag 932 may then be mixed by circulating the contents along the process loop 1110, before clearing the process loop 1110 by returning the entire contents to the process bag 932. As indicated above, in an embodiment, a portion of the enriched cells may be stored at this point by transferring a portion of the contents of the process bag 932 to the first storage bag 938 (step 1016). The process line 1112 and first storage bag line 1114 may then be cleared.

In embodiments where the bead washing step is not utilized, beads are then injected into the process loop 1110 using the syringe 952 and the process loop 1110 is cleared (step 1018). In embodiments where the bead washing step is utilized, the beads are resuspended and circulated through the process loop 1110 (step 1018) and column 968, and the process loop is cleared through the column 968.

As discussed above, after adding the magnetic isolation beads, the cells may be incubated for a period of time (step 1020). In an embodiment, prior to incubation, the contents of process bag 932 may be transferred to the second storage bag 940, and the second storage bag 940 is agitated (such as using the heating-cooling-mixing chamber 922). The contents of the second storage bag 940 are then transferred back to the process bag 932. Buffer from the isolation buffer bag 934 is then drawn into the processing chamber 912, and the chamber contents are expelled to the second storage bag 940, and then transferred to the process bag 932 to rinse the second storage bag 940.

In either embodiment, the cells are then incubated along with the magnetic isolation beads by circulating the cells along the process loop 1110 for a prescribed incubation time. After incubation, the process loop 1110 is cleared.

As discussed above, after incubation, the optional step of washing out excess beads (e.g., nano-sized beads) may be carried out (step 1022). Washing out excess nano-sized beads includes initiating a flow from the process bag 932 to the second storage bag 940, drawing the contents of the second storage bag 940 into the processing chamber 912, transferring buffer from the isolation buffer bag 934 to the process bag 932, transferring the contents of the process bag 932 to the second storage bag 940, and drawing the contents of the second storage bag 940 into the processing chamber. The steps of flowing from the isolation buffer bag 934 to the process bag 932, and then to the second storage bag 940 may be repeated as desired to wash out excess beads. In an embodiment, the chamber 912 may then be filled with buffer from the isolation buffer bag 934, initiating rotation of the chamber 912, and then expelling supernatant to the waste bag 742. These steps may be repeated as desired. In an embodiment, cells in the chamber are expelled to the process bag 932, buffer from isolation buffer bag 934 is drawn into the chamber 932, and the chamber is then expelled to the process bag 932. This process may likewise be repeated as desired. Mixing of the process loop and clearing of the process loop are then carried out.

In some embodiments, a portion of the incubated cell population may be stored in the second storage bag 940 (step 1024). To do so, a portion of the contents of the process bag 932 may be transferred to the second storage bag 940, and then the process line and second storage line 1116 are cleared.

In any of the processes described above, after incubation, the bead-bound cells are isolated using the magnets 964, 966 (step 1026). This is accomplished by flowing from the process bag 932 to the waste bag 942 while the magnetic field generator 962 is 'ON'. Residual waste is then cleared by pumping buffer from the isolation buffer bag 934 to the process bag 932, and then pumping from the process bag 932 to the waste bag 942 with the magnetic field generator 962 'ON'.

In an embodiment, rinsing without re-suspension may be carried out by pumping buffer from the isolation buffer bag 934 to the process bag 932, rinsing the process loop 1110, clearing the process loop 1110, and flowing from the process bag 932 to the waste bag 942 with the magnetic field generator 962 'ON'.

In another embodiment, rinsing via re-suspension may be carried out by pumping buffer from the isolation buffer bag 934 to the process bag 932 with the magnetic field generator 962 'OFF', circulating in the process loop 1110, clearing the process loop, and flowing from the process bag 932 to the waste bag 942 with the magnetic field generator 962 'ON'.

In an embodiment, residual waste may be cleared by pumping buffer from the isolation buffer bag 934 to the process bag 932, and flowing from the process bag 932 to the waste bag 942 with the magnetic field generator 962 'ON'.

After rinsing and isolating the residual bead-bound cells, the isolated bead bound cells are then collected (step 1028). Where the bead-bound cells are to be collected without releasing the cells from the beads, in one method, the media from media bag 946 is simply pumped through the column 968 to the collection bag 950 with the magnetic field generator 962 'OFF'. In another method, buffer from Isolation buffer bag 934 is pumped to the process bag 932, and the process bag 932 is then pumped to the collection bag 950 with the magnetic field generator 962 'OFF'. This second method provides for post-isolation washing. In a third method, media from the media bag 946 is pumped to the process bag 932 through the column 966 (if no post-isolation wash is needed). Alternatively, buffer from isolation buffer bag 934 is pumped to the process bag 932 through the column 966 (if post-isolation wash is desired). In either process, the contents of the process bag 932 are then circulated in the process loop 1110, the process loop 1110 is cleared by returning to the process bag 932, and the contents of the process bag 932 are pumped to the collection bag 950 to collect the bead-bound cells.

Where the bead-bound cells are to be collected after releasing the cells from the beads, a number of potential processes may be carried out. For example, in an embodiment, the cells/beads may be resuspended with the magnet 'OFF' by pumping a release buffer from bag 948 through the column to the process bag 932, circulating in the process loop 1110, and then clearing the process loop by returning the fluid to the process bag 932. Then, incubation and collection is carried out with the magnet 'ON' by incubating in the process loop 1110, clearing the process loop 1110, collecting the released cells by pumping from the process bag 932 through the column 966 to the collection bag 950, pumping buffer from the isolation buffer bag 934 to the process bag 932, and collecting residuals by pumping the contents of the process bag 932 through the column 966 to the collection bag 950. The released beads (step 1032) may then be discarded by, with the magnet 'OFF', pumping buffer from the isolation buffer bag 934 through the column 966 to the process bag 932, circulating in the process loop 1110, clearing the process loop 1110, and pumping the contents of the process bag 932 to the waste bag 942.

In connection with the above, in an embodiment, washing/concentration (step 1034) may be carried out by pumping the contents of the collection bag 950 to the processing chamber 912, pumping buffer from the isolation buffer bag 934 to the process bag 932, and transferring the buffer from the process bag 932 to the processing chamber 912. Wash cycles may then be carried out by filling the processing chamber 912 with buffer form isolation buffer bag 934, spinning the chamber 912, expelling supernatant to the waste bag 942, an repeating the spinning and expelling steps as desired. Finally, transferring the cells to the collection bag after wash/concentration may be accomplished by transferring media from the media bag 946 to the collection bag 950, pumping the collection bag contents into the processing chamber 912, expelling the contents of the processing chamber 912 to the collection bag 950, then manually clearing the line between the processing chamber 912 and the collection bag 950.

In an embodiment, one of the bags, e.g., process bag 932 may include a top port 1118 having a filter so that sterile air may be introduced into the system (when the process bag 932 is empty) for clearing the lines, as needed, such as in the various process steps discussed above. Clearing of the lines may be accomplished as a first step in the enrichment/isolation process and/or during the process. In an embodiment, air from the collection bag 950 may be used to clear any of the lines of the system (e.g., air from the collection bag 950 can be used to clear the process line 1112, then the air in the process line 1112 can be used to clear the desired tubing line (i.e., line 1114, 1116, etc.), thereby filling the process line 1112 with liquid from the process bag 932, and finally clearing the process line 1112 again using air from the collection bag 950).

In an embodiment, the processing bag 932 be blow-molded and have a high angle on the sides (having a 3D shape with a defined air pocket above liquid level) to limit micron-sized beads from sticking to side walls, particularly during long promote mixing during circulation-based incubation.

In an embodiment the syringe 952 allows for addition of small volumes (such as bead suspension aliquots) to the circulation-based flow loop 1110. Moreover, fluid from the flow loop 1110 can be pulled into the syringe 952 to further clear any residuals from the syringe 952.

In an embodiment, one of the sensors 920 may configured to measure the flow of fluid. For example, one of the sensor 920 may be a bubble detector or an optical detector which can be used as a secondary confirmatory measure to ensure accurate flow control (in addition to the load cells integrated with the hooks 926. This can be used in practice during isolation where it is desired to flow the volume in the process bag through the magnet without introducing air into the column. The load cell indicates that the process bag is close to empty within some expected tolerance of load cell variability, and then the bubble detector 920 identifies the trailing liquid/air interface in order to stop the flow. The sensor 920 can therefore be used by the controller to prevent the pulling of air into the loop which can generate slugs to dislodge cells, or expose cells to dry environment, or by inadvertently pulling material into the waste bags in situations where the pump is not stopped after full draining of the process bag. In an embodiment, the bubble detector 920 can therefore be used in combination with the load cells integrated with the hooks to improve volume control accuracy, thereby reducing cells loss and/or preventing air from entering column tubing and column.

As alluded to above in an embodiment, air may be pulled into the loop for the purposeful generation of an air slug that can used to dislodge bead-bound cells within the isolation column/tube, for collection. In an embodiment, a buffer solution may be circulated through the isolation column to elute the bead-bound cells from the isolation column, either in place of, or in addition to, using an air slug.

In an embodiment, two or more peristaltic pump tubes with different inside diameters connected serially can be employed, in order to enable expanded range of flow rates for a single pump. To switch between tubes, the pump cover is opened, the existing tube physically removed, the desired tube physically inserted, and the pump head is then closed.

In some embodiments, the system 900 can be used for elution of isolated/captured bead-cell complexes. In particular, it is contemplated that an air-liquid interface can be used to aid in the removal of complexes from tube sidewalls or column interstitial spaces. Air can be circulated through or shuffled back-and-forth through the column/tube. Without the air/liquid interface, a packed bed of beads/bead-bound cells can be difficult to remove with flow rate control alone, without significantly increasing shear rate (which has a potential negative impact on cell viability). Coupled with flow rate, it is therefore possible to remove bead-cell complexes without removing from the magnet.

In connection with the above, the system 900 supports the concept of eluting the positively selected bead-cell complexes directly into media of choice (based on downstream steps). This eliminates a buffer exchange/washing step. In an embodiment, it is also envisioned to elute directly into media and the viral vector to start incubation. This concept can also enable adding viral vector to the final bag. In an embodiment, instead of eluting bead-bound cells with buffer, media may be used as the elution fluid. Similarly, release buffer can be used to elute StemCell beads for subsequent cell release from beads. By replacing buffer in portions of the system 900 with media, dilution can be minimized.

As disclosed above, the apparatus 900 of the first module 100 is a single kit that provides for platelet- and plasma-reduced enrichment followed by magnetic isolation of target cells. The apparatus 900 is automated so as to allow the enrichment, isolation and collection steps, and all intervening steps, to be carried out with minimal human intervention. Like the second module 200, the first module 100 and apparatus 900 thereof is functional closed to minimize the risk of contamination, and is flexible so as to handle various therapy volumes/dosages/cell concentrations, and is able to support multiple cell types in addition to CAR-T cells.

It is to be understood that the system of the present invention may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller(s), e.g., controller 110, 210 and/or 310, to perform the methods disclosed herein may be read into a main memory of the at least one processor from a computer-readable medium. The term "computer-readable medium", as used herein, refers to any medium that provides or participates in providing instructions to the at least one processor of the system (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software. Moreover, it is envisioned that all methods, protocols and workflows described herein can be carried out via software, which software may a single or multiple applications, programs, etc.

Furthermore, it is contemplated that the software may be configured to carry out the methods, protocols and/or workflows in a fully autonomous mode, a semi-autonomous mode, or in a gated manner. In a fully autonomous mode, the software includes instructions configured to adapt the controller(s) of the system to run substantially an entire operation, method, protocol or workflow from start to finish automatically once initiated by a user or operator (i.e., without intervention by an operator and without requiring human touchpoints). In a semi-autonomous mode of operation, the software includes instructions configured to adapt the controller(s) of the system to run substantially an entire operation method, protocol or workflow from start to finish once initiated by a user or operator, except that the software may instruct the controller(s) to pause operation of the bioprocessing system or components thereof and prompt a user or operator to take certain specific actions necessary to carry out the operation method, protocol or workflow, such as connecting or disconnecting collection, waste, media, cell, or other bags or reservoirs, to take a sample, etc. In a gated mode of operation, the software includes instructions configured to adapt the controller(s) of the system to generate a series of prompts directing a user or operator to take certain specific actions necessary to carry out a given operation method, protocol or workflow such as connecting or disconnecting collection, waste, media, cell, or other bags or reservoirs, to take a sample, etc., and to autonomously control system operation between each discrete operator intervention. In the gated mode of operation, the bioprocessing system is much more heavily operator dependent, whereby the controller(s) only carry out preprogrammed bioprocessing steps once initiated by an operator.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system for bioprocessing, comprising:
   a tray having an interior compartment and being configured to receive a bioreactor vessel;
   a pump assembly;
   a pinch valve array;
   a first tubing holder block configured for selective engagement with the pump assembly; and
   a second tubing holder block configured for selective engagement with a respective actuator of the pinch valve array.

2. The system of claim 1, wherein:
   the tray includes a plurality of sidewalls, a bottom surface and a generally open top.

3. The system of claim 2, wherein:
   the pump assembly is positioned adjacent to a rear sidewall of the plurality of sidewalls of the tray; and
   wherein a pinch valve array positioned adjacent to the rear sidewall of the tray.

4. The system of claim 1, wherein:
   the first tubing holder block is configured to receive at least one pump tube and hold the at least one pump tube in position for selective engagement with the pump assembly.

5. The system of claim 4, wherein:
   the first tubing holder block and the second tubing holder block define a tubing module positioned at a rear of the tray.

6. The system of claim 5, wherein:
   the tubing module is integral with the tray.

7. The system of claim 5, wherein:
   the tubing module is removably received by an opening formed in a rear wall of the tray.

8. The system of claim 5, further comprising:
   a temperature-controlled processing chamber configured to receive the tray.

9. The system of claim 8, wherein:
   the temperature-controlled processing chamber has a plurality of sidewalls, a bottom surface, and a generally open top;
   wherein the temperature-controlled processing chamber includes a shoe that extends upwardly from the processing chamber and is received through a first clearance opening in the tubing module; and wherein the at least one pump tube is received intermediate the pump assembly and the shoe.

10. The system of claim 8, wherein:

the temperature-controlled processing chamber includes an anvil that extends upwardly from the processing chamber and is received through a second clearance opening in the tubing module.

11. The system of claim 1, wherein:

at least one of the first tubing holder block and the second tubing holder block is integral with the tray.

12. The system of claim 1, wherein:

at least one of the first tubing holder block and the second tubing holder block is removably received by an opening formed in a wall of the tray.

13. The system of claim 12, wherein:

the wall is a rear sidewall of the tray.

14. The system of claim 1, wherein:

the second tubing holder block is configured to receive a plurality of pinch valve tubes and hold each pinch valve tube of the plurality of pinch valve tubes in position for selective engagement with a respective actuator of the pinch valve array;

wherein the second tubing holder block of the tubing module includes a back plate having a plurality of apertures corresponding to the plurality of pinch valve tubes;

wherein the plurality of pinch valve tubes are positioned adjacent to the back plate.

15. The system of claim 14, wherein:

the plurality of apertures includes a first column of apertures and a second column of apertures;

wherein the apertures in the first column of apertures are offset in a vertical direction with respect to the apertures on the second column of apertures so that the apertures in the first column of apertures are not in horizontal alignment with the apertures in the second column of apertures.

16. The system of claim 15, wherein:

each aperture of the plurality of apertures is arranged so as to be aligned with an actuator of the pinch valve array so as to allow engagement of the actuator with the plurality of pinch valve tubes through the plurality of apertures.

17. The system of claim 1, wherein:

at least one of the first tubing holder block and the second tubing holder block includes at least one of a hollow fiber filter and/or a tangential flow filtration device.

18. The system of claim 1, wherein:

at least one of the first tubing holder block and the second tubing holder block includes at least one vessel tubing clip for retaining one of a drain line and a feed line connected to the bioreactor vessel.

19. A system for bioprocessing, comprising:

a tray having a plurality of sidewalls and a bottom surface defining an interior compartment, and a generally open top, the tray being configured to receive a bioreactor vessel;

a pump assembly positioned adjacent to the rear sidewall of the tray;

a pinch valve array positioned adjacent to the rear sidewall of the tray;

a first tubing holder block configured for selective engagement with the pump assembly; and a second tubing holder block configured for selective engagement with at least one actuator of the pinch valve array.

20. The system of claim 19, wherein:

the first tubing holder block and the second tubing holder block form an integrated unit.

21. The system of claim 19, wherein:

wherein the first tubing holder block and the second tubing holder block, together, form at least a portion of a rear sidewall of the tray and defines a portion of a boundary of the interior compartment.

* * * * *